(12) United States Patent
Anderberg et al.

(10) Patent No.: US 8,993,250 B2
(45) Date of Patent: Mar. 31, 2015

(54) METHODS AND COMPOSITIONS FOR DIAGNOSIS AND PROGNOSIS OF RENAL INJURY AND RENAL FAILURE

(75) Inventors: Joseph Anderberg, Encinitas, CA (US); Jeff Gray, Solana Beach, CA (US); Paul McPherson, Encinitas, CA (US); Kevin Nakamura, Cardiff by the Sea, CA (US)

(73) Assignee: Astute Medical, Inc., San Diego, CA (US)

( * ) Notice: Subject to any disclaimer, the term of this patent is extended or adjusted under 35 U.S.C. 154(b) by 851 days.

(21) Appl. No.: 13/128,392

(22) PCT Filed: Nov. 10, 2009

(86) PCT No.: PCT/US2009/063906
§ 371 (c)(1),
(2), (4) Date: Jun. 9, 2011

(87) PCT Pub. No.: WO2010/054389
PCT Pub. Date: May 14, 2010

(65) Prior Publication Data
US 2011/0306063 A1 Dec. 15, 2011

Related U.S. Application Data

(60) Provisional application No. 61/113,074, filed on Nov. 10, 2008, provisional application No. 61/115,049, filed on Nov. 15, 2008, provisional application No. 61/117,180, filed on Nov. 22, 2008, provisional application No. 61/117,168, filed on Nov. 22, 2008, provisional application No. 61/117,178, filed on Nov. 22, 2008, provisional application No. 61/117,163, filed on Nov. 22, 2008, provisional application No. 61/117,158, filed on Nov. 22, 2008, provisional application No. 61/117,162, filed on Nov. 22, 2008, provisional application No. 61/117,160, filed on Nov. 22, 2008, provisional application No. 61/117,161, filed on Nov. 22, 2008, provisional application No. 61/117,151, filed on Nov. 22, 2008.

(51) Int. Cl.
*G01N 31/00* (2006.01)
*G01N 33/53* (2006.01)
*G01N 33/68* (2006.01)

(52) U.S. Cl.
CPC ...... *G01N 33/6893* (2013.01); *G01N 2800/347* (2013.01)
USPC ........... 435/7.21; 435/7.1; 436/501; 436/518; 424/9.1; 424/520; 422/430; 530/300; 530/350

(58) Field of Classification Search
CPC ... A61K 45/06; A61K 2300/00; C12Q 1/6886
See application file for complete search history.

(56) References Cited

U.S. PATENT DOCUMENTS

| | | |
|---|---|---|
| 6,218,122 B1 | 4/2001 | Friend et al. |
| 6,664,385 B1 | 12/2003 | Sanicola-Nadel et al. |
| 6,784,154 B2 | 8/2004 | Westenfelder |
| 6,861,404 B1 | 3/2005 | Cohen et al. |
| 6,941,172 B2 | 9/2005 | Nachum |
| 7,138,230 B2 | 11/2006 | Hu et al. |
| 7,141,382 B1 | 11/2006 | Parikh et al. |
| 7,235,358 B2 | 6/2007 | Wohlgemuth et al. |
| 7,608,413 B1 | 10/2009 | Joseloff et al. |
| 7,662,578 B2 | 2/2010 | Devarajan |
| 7,981,684 B2 | 7/2011 | Levin et al. |
| 7,998,744 B2 | 8/2011 | Stevenson et al. |
| 8,008,008 B2 | 8/2011 | Parr et al. |
| 8,071,293 B2 | 12/2011 | High et al. |
| 8,080,394 B2 | 12/2011 | Levy et al. |
| 8,241,861 B1 | 8/2012 | Heinecke et al. |
| 2003/0003588 A1 | 1/2003 | Comper |
| 2004/0053309 A1 | 3/2004 | Holt et al. |
| 2004/0106155 A1 | 6/2004 | Comper |
| 2005/0002934 A1 | 1/2005 | Reed |
| 2005/0048033 A1 | 3/2005 | Fraser et al. |
| 2005/0112688 A1 | 5/2005 | Hu et al. |
| 2005/0137481 A1 | 6/2005 | Sheard et al. |
| 2005/0148029 A1 | 7/2005 | Buechler et al. |

(Continued)

FOREIGN PATENT DOCUMENTS

| | | |
|---|---|---|
| CN | 1791797 A | 6/2006 |
| EP | 0828159 A1 | 3/1998 |

(Continued)

OTHER PUBLICATIONS

Kawai et al. Ameican Journal of Pathology, Nov. 2004, 165(5), pp. 1603-1612.*
Grigoryev et al., The Local and Systemic Inflammatory Transcriptome after Acute Kidney Injury. J Am Soc Nephrol. Mar. 2008;19(3):547-558.
Gümüs et al., Serum Levels of Total Acid Phosphatase, Prostatic Acid Phosphatase, Total and Free Prostate-Specific Antigen in Patients Within Chronic Hemodialysis Program. Braz J Urol, Mar.-Apr. 2001;27(2):133-135.
Gupta et al., Role of Protein C in Renal Dysfunction after Polymicrobial Sepsis. J Am Soc Nephrol. Mar. 2007;18 (3):860-867.

(Continued)

*Primary Examiner* — Lisa Cook
(74) *Attorney, Agent, or Firm* — Michael A. Whittaker; Acuity Law Group, P.C.

(57) ABSTRACT

The present invention relates to methods and compositions for monitoring, diagnosis, prognosis, and determination of treatment regimens in subjects suffering from or suspected of having a renal injury. In particular, the invention relates to using assays that detect one or more markers selected from the group consisting of Clusterin, Heart-type fatty acid binding protein, Hepatocyte growth factor, Interferon gamma, Interleukin-12 subunit beta, Interleukin-16, Interleukin-2, 72 kDa type IV collagenase, Matrix metalloproteinase-9, Midkine, and Serum amyloid P-component as diagnostic and prognostic biomarkers in renal injuries.

25 Claims, 120 Drawing Sheets

(56) References Cited

U.S. PATENT DOCUMENTS

| | | |
|---|---|---|
| 2005/0158801 A1 | 7/2005 | Hu et al. |
| 2005/0256075 A1 | 11/2005 | Alitalo et al. |
| 2005/0272101 A1 | 12/2005 | Devarajan et al. |
| 2006/0003327 A1 | 1/2006 | Achiron et al. |
| 2006/0057066 A1 | 3/2006 | Natsoulis et al. |
| 2006/0088823 A1 | 4/2006 | Haab et al. |
| 2006/0204951 A1 | 9/2006 | Folkman et al. |
| 2006/0223077 A1 | 10/2006 | Ni et al. |
| 2006/0240437 A1 | 10/2006 | Krolewski et al. |
| 2006/0246485 A1 | 11/2006 | Sarwal et al. |
| 2007/0031905 A1 | 2/2007 | Shariat |
| 2007/0087387 A1 | 4/2007 | Devarajan et al. |
| 2007/0093969 A1 | 4/2007 | Mendrick et al. |
| 2007/0105142 A1 | 5/2007 | Wilhelm |
| 2007/0112327 A1 | 5/2007 | Yun et al. |
| 2007/0154897 A1 | 7/2007 | Yen et al. |
| 2007/0248989 A1 | 10/2007 | Devarajan |
| 2007/0249002 A1 | 10/2007 | Hu et al. |
| 2008/0014644 A1 | 1/2008 | Barasch et al. |
| 2008/0038192 A1 | 2/2008 | Gervais |
| 2008/0038269 A1 | 2/2008 | Susan |
| 2008/0090304 A1 | 4/2008 | Barasch et al. |
| 2008/0133141 A1 | 6/2008 | Frost |
| 2008/0153092 A1 | 6/2008 | Kienle et al. |
| 2008/0206794 A1 | 8/2008 | Hu et al. |
| 2008/0254483 A1 | 10/2008 | Darbouret et al. |
| 2008/0254485 A1 | 10/2008 | Valkirs et al. |
| 2009/0022730 A1 | 1/2009 | Raulf et al. |
| 2009/0047689 A1 | 2/2009 | Kolman et al. |
| 2009/0081713 A1 | 3/2009 | Klein et al. |
| 2009/0088409 A1 | 4/2009 | Charlton |
| 2009/0090856 A1 | 4/2009 | Grant et al. |
| 2009/0148539 A1 | 6/2009 | Elias et al. |
| 2009/0176656 A1 | 7/2009 | Halloran |
| 2009/0197287 A1 | 8/2009 | Hu et al. |
| 2009/0203588 A1 | 8/2009 | Willman et al. |
| 2009/0220526 A1 | 9/2009 | Hamid |
| 2009/0258002 A1 | 10/2009 | Barrett et al. |
| 2009/0298073 A1 | 12/2009 | Gerhold et al. |
| 2009/0298106 A1 | 12/2009 | Hooper |
| 2010/0022627 A1 | 1/2010 | Scherer |
| 2010/0081148 A1 | 4/2010 | Singbartl et al. |
| 2010/0190164 A1 | 7/2010 | Tammen et al. |
| 2010/0240078 A1 | 9/2010 | Lee et al. |
| 2010/0267041 A1 | 10/2010 | Shuber et al. |
| 2011/0065608 A1 | 3/2011 | Labrie et al. |
| 2011/0104726 A1 | 5/2011 | Valkirs et al. |
| 2011/0174062 A1 | 7/2011 | Anderberg et al. |
| 2011/0195429 A1 | 8/2011 | Anderberg et al. |
| 2011/0201038 A1 | 8/2011 | Anderberg et al. |
| 2011/0207161 A1 | 8/2011 | Anderberg et al. |
| 2012/0190044 A1 | 7/2012 | Anderberg et al. |
| 2012/0190051 A1 | 7/2012 | Anderberg et al. |
| 2013/0035290 A1 | 2/2013 | Elias et al. |

FOREIGN PATENT DOCUMENTS

| | | |
|---|---|---|
| EP | 1905846 A2 | 4/2008 |
| EP | 2261660 A1 | 12/2010 |
| EP | 2480882 A1 | 8/2012 |
| EP | 2513649 A1 | 10/2012 |
| RU | 2180965 C1 | 3/2002 |
| SU | 1429031 A1 | 10/1988 |
| WO | 9855508 A2 | 12/1998 |
| WO | 03054004 A2 | 7/2003 |
| WO | 03075016 A1 | 9/2003 |
| WO | 2004005934 A2 | 1/2004 |
| WO | 2005087264 A1 | 9/2005 |
| WO | 2006083986 A3 | 8/2006 |
| WO | 2007013919 A2 | 2/2007 |
| WO | 2007041623 A2 | 4/2007 |
| WO | 2008060607 A2 | 5/2008 |
| WO | 2008084331 A2 | 7/2008 |
| WO | 2008104804 A2 | 9/2008 |
| WO | 2008116867 A1 | 10/2008 |
| WO | 2008122670 A2 | 10/2008 |
| WO | 2008154238 A1 | 12/2008 |
| WO | 2009038742 A2 | 3/2009 |
| WO | 2010025424 A1 | 3/2010 |
| WO | 2010025434 A1 | 3/2010 |
| WO | 2010048346 A1 | 4/2010 |
| WO | 2010048347 A2 | 4/2010 |
| WO | 2010054389 A1 | 5/2010 |
| WO | 2010091236 A1 | 8/2010 |
| WO | 2010111746 A1 | 10/2010 |
| WO | 2010128158 A1 | 11/2010 |
| WO | 2011035323 A1 | 3/2011 |
| WO | 2011075744 A1 | 6/2011 |

OTHER PUBLICATIONS

Han et al, Urinary biomarkers in the early diagnosis of acute kidney injury, Kidney Int. Apr. 2008;73(7):863-869.

Han et al., Upregulation of hyaluronan and its binding receptors in an experimental model of chronic cyclosporine nephropathy. Nephrology (Carlton). Mar. 2010;15(2):216-224.

Han, Biomarkers for Early Detection of Acute Kidney Injury. Nephrology Rounds Apr. 2008;6(4):6 pp.

Harris et al., Growth Factors and Cytokines in Acute Renal Failure. Adv Ren Replace Ther. Apr. 1997;4(2 Suppl):43-53.

He et al., Interleukin-18 binding protein transgenic mice are protected against ischemic acute kidney injury. Am J Physiol Renal Physiol. Nov. 2008;295(5):F1414-F1421.

Herget-Rosenthal et al., Early detection of acute renal failure by serum cystatin C. Kidney Int. Sep. 2004;66 (3):1115-1122.

Hidaka et al., Urinary clusterin levels in the rat correlate with the severity of tubular damage and may help to differentiate between glomerular and tubular injuries. Cell Tissue Res. Dec. 2002;310(3):289-296.

Hirschberg et al. Factors Predicting Poor Outcome in Patients with Acute Renal Failure (ARF). J. Am. Soc. Nephrol. Sep. 1, 1996;7(9):1374.

Hoste et al., RIFLE criteria for acute kidney injury are associated with hospital mortality in critically ill patients: a cohort analysis. Crit Care, 2006;10(3):R73 (10 pages).

Hugo and Daniel, Thrombospondin in Renal Disease. Nephron Exp Nephrol. 2009;111(3):e61-e66.

Hugo et al. ,Thrombospondin 1 precedes and predicts the development of tubulointerstitial fibrosis in glomerular disease in the rat. Kidney Int. Feb. 1998;53(2):302-311.

Jang and Rabb, The innate immune response in ischemic acute kidney injury. Clin Immunol. Jan. 2009;130(1):41-50.

Jonsson, The role of fibroblast growth factor 23 in renal disease. Nephrol. Dial. Transplant Mar. 2005;20(3):479-482.

Julian et al., Sources of Urinary Proteins and their Analysis by Urinary Proteomics for the Detection of Biomarkers of Disease. Proteomics Clin Appl., 2009;3(9):1029-1043.

Kadiroglu et al., The Evaluation of Effects of Demographic Features, Biochemical Parameters, and Cytokines on Clinical Outcomes in Patients with Acute Renal Failure. Ren Fail. 2007;29(4):503-508.

Kalousova et al., Soluble Receptor for Advanced Glycation End Products in Patients With Decreased Renal Function. Am. J. Kidney Dis. Mar. 2006;47(3): 406-411.

Kamata et al., Up-regulation of glomerular extracellular matrix and transforming growth factor-beta expression in RF/J mice. Kidney Int. Mar. 1999;55(3):864-876.

Kehoe et al. Elevated Plasma Renin Activity Associated with Renal Dysfunction. Nephron 1986;44:51-57 (abstract only).

Kellum et al. Definition and Classification of Acute Kidney Injury. Nephron Clin Pract 2008;109(4):c182-c187.

Kellum., Acute kidney injury, Crit Care Med, 2008;36(4):S141-S145.

Keyes and Bagshaw, Early diagnosis of acute kidney injury in critically ill patients. Expert Rev Mol Diagn. Jul. 2008;8(4):455-464.

Khanna et al., Expression of TGF-beta and fibrogenic genes in transplant recipients with tacrolimus and cyclosporine nephrotoxicity. Kidney Int. Dec. 2002;62(6):2257-2263.

(56) References Cited

OTHER PUBLICATIONS

Kharasch et al., Gene Expression Profiling of Nephrotoxicity from the Sevoflurane Degradation Product Fluoromethyl-2,2-difluoro-1-(trifluoromethyl)vinyl Ether ("Compound A") in Rats. Toxicol Sci. Apr. 2006;90(2):419-431.
Kiley and Chevalier, Urinary biomarkers: The future looks promising. Kidney Int. Jul. 2009;76(2): 133-134.
Kilis-Pstrusinska et al., [Levels of selected soluble adhesion molecules in blood serum of children with chronic glomerulonephritis]. Pol Merkur Lekarski. Apr. 2001;10(58):247-249.
Kilis-Pstrusinska et al., Serum levels of soluble adhesion molecules in children with glomerulonephritis (GN). Nephrol Dialysis Transplant. Jun. 2001;16(6):A62.
Kinsey et al., Inflammation in Acute Kidney Injury. Nephron Exp Nephrol. 2008; 109(4):e102-e107.
Koo et al., Cadaver versus living donor kidneys: Impact of donor factors on antigen induction before transplantation. Kidney Int. Oct. 1999;56(4):1551-1559.
Landray et al., Inflammation, Endothelial Dysfunction, and Platelet Activation in Patients With Chronic Kidney Disease: The Chronic Renal Impairment in Birmingham (CRIB) Study. Am J Kidney Dis. Feb. 2004;43(2):244-253.
Lang et al., Heat Shock Protein 60 Is Released in Immune-Mediated Glomerulonephritis and Aggravates Disease: In Vivo Evidence for an Immunologic Danger Signal. J Am Soc Nephrol. Feb. 2005;16(2):383-391.
Lapsley et al., Beta2-glycoprotein-1 (apolipoprotein H) excretion in chronic renal tubular disorders: Comparison with other protein markers of tubular malfunction. J Clin Pathol. Oct. 1991;44(10):812-816.
Larsson et al., Circulating concentration of FGF-23 increases as renal function declines in patients with chronic kidney disease, but does not change in response to variation in Phosphate intake in healthy volunteers. Kidney Int. Dec. 2003;64(6):2272-2279.
Liu et al., Predictive and pathogenetic value of plasma biomarkers for acute kidney injury in patients with acute lung injury. Crit Care Med Dec. 2007;35(12):2755-2761.
Liu et al., Serum Interleukin-6 and interleukin-8 are early biomarkers of acute kidney injury and predict prolonged mechanical ventilation in children undergoing cardiac surgery: a case-control study. Critical Care 2009;13(4):R104 (9 pp.).
Lopes-Virella et al., Urinary high density lipoprotein in minimal change glomerular disease and chronic glomerulopathies. Clin Chim Acta. May 16, 1979;94(1):73-81.
Lu et al., Increased Macrophage Infiltration and Fractalkine Expression in Cisplatin-Induced Acute Renal Failure in Mice. J Pharmacol Exp Ther. Jan. 2008;324(1):111-117.
Malyszko et al., Visfatin and apelin, new adipocytokines, and their relation to endothelial function in patients with chronic renal failure. Adv Med Sci. 2008;53(1):32-36.
Matousovic et al., IgA-containing immune complexes in the urine of IgA nephropathy patients. Nephrol Dial Transplant Sep. 2006;21(9):2478-2484.
Mattes, Experience With a Biomarker Consortium. CPath Predictive Safety Training Consortium, Critical Path Institute:48 pp., Mar. 2006.
Melnikov et al., Impaired IL-18 processing protects caspase-1-deficient mice from ischemic acute renal failure. J Clin Invest, May 2001;107(9):1145-1152.
Milford et al., Prognostic Markers in Diarrhoea-Associated Haemolytic-Uraemic Syndrome: Initial Neutrophil Count, Human Neutrophil Elastase and Von Willebrand Factor Antigen. Nephrol Dial Transplant 1991;6(4):232-237.
Montagna et al., Impairment of cellular redox status and membrane protein activities in kidneys from rats with ischemic acute renal failure. Biochim Biophys Acta Aug. 14, 1998;1407(2):99-108.
Musial et al., Soluble adhesion molecules in chronic renal failure (CRF) children treated conservatively. Nephrol Dialysis Transplant. 2002;17(Abstracts Suppl 1):232.
Nguyen et al., Heparin-Binding EGF-Like Growth Factor Is Up-Regulated in the Obstructed Kidney in a Cell- and Region-Specific Manner and Acts to Inhibit Apoptosis. Am J Pathol. Mar. 2000;156(3):889-898.
Nishiyama et al., Up-Regulation of Galectin-3 in Acute Renal Failure of the Rat. Am J Pathol. Sep. 2000;157 (3):815-823.
Ohno et al., Prognostic significance of tenascin-C expression in clear cell renal cell carcinoma. Oncol Rep. 2008;20 (3):511-516.
Ozer et al., A panel of urinary biomarkers to monitor reversibility of renal injury and a serum marker with improved potential to assess renal function. Nat Biotechnol. May 2010;28(5):486-494.
Yuen et al., Ischemic and Nephrotoxic Acute Renal Failure are Distinguished by their Broad Transcriptomic Responses. Physiol Genomics. May 16, 2006;25(3):375-386.
Zager et al. Proximal tubular cytochrome c efflux: Determinant, and potential marker, of mitochondrial injury. Kidney Int. Jun. 2004;65(6):2123-2134.
Parikh and Devarajan, New biomarkers of acute kidney injury. Crit Care Med 2008;36(4 Suppl):S159-S165.
Parikh et al., Urinary IL-18 is an early predictive biomarker of acute kidney injury after cardiac surgery. Kidney Int, 2006;70(1):199-203.
Perco et al., Protein biomarkers associated with acute renal failure and chronic kidney disease. Eur J Clin Invest. Nov. 2006;36(11):753-763.
Picard et al., Origin of renal myofibroblasts in the model of unilateral ureter obstruction in the rat. Histochem Cell Biol. Jul. 2008;130(1):141-155.
Price, Abrupt Changes in Prostate-Specific Antigen Concentration in Acute Renal Failure. Clin Chem. Jan. 1993;39 (1):161-162.
Prozialeck and Edwards, Cell Adhesion Molecules in Chemically-Induced Renal Injury. Pharmacol Ther. Apr. 2007;114(1):74-93.
Radford et al. Predicting renal outcome in IgA nephropathy. J Am Soc Nephrol Feb. 1997;8(2):199-207.
Ramesh and Reeves, TNF-α mediates chemokine and cytokine expression and renal injury in cisplatin nephrotoxicity. J. Clin. Invest. Sep. 2002;110(6):835-842.
Ramesh et al., Endotoxin and cisplatin synergistically induce renal dysfunction and cytokine production in mice. Am J Physiol Renal Physiol. Jul. 2007;293(1):F325-F332.
Ramirez et al., Prospective Study on Autoantibodies Against Apolipoprotein H ( B2GPI) in Several Clinical Parameters From Patients With Terminal Renal Failure and Functioning Renal Transplants. Transplantation Proceedings Jul. 2009;41(6):2370-2372.
Ricci et al., The RIFLE criteria and mortality in acute kidney injury: A systematic review. Kidney Int Mar. 2008;73 (5):538-546.
Rosenkranz et al., P-selectin deficiency exacerbates experimental glomerulonephritis: a protective role for endothelial P-selectin in inflammation. J Clin Invest Mar. 1999;103(5):649-659.
Rouschop et al., Pre-transplant plasma and cellular levels of CD44 correlate with acute renal allograft rejection. Nephrol Dial Transplant Oct. 2005;20(10):2248-2254.
Rouschop et al., Renal expression of CD44 correlates with acute renal allograft rejection. Kidney Int. Sep. 2006;70 (6):1127-1134.
Schena et al., EGF and MCP-1 Urinary Excretion Is a Suitable Prognostic Marker in Iga Nephropathy. J Am Soc of Nephrology; Meeting of the American Society of Nephrology. Sep. 1, 2002;13(Program and Abstracts Issue): 458A.
Schiffer et al., Activated Renal Macrophages Are Markers of Disease Onset and Disease Remission in Lupus Nephritis, J Immunol Feb. 1, 2008;180(3):1938-1947.
Schmaldienst et al., Angiogenin: a novel inhibitor of neutrophil-lactoferrin release during extracorporeal circulation. Kidney Blood Press Res. 2003;26(2):107-112.
Schmidt et al., Sexual hormone abnormalities in male patients with renal failure. Nephrol Dial Transplant. Mar. 2002;17(3):368-371.
Segawa et al., In situ expression and soluble form of P-selectin in human glomerulonephritis. Kidney Int. Oct. 1997;52 (4):1054-1063.
Segerer et al., Chemokines, Chemokine Receptors, and Renal Disease: From Basic Science to Pathophysiologic and Therapeutic Studies. J Am Soc Nephrol Jan. 2000;11(1):152-176.

(56) References Cited

OTHER PUBLICATIONS

Severini and Aliberti, Diagnostic significance of urinary enzymes: Development of a high performance liquid chromatographic method for the measurement of urinary lysozyme. Clin Chim Acta Feb. 27, 1987;163(1):97-103.
Shlipak et al., Elevations of Inflammatory and Procoagulant Biomarkers in Elderly Persons With Renal Insufficiency. Circulation Jan. 2003;107(1):87-92.
Shoji et al., Plasma angiopoietin-like protein 3 (ANGPTL3) concentration is associated with uremic dyslipidemia. Atherosclerosis. Dec. 2009;207(2):579-584.
Stafford-Smith et al., Acute Kidney Injury and Chronic Kidney Disease After Cardiac Surgery. Adv Chronic Kidney Dis. Jul. 2008;15(3):257-277.
Stasko et al., Soluble P-Selectin During a Single Hemodialysis Session in Patients With Chronic Renal Failure and Erythropoietin Treatment. Clin Appl Thromb Hemost. Oct. 2007;13(4):410-415.
Stuard et al., Soluble adhesion molecules in chronic renal failure patients. Nephrol Dialysis Transplant. 1997;12(9): A100.
Supavekin et al., Differential gene expression following early renal ischemia/reperfusion. Kidney Int. May 2003;63 (5):1714-1724.
Sutton et al., Injury of the renal microvascular endothelium alters barrier function after ischemia. Am J Physiol Renal Physiol Aug. 2003;285(2):F191-F198.
Sutton et al., Microvascular endothelial injury and dysfunction during ischemic acute renal failure. Kidney Int. Nov. 2002;62(5):1539-1549.
Sutton, Alteration of microvascular permeability in acute kidney injury. Microvasc Res. Jan. 2009;77(1):4-7.
Symon et al., The endogenous insulin-like growth factor system in radiocontrast nephropathy. Am. J. Physiol. Renal Physiol. Mar. 1998;274(3 Pt 2):F490-497.
Takada et al., The Cytokine-adhesion Molecule Cascade in Ischemia/Reperfusion Injury of the Rat Kidney. Inhibition by a Soluble P-selectin Ligand. J. Clin. Invest. Jun. 1997; 99(11):2682-2690.
Taulan et al., Comprehensive analysis of the renal transcriptional response to acute uranyl nitrate exposure. BMC Genomics Jan. 11, 2006;7(2) 14 pages.
Teppo et al., Soluble Intercellular Adhesion Molecule-1 (Sicam-1) after Kidney Transplantation: The Origin and Role of Urinary Sicam-1? Transplantation Apr. 27, 2001;71(8):1113-1119.
Thorburn et al., CXC and CC chemokines induced in human renal epithelial cells by inflammatory cytokines. APMIS Jul. 2009;117(7):477-487.
Timoshanko et al., Interleukin-12 from Intrinsic Cells Is an Effector of Renal Injury in Crescentic Glomerulonephritis. J. Am. Soc. Nephrol. Mar. 2001;12(3):464-471.
Torres et al., The ratio of epidermal growth factor to monocyte chemotactic peptide-1 in the urine predicts renal prognosis in IgA nephropathy. Kidney Int. Feb. 2008;73(3):327-333.
Vaidya and Bonventre, Mechanistic biomarkers for cytotoxic acute kidney injury. Expert Opin Drug Metab Toxicol. Oct. 2006;2(5):697-713.
Vaidya et al., Biomarkers of Acute Kidney Injury. Annu Rev Pharmacol Toxicol. Feb. 2008;48:463-493.
Vanhoutte et al., Biomarker discovery with SELDI-TOF MS in human urine associated with early renal injury: evaluation with computational analytical tools. Nephrol Dial Transplant Oct. 2007;22(10):2932-2943.
Villanueva et al., Ischemic acute renal failure induces the expression of a wide range of nephrogenic proteins. Am J Physiol Regul Integr Comp Physiol Apr. 2006;290(4):R861-R870.
Vonderscher, Biomarker of Drug Induced Kidney Injury Qualification for Regulatory Decision Making (CRADA). IOM/FDA, Silver Spring, MD Apr. 23, 2007:31 pp.
Waikar et al., Diagnosis, Epidemiology and Outcomes of Acute Kidney Injury. Clin J Am Soc Nephrol. May 2008;3 (3):844-861.
Wan et al., The pathogenesis of septic acute renal failure. Curr Opin Crit Care Dec. 2003;9(6):496-502.
Wang et al., Netrin-1 and kidney injury. I. Netrin-1 protects against ischemia-reperfusion injury of the kidney. Am J Physiol Renal Physiol. Apr. 2008;294(4):F739-F747.
Wang et al., Validation of putative genomic biomarkers of nephrotoxicity in rats. Toxicology Apr. 18, 2008;246(2-3):91-100.
Wilson and Hadley, Urinary lysozyme. J Pediatr. Feb. 1950;36(2):199-211.
Winchester et al., Sorbents in Acute Renal Failure and End-Stage Renal Disease: Middle Molecule and Cytokine Removal. Blood Purif. 2004;22(1):73-77.
Yang et al. Frequency of anti-bactericidal/permeability-increasing protein (BPI) and anti-azurocidin in patients with renal disease. Clin. Exp. Immunol. Jul. 1996;105(1):125-131.
Yu et al., Urinary biomarkers trefoil factor 3 and albumin enable early detection of kidney tubular injury. Nat Biotechnol May 2010;128(5):470-477.
International Preliminary Report on Patentability issued on Sep. 7, 2012 in PCT/US2011/026384.
Non-Final Office Action issued by the US Patent and Trademark Office on Nov. 16, 2012 in U.S. Appl. No. 13/389,351.
Non-Final Office Action issued by the US Patent and Trademark Office on Nov. 27, 2012 in U.S. Appl. No. 13/130,474.
Flynn et al., Urinary excretion of beta2 -glycoprotein-1 (apolipoprotein H) and other markers of tubular malfunction in "non-tubular" renal disease J Clin Pathol. Jul. 1992;45(7):561-567.
Kasahara et al Clinical Significance of Serum Oxidized Low-Density Lipoprotein/beta2-Glycoprotein I Complexes in Patients with Chronic Renal Diseases. Nephron Clin Pract. 2004;98(1):15-24.
Lapsley et al., Beta 2-glycoprotein-1 (apolipoprotein H) excretion in chronic renal tubular disorders: Comparison with other protein markers of tubular malfunction. J Clin Pathol. Oct. 1991;44(10):812-816.
Matsuda et al., Beta 2-Glycoprotein I-Dependent and -Independent Anticardiolipin Antibody in Patients with End-Stage Renal Disease. Thromb Res. Oct. 15, 1993;72(2):109-117.
Ramirez et al., Prospective Study on Autoantibodies Against Apolipoprotein H (beta2GPI) in Several Clinical Parameters From Patients With Terminal Renal Failure and Functioning Renal Transplants. Transplant Proc. Jul.-Aug. 2009;41(6):2370-2.
Zheng et al., Antiphospholipid antibody profiles in lupus nephritis with glomerular microthrombosis: a prospective study of 124 cases. Arthritis Res Ther. 2009;11(3):1-9.
Extended European Search Report and Written Opinion issued in PCT/US2010044772 dated Dec. 3, 2012.
Voshol et al., Evaluation of Biomarker Discovery Approaches to Detect Protein Biomarkers of Acute Renal Allograft Rejection. J Proteome Res. Jul.-Aug. 2005;4(4):1192-1199.
Extended European Search Report and Written Opinion issued in PCT/US2010044708 dated Dec. 3, 2012.
Neziri et al., Cloning and molecular characterization of Dashurin encoded by C20orf116, a PCI-domain containing protein. Biochim Biophys Acta. Apr. 2010;1800(4):430-438.
Non Final Office Action issued by the US Patent and Trademark Office in U.S. Appl. No. 13/164,768 on Dec. 18, 2012.
Non Final Office Action issued by the US Patent and Trademark Office in U.S. Appl. No. 13/061,413 on Jan. 2, 2013.
Norman et al., Progressive Renal Disease: Fibroblasts, Extracellular Matrix, and Integrins. Exp Nephrol. Mar.-Apr. 1999;7(2):167-177.
International Search Report and Written Opinion issued in 200980154224.5 dated Nov. 23, 2012.
English Translation of International Search Report and Written Opinion issued in 200980154224.5 dated Nov. 23, 2012.
Zhu et al., Expression of Urinary Epidermal Growth Factor and Renal Function. J Clin Urol Dec. 31, 1998;13 (8):374-379.
Zhu et al., Expression of Urinary Epidermal Growth Factor and Renal Function. J Clin Urol Dec. 31, 1998;13 (8):374-379 (abstract English translation).
Sun et al., A Survey on the Relationship between the Epidermal Growth Factor and Renal Function. Int J Transpl Hemopurific Dec. 31, 2006;4(1):41-44.
Sun et al., A Survey on the Relationship between the Epidermal Growth Factor and Renal Function. Int J Transpl Hemopurific Dec. 31, 2006;4(1):41-44 (abstract English translation).

(56) References Cited

OTHER PUBLICATIONS

Non Final Office Action issued in 2009801542245 dated Dec. 17, 2012.
Non Final Office Action issued by the US Patent and Trademark Office in U.S. Appl. No. 13/125,360 on Jan. 24, 2013.
Caron et al. Ischemic injury alters endothelial cell properties of kidney cortex:stimulation of MMP-9. Exp Cell Res. Oct. 15, 2005;301(1):105-116.
Non Final Office Action issued by the US Patent and Trademark Office in U.S. Appl. No. 13/508,363 on Feb. 1, 2013.
Non Final Office Action issued by the US Patent and Trademark Office in U.S. Appl. No. 13/577,243 on Feb. 14, 2013.
Non Final Office Action issued in Japanese Patent Application No. 2011-525262 on Feb. 5, 2013.
Non Final Office Action issued in Japanese Patent Application No. 2011-525262 on Feb. 5, 2013 (English translation).
International Search Report and Written Opinion issued in PCT/US2012/066152 dated Mar. 15, 2013.
Extended European Search Report and Written Opinion issued in EP 10817878 dated Apr. 15, 2013.
Mezzano et al., Endothelial Cell Markers in Chronic Uremia: Relationship with Hemostatic Defects and Severity of Renal Failure. Thromb Res. Dec. 15, 1997;88(6):465-472.
Tan et al., The level of urinary secretory immunoglobulin A (sIgA) of patients with IgA nephropathy is elevated and associated with pathological phenotypes. Clin Exp Immunol. Apr. 2009;156(1):111-116.
Zhang et al., The level of serum secretory IgA of patients with IgA nephropathy is elevated and associated with pathological phenotypes. Nephrol Dial Transplant Jan. 2008;23(1):207-212.
Search Report and Written Opinion issued by SIPO in 2009801406946 dated Apr. 15, 2013—includes English translation.
Office Action issued by SIPO in 2009801406946 dated May 29, 2013—includes English translation.
Search Report and Written Opinion issued in PCT/US2013/023479 dated May 15, 2013.
Choi et al., Expression of Vascular Endothelial Growth Factor-C and Its Receptor mRNA in the Rat Kidney With Ischemia-Reperfusion Injury. Clinical Kidney J. Jun. 2, 2011;4(Suppl 2):2 pages.
Cooper, Effect of Tobacco Smoking on Renal Function. Indian J Med Res Sep. 2006;124(3):261-268.
Extended European Search Report and Written Opinion issued in EP 10829198 dated May 21, 2013.
Senatorski et al., Urine activity of cathepsin B, collagenase and urine excretion of TGF-beta1 and fibronectin in membranous glomerulonephritis. Res Exp Med (Berl). Dec. 1998;198(4):199-206.
Schaefer et al., Urinary excretion of cathepsin B and cystatins as parameters of tubular damage. Kidney Int Suppl. Nov. 1994;47:S64-S67.
Kos et al., Cathepsins B,H and L and Their Inhibitors Stefin A and Cystatin C in Sera of Melanoma Patients. Clin Cancer Res. Oct. 1997;3(10):1815-1822.
Nambi et al., Down regulation of kidney neutral endopeptidase mRNA, protein and activity during acute renal failure: possible mechanism for ischemia-induced acute renal failure in rats? Mol Cell Biochem. Jul. 1999;197(1-2):53-59.
Li et al., Predictive value of RIFLE classification on prognosis of critically ill patients with acute kidney injury treated with continuous renal replacement therapy. Chin Med J (Engl). May 5, 2009;122(9):1020-1025.
Extended European Search Report and Written Opinion issued in EP 10829191 dated May 24, 2013.
Berahovich et al., Proteolytic activation of alternative CCR1 ligands in inflammation. J Immunol. Jun. 1, 2005;174 (11)1341-7351.
Hatta et al., Cytokine Array Comparisons of Plasma from Cycling Fertile Women on Cycle Day 5 and Ovulation. Am J Reprod Immunol. Sep. 2009;62(3):158-164.
Office Action and Search Report issued by SIPO in Application No. 200980140805.3 dated Apr. 23, 2013—includes English Translation.
Mishra et al., Neutrophil gelatinase-associated lipocalin (NGAL) as a biomarker for acute renal injury after cardiac surgery. Lancet. Apr. 2-8, 2005;365(9466):1231-1238.
International Preliminary Report on Patentability issued in PCT/US2011/055055 dated May 24, 2013.
Extended European Search Report and Written Opinion issued in EP 10838357 dated Jun. 3, 2013.
Stenvinkel et al., High Serum Hyaluronan Indicates Poor Survival in Renal Replacement Therapy. Am J Kidney Dis. Dec. 1999;34(6):1083-1088.
Non-Final Office Action issued by the United States Patent and Trade Office in U.S. Appl. No. 13/577,242 dated Jun. 20, 2013.
Extended European Search Report and Written Opinion issued in EP 10818036 dated Jun. 6, 2013.
Extended European Search Report and Written Opinion issued in EP 11740470 dated Jun. 18, 2013.
Tary-Lehmann et al., Enzyme-Linked Immunosorbent Assay Spot Detection of Interferon-Gamma and Interleukin 5-Producing Cells as a Predictive Marker for Renal Allograft Failure. Transplantation. Jul. 27, 1998;66(2):219-224.
Kimmel et al., Immunologic function and survival in hemodialysis patients. Kidney Int. Jul. 1998;54(1):236-244.
Simmons et al., Plasma cytokine levels predict mortality in patients with acute renal failure. Kidney Int. Apr. 2004;65 (4):1357-1365.
Search Report issued by SIPO in Application No. 200980149555.X dated May 23, 2013—includes English translation.
Cai, Detection and Application for the biomarker of Rental Injury in Early Stage. Laboratory Med Clinic. Jun. 2005;2 (3):124-127—incl Engl trans! abstract only.
Office Action issued by SIPO in Application No. 200980149555.X dated Jul. 1, 2013—includes English translation.
Search Report issued by SIPO in Application No. 201080014932.1 dated Jun. 9, 2013—includes English translation.
Office Action issued by SIPO in Application No. 201080014932.1 dated Jun. 25, 2013—includes English translation.
Jung et al., Diagnostic significance of urinary enzymes in detecting acute rejection crises in renal transplant recipients depending on expression of results illustrated through the example of alanine aminopeptidase. Clin Biochem. Aug. 1985;18(4):257-260.
Search Report issued by SIPO in Application No. 200980149636.X dated Jun. 17, 2013—includes English translation.
Office Action issued by SIPO in Application No. 200980149636.X dated Jul. 1, 2013—includes English translation.
Extended European Search Report and Written Opinion issued in EP 11740468 dated Jun. 13, 2013.
Fried et al., Inflammatory and Prothrombotic Markers and the Progression of Renal Disease in Elderly Individuals. J Am Soc Nephrol. Dec. 2004;15(12):3184-3191.
Edelstein, Biomarkers of Acute Kidney Injury. Adv Chronic Kidney Dis. Jul. 2008;15(3)222-234.
Extended European Search Report and Written Opinion issued in EP 11740469 dated Jun. 13, 2013.
Fujisaki et al., Infusion of radiocontrast agents induces exaggerated release of urinary endothelin in patients with impaired renal function. Clin Exp Nephrol. Dec. 2003;7(4):279-283.
Hirai et al., Plasma endothelin-1(ET-1) is a useful marker for renal dysfunction. Atheroscler Suppl. Jun. 19, 2006;7 (3):60[Mo-P1:65].
Cottone et al., Endothelin-1 and F2-isoprostane relate to and predict renal dysfunction in hypertensive patients. Nephrol Dial Transpl. Feb. 2009;24(2):497-503.
Schulz et al., Endothelin-1 as an early prognostic marker in acute renal failure (ARF) and sepsis. Kidney Blood Press Res. 2000;23(3-5):341-342.
Search Report issued by SIPO in Application No. 201080057014.7 dated Jul. 8, 2013—includes English translation.
Office Action issued by SIPO in Application No. 201080057014.7 dated Jul. 18, 2013—includes English translation.
Extended European Search Report and Written Opinion issued in EP 10812639 dated Jul. 16, 2013.
Song et al., Expression of TRAIL, DR4, and DR5 in kidney and serum from patients receiving renal transplantation. Transplant Proc. Jun. 2004;36(5):1340-1343.

(56) References Cited

OTHER PUBLICATIONS

FDA, European Medicines Agency to Consider Additional Test Results When Assessing New Drug Safety—Collaborative effort by FDA and EMEA expected to yield additional safety data. http://www.natap.org/2008/newsUpdates/071608_01.htm dated Jun. 12, 2008.
Harpur et al., Biological Qualification of Biomarkers of Chemical-Induced Renal Toxicity in Two Strains of Male Rat. Toxicol Sci. Aug. 2011;122(2):235-252.
Final Office Action issued by the United States Patent and Trademark Office in U.S. Appl. No. 13/061,446 dated Jun. 7, 2013.
Non Final Office Action issued by the United States Patent and Trademark Office in U.S. Appl. No. 13/125,454 dated Mar. 5, 2013.
Thaker et al., Identification of thrombospondin 1 (TSP-1) as a novel mediator of cell injury in kidney ischemia. J Clin Invest Dec. 2005;115(12):3451-3458.
Restriction Requirement issued by the United States Patent and Trademark Office in U.S. Appl. No. 13/061,413 dated Sep. 5, 2012.
Response to Restriction Requirement in U.S. Appl. No. 13/061,413 dated Oct. 16, 2012.
Response to Non Final Office Action issued in U.S. Appl. No. 13/061,413 dated Jul. 2, 2013.
Final Office Action issued by the United States Patent and Trademark Office in U.S. Appl. No. 13/061,413 dated Aug. 23, 2013.
Restriction Requirement issued by the United States Patent and Trademark Office in U.S. Appl. No. 13/148,031 dated Mar. 20, 2013.
Mast et al., Clinical utility of the soluble transferrin receptor and comparison with serum ferritin in several populations. Clin Chem. Jan. 1998;44(1):45-51.
Non Final Office Action issued by the United States Patent and Trademark Office in U.S. Appl. No. 13/389,363 dated Apr. 18, 2013.
Iglesias et al., Thyroid Dysfunction and Kidney Disease (Revised version). Eur J Endocrinol. Dec. 18, 2008:32 pages. retrieved from URL:///www.eje.org/contentlearly/2008/12/18/EJE-08-0837.full.pdf.
Rajashekar et al., Systemic diseases with renal manifestations. Prim Care. Jun. 2008;35(2):297-328.abstract retrieved from URL:www.ncbi.nlm.nih.gov/pubmed/18486717.
Rini et al., Renal cell carcinoma. Lancet. Mar. 28, 2009;373(9669):1119-1132.
Non Final Office Action issued by the United States Patent and Trademark Office in U.S. Appl. No. 13/125,360 dated Aug. 27, 2013.
Sharma et al. Two-dimensional fluorescence difference gel electrophoresis analysis of the urine proteome in human diabetic nephropathy. Proteomics. Jul. 2005;5(10):2648-2655.
Non Final Office Action issued by the United States Patent and Trademark Office in U.S. Appl. No. 13/130,474 dated Nov. 27, 2012.
Non Final Office Action issued by the United States Patent and Trademark Office in U.S. Appl. No. 13/148,030 dated May 1, 2013.
Malm et al., Changes in the plasma levels of vitamin K-dependent proteins C and S and of C4b-binding protein during pregnancy and oral contraception. Br J Haematol. Apr. 1988;68(4):437-443.
Matsuzaka et al., Relationship between vitamin K dependent coagulation factors and anticoagulants (protein C and protein S) in neonatal vitamin K deficiency. Arch Dis Child. Mar. 1993;68(3 Spec No):297-302.
International Search Report and Written Opinion issued in PCT/US2013/028005 dated Jun. 18, 2013.
Maddens et al., Chitinase-like Proteins are Candidate Biomarkers for Sepsis-induced Acute Kidney Injury. Mol Cell Proteomics. Jan. 10, 2012;11(6):1-13.
Restriction Requirement issued by the United States Patent and Trademark Office in U.S. Appl. No. 13/517,244 dated Jul. 1, 2013.
Extended European Search Report and Written Opinion issued in EP 11751238 dated Aug. 13, 2013.
Haase et al., A comparison of the RIFLE and Acute Kidney Injury Network classifications for cardiac surgery-associated acute kidney injury: A prospective cohort study. J Thorac Cardiovasc Surg. Dec. 2009;138(6):1370-1376.
Zaffanello M et al., Early diagnosis of acute kidney injury with urinary biomarkers in the newborn. J Matern Fetal Neonatal Med. 2009;22 Suppl 3:62-66.
Extended European Search Report and Written Opinion issued in EP 11748210 dated Aug. 16, 2013.
Calabrese et al., Oxidative stress and cellular stress response in diabetic nephropathy. Database Biosis [Online]. Biosciences Information Service Jan. 2007; XP002705326. Database accession No. PREV200800097004 (abstract):3 pages & Cell Stress Chaperones. 2007 Winter;12(4):299-306.
Musial et al., The Heat Shock Protein Profile in Children with Chronic Kidney Disease. Perit Dial Int. Mar.-Apr. 2010;30 (2):227-232.
Tao et al., Expression of 60-kDa and Inducible 70-kDa Stress Proteins in Gentamicin-Induced Acute Renal Failure. Clin Exp Nephrol. Jul. 1997;1:254-260.
Response dated May 16, 2012 to Extended European Search Report and Written Opinion in PCT/US2009/055449.
Extended European Search Report and Written Opinion issued on Feb. 23, 2012 in PCT/US2009/065419.
Extended European Search Report and Written Opinion issued on Jul. 27, 2012 in PCT/US2010/023294.
Extended European Search Report and Written Opinion issued on Oct. 24, 2011 in PCT/US2009/055449.
Extended European Search Report and Written Opinion issued on Feb. 22, 2012 in PCT/US2009/055460.
Extended European Search Report and Written Opinion issued on Jul. 9, 2012 in PCT/US2009/061561.
Extended European Search Report and Written Opinion issued on Aug. 23, 2012 in PCT/US2009/061562.
Extended European Search Report and Written Opinion issued on Jul. 9, 2012 in PCT/US2010/023292.
Extended European Search Report and Written Opinion issued on Aug. 23, 2012 in PCT/US2010/023297.
Extended European Search Report and Written Opinion issued on Jun. 8, 2012 in PCT/US2009/063906.
International Preliminary Report on Patentability issued on Oct. 21, 2011 in PCT/US2010/023297.
International Preliminary Report on Patentability issued on Mar. 29, 2011 in PCT/US2010/049234.
International Preliminary Report on Patentability issued on May 18, 2012 in PCT/US2010/055730.
International Preliminary Report on Patentability issued on Mar. 10, 2011 in PCT/US2009/055449.
International Preliminary Report on Patentability issued on Mar. 10, 2011 in PCT/US2009/055460.
International Preliminary Report on Patentability issued on Aug. 16, 2012 in PCT/US2011/023830.
International Preliminary Report on Patentability issued on Aug. 16, 2012 in PCT/US2011/023831.
International Preliminary Report on Patentability issued on Aug. 16, 2012 in PCT/US2011/023832.
International Preliminary Report on Patentability issued on Apr. 5, 2012 in PCT/US2010/049695.
International Preliminary Report on Patentability issued on May 5, 2011 in PCT/US2009/061561.
International Preliminary Report on Patentability issued on May 5, 2011 in PCT/US2009/061562.
International Preliminary Report on Patentability issued on Jun. 3, 2011 in PCT/US2009/065419.
International Preliminary Report on Patentability issued on Jul. 5, 2012 in PCT/US2010/061377.
International Preliminary Report on Patentability issued on Aug. 18, 2011 in PCT/US2010/023292.
International Preliminary Report on Patentability issued on Aug. 18, 2011 in PCT/US2010/023294.
International Preliminary Report on Patentability issued on May 10, 2011 in PCT/US2009/063906.
International Search Report and Written Opinion issued on Dec. 3, 2010 in PCT/US2010/049234.
International Search Report and Written Opinion issued on Feb. 8, 2011 in PCT/US2010/055730.

(56) References Cited

OTHER PUBLICATIONS

International Search Report and Written Opinion issued on Oct. 28, 2010 in PCT/US2010/044772.
International Search Report and Written Opinion issued on Oct. 8, 2010 in PCT/US2010/044708.
International Search Report and Written Opinion issued on Dec. 10, 2009 in PCT/US2009/055449.
International Search Report and Written Opinion issued on Dec. 31, 2009 in PCT/US2009/055460.
International Search Report and Written Opinion issued on Dec. 3, 2010 in PCT/US2010/049695.
International Search Report and Written Opinion issued on Jan. 20, 2010 in PCT/US2009/061561.
International Search Report and Written Opinion issued on Apr. 13, 2010 in PCT/US2009/061562.
International Search Report and Written Opinion issued on Mar. 30, 2010 in PCT/US2009/065419.
International Search Report and Written Opinion issued on Mar. 8, 2011 in PCT/US2010/061377.
International Search Report and Written Opinion issued on Apr. 30, 2010 in PCT/US2010/023292.
International Search Report and Written Opinion issued on Apr. 22, 2010 in PCT/US2010/023294.
International Search Report and Written Opinion issued on Jun. 3, 2010 in PCT/US2010/023297.
International Search Report and Written Opinion issued on Jan. 15, 2010 in PCT/US2009/063906.
International Search Report and Written Opinion issued on Nov. 18, 2010 in PCT/US2010/046910.
International Search Report and Written Opinion issued on Jan. 18, 2012 in PCT/US2011/053015.
International Search Report and Written Opinion issued on Feb. 24, 2012 in PCT/US2011/055055.
International Search Report and Written Opinion issued on Jan. 19, 2011 in PCT/US2010/055721.
International Search Report and Written Opinion issued on May 10, 2012 in PCT/US2012/020571.
International Search Report and Written Opinion issued on Apr. 27, 2011 in PCT/US2011/023830.
International Search Report and Written Opinion issued on Apr. 27, 2011 in PCT/US2011/023831.
International Search Report and Written Opinion issued on Apr. 29, 2011 in PCT/US2011/023832.
International Search Report and Written Opinion issued on May 17, 2011 in PCT/US2011/026384.
International Search Report and Written Opinion issued on Jun. 3, 2011 in PCT/US2011/026759.
International Search Report and Written Opinion issued on Sep. 7, 2012 in PCT/US2012/043279.
International Search Report and Written Opinion issued on Dec. 15, 2011 in PCT/US2011/001126.
International Search Report and Written Opinion issued on Nov. 25, 2011 in PCT/US2011/001127.
International Search Report and Written Opinion issued on Nov. 25, 2011 in PCT/US2011/001128.
International Search Report and Written Opinion issued on Nov. 25, 2011 in PCT/US2011/001125.
International Search Report and Written Opinion issued on Jun. 20, 2012 in PCT/US2012/020572.
International Search Report and Written Opinion issued on May 2, 2012 in PCT/US2012/022926.
International Search Report and Written Opinion issued on Sep. 21, 2012 in PCT/US2012/045583.
Non Final Office Action issued by the USPTO in U.S. Appl. No. 13/061,446 on Oct. 12, 2012.
Abd El Latif et al., Urinary epidermal growth factor excretion: A useful prognostic marker for progression of renal damage in children. J Med Sci Oct. 2007; 7(7): 1171-1176.
Abou-Shousha and Youssef, Interleukin-2 Regulatory Effect on P-Selectin and Interleukin-8 Production in Patients with Chronic Renal Failure. Egypt J Immunol. 2006;13(1):11-18.
Akcay et al., Mediators of Inflammation in Acute Kidney Injury. Mediators Inflamm. 2009;2009:137072 (12 pp).
Albright, Acute Renal Failure: A Practical Update. Mayo Clin. Proc. Jan. 2001;76(1):67-74.
Anders et al., Chemokines and chemokine receptors are involved in the resolution or progression of renal disease. Kidney Int. Feb. 2003;63(2):401-415.
Anilkumar et al., Trimeric assembly of the C-terminal region of Thrombospondin-1 or Thrombospondin-2 is necessary for cell spreading and fascin spike organisation. J Cell Sci. Jun. 1, 2002;115(Pt 11):2357-2366.
Arribas and Esselens, ADAM17 as a Therapeutic Target in Multiple Diseases. Curr Pharm Des. 2009;15 (20):2319-2335.
Arrizabalaga et al., Tubular and Interstitial Expression of ICAM-1 as a Marker of Renal Injury in IgA Nephropathy. Am J Nephrol May-Jun. 2003;23(3):121-128.
Bagshaw et al., Urinary biomarkers in septic acute kidney injury. Intensive Care Med. Jul. 2007;33(7):1285-1296.
Bajwa et al., Immune Mechanisms and Novel Pharmacological Therapies of Acute Kidney Injury. Curr Drug Targets Dec. 2009;10(12):1196-1204.
Barrera-Chimal et al., Hsp72 is an early and sensitive biomarker to detect acute kidney injury. EMBO Mol Med. Jan. 2011;3(1):5-20.
Beushausen, NWG Biomarker Objectives. ILSI Health and Environmental Sciences Institute, ILSI-HESI Annual Meeting 2006:17 pp.
Bicik et al., Role of Transforming Growth Factor-.beta.2 in, and a Possible Transforming Growth Factor-beta2 Gene Polymorphism as a Marker of, Renal Dysfunction in Essential Hypertension: A Study in Turkish Patients, Current Therapeutic Research, 2005;44(4):266-278.
Biotrin International, Biotrin Biomarkers: How late do you want to detect preclinical kidney damage? Biotrin's acute kidney injury test (AKI Test). Biotrin's Preclinical Kidney Biomarkers: 8 pp., 2007.
Bonomini et al., Serum Levels of Soluble Adhesion Molecules in Chronic Renal Failure and Dialysis Patients. Nephron. Aug. 1998;79(4):399-407.
Bonventre and Zuk, Ischemic acute renal failure: An inflammatory disease? Kidney Int. Aug. 2004;66(2):480-485.
Bonventre, Dedifferentiation and Proliferation of Surviving Epithelial Cells in Acute Renal Failure. J Am Soc Nephrol Jun. 2003;14 Suppl 1:S55-S61.
Bonventre, Pathophysiology of Acute Kidney Injury: Roles of Potential Inhibitors of Inflammation. Contrib Nephrol. 2007; 156: 39-46.
Burne et al., IL-1 and TNF independent pathways mediate ICAM-1/VCAM-1 up-regulation in ischemia reperfusion injury. J Leukoc Biol. Aug. 2001;70(2):192-198.
Burne-Taney and Rabb, The role of adhesion molecules and T cells in ischemic renal injury. Curr Opin Nephrol Hypertens. Jan. 2003;12(1):85-90.
Canani et al., The Fatty Acid-Binding Protein-2 A54T Polymorphism Is Associated With Renal Disease in Patients With Type 2 Diabetes. Diabetes Nov. 2005;54(11):3326-3330.
Catania et al., Role of matrix metalloproteinases in renal pathophysiologies. Am J Physiol Renal Physiol Mar. 2007;292(3):F905-F911.
Coca et al., Biomarkers for the diagnosis and risk stratification of acute kidney injury: A systematic review. Kidney Int May 2008;73(9):1008-1016.
Cruz et al., North East Italian Prospective Hospital Renal Outcome Survey on Acute Kidney Injury (NEiPHROS-AKI): Targeting the Problem with the RIFLE Criteria. Clin J Amer. Soc. Nephrol. May 2007;2(3):418-425.
Daha and Van Kooten, Is the proximal tubular cell a proinflammatory cell? Nephrol Dial Transplant 2000;15 Suppl 6:41-43.
De Sa et al., Leukocyte, platelet and endothelial activation in patients with acute renal failure treated by intermittent hemodialysis. Am J Nephrol. Jul.-Aug. 2001;21(4):264-273.
Devarajan and Williams, Proteomics for Biomarker Discovery in Acute Kidney Injury. Semin Nephrol. Nov. 2007;27(6):637-651.

(56) References Cited

OTHER PUBLICATIONS

Devarajan, Cellular and molecular derangements in acute tubular necrosis. Curr Opin Pediatr. Apr. 2005;17(2):193-199.

Devarajan, Novel biomarkers for the early prediction of acute kidney injury. Cancer Therapy Sep. 2005;3:477-488.

Devarajan, Update on Mechanisms of Ischemic Acute Kidney Injury. J Am Soc Nephrol. Jun. 2006;17(6):1503-1520.

Domanski et al., Purine and Cytokine Concentrations in the Renal Vein of the Allograft During Reperfusion. Transplant Proc. Jun. 2007;39(5):1319-1322.

FDA, European Medicines Agency to Consider Additional Test Results When Assessing New Drug Safety—Collaborative effort by FDA and EMEA expected to yield additional safety data. http://www.natap.org/2008/newsUpdates/071608_01.htm.

Ferguson et al., Biomarkers of nephrotoxic acute kidney injury. Toxicology Mar. 20, 2008;245(3):182-193.

Frangogiannis, Chemokines in ischemia and reperfusion. Thromb Haemost May 2007;97(5):738-747.

Furuichi et al., Chemokine/chemokine receptor-mediated inflammation regulates pathologic changes from acute kidney injury to chronic kidney disease. Clin Exp Nephrol Feb. 2009;13(1):9-14.

Furuichi et al., Roles of chemokines in renal ischemia/reperfusion injury. Front Biosci. May 1, 2008;13:4021-4028.

Galkina and Ley, Leukocyte Recruitment and Vascular Injury in Diabetic Nephropathy. J Am Soc Nephrol. Feb. 2006;17(2):368-377.

Garcia et al., Adenosine A2A receptor activation and macrophagemediated experimental glomerulonephritis. FASEB J. Feb. 2008;22(2):445-454.

Gbadegesin et al., Plasma and urinary soluble adhesion molecule expression is increased during first documented acute pyelonephritis. Arch Dis Child. Mar. 2002;86(3):218-221.

Goes et al., Effect of Recombinant Human Insulin-Like Growth Factor-1 on the Inflammatory Response to Acute Renal Injury. J Am Soc Nephrol. May 1996;7(5):710-720.

Extended European Search Report dated Jun. 8, 2012 issued in EP 09825600.

Hidaka et al., Urinary clusterin levels in the rat correlate with the severity of tubular damage and may help to differentiate between glomerular and tubular injuries. Cell Tissue Res Dec. 2002;310(3):289-296.

Vaidya et al., Biomarkers of Acute Kidney Injury. Annu Rev Pharmacol Toxicol. 2008;48:463-493.

International Search Report and Written Opinion issued in PCT/US2009/063906, dated Jan. 15, 2010.

Han et al., Urinary Biomarkers in the Early Diagnosis of Acute Kidney Injury, Kidney Int., 2007, 73(7):863-869.

\* cited by examiner

Clusterin sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 67.620 | 108.140 | 67.620 | 96.933 | 67.620 | 62.170 |
| average | 167.548 | 184.717 | 167.548 | 236.137 | 167.548 | 206.308 |
| stdev | 302.129 | 175.724 | 302.129 | 507.042 | 302.129 | 496.203 |
| p (t-test) |  | 0.706 |  | 0.262 |  | 0.605 |
| min | 3.849 | 7.464 | 3.849 | 1.319 | 3.849 | 0.736 |
| max | 2047.880 | 694.106 | 2047.880 | 3450.639 | 2047.880 | 2507.730 |
| n (Samp) | 117 | 51 | 117 | 60 | 117 | 26 |
| n (Pat) | 99 | 51 | 99 | 60 | 99 | 26 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 83.981 | 80.931 | 83.981 | 77.813 | 83.981 | 53.541 |
| average | 184.237 | 113.963 | 184.237 | 169.101 | 184.237 | 172.784 |
| stdev | 349.940 | 133.990 | 349.940 | 322.010 | 349.940 | 273.867 |
| p (t-test) |  | 0.411 |  | 0.842 |  | 0.904 |
| min | 0.736 | 7.794 | 0.736 | 1.543 | 0.736 | 14.404 |
| max | 3450.639 | 526.949 | 3450.639 | 1561.833 | 3450.639 | 881.911 |
| n (Samp) | 260 | 17 | 260 | 23 | 260 | 14 |
| n (Pat) | 160 | 17 | 160 | 23 | 160 | 14 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 72.627 | 111.483 | 72.627 | 102.636 | 72.627 | 64.232 |
| average | 162.079 | 416.324 | 162.079 | 245.577 | 162.079 | 200.119 |
| stdev | 290.142 | 1497.119 | 290.142 | 517.556 | 290.142 | 514.718 |
| p (t-test) |  | 0.096 |  | 0.201 |  | 0.628 |
| min | 3.849 | 7.464 | 3.849 | 1.319 | 3.849 | 0.736 |
| max | 2047.880 | 10168.806 | 2047.880 | 3450.639 | 2047.880 | 2507.730 |
| n (Samp) | 105 | 45 | 105 | 50 | 105 | 23 |
| n (Pat) | 84 | 45 | 84 | 50 | 84 | 23 | sCr or UO

| Time prior AKI stage | AUC | SE | nCohort 1 | nCohort 2 | p |
|---|---|---|---|---|---|
| 0 hours | 0.61 | 0.048 | 117 | 51 | 0.020 |
| 24 hours | 0.54 | 0.046 | 117 | 60 | 0.339 |
| 48 hours | 0.48 | 0.062 | 117 | 26 | 0.808 | sCr only

| Time prior AKI stage | AUC | SE | nCohort 1 | nCohort 2 | p |
|---|---|---|---|---|---|
| 0 hours | 0.46 | 0.070 | 260 | 17 | 0.582 |
| 24 hours | 0.47 | 0.062 | 260 | 23 | 0.651 |
| 48 hours | 0.47 | 0.078 | 260 | 14 | 0.683 |

UO only

| Time prior AKI stage | AUC | SE | nCohort 1 | nCohort 2 | p |
|---|---|---|---|---|---|
| 0 hours | 0.64 | 0.051 | 105 | 45 | 0.008 |
| 24 hours | 0.57 | 0.050 | 105 | 50 | 0.176 |
| 48 hours | 0.48 | 0.066 | 105 | 23 | 0.718 | sCr or UO

| Time prior AKI stage | Cutoff value | sens | spec | Quartile | OR | 95% CI of OR | |
|---|---|---|---|---|---|---|---|
| 0 hours | 68.062234 | 71% | 51% | 1 |  |  |  |
|  | 46.123708 | 80% | 41% | 2 | 1.3 | 0.8 | 2.3 |
|  | 20.118859 | 90% | 19% | 3 | 2.1 | 1.3 | 3.5 |
|  | 125.66895 | 45% | 70% | 4 | 3.5 | 2.1 | 5.7 |
|  | 194.16184 | 39% | 80% |  |  |  |  |
|  | 390.92356 | 12% | 91% |  |  |  |  |

Fig. 1 - 1

| | | | | | | | |
|---|---|---|---|---|---|---|---|
| 24 hours | 42.128889 | 70% | 40% | 1 | | | |
| | 20.118859 | 80% | 19% | 2 | 0.6 | 0.4 | 0.9 |
| | 12.351171 | 90% | 11% | 3 | 1.2 | 0.8 | 1.8 |
| | 125.66895 | 38% | 70% | 4 | 1.3 | 0.9 | 1.9 |
| | 194.16184 | 23% | 80% | | | | |
| | 390.92356 | 15% | 91% | | | | |
| 48 hours | 35.544963 | 73% | 34% | 1 | | | |
| | 23.299936 | 81% | 24% | 2 | 2.3 | 1.0 | 5.4 |
| | 5.0656624 | 92% | 3% | 3 | 2.3 | 1.0 | 5.4 |
| | 125.66895 | 31% | 70% | 4 | 1.7 | 0.6 | 4.3 |
| | 194.16184 | 15% | 80% | | | | |
| | 390.92356 | 15% | 91% | | | | | sCr only

| Time prior AKI stage | Cutoff value | sens | spec | Quartile | OR | 95% CI of OR | |
|---|---|---|---|---|---|---|---|
| 0 hours | 35.544963 | 71% | 28% | 1 | | | |
| | 23.299936 | 82% | 21% | 2 | 1.7 | 0.6 | 5.3 |
| | 20.118859 | 94% | 17% | 3 | 1.4 | 0.4 | 4.6 |
| | 147.85684 | 18% | 70% | 4 | 1.7 | 0.6 | 5.3 |
| | 247.36505 | 12% | 80% | | | | |
| | 400 | 6% | 92% | | | | |
| 24 hours | 33.416142 | 74% | 27% | 1 | | | |
| | 21.410305 | 83% | 19% | 2 | 1.2 | 0.6 | 2.7 |
| | 7.1564891 | 91% | 5% | 3 | 1.2 | 0.6 | 2.7 |
| | 147.85684 | 30% | 70% | 4 | 1.2 | 0.6 | 2.7 |
| | 247.36505 | 13% | 80% | | | | |
| | 400 | 4% | 92% | | | | |
| 48 hours | 35.544963 | 71% | 28% | 1 | | | |
| | 22.08047 | 86% | 20% | 2 | 2.1 | 0.5 | 9.7 |
| | 16.79504 | 93% | 14% | 3 | 2.1 | 0.4 | 9.5 |
| | 147.85684 | 21% | 70% | 4 | 2.1 | 0.5 | 9.7 |
| | 247.36505 | 14% | 80% | | | | |
| | 400 | 14% | 92% | | | | |

UO only

| Time prior AKI stage | Cutoff value | sens | spec | Quartile | OR | 95% CI of OR | |
|---|---|---|---|---|---|---|---|
| 0 hours | 68.371454 | 71% | 49% | 1 | | | |
| | 50.270477 | 80% | 42% | 2 | 3.0 | 1.5 | 5.9 |
| | 19.168593 | 91% | 17% | 3 | 1.8 | 0.8 | 3.8 |
| | 147.85684 | 47% | 70% | 4 | 7.1 | 3.7 | 13.8 |
| | 181.21256 | 44% | 80% | | | | |
| | 387.05066 | 16% | 90% | | | | |
| 24 hours | 53.596005 | 70% | 44% | 1 | | | |
| | 21.840385 | 80% | 23% | 2 | 0.7 | 0.4 | 1.3 |
| | 16.227818 | 90% | 15% | 3 | 1.4 | 0.9 | 2.2 |
| | 147.85684 | 36% | 70% | 4 | 1.7 | 1.1 | 2.7 |
| | 181.21256 | 32% | 80% | | | | |
| | 387.05066 | 18% | 90% | | | | |
| 48 hours | 35.544963 | 74% | 35% | 1 | | | |
| | 24.383414 | 83% | 28% | 2 | 1.6 | 0.6 | 4.2 |
| | 5.0656624 | 91% | 2% | 3 | 2.7 | 1.2 | 6.5 |
| | 147.85684 | 22% | 70% | 4 | 1.0 | 0.3 | 3.1 |
| | 181.21256 | 17% | 80% | | | | |
| | 387.05066 | 13% | 90% | | | | |

Fig. 1 - 2

Fatty acid binding protein, heart sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 32.900 | 165.000 | 32.900 | 139.000 | 32.900 | 122.000 |
| average | 293.148 | 586.377 | 293.148 | 1011.722 | 293.148 | 769.790 |
| stdev | 752.839 | 1016.672 | 752.839 | 2426.368 | 752.839 | 1655.881 |
| p (t-test) |  | 0.017 |  | 0.000 |  | 0.008 |
| min | 0.371 | 0.268 | 0.371 | 1.130 | 0.371 | 1.210 |
| max | 8087.000 | 4500.000 | 8087.000 | 14771.000 | 8087.000 | 8087.000 |
| n (Samp) | 249 | 53 | 249 | 62 | 249 | 27 |
| n (Pat) | 104 | 53 | 104 | 62 | 104 | 27 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 60.800 | 106.400 | 60.800 | 74.350 | 60.800 | 111.450 |
| average | 476.484 | 1099.031 | 476.484 | 1865.080 | 476.484 | 647.192 |
| stdev | 1336.601 | 2451.620 | 1336.601 | 3575.691 | 1336.601 | 955.881 |
| p (t-test) |  | 0.052 |  | 0.000 |  | 0.636 |
| min | 0.371 | 0.268 | 0.371 | 1.130 | 0.371 | 5.510 |
| max | 13231.000 | 8087.000 | 13231.000 | 14771.000 | 13231.000 | 2840.000 |
| n (Samp) | 441 | 20 | 441 | 26 | 441 | 14 |
| n (Pat) | 170 | 20 | 170 | 26 | 170 | 14 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 37.800 | 214.000 | 37.800 | 180.000 | 37.800 | 163.000 |
| average | 339.709 | 629.554 | 339.709 | 715.528 | 339.709 | 746.260 |
| stdev | 954.316 | 1029.634 | 954.316 | 1411.219 | 954.316 | 1668.700 |
| p (t-test) |  | 0.064 |  | 0.023 |  | 0.068 |
| min | 0.371 | 5.470 | 0.371 | 2.380 | 0.371 | 1.210 |
| max | 8087.000 | 4500.000 | 8087.000 | 8087.000 | 8087.000 | 8087.000 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
| --- | --- | --- | --- | --- | --- |
| 0 hours | 0.64 | 0.044 | 249 | 53 | 0.001 |
| 24 hours | 0.63 | 0.041 | 249 | 62 | 0.001 |
| 48 hours | 0.62 | 0.060 | 249 | 27 | 0.045 | sCr only

| Time prior AKI stage | AUC | SE | nCohort 1 | nCohort 2 | p |
| --- | --- | --- | --- | --- | --- |
| 0 hours | 0.54 | 0.067 | 441 | 20 | 0.550 |
| 24 hours | 0.54 | 0.059 | 441 | 26 | 0.489 |
| 48 hours | 0.57 | 0.081 | 441 | 14 | 0.420 |

UO only

| Time prior AKI stage | AUC | SE | nCohort 1 | nCohort 2 | p |
| --- | --- | --- | --- | --- | --- |
| 0 hours | 0.70 | 0.046 | 212 | 47 | 0.000 |
| 24 hours | 0.68 | 0.044 | 212 | 52 | 0.000 |
| 48 hours | 0.64 | 0.062 | 212 | 25 | 0.022 | sCr or UO

| Time prior AKI stage | Cutoff value | sens | spec | Quartile | OR | 95% CI of OR | |
| --- | --- | --- | --- | --- | --- | --- | --- |
| 0 hours | 43.8 | 72% | 54% | 1 |  |  |  |
|  | 14.9 | 81% | 35% | 2 | 1.3 | 0.7 | 2.3 |
|  | 7.78 | 91% | 17% | 3 | 2.6 | 1.7 | 4.2 |
|  | 151 | 55% | 70% | 4 | 3.7 | 2.4 | 5.7 |
|  | 274 | 32% | 80% |  |  |  |  |
|  | 845 | 21% | 90% |  |  |  |  |
| 24 hours | 35 | 71% | 51% | 1 |  |  |  |
|  | 18.4 | 81% | 39% | 2 | 0.7 | 0.5 | 1.1 |

Fig. 1 - 3

|  | Cutoff value | sens | spec | Quartile | OR | 95% CI of OR | |
|---|---|---|---|---|---|---|---|
|  | 6.02 | 90% | 14% | 3 | 1.5 | 1.1 | 2.1 |
|  | 151 | 47% | 70% | 4 | 2.4 | 1.8 | 3.3 |
|  | 274 | 32% | 80% |  |  |  |  |
|  | 845 | 21% | 90% |  |  |  |  |
| 48 hours | 39.5 | 70% | 53% | 1 |  |  |  |
|  | 10.4 | 81% | 24% | 2 | 0.3 | 0.1 | 1.2 |
|  | 5.46 | 93% | 14% | 3 | 1.2 | 0.6 | 2.3 |
|  | 151 | 48% | 70% | 4 | 2.2 | 1.3 | 3.9 |
|  | 274 | 41% | 80% |  |  |  |  |
|  | 845 | 22% | 90% |  |  |  |  | sCr only

| Time prior AKI stage | Cutoff value | sens | spec | Quartile | OR | 95% CI of OR | |
|---|---|---|---|---|---|---|---|
| 0 hours | 20 | 70% | 33% | 1 |  |  |  |
|  | 7.86 | 80% | 15% | 2 | 0.8 | 0.3 | 2.0 |
|  | 5.13 | 90% | 10% | 3 | 0.8 | 0.3 | 2.0 |
|  | 191 | 35% | 70% | 4 | 1.4 | 0.7 | 2.9 |
|  | 306 | 35% | 80% |  |  |  |  |
|  | 1120 | 20% | 90% |  |  |  |  |
| 24 hours | 10.1 | 73% | 19% | 1 |  |  |  |
|  | 8.2 | 81% | 15% | 2 | 0.4 | 0.2 | 0.9 |
|  | 3.98 | 92% | 8% | 3 | 0.3 | 0.1 | 0.8 |
|  | 191 | 42% | 70% | 4 | 1.1 | 0.7 | 1.7 |
|  | 306 | 38% | 80% |  |  |  |  |
|  | 1120 | 31% | 90% |  |  |  |  |
| 48 hours | 16.2 | 71% | 29% | 1 |  |  |  |
|  | 9.32 | 86% | 17% | 2 | 0.7 | 0.2 | 2.4 |
|  | 9.27 | 93% | 17% | 3 | 0.2 | 0.0 | 2.9 |
|  | 191 | 43% | 70% | 4 | 1.5 | 0.6 | 3.6 |
|  | 306 | 43% | 80% |  |  |  |  |
|  | 1120 | 14% | 90% |  |  |  |  |

UO only

| Time prior AKI stage | Cutoff value | sens | spec | Quartile | OR | 95% CI of OR | |
|---|---|---|---|---|---|---|---|
| 0 hours | 98.8 | 70% | 64% | 1 |  |  |  |
|  | 43.8 | 81% | 52% | 2 | 2.1 | 0.9 | 4.7 |
|  | 14.9 | 91% | 33% | 3 | 4.1 | 2.0 | 8.3 |
|  | 156 | 62% | 70% | 4 | 7.2 | 3.7 | 13.9 |
|  | 267 | 38% | 80% |  |  |  |  |
|  | 1020 | 17% | 90% |  |  |  |  |
| 24 hours | 64.4 | 71% | 55% | 1 |  |  |  |
|  | 35 | 81% | 49% | 2 | 1.6 | 0.9 | 2.9 |
|  | 11.2 | 90% | 25% | 3 | 2.9 | 1.7 | 5.0 |
|  | 156 | 52% | 70% | 4 | 5.0 | 3.1 | 8.2 |
|  | 267 | 38% | 80% |  |  |  |  |
|  | 1020 | 19% | 90% |  |  |  |  |
| 48 hours | 43.8 | 72% | 52% | 1 |  |  |  |
|  | 31.5 | 80% | 47% | 2 | 1.0 | 0.3 | 2.9 |
|  | 9.27 | 92% | 19% | 3 | 1.3 | 0.5 | 3.3 |
|  | 156 | 52% | 70% | 4 | 3.4 | 1.7 | 7.1 |
|  | 267 | 44% | 80% |  |  |  |  |
|  | 1020 | 20% | 90% |  |  |  |  |

Fig. 1 - 4

Hepatocyte growth factor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 332.751 | 606.005 | 332.751 | 605.973 | 332.751 | 713.738 |
| average | 467.138 | 779.409 | 467.138 | 992.715 | 467.138 | 750.183 |
| stdev | 455.556 | 644.938 | 455.556 | 1315.054 | 455.556 | 650.933 |
| p (t-test) |  | 0.000 |  | 0.000 |  | 0.009 |
| min | 27.880 | 42.096 | 27.880 | 14.776 | 27.880 | 38.014 |
| max | 2833.841 | 2726.014 | 2833.841 | 7839.221 | 2833.841 | 3067.704 |
| n (Samp) | 117 | 51 | 117 | 59 | 117 | 26 |
| n (Pat) | 99 | 51 | 99 | 59 | 99 | 26 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 452.538 | 459.687 | 452.538 | 638.601 | 452.538 | 655.061 |
| average | 652.139 | 572.674 | 652.139 | 886.286 | 652.139 | 648.386 |
| stdev | 759.885 | 648.438 | 759.885 | 982.315 | 759.885 | 380.882 |
| p (t-test) |  | 0.674 |  | 0.168 |  | 0.985 |
| min | 22.466 | 42.096 | 22.466 | 14.776 | 22.466 | 64.024 |
| max | 7839.221 | 2366.004 | 7839.221 | 4229.981 | 7839.221 | 1318.065 |
| n (Samp) | 260 | 17 | 260 | 23 | 260 | 14 |
| n (Pat) | 160 | 17 | 160 | 23 | 160 | 14 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 359.932 | 750.965 | 359.932 | 655.623 | 359.932 | 723.983 |
| average | 458.895 | 839.663 | 458.895 | 1011.170 | 458.895 | 765.779 |
| stdev | 404.053 | 584.266 | 404.053 | 1308.137 | 404.053 | 680.092 |
| p (t-test) |  | 0.000 |  | 0.000 |  | 0.005 |
| min | 27.880 | 71.485 | 27.880 | 29.280 | 27.880 | 38.014 |
| max | 2258.303 | 2726.014 | 2258.303 | 7839.221 | 2258.303 | 3067.704 |
| n (Samp) | 105 | 45 | 105 | 49 | 105 | 23 |
| n (Pat) | 84 | 45 | 84 | 49 | 84 | 23 | sCr or UO

| Time prior AKI stage | AUC | SE | nCohort 1 | nCohort 2 | p |
| --- | --- | --- | --- | --- | --- |
| 0 hours | 0.65 | 0.048 | 117 | 51 | 0.002 |
| 24 hours | 0.66 | 0.045 | 117 | 59 | 0.000 |
| 48 hours | 0.64 | 0.063 | 117 | 26 | 0.024 | sCr only

| Time prior AKI stage | AUC | SE | nCohort 1 | nCohort 2 | p |
| --- | --- | --- | --- | --- | --- |
| 0 hours | 0.44 | 0.069 | 260 | 17 | 0.353 |
| 24 hours | 0.57 | 0.065 | 260 | 23 | 0.299 |
| 48 hours | 0.57 | 0.082 | 260 | 14 | 0.380 |

UO only

| Time prior AKI stage | AUC | SE | nCohort 1 | nCohort 2 | p |
| --- | --- | --- | --- | --- | --- |
| 0 hours | 0.72 | 0.048 | 105 | 45 | 0.000 |
| 24 hours | 0.69 | 0.048 | 105 | 49 | 0.000 |
| 48 hours | 0.64 | 0.067 | 105 | 23 | 0.041 | sCr or UO

| Time prior AKI stage | Cutoff value | sens | spec | Quartile | OR | 95% CI of OR | |
| --- | --- | --- | --- | --- | --- | --- | --- |
| 0 hours | 373.50372 | 71% | 55% | 1 |  |  |  |
|  | 237.5733 | 80% | 38% | 2 | 0.6 | 0.4 | 1.2 |
|  | 85.423471 | 90% | 9% | 3 | 1.3 | 0.8 | 2.1 |
|  | 518.2926 | 55% | 70% | 4 | 3.5 | 2.3 | 5.5 |
|  | 756.62964 | 45% | 80% |  |  |  |  |
|  | 1015.7457 | 29% | 91% |  |  |  |  |
| 24 hours | 314.08152 | 71% | 49% | 1 |  |  |  |
|  | 237.5733 | 81% | 38% | 2 | 1.3 | 0.8 | 2.2 |
|  | 85.423471 | 92% | 9% | 3 | 2.4 | 1.5 | 3.9 |

Fig. 1 - 5

|  | Cutoff value | sens | spec | Quartile | OR | 95% CI of OR | |
|---|---|---|---|---|---|---|---|
|  | 518.2926 | 58% | 70% | 4 | 3.9 | 2.5 | 6.1 |
|  | 756.62964 | 41% | 80% |  |  |  |  |
|  | 1015.7457 | 31% | 91% |  |  |  |  |
| 48 hours | 315.00269 | 73% | 49% | 1 |  |  |  |
|  | 210.92416 | 81% | 35% | 2 | 0.8 | 0.3 | 2.1 |
|  | 62.722752 | 92% | 3% | 3 | 1.2 | 0.5 | 2.8 |
|  | 518.2926 | 54% | 70% | 4 | 2.6 | 1.3 | 5.4 |
|  | 756.62964 | 42% | 80% |  |  |  |  |
|  | 1015.7457 | 27% | 91% |  |  |  |  | sCr only

| Time prior AKI stage | Cutoff value | sens | spec | Quartile | OR | 95% CI of OR | |
|---|---|---|---|---|---|---|---|
| 0 hours | 130.16184 | 71% | 15% | 1 |  |  |  |
|  | 72.246896 | 82% | 7% | 2 | 1.3 | 0.5 | 3.3 |
|  | 42.09614 | 94% | 4% | 3 | 0.5 | 0.1 | 2.3 |
|  | 756.62964 | 24% | 70% | 4 | 1.6 | 0.7 | 3.8 |
|  | 980.60521 | 12% | 80% |  |  |  |  |
|  | 1331.9074 | 12% | 90% |  |  |  |  |
| 24 hours | 340.9225 | 74% | 39% | 1 |  |  |  |
|  | 144.77821 | 83% | 17% | 2 | 0.8 | 0.3 | 2.0 |
|  | 62.722752 | 91% | 4% | 3 | 1.0 | 0.4 | 2.3 |
|  | 756.62964 | 43% | 70% | 4 | 1.9 | 1.0 | 3.7 |
|  | 980.60521 | 35% | 80% |  |  |  |  |
|  | 1331.9074 | 17% | 90% |  |  |  |  |
| 48 hours | 388.05005 | 71% | 43% | 1 |  |  |  |
|  | 340.9225 | 86% | 39% | 2 | 2.0 | 0.4 | 9.4 |
|  | 210.92416 | 93% | 25% | 3 | 2.1 | 0.4 | 9.5 |
|  | 756.62964 | 36% | 70% | 4 | 2.0 | 0.4 | 9.4 |
|  | 980.60521 | 21% | 80% |  |  |  |  |
|  | 1331.9074 | 0% | 90% |  |  |  |  |

UO only

| Time prior AKI stage | Cutoff value | sens | spec | Quartile | OR | 95% CI of OR | |
|---|---|---|---|---|---|---|---|
| 0 hours | 450.47234 | 71% | 64% | 1 |  |  |  |
|  | 373.50372 | 80% | 52% | 2 | 2.2 | 0.9 | 5.2 |
|  | 237.5733 | 91% | 36% | 3 | 4.0 | 1.8 | 8.7 |
|  | 533.02014 | 62% | 70% | 4 | 10.2 | 4.8 | 21.7 |
|  | 703.49241 | 51% | 80% |  |  |  |  |
|  | 1013.5018 | 31% | 90% |  |  |  |  |
| 24 hours | 387.20019 | 71% | 55% | 1 |  |  |  |
|  | 272.17607 | 82% | 42% | 2 | 2.3 | 1.1 | 4.7 |
|  | 181.96421 | 92% | 26% | 3 | 3.4 | 1.7 | 6.8 |
|  | 533.02014 | 59% | 70% | 4 | 7.7 | 4.0 | 14.8 |
|  | 703.49241 | 47% | 80% |  |  |  |  |
|  | 1013.5018 | 33% | 90% |  |  |  |  |
| 48 hours | 329.88007 | 74% | 46% | 1 |  |  |  |
|  | 110.21965 | 83% | 16% | 2 | 0.4 | 0.1 | 1.6 |
|  | 70.941928 | 91% | 8% | 3 | 1.0 | 0.4 | 2.5 |
|  | 533.02014 | 52% | 70% | 4 | 2.8 | 1.4 | 5.9 |
|  | 703.49241 | 52% | 80% |  |  |  |  |
|  | 1013.5018 | 30% | 90% |  |  |  |  |

Fig. 1 - 6

Interferon gamma sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 8.780 | 10.200 | 8.780 | 12.700 | 8.780 | 13.000 |
| average | 11.553 | 13.182 | 11.553 | 14.609 | 11.553 | 15.863 |
| stdev | 8.616 | 8.790 | 8.616 | 10.039 | 8.616 | 11.674 |
| p (t-test) |  | 0.214 |  | 0.016 |  | 0.018 |
| min | 0.670 | 0.819 | 0.670 | 0.018 | 0.670 | 0.381 |
| max | 45.400 | 37.700 | 45.400 | 51.900 | 45.400 | 50.700 |
| n (Samp) | 249 | 53 | 249 | 62 | 249 | 27 |
| n (Pat) | 104 | 53 | 104 | 62 | 104 | 27 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 9.770 | 9.690 | 9.770 | 14.700 | 9.770 | 13.000 |
| average | 12.213 | 10.669 | 12.213 | 14.294 | 12.213 | 14.816 |
| stdev | 8.874 | 7.393 | 8.874 | 10.999 | 8.874 | 10.447 |
| p (t-test) |  | 0.444 |  | 0.252 |  | 0.283 |
| min | 0.381 | 0.819 | 0.381 | 0.018 | 0.381 | 1.100 |
| max | 51.900 | 22.400 | 51.900 | 37.300 | 51.900 | 35.400 |
| n (Samp) | 441 | 20 | 441 | 26 | 441 | 14 |
| n (Pat) | 170 | 20 | 170 | 26 | 170 | 14 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 8.940 | 11.800 | 8.940 | 14.100 | 8.940 | 12.800 |
| average | 10.821 | 14.603 | 10.821 | 15.395 | 10.821 | 15.231 |
| stdev | 7.375 | 8.769 | 7.375 | 8.785 | 7.375 | 10.309 |
| p (t-test) |  | 0.002 |  | 0.000 |  | 0.007 |
| min | 0.670 | 3.850 | 0.670 | 1.560 | 0.670 | 0.381 |
| max | 37.300 | 37.700 | 37.300 | 51.900 | 37.300 | 50.700 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
|---|---|---|---|---|---|
| 0 hours | 0.56 | 0.044 | 249 | 53 | 0.153 |
| 24 hours | 0.60 | 0.042 | 249 | 62 | 0.017 |
| 48 hours | 0.61 | 0.060 | 249 | 27 | 0.066 | sCr only

| Time prior AKI stage | AUC | SE | nCohort 1 | nCohort 2 | p |
|---|---|---|---|---|---|
| 0 hours | 0.46 | 0.064 | 441 | 20 | 0.517 |
| 24 hours | 0.54 | 0.059 | 441 | 26 | 0.524 |
| 48 hours | 0.57 | 0.081 | 441 | 14 | 0.371 |

UO only

| Time prior AKI stage | AUC | SE | nCohort 1 | nCohort 2 | p |
|---|---|---|---|---|---|
| 0 hours | 0.63 | 0.047 | 212 | 47 | 0.006 |
| 24 hours | 0.67 | 0.044 | 212 | 52 | 0.000 |
| 48 hours | 0.65 | 0.062 | 212 | 25 | 0.019 | sCr or UO

| Time prior AKI stage | Cutoff value | sens | spec | Quartile | OR | 95% CI of OR | |
|---|---|---|---|---|---|---|---|
| 0 hours | 6.86 | 72% | 42% | 1 |  |  |  |
|  | 4.85 | 83% | 24% | 2 | 1.1 | 0.7 | 1.6 |
|  | 3.87 | 92% | 15% | 3 | 1.3 | 0.9 | 2.0 |
|  | 14.1 | 40% | 70% | 4 | 1.6 | 1.1 | 2.2 |
|  | 18.9 | 26% | 80% |  |  |  |  |
|  | 24.9 | 11% | 90% |  |  |  |  |
| 24 hours | 9.04 | 71% | 52% | 1 |  |  |  |
|  | 6.71 | 81% | 40% | 2 | 0.8 | 0.5 | 1.2 |

Fig. 1 - 7

| Time prior AKI stage | Cutoff value | sens | spec | Quartile | OR | 95% CI of OR | |
|---|---|---|---|---|---|---|---|
| | 2.8 | 90% | 7% | 3 | 2.2 | 1.6 | 3.1 |
| | 14.1 | 47% | 70% | 4 | 2.2 | 1.6 | 3.1 |
| | 18.9 | 27% | 80% | | | | |
| | 24.9 | 15% | 90% | | | | |
| 48 hours | 9.28 | 70% | 53% | 1 | | | |
| | 5.8 | 81% | 33% | 2 | 0.6 | 0.2 | 1.8 |
| | 1.41 | 93% | 2% | 3 | 1.7 | 0.8 | 3.4 |
| | 14.1 | 48% | 70% | 4 | 2.4 | 1.3 | 4.6 |
| | 18.9 | 33% | 80% | | | | |
| | 24.9 | 19% | 90% | | | | | sCr only

| Time prior AKI stage | Cutoff value | sens | spec | Quartile | OR | 95% CI of OR | |
|---|---|---|---|---|---|---|---|
| 0 hours | 4.87 | 70% | 22% | 1 | | | |
| | 3.79 | 80% | 15% | 2 | 1.0 | 0.4 | 2.3 |
| | 2.3 | 90% | 7% | 3 | 0.6 | 0.2 | 1.8 |
| | 15.6 | 30% | 70% | 4 | 1.4 | 0.7 | 2.9 |
| | 19.5 | 20% | 80% | | | | |
| | 24.6 | 0% | 90% | | | | |
| 24 hours | 3.33 | 73% | 12% | 1 | | | |
| | 3.14 | 81% | 11% | 2 | 0.1 | 0.0 | 0.9 |
| | 1.56 | 92% | 3% | 3 | 0.5 | 0.3 | 1.0 |
| | 15.6 | 42% | 70% | 4 | 1.2 | 0.8 | 1.9 |
| | 19.5 | 31% | 80% | | | | |
| | 24.6 | 19% | 90% | | | | |
| 48 hours | 8.66 | 71% | 44% | 1 | | | |
| | 4.4 | 86% | 19% | 2 | 0.7 | 0.1 | 3.5 |
| | 1.56 | 93% | 3% | 3 | 1.7 | 0.6 | 5.0 |
| | 15.6 | 43% | 70% | 4 | 1.3 | 0.4 | 4.3 |
| | 19.5 | 29% | 80% | | | | |
| | 24.6 | 21% | 90% | | | | |

UO only

| Time prior AKI stage | Cutoff value | sens | spec | Quartile | OR | 95% CI of OR | |
|---|---|---|---|---|---|---|---|
| 0 hours | 8.22 | 70% | 45% | 1 | | | |
| | 6.63 | 81% | 39% | 2 | 1.8 | 1.1 | 3.1 |
| | 4.43 | 91% | 20% | 3 | 1.3 | 0.7 | 2.3 |
| | 13.7 | 49% | 70% | 4 | 3.4 | 2.1 | 5.3 |
| | 17.6 | 36% | 80% | | | | |
| | 21.9 | 17% | 92% | | | | |
| 24 hours | 10 | 71% | 57% | 1 | | | |
| | 8.65 | 81% | 49% | 2 | 4.7 | 1.9 | 11.3 |
| | 6.84 | 90% | 40% | 3 | 7.3 | 3.1 | 16.9 |
| | 13.7 | 50% | 70% | 4 | 9.1 | 4.0 | 20.8 |
| | 17.6 | 33% | 80% | | | | |
| | 21.9 | 17% | 92% | | | | |
| 48 hours | 9.89 | 72% | 57% | 1 | | | |
| | 8.62 | 80% | 49% | 2 | 2.6 | 0.6 | 11.2 |
| | 5.8 | 92% | 32% | 3 | 5.1 | 1.4 | 18.3 |
| | 13.7 | 40% | 70% | 4 | 5.0 | 1.4 | 17.9 |
| | 17.6 | 36% | 80% | | | | |
| | 21.9 | 20% | 92% | | | | |

Fig. 1 - 8

Interleukin-16 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 7.710 | 10.500 | 7.710 | 15.500 | 7.710 | 11.000 |
| average | 35.934 | 33.794 | 35.934 | 76.873 | 35.934 | 44.054 |
| stdev | 121.825 | 63.390 | 121.825 | 172.802 | 121.825 | 108.934 |
| p (t-test) |  | 0.901 |  | 0.031 |  | 0.740 |
| min | 0.265 | 0.265 | 0.265 | 0.265 | 0.265 | 0.265 |
| max | 1100.000 | 294.000 | 1100.000 | 1010.000 | 1100.000 | 531.000 |
| n (Samp) | 249 | 53 | 249 | 62 | 249 | 27 |
| n (Pat) | 104 | 53 | 104 | 62 | 104 | 27 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 8.280 | 14.785 | 8.280 | 16.450 | 8.280 | 14.600 |
| average | 38.429 | 114.060 | 38.429 | 108.640 | 38.429 | 74.289 |
| stdev | 116.686 | 244.440 | 116.686 | 209.378 | 116.686 | 132.743 |
| p (t-test) |  | 0.008 |  | 0.005 |  | 0.260 |
| min | 0.265 | 0.265 | 0.265 | 0.265 | 0.265 | 0.265 |
| max | 1100.000 | 1080.000 | 1100.000 | 857.000 | 1100.000 | 439.000 |
| n (Samp) | 441 | 20 | 441 | 26 | 441 | 14 |
| n (Pat) | 170 | 20 | 170 | 26 | 170 | 14 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 8.235 | 12.600 | 8.235 | 17.450 | 8.235 | 14.500 |
| average | 30.693 | 33.302 | 30.693 | 77.489 | 30.693 | 56.810 |
| stdev | 103.693 | 61.162 | 103.693 | 172.208 | 103.693 | 119.805 |
| p (t-test) |  | 0.868 |  | 0.012 |  | 0.243 |
| min | 0.265 | 0.265 | 0.265 | 0.265 | 0.265 | 0.265 |
| max | 891.000 | 294.000 | 891.000 | 1010.000 | 891.000 | 531.000 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
| --- | --- | --- | --- | --- | --- |
| 0 hours | 0.56 | 0.044 | 249 | 53 | 0.205 |
| 24 hours | 0.61 | 0.042 | 249 | 62 | 0.011 |
| 48 hours | 0.56 | 0.060 | 249 | 27 | 0.297 | sCr only

| Time prior AKI stage | AUC | SE | nCohort 1 | nCohort 2 | p |
| --- | --- | --- | --- | --- | --- |
| 0 hours | 0.62 | 0.068 | 441 | 20 | 0.071 |
| 24 hours | 0.63 | 0.060 | 441 | 26 | 0.034 |
| 48 hours | 0.60 | 0.081 | 441 | 14 | 0.214 |

UO only

| Time prior AKI stage | AUC | SE | nCohort 1 | nCohort 2 | p |
| --- | --- | --- | --- | --- | --- |
| 0 hours | 0.56 | 0.047 | 212 | 47 | 0.195 |
| 24 hours | 0.65 | 0.045 | 212 | 52 | 0.001 |
| 48 hours | 0.63 | 0.063 | 212 | 25 | 0.038 | sCr or UO

| Time prior AKI stage | Cutoff value | sens | spec | Quartile | OR | 95% CI of OR | |
| --- | --- | --- | --- | --- | --- | --- | --- |
| 0 hours | 4.65 | 72% | 33% | 1 |  |  |  |
|  | 0 | 100% | 0% | 2 | 1.0 | 0.6 | 1.5 |
|  | 0 | 100% | 0% | 3 | 1.2 | 0.8 | 1.8 |
|  | 14.4 | 45% | 70% | 4 | 1.8 | 1.3 | 2.6 |
|  | 22.2 | 25% | 80% |  |  |  |  |
|  | 59.7 | 17% | 90% |  |  |  |  |
| 24 hours | 5.64 | 71% | 38% | 1 |  |  |  |
|  | 0 | 100% | 0% | 2 | 1.0 | 0.7 | 1.5 |
|  | 0 | 100% | 0% | 3 | 1.9 | 1.4 | 2.7 |

Fig. 1 - 9

|  | 14.4 | 53% | 70% | 4 | 2.2 | 1.6 | 3.1 |
|---|---|---|---|---|---|---|---|
|  | 22.2 | 34% | 80% |  |  |  |  |
|  | 59.7 | 19% | 90% |  |  |  |  |
| 48 hours | 6.22 | 70% | 44% | 1 |  |  |  |
|  | 0 | 100% | 0% | 2 | 0.8 | 0.4 | 1.8 |
|  | 0 | 100% | 0% | 3 | 1.4 | 0.7 | 2.6 |
|  | 14.4 | 48% | 70% | 4 | 1.4 | 0.7 | 2.6 |
|  | 22.2 | 22% | 80% |  |  |  |  |
|  | 59.7 | 11% | 90% |  |  |  |  | sCr only

| Time prior AKI stage | Cutoff value | sens | spec | Quartile | OR | 95% CI of OR | |
|---|---|---|---|---|---|---|---|
| 0 hours | 7.57 | 70% | 47% | 1 |  |  |  |
|  | 5.2 | 80% | 35% | 2 | 0.7 | 0.2 | 2.4 |
|  | 0 | 100% | 0% | 3 | 1.0 | 0.4 | 2.8 |
|  | 16.6 | 50% | 70% | 4 | 2.3 | 1.1 | 4.9 |
|  | 23.7 | 45% | 80% |  |  |  |  |
|  | 69.8 | 30% | 90% |  |  |  |  |
| 24 hours | 8.57 | 73% | 52% | 1 |  |  |  |
|  | 0 | 100% | 0% | 2 | 0.4 | 0.1 | 1.6 |
|  | 0 | 100% | 0% | 3 | 1.6 | 0.8 | 3.2 |
|  | 16.6 | 50% | 70% | 4 | 2.3 | 1.3 | 4.2 |
|  | 23.7 | 38% | 80% |  |  |  |  |
|  | 69.8 | 27% | 90% |  |  |  |  |
| 48 hours | 6.22 | 71% | 41% | 1 |  |  |  |
|  | 0 | 100% | 0% | 2 | 0.7 | 0.1 | 3.5 |
|  | 0 | 100% | 0% | 3 | 1.7 | 0.6 | 5.0 |
|  | 16.6 | 43% | 70% | 4 | 1.3 | 0.4 | 4.3 |
|  | 23.7 | 29% | 80% |  |  |  |  |
|  | 69.8 | 21% | 90% |  |  |  |  |

UO only

| Time prior AKI stage | Cutoff value | sens | spec | Quartile | OR | 95% CI of OR | |
|---|---|---|---|---|---|---|---|
| 0 hours | 4.65 | 70% | 32% | 1 |  |  |  |
|  | 0 | 100% | 0% | 2 | 0.6 | 0.4 | 1.0 |
|  | 0 | 100% | 0% | 3 | 0.8 | 0.5 | 1.2 |
|  | 13.8 | 49% | 70% | 4 | 1.5 | 1.1 | 2.2 |
|  | 21.9 | 26% | 80% |  |  |  |  |
|  | 52 | 15% | 90% |  |  |  |  |
| 24 hours | 9.26 | 71% | 56% | 1 |  |  |  |
|  | 4.95 | 81% | 33% | 2 | 0.9 | 0.5 | 1.6 |
|  | 0 | 100% | 0% | 3 | 2.7 | 1.8 | 4.2 |
|  | 13.8 | 60% | 70% | 4 | 2.9 | 1.9 | 4.5 |
|  | 21.9 | 35% | 80% |  |  |  |  |
|  | 52 | 21% | 90% |  |  |  |  |
| 48 hours | 7.71 | 72% | 48% | 1 |  |  |  |
|  | 6.22 | 80% | 42% | 2 | 1.3 | 0.5 | 3.3 |
|  | 0 | 100% | 0% | 3 | 1.9 | 0.8 | 4.3 |
|  | 13.8 | 56% | 70% | 4 | 2.4 | 1.1 | 5.3 |
|  | 21.9 | 28% | 80% |  |  |  |  |
|  | 52 | 16% | 90% |  |  |  |  |

Fig. 1 - 10

Interleukin-2 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.323 | 0.424 | 0.323 | 0.370 | 0.323 | 0.270 |
| average | 1.495 | 0.952 | 1.495 | 0.765 | 1.495 | 0.480 |
| stdev | 8.995 | 1.687 | 8.995 | 1.883 | 8.995 | 0.740 |
| p (t-test) |  | 0.670 |  | 0.535 |  | 0.567 |
| min | 0.000 | 0.000 | 0.000 | 0.000 | 0.000 | 0.000 |
| max | 96.860 | 8.363 | 96.860 | 13.553 | 96.860 | 3.002 |
| n (Samp) | 117 | 51 | 117 | 60 | 117 | 26 |
| n (Pat) | 99 | 51 | 99 | 60 | 99 | 26 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 0.335 | 0.349 | 0.335 | 0.376 | 0.335 | 0.450 |
| average | 1.218 | 0.825 | 1.218 | 1.105 | 1.218 | 0.765 |
| stdev | 6.423 | 1.504 | 6.423 | 2.824 | 6.423 | 0.972 |
| p (t-test) |  | 0.801 |  | 0.934 |  | 0.792 |
| min | 0.000 | 0.000 | 0.000 | 0.000 | 0.000 | 0.022 |
| max | 96.860 | 5.938 | 96.860 | 13.553 | 96.860 | 3.002 |
| n (Samp) | 261 | 17 | 261 | 23 | 261 | 14 |
| n (Pat) | 160 | 17 | 160 | 23 | 160 | 14 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 0.324 | 0.424 | 0.324 | 0.358 | 0.324 | 0.274 |
| average | 1.653 | 0.881 | 1.653 | 0.498 | 1.653 | 0.297 |
| stdev | 9.498 | 1.626 | 9.498 | 0.791 | 9.498 | 0.242 |
| p (t-test) |  | 0.589 |  | 0.393 |  | 0.496 |
| min | 0.000 | 0.000 | 0.000 | 0.000 | 0.000 | 0.000 |
| max | 96.860 | 8.363 | 96.860 | 5.260 | 96.860 | 0.831 |
| n (Samp) | 105 | 45 | 105 | 50 | 105 | 23 |
| n (Pat) | 84 | 45 | 84 | 50 | 84 | 23 | sCr or UO

| Time prior AKI stage | AUC | SE | nCohort 1 | nCohort 2 | p |
| --- | --- | --- | --- | --- | --- |
| 0 hours | 0.58 | 0.049 | 117 | 51 | 0.106 |
| 24 hours | 0.56 | 0.046 | 117 | 60 | 0.160 |
| 48 hours | 0.51 | 0.063 | 117 | 26 | 0.935 | sCr only

| Time prior AKI stage | AUC | SE | nCohort 1 | nCohort 2 | p |
| --- | --- | --- | --- | --- | --- |
| 0 hours | 0.52 | 0.073 | 261 | 17 | 0.749 |
| 24 hours | 0.56 | 0.064 | 261 | 23 | 0.353 |
| 48 hours | 0.58 | 0.082 | 261 | 14 | 0.351 |

UO only

| Time prior AKI stage | AUC | SE | nCohort 1 | nCohort 2 | p |
| --- | --- | --- | --- | --- | --- |
| 0 hours | 0.55 | 0.052 | 105 | 45 | 0.313 |
| 24 hours | 0.54 | 0.050 | 105 | 50 | 0.398 |
| 48 hours | 0.47 | 0.066 | 105 | 23 | 0.616 | sCr or UO

| Time prior AKI stage | Cutoff value | sens | spec | Quartile | OR | 95% CI of OR | |
| --- | --- | --- | --- | --- | --- | --- | --- |
| 0 hours | 0.2399449 | 71% | 44% | 1 |  |  |  |
|  | 0.1435391 | 80% | 40% | 2 | 2.8 | 1.6 | 4.8 |
|  | 0 | 100% | 0% | 3 | 2.5 | 1.4 | 4.3 |
|  | 0.4896804 | 43% | 70% | 4 | 2.8 | 1.6 | 4.8 |
|  | 0.7486972 | 25% | 80% |  |  |  |  |
|  | 1.7654847 | 14% | 91% |  |  |  |  |
| 24 hours | 0.2365948 | 70% | 44% | 1 |  |  |  |
|  | 0.1007266 | 80% | 38% | 2 | 5.3 | 3.0 | 9.2 |
|  | 0.0027535 | 90% | 32% | 3 | 4.8 | 2.7 | 8.4 |

Fig. 1 - 11

|  | Cutoff value | sens | spec | Quartile | OR | 95% CI of OR | |
|---|---|---|---|---|---|---|---|
|  | 0.4896804 | 35% | 70% | 4 | 3.2 | 1.8 | 5.6 |
|  | 0.7486972 | 17% | 80% |  |  |  |  |
|  | 1.7654847 | 7% | 91% |  |  |  |  |
| 48 hours | 0.1603607 | 73% | 42% | 1 |  |  |  |
|  | 0.0713336 | 81% | 36% | 2 | 10.5 | 3.0 | 37.3 |
|  | 0 | 100% | 0% | 3 | 2.1 | 0.4 | 10.1 |
|  | 0.4896804 | 23% | 70% | 4 | 3.3 | 0.8 | 13.8 |
|  | 0.7486972 | 12% | 80% |  |  |  |  |
|  | 1.7654847 | 8% | 91% |  |  |  |  | sCr only

| Time prior AKI stage | Cutoff value | sens | spec | Quartile | OR | 95% CI of OR | |
|---|---|---|---|---|---|---|---|
| 0 hours | 0.1767872 | 71% | 34% | 1 |  |  |  |
|  | 0.0027535 | 82% | 23% | 2 | 1.0 | 0.3 | 2.8 |
|  | 0 | 100% | 0% | 3 | 1.0 | 0.4 | 2.8 |
|  | 0.5364781 | 35% | 70% | 4 | 1.3 | 0.5 | 3.2 |
|  | 0.7080363 | 24% | 80% |  |  |  |  |
|  | 1.7097552 | 12% | 90% |  |  |  |  |
| 24 hours | 0.2570186 | 74% | 41% | 1 |  |  |  |
|  | 0.1335295 | 83% | 30% | 2 | 4.4 | 1.2 | 15.8 |
|  | 0.0944585 | 91% | 28% | 3 | 3.8 | 1.0 | 14.1 |
|  | 0.5364781 | 30% | 70% | 4 | 3.2 | 0.8 | 12.5 |
|  | 0.7080363 | 17% | 80% |  |  |  |  |
|  | 1.7097552 | 9% | 90% |  |  |  |  |
| 48 hours | 0.189991 | 71% | 34% | 1 |  |  |  |
|  | 0.1435391 | 86% | 30% | 2 | 5.2 | 0.5 | 58.4 |
|  | 0.0642177 | 93% | 26% | 3 | 4.1 | 0.3 | 50.7 |
|  | 0.5364781 | 36% | 70% | 4 | 4.1 | 0.3 | 50.7 |
|  | 0.7080363 | 21% | 80% |  |  |  |  |
|  | 1.7097552 | 14% | 90% |  |  |  |  |

UO only

| Time prior AKI stage | Cutoff value | sens | spec | Quartile | OR | 95% CI of OR | |
|---|---|---|---|---|---|---|---|
| 0 hours | 0.1570865 | 71% | 38% | 1 |  |  |  |
|  | 1E-09 | 80% | 30% | 2 | 2.5 | 1.4 | 4.4 |
|  | 0 | 100% | 0% | 3 | 1.8 | 1.0 | 3.3 |
|  | 0.4943534 | 40% | 70% | 4 | 2.2 | 1.3 | 4.0 |
|  | 0.7080363 | 22% | 80% |  |  |  |  |
|  | 2.092275 | 9% | 90% |  |  |  |  |
| 24 hours | 0.1762841 | 70% | 41% | 1 |  |  |  |
|  | 0.0683632 | 80% | 33% | 2 | 4.1 | 2.3 | 7.5 |
|  | 1E-09 | 90% | 30% | 3 | 3.7 | 2.0 | 6.7 |
|  | 0.4943534 | 36% | 70% | 4 | 2.1 | 1.1 | 4.0 |
|  | 0.7080363 | 16% | 80% |  |  |  |  |
|  | 2.092275 | 4% | 90% |  |  |  |  |
| 48 hours | 0.1603607 | 74% | 40% | 1 |  |  |  |
|  | 0.0356614 | 83% | 32% | 2 | 1.0 | 0.3 | 3.1 |
|  | 0 | 100% | 0% | 3 | 4.2 | 1.8 | 9.5 |
|  | 0.4943534 | 17% | 70% | 4 | 0.7 | 0.2 | 2.6 |
|  | 0.7080363 | 9% | 80% |  |  |  |  |
|  | 2.092275 | 0% | 90% |  |  |  |  |

Fig. 1 - 12

Interleukin-12 p40 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 4.780 | 8.387 | 4.780 | 5.527 | 4.780 | 4.714 |
| average | 9.944 | 10.736 | 9.944 | 8.429 | 9.944 | 9.110 |
| stdev | 13.422 | 10.485 | 13.422 | 10.716 | 13.422 | 11.666 |
| p (t-test) |  | 0.708 |  | 0.452 |  | 0.770 |
| min | 0.000 | 0.000 | 0.000 | 0.000 | 0.000 | 0.000 |
| max | 66.881 | 41.351 | 66.881 | 52.713 | 66.881 | 44.714 |
| n (Samp) | 117 | 51 | 117 | 59 | 117 | 26 |
| n (Pat) | 99 | 51 | 99 | 59 | 99 | 26 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 5.190 | 5.328 | 5.190 | 5.913 | 5.190 | 9.240 |
| average | 9.350 | 10.484 | 9.350 | 10.493 | 9.350 | 11.956 |
| stdev | 12.119 | 10.274 | 12.119 | 10.495 | 12.119 | 14.308 |
| p (t-test) |  | 0.706 |  | 0.662 |  | 0.438 |
| min | 0.000 | 0.000 | 0.000 | 0.000 | 0.000 | 0.000 |
| max | 66.881 | 27.881 | 66.881 | 36.019 | 66.881 | 49.268 |
| n (Samp) | 260 | 17 | 260 | 23 | 260 | 14 |
| n (Pat) | 160 | 17 | 160 | 23 | 160 | 14 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 5.760 | 9.439 | 5.760 | 3.785 | 5.760 | 4.750 |
| average | 9.832 | 12.491 | 9.832 | 7.881 | 9.832 | 9.389 |
| stdev | 12.576 | 11.720 | 12.576 | 10.972 | 12.576 | 11.996 |
| p (t-test) |  | 0.228 |  | 0.353 |  | 0.878 |
| min | 0.000 | 0.000 | 0.000 | 0.000 | 0.000 | 0.000 |
| max | 61.635 | 41.936 | 61.635 | 52.713 | 61.635 | 44.714 |
| n (Samp) | 105 | 45 | 105 | 49 | 105 | 23 |
| n (Pat) | 84 | 45 | 84 | 49 | 84 | 23 | sCr or UO

| Time prior AKI stage | AUC | SE | nCohort 1 | nCohort 2 | p |
|---|---|---|---|---|---|
| 0 hours | 0.57 | 0.049 | 117 | 51 | 0.163 |
| 24 hours | 0.50 | 0.046 | 117 | 59 | 0.992 |
| 48 hours | 0.49 | 0.062 | 117 | 26 | 0.852 | sCr only

| Time prior AKI stage | AUC | SE | nCohort 1 | nCohort 2 | p |
|---|---|---|---|---|---|
| 0 hours | 0.56 | 0.074 | 260 | 17 | 0.403 |
| 24 hours | 0.55 | 0.064 | 260 | 23 | 0.414 |
| 48 hours | 0.53 | 0.081 | 260 | 14 | 0.669 |

UO only

| Time prior AKI stage | AUC | SE | nCohort 1 | nCohort 2 | p |
|---|---|---|---|---|---|
| 0 hours | 0.59 | 0.052 | 105 | 45 | 0.072 |
| 24 hours | 0.47 | 0.050 | 105 | 49 | 0.522 |
| 48 hours | 0.49 | 0.066 | 105 | 23 | 0.854 | sCr or UO

| Time prior AKI stage | Cutoff value | sens | spec | Quartile | OR | 95% CI of OR | |
|---|---|---|---|---|---|---|---|
| 0 hours | 3.1997977 | 71% | 44% | 1 |  |  |  |
|  | 1.1104935 | 80% | 36% | 2 | 3.4 | 2.0 | 5.8 |
|  | 0 | 100% | 0% | 3 | 1.8 | 1.0 | 3.2 |
|  | 12.058681 | 37% | 70% | 4 | 3.1 | 1.8 | 5.2 |
|  | 18.160458 | 24% | 80% |  |  |  |  |
|  | 26.148501 | 10% | 91% |  |  |  |  |
| 24 hours | 1.2625972 | 71% | 37% | 1 |  |  |  |
|  | 0 | 100% | 0% | 2 | 1.8 | 1.2 | 2.8 |
|  | 0 | 100% | 0% | 3 | 1.7 | 1.1 | 2.5 |

Fig. 1 - 13

|  | Cutoff value | sens | spec | Quartile | OR | 95% CI of OR | |
|---|---|---|---|---|---|---|---|
|  | 12.058681 | 25% | 70% | 4 | 1.0 | 0.6 | 1.6 |
|  | 18.160458 | 12% | 80% |  |  |  |  |
|  | 26.148501 | 7% | 91% |  |  |  |  |
| 48 hours | 0 | 100% | 0% | 1 |  |  |  |
|  | 0 | 100% | 0% | 2 | 1.8 | 0.8 | 3.8 |
|  | 0 | 100% | 0% | 3 | 0.8 | 0.3 | 2.1 |
|  | 12.058681 | 23% | 70% | 4 | 2.1 | 1.0 | 4.5 |
|  | 18.160458 | 19% | 80% |  |  |  |  |
|  | 26.148501 | 8% | 91% |  |  |  |  | sCr only

| Time prior AKI stage | Cutoff value | sens | spec | Quartile | OR | 95% CI of OR | |
|---|---|---|---|---|---|---|---|
| 0 hours | 3.1531486 | 71% | 42% | 1 |  |  |  |
|  | 0.3767903 | 82% | 30% | 2 | 1.7 | 0.6 | 5.2 |
|  | 0 | 100% | 0% | 3 | 1.0 | 0.3 | 3.9 |
|  | 11.13881 | 41% | 70% | 4 | 2.1 | 0.7 | 5.8 |
|  | 15.281897 | 35% | 80% |  |  |  |  |
|  | 23.495933 | 18% | 90% |  |  |  |  |
| 24 hours | 2.5686249 | 74% | 40% | 1 |  |  |  |
|  | 0 | 100% | 0% | 2 | 0.5 | 0.2 | 1.3 |
|  | 0 | 100% | 0% | 3 | 1.0 | 0.5 | 2.0 |
|  | 11.13881 | 39% | 70% | 4 | 1.4 | 0.7 | 2.6 |
|  | 15.281897 | 30% | 80% |  |  |  |  |
|  | 23.495933 | 13% | 90% |  |  |  |  |
| 48 hours | 0 | 100% | 0% | 1 |  |  |  |
|  | 0 | 100% | 0% | 2 | 0.2 | 0.0 | 2.1 |
|  | 0 | 100% | 0% | 3 | 0.6 | 0.2 | 1.8 |
|  | 11.13881 | 43% | 70% | 4 | 1.0 | 0.4 | 2.3 |
|  | 15.281897 | 36% | 80% |  |  |  |  |
|  | 23.495933 | 14% | 90% |  |  |  |  |

UO only

| Time prior AKI stage | Cutoff value | sens | spec | Quartile | OR | 95% CI of OR | |
|---|---|---|---|---|---|---|---|
| 0 hours | 4.0303087 | 71% | 45% | 1 |  |  |  |
|  | 2.9891225 | 80% | 40% | 2 | 2.2 | 1.3 | 4.0 |
|  | 0 | 100% | 0% | 3 | 1.4 | 0.7 | 2.6 |
|  | 12.058681 | 40% | 70% | 4 | 3.1 | 1.8 | 5.4 |
|  | 16.350232 | 36% | 80% |  |  |  |  |
|  | 24.423486 | 20% | 90% |  |  |  |  |
| 24 hours | 0.1995976 | 71% | 30% | 1 |  |  |  |
|  | 0 | 100% | 0% | 2 | 1.7 | 1.0 | 2.7 |
|  | 0 | 100% | 0% | 3 | 1.5 | 0.9 | 2.4 |
|  | 12.058681 | 24% | 70% | 4 | 1.3 | 0.8 | 2.2 |
|  | 16.350232 | 10% | 80% |  |  |  |  |
|  | 24.423486 | 6% | 90% |  |  |  |  |
| 48 hours | 0 | 100% | 0% | 1 |  |  |  |
|  | 0 | 100% | 0% | 2 | 1.0 | 0.4 | 2.5 |
|  | 0 | 100% | 0% | 3 | 1.5 | 0.7 | 3.4 |
|  | 12.058681 | 26% | 70% | 4 | 1.2 | 0.5 | 3.0 |
|  | 16.350232 | 22% | 80% |  |  |  |  |
|  | 24.423486 | 9% | 90% |  |  |  |  |

Fig. 1 - 14

Matrix metalloproteinase-2 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 19.300 | 27.700 | 19.300 | 24.900 | 19.300 | 23.700 |
| average | 24.737 | 34.357 | 24.737 | 59.008 | 24.737 | 35.013 |
| stdev | 25.360 | 27.697 | 25.360 | 165.081 | 25.360 | 43.441 |
| p (t-test) |  | 0.014 |  | 0.002 |  | 0.067 |
| min | 0.600 | 0.600 | 0.600 | 0.600 | 0.600 | 2.470 |
| max | 293.000 | 190.000 | 293.000 | 1280.000 | 293.000 | 235.000 |
| n (Samp) | 249 | 53 | 249 | 62 | 249 | 27 |
| n (Pat) | 104 | 53 | 104 | 62 | 104 | 27 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 21.000 | 29.250 | 21.000 | 33.350 | 21.000 | 28.400 |
| average | 30.159 | 32.912 | 30.159 | 41.482 | 30.159 | 36.436 |
| stdev | 67.363 | 17.263 | 67.363 | 26.611 | 67.363 | 24.845 |
| p (t-test) |  | 0.855 |  | 0.394 |  | 0.728 |
| min | 0.600 | 6.640 | 0.600 | 4.660 | 0.600 | 8.610 |
| max | 1280.000 | 76.800 | 1280.000 | 96.100 | 1280.000 | 98.400 |
| n (Samp) | 441 | 20 | 441 | 26 | 441 | 14 |
| n (Pat) | 170 | 20 | 170 | 26 | 170 | 14 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 19.400 | 27.700 | 19.400 | 24.600 | 19.400 | 23.700 |
| average | 24.609 | 36.368 | 24.609 | 62.193 | 24.609 | 36.338 |
| stdev | 25.694 | 29.111 | 25.694 | 179.932 | 25.694 | 44.747 |
| p (t-test) |  | 0.006 |  | 0.004 |  | 0.051 |
| min | 0.600 | 0.600 | 0.600 | 0.600 | 0.600 | 2.470 |
| max | 293.000 | 190.000 | 293.000 | 1280.000 | 293.000 | 235.000 |
| n (Samp) | 212 | 47 | 212 | 52 | 212 | 25 |
| n (Pat) | 85 | 47 | 85 | 52 | 85 | 25 | sCr or UO

| Time prior AKI stage | AUC | SE | nCohort 1 | nCohort 2 | p |
|---|---|---|---|---|---|
| 0 hours | 0.68 | 0.043 | 249 | 53 | 0.000 |
| 24 hours | 0.66 | 0.041 | 249 | 62 | 0.000 |
| 48 hours | 0.60 | 0.060 | 249 | 27 | 0.100 | sCr only

| Time prior AKI stage | AUC | SE | nCohort 1 | nCohort 2 | p |
|---|---|---|---|---|---|
| 0 hours | 0.68 | 0.067 | 441 | 20 | 0.008 |
| 24 hours | 0.69 | 0.059 | 441 | 26 | 0.001 |
| 48 hours | 0.68 | 0.080 | 441 | 14 | 0.021 |

UO only

| Time prior AKI stage | AUC | SE | nCohort 1 | nCohort 2 | p |
|---|---|---|---|---|---|
| 0 hours | 0.70 | 0.045 | 212 | 47 | 0.000 |
| 24 hours | 0.65 | 0.045 | 212 | 52 | 0.001 |
| 48 hours | 0.61 | 0.063 | 212 | 25 | 0.072 | sCr or UO

| Time prior AKI stage | Cutoff value | sens | spec | Quartile | OR | 95% CI of OR | |
|---|---|---|---|---|---|---|---|
| 0 hours | 22.9 | 72% | 64% | 1 |  |  |  |
|  | 18.1 | 81% | 46% | 2 | 1.0 | 0.5 | 2.0 |
|  | 12.7 | 91% | 27% | 3 | 3.9 | 2.4 | 6.4 |
|  | 25.4 | 60% | 70% | 4 | 4.7 | 2.9 | 7.6 |
|  | 32.1 | 36% | 81% |  |  |  |  |
|  | 49.5 | 15% | 90% |  |  |  |  |
| 24 hours | 21.4 | 71% | 57% | 1 |  |  |  |
|  | 17.6 | 81% | 45% | 2 | 2.2 | 1.2 | 3.7 |
|  | 12.8 | 90% | 28% | 3 | 4.1 | 2.5 | 6.6 |

Fig. 1 - 15

|  | Cutoff value | sens | spec | Quartile | OR | 95% CI of OR | |
|---|---|---|---|---|---|---|---|
|  | 25.4 | 47% | 70% | 4 | 5.3 | 3.3 | 8.4 |
|  | 32.1 | 35% | 81% |  |  |  |  |
|  | 49.5 | 23% | 90% |  |  |  |  |
| 48 hours | 17.8 | 70% | 46% | 1 |  |  |  |
|  | 12.3 | 81% | 25% | 2 | 0.5 | 0.2 | 1.4 |
|  | 8.5 | 93% | 13% | 3 | 1.4 | 0.7 | 2.6 |
|  | 25.4 | 48% | 70% | 4 | 1.8 | 1.0 | 3.2 |
|  | 32.1 | 30% | 81% |  |  |  |  |
|  | 49.5 | 19% | 90% |  |  |  |  | sCr only

| Time prior AKI stage | Cutoff value | sens | spec | Quartile | OR | 95% CI of OR | |
|---|---|---|---|---|---|---|---|
| 0 hours | 25.4 | 70% | 66% | 1 |  |  |  |
|  | 22.9 | 80% | 58% | 2 | 3.1 | 0.2 | 43.1 |
|  | 14.3 | 90% | 31% | 3 | 8.5 | 0.9 | 80.1 |
|  | 27.7 | 65% | 71% | 4 | 8.4 | 0.9 | 79.3 |
|  | 34.9 | 30% | 80% |  |  |  |  |
|  | 53.4 | 10% | 90% |  |  |  |  |
| 24 hours | 20.6 | 73% | 49% | 1 |  |  |  |
|  | 18.7 | 81% | 44% | 2 | 1.7 | 0.6 | 5.0 |
|  | 10.9 | 92% | 17% | 3 | 1.3 | 0.4 | 4.3 |
|  | 27.7 | 54% | 71% | 4 | 5.1 | 2.2 | 11.7 |
|  | 34.9 | 50% | 80% |  |  |  |  |
|  | 53.4 | 27% | 90% |  |  |  |  |
| 48 hours | 26.4 | 71% | 68% | 1 |  |  |  |
|  | 21 | 86% | 51% | 2 | 2.0 | 0.1 | 39.2 |
|  | 17.6 | 93% | 41% | 3 | 6.2 | 0.6 | 63.5 |
|  | 27.7 | 50% | 71% | 4 | 5.1 | 0.5 | 55.9 |
|  | 34.9 | 29% | 80% |  |  |  |  |
|  | 53.4 | 14% | 90% |  |  |  |  |

UO only

| Time prior AKI stage | Cutoff value | sens | spec | Quartile | OR | 95% CI of OR | |
|---|---|---|---|---|---|---|---|
| 0 hours | 23.3 | 70% | 65% | 1 |  |  |  |
|  | 19 | 81% | 47% | 2 | 1.2 | 0.5 | 2.6 |
|  | 12.7 | 91% | 25% | 3 | 3.2 | 1.8 | 5.9 |
|  | 24.9 | 62% | 70% | 4 | 6.0 | 3.4 | 10.6 |
|  | 30.3 | 43% | 80% |  |  |  |  |
|  | 43.7 | 26% | 90% |  |  |  |  |
| 24 hours | 21.1 | 71% | 56% | 1 |  |  |  |
|  | 17.6 | 81% | 43% | 2 | 1.4 | 0.7 | 2.6 |
|  | 12.8 | 90% | 26% | 3 | 3.5 | 2.1 | 5.8 |
|  | 24.9 | 48% | 70% | 4 | 4.7 | 2.8 | 7.7 |
|  | 30.3 | 37% | 80% |  |  |  |  |
|  | 43.7 | 21% | 90% |  |  |  |  |
| 48 hours | 17.8 | 72% | 44% | 1 |  |  |  |
|  | 15 | 80% | 35% | 2 | 0.8 | 0.3 | 2.0 |
|  | 8.77 | 92% | 13% | 3 | 1.2 | 0.6 | 2.7 |
|  | 24.9 | 48% | 70% | 4 | 2.2 | 1.1 | 4.2 |
|  | 30.3 | 36% | 80% |  |  |  |  |
|  | 43.7 | 24% | 90% |  |  |  |  |

Fig. 1 - 16

Midkine sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.056 | 0.082 | 0.056 | 0.097 | 0.056 | 0.108 |
| average | 0.240 | 0.156 | 0.240 | 0.286 | 0.240 | 0.395 |
| stdev | 0.855 | 0.200 | 0.855 | 0.630 | 0.855 | 1.018 |
| p (t-test) |  | 0.554 |  | 0.733 |  | 0.450 |
| min | 0.000 | 0.000 | 0.000 | 0.000 | 0.000 | 0.000 |
| max | 8.902 | 0.923 | 8.902 | 4.142 | 8.902 | 4.857 |
| n (Samp) | 120 | 37 | 120 | 48 | 120 | 22 |
| n (Pat) | 67 | 37 | 67 | 48 | 67 | 22 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 0.077 | 0.118 | 0.077 | 0.129 | 0.077 | 0.105 |
| average | 0.228 | 0.393 | 0.228 | 0.455 | 0.228 | 0.255 |
| stdev | 0.695 | 0.820 | 0.695 | 0.940 | 0.695 | 0.281 |
| p (t-test) |  | 0.393 |  | 0.174 |  | 0.897 |
| min | 0.000 | 0.000 | 0.000 | 0.000 | 0.000 | 0.003 |
| max | 8.902 | 3.139 | 8.902 | 4.142 | 8.902 | 0.817 |
| n (Samp) | 242 | 14 | 242 | 20 | 242 | 11 |
| n (Pat) | 116 | 14 | 116 | 20 | 116 | 11 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 0.063 | 0.111 | 0.063 | 0.107 | 0.063 | 0.105 |
| average | 0.273 | 0.176 | 0.273 | 0.225 | 0.273 | 0.360 |
| stdev | 0.923 | 0.204 | 0.923 | 0.296 | 0.923 | 1.039 |
| p (t-test) |  | 0.557 |  | 0.741 |  | 0.701 |
| min | 0.000 | 0.000 | 0.000 | 0.000 | 0.000 | 0.000 |
| max | 8.902 | 0.923 | 8.902 | 1.238 | 8.902 | 4.857 |
| n (Samp) | 98 | 32 | 98 | 43 | 98 | 21 |
| n (Pat) | 51 | 32 | 51 | 43 | 51 | 21 | sCr or UO

| Time prior AKI stage | AUC | SE | nCohort 1 | nCohort 2 | p |
| --- | --- | --- | --- | --- | --- |
| 0 hours | 0.57 | 0.055 | 120 | 37 | 0.237 |
| 24 hours | 0.62 | 0.049 | 120 | 48 | 0.013 |
| 48 hours | 0.65 | 0.068 | 120 | 22 | 0.032 | sCr only

| Time prior AKI stage | AUC | SE | nCohort 1 | nCohort 2 | p |
| --- | --- | --- | --- | --- | --- |
| 0 hours | 0.54 | 0.081 | 242 | 14 | 0.642 |
| 24 hours | 0.63 | 0.069 | 242 | 20 | 0.057 |
| 48 hours | 0.63 | 0.092 | 242 | 11 | 0.158 |

UO only

| Time prior AKI stage | AUC | SE | nCohort 1 | nCohort 2 | p |
| --- | --- | --- | --- | --- | --- |
| 0 hours | 0.58 | 0.060 | 98 | 32 | 0.160 |
| 24 hours | 0.60 | 0.053 | 98 | 43 | 0.063 |
| 48 hours | 0.56 | 0.071 | 98 | 21 | 0.362 | sCr or UO

| Time prior AKI stage | Cutoff value | sens | spec | Quartile | OR | 95% CI of OR | |
| --- | --- | --- | --- | --- | --- | --- | --- |
| 0 hours | 0.0373657 | 70% | 44% | 1 |  |  |  |
|  | 0.0157077 | 81% | 28% | 2 | 1.7 | 0.8 | 3.2 |
|  | 0.0016104 | 92% | 20% | 3 | 2.8 | 1.5 | 5.1 |
|  | 0.1443816 | 35% | 70% | 4 | 1.6 | 0.8 | 3.1 |
|  | 0.2485795 | 16% | 80% |  |  |  |  |
|  | 0.4342297 | 14% | 90% |  |  |  |  |
| 24 hours | 0.0581948 | 71% | 52% | 1 |  |  |  |
|  | 0.0422102 | 81% | 47% | 2 | 1.4 | 0.7 | 2.5 |
|  | 0.0058384 | 92% | 24% | 3 | 3.8 | 2.2 | 6.3 |

Fig. 1 - 17

|  | | Cutoff value | sens | spec | Quartile | OR | 95% CI of OR | |
|---|---|---|---|---|---|---|---|---|
|  |  | 0.1443816 | 40% | 70% | 4 | 2.5 | 1.4 | 4.3 |
|  |  | 0.2485795 | 29% | 80% |  |  |  |  |
|  |  | 0.4342297 | 13% | 90% |  |  |  |  |
|  | 48 hours | 0.0631003 | 73% | 53% | 1 |  |  |  |
|  |  | 0.056067 | 82% | 51% | 2 | 2.7 | 0.6 | 11.9 |
|  |  | 0.0404793 | 91% | 45% | 3 | 5.7 | 1.5 | 21.7 |
|  |  | 0.1443816 | 32% | 70% | 4 | 3.3 | 0.8 | 13.8 |
|  |  | 0.2485795 | 23% | 80% |  |  |  |  |
|  |  | 0.4342297 | 23% | 90% |  |  |  |  | sCr only

| Time prior AKI stage | Cutoff value | sens | spec | Quartile | OR | 95% CI of OR | |
|---|---|---|---|---|---|---|---|
| 0 hours | 0.023441 | 71% | 26% | 1 |  |  |  |
|  | 0.0140548 | 86% | 23% | 2 | 0.7 | 0.2 | 2.5 |
|  | 0.0001464 | 93% | 0% | 3 | 0.2 | 0.0 | 2.9 |
|  | 0.1555932 | 50% | 70% | 4 | 1.6 | 0.6 | 3.8 |
|  | 0.2771893 | 29% | 80% |  |  |  |  |
|  | 0.4620882 | 21% | 90% |  |  |  |  |
| 24 hours | 0.0741531 | 70% | 49% | 1 |  |  |  |
|  | 0.0704339 | 80% | 48% | 2 | 2.6 | 0.6 | 10.8 |
|  | 0.0581948 | 90% | 43% | 3 | 3.2 | 0.8 | 12.6 |
|  | 0.1555932 | 45% | 70% | 4 | 3.7 | 1.0 | 14.1 |
|  | 0.2771893 | 35% | 80% |  |  |  |  |
|  | 0.4620882 | 15% | 90% |  |  |  |  |
| 48 hours | 0.0704339 | 73% | 48% | 1 |  |  |  |
|  | 0.0634663 | 82% | 46% | 2 | 3.1 | 0.2 | 45.1 |
|  | 0.0486198 | 91% | 39% | 3 | 3.1 | 0.2 | 45.1 |
|  | 0.1555932 | 45% | 70% | 4 | 4.1 | 0.3 | 51.1 |
|  | 0.2771893 | 27% | 80% |  |  |  |  |
|  | 0.4620882 | 27% | 90% |  |  |  |  |

UO only

| Time prior AKI stage | Cutoff value | sens | spec | Quartile | OR | 95% CI of OR | |
|---|---|---|---|---|---|---|---|
| 0 hours | 0.0608593 | 72% | 49% | 1 |  |  |  |
|  | 0.0404793 | 81% | 42% | 2 | 1.2 | 0.5 | 2.8 |
|  | 0.0056671 | 91% | 20% | 3 | 4.8 | 2.3 | 9.7 |
|  | 0.2039195 | 22% | 70% | 4 | 1.2 | 0.5 | 2.8 |
|  | 0.3942587 | 16% | 81% |  |  |  |  |
|  | 0.4986167 | 9% | 91% |  |  |  |  |
| 24 hours | 0.0550031 | 72% | 46% | 1 |  |  |  |
|  | 0.0404793 | 81% | 42% | 2 | 2.1 | 1.0 | 4.4 |
|  | 0.0137202 | 91% | 24% | 3 | 6.4 | 3.2 | 12.6 |
|  | 0.2039195 | 28% | 70% | 4 | 2.6 | 1.3 | 5.4 |
|  | 0.3942587 | 14% | 81% |  |  |  |  |
|  | 0.4986167 | 9% | 91% |  |  |  |  |
| 48 hours | 0.0608593 | 71% | 49% | 1 |  |  |  |
|  | 0.0417811 | 81% | 42% | 2 | 1.7 | 0.5 | 5.7 |
|  | 0.0056671 | 90% | 20% | 3 | 4.3 | 1.6 | 12.0 |
|  | 0.2039195 | 29% | 70% | 4 | 1.0 | 0.2 | 4.1 |
|  | 0.3942587 | 14% | 81% |  |  |  |  |
|  | 0.4986167 | 10% | 91% |  |  |  |  |

Fig. 1 - 18

Serum amyloid P-component sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 1.447 | 2.273 | 1.447 | 2.398 | 1.447 | 2.171 |
| average | 4.827 | 5.940 | 4.827 | 7.802 | 4.827 | 4.854 |
| stdev | 10.143 | 8.522 | 10.143 | 20.452 | 10.143 | 6.028 |
| p (t-test) |  | 0.499 |  | 0.203 |  | 0.990 |
| min | 0.089 | 0.038 | 0.089 | 0.129 | 0.089 | 0.269 |
| max | 58.307 | 34.528 | 58.307 | 152.000 | 58.307 | 21.775 |
| n (Samp) | 114 | 50 | 114 | 58 | 114 | 25 |
| n (Pat) | 96 | 50 | 96 | 58 | 96 | 25 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 1.804 | 3.185 | 1.804 | 7.024 | 1.804 | 2.919 |
| average | 5.624 | 4.863 | 5.624 | 8.986 | 5.624 | 5.778 |
| stdev | 12.561 | 5.755 | 12.561 | 10.583 | 12.561 | 6.871 |
| p (t-test) |  | 0.810 |  | 0.215 |  | 0.964 |
| min | 0.025 | 0.038 | 0.025 | 0.143 | 0.025 | 0.226 |
| max | 152.000 | 21.427 | 152.000 | 37.076 | 152.000 | 21.775 |
| n (Samp) | 253 | 16 | 253 | 23 | 253 | 14 |
| n (Pat) | 157 | 16 | 157 | 23 | 157 | 14 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 1.543 | 2.517 | 1.543 | 2.398 | 1.543 | 3.388 |
| average | 5.100 | 6.629 | 5.100 | 9.575 | 5.100 | 6.648 |
| stdev | 10.027 | 8.785 | 10.027 | 23.142 | 10.027 | 10.167 |
| p (t-test) |  | 0.382 |  | 0.099 |  | 0.513 |
| min | 0.089 | 0.038 | 0.089 | 0.129 | 0.089 | 0.320 |
| max | 58.307 | 34.528 | 58.307 | 152.000 | 58.307 | 44.971 |
| n (Samp) | 103 | 44 | 103 | 48 | 103 | 22 |
| n (Pat) | 82 | 44 | 82 | 48 | 82 | 22 | sCr or UO

| Time prior AKI stage | AUC | SE | nCohort 1 | nCohort 2 | p |
| --- | --- | --- | --- | --- | --- |
| 0 hours | 0.58 | 0.049 | 114 | 50 | 0.129 |
| 24 hours | 0.61 | 0.046 | 114 | 58 | 0.016 |
| 48 hours | 0.61 | 0.065 | 114 | 25 | 0.077 | sCr only

| Time prior AKI stage | AUC | SE | nCohort 1 | nCohort 2 | p |
| --- | --- | --- | --- | --- | --- |
| 0 hours | 0.52 | 0.075 | 253 | 16 | 0.778 |
| 24 hours | 0.63 | 0.065 | 253 | 23 | 0.040 |
| 48 hours | 0.56 | 0.081 | 253 | 14 | 0.467 |

UO only

| Time prior AKI stage | AUC | SE | nCohort 1 | nCohort 2 | p |
| --- | --- | --- | --- | --- | --- |
| 0 hours | 0.58 | 0.052 | 103 | 44 | 0.108 |
| 24 hours | 0.61 | 0.050 | 103 | 48 | 0.029 |
| 48 hours | 0.64 | 0.069 | 103 | 22 | 0.041 | sCr or UO

| Time prior AKI stage | Cutoff value | sens | spec | Quartile | OR | 95% CI of OR | |
| --- | --- | --- | --- | --- | --- | --- | --- |
| 0 hours | 0.9853183 | 70% | 43% | 1 |  |  |  |
|  | 0.4746547 | 80% | 20% | 2 | 0.8 | 0.5 | 1.3 |
|  | 0.2212973 | 92% | 7% | 3 | 1.4 | 0.9 | 2.2 |
|  | 2.7653229 | 44% | 70% | 4 | 1.7 | 1.1 | 2.7 |
|  | 4.2737938 | 32% | 81% |  |  |  |  |
|  | 11.50007 | 16% | 90% |  |  |  |  |
| 24 hours | 1.0844797 | 71% | 46% | 1 |  |  |  |
|  | 0.5885975 | 81% | 27% | 2 | 0.9 | 0.6 | 1.4 |
|  | 0.4557392 | 91% | 18% | 3 | 1.1 | 0.7 | 1.7 |

Fig. 1 - 19

|  | Cutoff value | sens | spec | Quartile | OR | 95% CI of OR | |
|---|---|---|---|---|---|---|---|
|  | 2.7653229 | 47% | 70% | 4 | 2.7 | 1.8 | 4.1 |
|  | 4.2737938 | 40% | 81% |  |  |  |  |
|  | 11.50007 | 16% | 90% |  |  |  |  |
| 48 hours | 1.1846337 | 72% | 47% | 1 |  |  |  |
|  | 0.9490725 | 80% | 43% | 2 | 4.7 | 1.2 | 18.4 |
|  | 0.5885975 | 92% | 27% | 3 | 2.7 | 0.6 | 11.9 |
|  | 2.7653229 | 48% | 70% | 4 | 6.4 | 1.7 | 23.9 |
|  | 4.2737938 | 32% | 81% |  |  |  |  |
|  | 11.50007 | 12% | 90% |  |  |  |  | sCr only

| Time prior AKI stage | Cutoff value | sens | spec | Quartile | OR | 95% CI of OR | |
|---|---|---|---|---|---|---|---|
| 0 hours | 0.4557392 | 75% | 13% | 1 |  |  |  |
|  | 0.3460298 | 81% | 11% | 2 | 0.2 | 0.0 | 2.1 |
|  | 0.037612 | 94% | 0% | 3 | 1.0 | 0.4 | 2.3 |
|  | 4.10741 | 38% | 70% | 4 | 1.0 | 0.4 | 2.3 |
|  | 6.5771402 | 31% | 80% |  |  |  |  |
|  | 13.062464 | 6% | 90% |  |  |  |  |
| 24 hours | 1.0374191 | 74% | 34% | 1 |  |  |  |
|  | 0.9853183 | 83% | 33% | 2 | 1.0 | 0.4 | 2.8 |
|  | 0.3715084 | 91% | 11% | 3 | 0.7 | 0.2 | 2.5 |
|  | 4.10741 | 57% | 70% | 4 | 3.4 | 1.7 | 7.0 |
|  | 6.5771402 | 52% | 80% |  |  |  |  |
|  | 13.062464 | 22% | 90% |  |  |  |  |
| 48 hours | 1.028192 | 71% | 34% | 1 |  |  |  |
|  | 0.6630833 | 86% | 23% | 2 | 0.6 | 0.1 | 3.5 |
|  | 0.2564023 | 93% | 7% | 3 | 1.3 | 0.4 | 4.5 |
|  | 4.10741 | 43% | 70% | 4 | 1.7 | 0.6 | 5.1 |
|  | 6.5771402 | 29% | 80% |  |  |  |  |
|  | 13.062464 | 14% | 90% |  |  |  |  |

UO only

| Time prior AKI stage | Cutoff value | sens | spec | Quartile | OR | 95% CI of OR | |
|---|---|---|---|---|---|---|---|
| 0 hours | 1.1846337 | 70% | 46% | 1 |  |  |  |
|  | 0.5885975 | 82% | 26% | 2 | 1.0 | 0.5 | 1.7 |
|  | 0.2212973 | 91% | 7% | 3 | 1.4 | 0.8 | 2.5 |
|  | 3.1950229 | 43% | 71% | 4 | 1.8 | 1.1 | 3.1 |
|  | 6.3585829 | 30% | 81% |  |  |  |  |
|  | 12.688918 | 20% | 90% |  |  |  |  |
| 24 hours | 1.1846337 | 71% | 46% | 1 |  |  |  |
|  | 0.5885975 | 81% | 26% | 2 | 0.8 | 0.5 | 1.5 |
|  | 0.513498 | 92% | 23% | 3 | 1.2 | 0.8 | 2.1 |
|  | 3.1950229 | 48% | 71% | 4 | 2.2 | 1.4 | 3.5 |
|  | 6.3585829 | 33% | 81% |  |  |  |  |
|  | 12.688918 | 17% | 90% |  |  |  |  |
| 48 hours | 1.4165129 | 73% | 48% | 1 |  |  |  |
|  | 1.1846337 | 82% | 46% | 2 | 3.5 | 0.8 | 14.9 |
|  | 0.8267137 | 91% | 36% | 3 | 3.5 | 0.8 | 14.9 |
|  | 3.1950229 | 55% | 71% | 4 | 4.8 | 1.2 | 19.1 |
|  | 6.3585829 | 27% | 81% |  |  |  |  |
|  | 12.688918 | 14% | 90% |  |  |  |  |

Fig. 1 - 20

Fatty acid binding protein, heart sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 55.900 | 150.000 | 55.900 | 155.500 | 55.900 | 127.000 |
| average | 410.197 | 688.950 | 410.197 | 1158.180 | 410.197 | 639.412 |
| stdev | 1121.958 | 1612.525 | 1121.958 | 2840.633 | 1121.958 | 1339.887 |
| p (t-test) |  | 0.225 |  | 0.001 |  | 0.400 |
| min | 0.268 | 0.689 | 0.268 | 4.070 | 0.268 | 4.140 |
| max | 8087.000 | 8087.000 | 8087.000 | 14771.000 | 8087.000 | 5160.000 |
| n (Samp) | 419 | 27 | 419 | 36 | 419 | 18 |
| n (Pat) | 164 | 27 | 164 | 36 | 164 | 18 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 64.550 | 412.000 | 64.550 | 93.900 | 64.550 | 128.000 |
| average | 502.660 | 1851.436 | 502.660 | 2756.591 | 502.660 | 2006.600 |
| stdev | 1333.784 | 3492.966 | 1333.784 | 5207.291 | 1333.784 | 3270.907 |
| p (t-test) |  | 0.028 |  | 0.000 |  | 0.004 |
| min | 0.268 | 5.180 | 0.268 | 4.070 | 0.268 | 10.700 |
| max | 13231.000 | 8087.000 | 13231.000 | 14771.000 | 13231.000 | 8087.000 |
| n (Samp) | 518 | 5 | 518 | 9 | 518 | 7 |
| n (Pat) | 199 | 5 | 199 | 9 | 199 | 7 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 64.000 | 157.500 | 64.000 | 237.500 | 64.000 | 158.000 |
| average | 427.862 | 474.211 | 427.862 | 664.106 | 427.862 | 431.489 |
| stdev | 1179.546 | 667.924 | 1179.546 | 1106.648 | 1179.546 | 757.709 |
| p (t-test) |  | 0.843 |  | 0.291 |  | 0.990 |
| min | 0.371 | 0.689 | 0.371 | 6.340 | 0.371 | 4.140 |
| max | 8087.000 | 3040.000 | 8087.000 | 4420.000 | 8087.000 | 3000.000 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
| --- | --- | --- | --- | --- | --- |
| 0 hours | 0.62 | 0.059 | 419 | 27 | 0.045 |
| 24 hours | 0.63 | 0.052 | 419 | 36 | 0.014 |
| 48 hours | 0.58 | 0.072 | 419 | 18 | 0.239 | sCr only

| Time prior AKI stage | AUC | SE | nCohort 1 | nCohort 2 | p |
| --- | --- | --- | --- | --- | --- |
| 0 hours | 0.68 | 0.133 | 518 | 5 | 0.184 |
| 24 hours | 0.60 | 0.101 | 518 | 9 | 0.320 |
| 48 hours | 0.64 | 0.114 | 518 | 7 | 0.203 |

UO only

| Time prior AKI stage | AUC | SE | nCohort 1 | nCohort 2 | p |
| --- | --- | --- | --- | --- | --- |
| 0 hours | 0.63 | 0.060 | 352 | 26 | 0.035 |
| 24 hours | 0.64 | 0.056 | 352 | 30 | 0.011 |
| 48 hours | 0.59 | 0.076 | 352 | 16 | 0.217 | sCr or UO

| Time prior AKI stage | Cutoff value | sens | spec | Quartile | OR | 95% CI of OR | |
| --- | --- | --- | --- | --- | --- | --- | --- |
| 0 hours | 41.5 | 70% | 48% | 1 |  |  |  |
|  | 20.4 | 81% | 37% | 2 | 2.0 | 0.7 | 5.6 |
|  | 5.47 | 93% | 12% | 3 | 2.8 | 1.1 | 7.1 |
|  | 170 | 41% | 70% | 4 | 3.5 | 1.5 | 8.6 |
|  | 300 | 37% | 80% |  |  |  |  |
|  | 1120 | 11% | 90% |  |  |  |  |
| 24 hours | 33.3 | 72% | 44% | 1 |  |  |  |
|  | 29 | 81% | 42% | 2 | 1.2 | 0.6 | 2.2 |
|  | 8.2 | 92% | 17% | 3 | 1.3 | 0.7 | 2.5 |

Fig. 2 - 1

|  | | 170 | 50% | 70% | 4 | 2.7 | 1.6 | 4.4 |
|  | | 300 | 28% | 80% |  |  |  |  |
|  | | 1120 | 19% | 90% |  |  |  |  |
| 48 hours | | 39.5 | 72% | 47% | 1 |  |  |  |
|  | | 11.1 | 83% | 24% | 2 | 1.0 | 0.4 | 2.8 |
|  | | 4.54 | 94% | 10% | 3 | 1.0 | 0.4 | 2.8 |
|  | | 170 | 39% | 70% | 4 | 1.5 | 0.6 | 3.6 |
|  | | 300 | 28% | 80% |  |  |  |  |
|  | | 1120 | 11% | 90% |  |  |  |  | sCr only

| Time prior AKI stage | Cutoff value | sens | spec | Quartile | OR | 95% CI of OR | |
|---|---|---|---|---|---|---|---|
| 0 hours | 163 | 80% | 66% | 1 |  |  |  |
|  | 163 | 80% | 66% | 2 | 0.0 | 0.0 | na |
|  | 5.13 | 100% | 10% | 3 | 1.0 | 0.0 | 51.5 |
|  | 209 | 60% | 70% | 4 | 3.0 | 0.2 | 42.5 |
|  | 377 | 60% | 80% |  |  |  |  |
|  | 1260 | 20% | 90% |  |  |  |  |
| 24 hours | 33.3 | 78% | 41% | 1 |  |  |  |
|  | 8.2 | 89% | 15% | 2 | 1.0 | 0.1 | 7.3 |
|  | 3.98 | 100% | 8% | 3 | 0.5 | 0.0 | 9.6 |
|  | 209 | 44% | 70% | 4 | 2.0 | 0.4 | 9.0 |
|  | 377 | 44% | 80% |  |  |  |  |
|  | 1260 | 22% | 90% |  |  |  |  |
| 48 hours | 44.6 | 71% | 46% | 1 |  |  |  |
|  | 38.2 | 86% | 44% | 2 | 2.0 | 0.1 | 39.3 |
|  | 10.4 | 100% | 20% | 3 | 1.0 | 0.0 | 51.9 |
|  | 209 | 43% | 70% | 4 | 3.0 | 0.2 | 42.5 |
|  | 377 | 43% | 80% |  |  |  |  |
|  | 1260 | 29% | 90% |  |  |  |  |

UO only

| Time prior AKI stage | Cutoff value | sens | spec | Quartile | OR | 95% CI of OR | |
|---|---|---|---|---|---|---|---|
| 0 hours | 41.5 | 73% | 45% | 1 |  |  |  |
|  | 31.6 | 81% | 40% | 2 | 3.1 | 0.8 | 12.0 |
|  | 15 | 92% | 28% | 3 | 3.7 | 1.0 | 13.6 |
|  | 189 | 46% | 70% | 4 | 6.0 | 1.8 | 20.1 |
|  | 301 | 42% | 80% |  |  |  |  |
|  | 1120 | 8% | 90% |  |  |  |  |
| 24 hours | 60.6 | 70% | 49% | 1 |  |  |  |
|  | 31.6 | 80% | 40% | 2 | 1.5 | 0.6 | 3.6 |
|  | 11.5 | 90% | 22% | 3 | 1.5 | 0.6 | 3.6 |
|  | 189 | 57% | 70% | 4 | 3.9 | 2.0 | 7.6 |
|  | 301 | 30% | 80% |  |  |  |  |
|  | 1120 | 20% | 90% |  |  |  |  |
| 48 hours | 39.5 | 75% | 44% | 1 |  |  |  |
|  | 23.7 | 81% | 36% | 2 | 1.0 | 0.3 | 3.9 |
|  | 4.44 | 94% | 9% | 3 | 1.3 | 0.4 | 4.4 |
|  | 189 | 38% | 70% | 4 | 2.1 | 0.7 | 5.8 |
|  | 301 | 31% | 80% |  |  |  |  |
|  | 1120 | 6% | 90% |  |  |  |  |

Fig. 2 - 2

Hepatocyte growth factor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 391.184 | 648.731 | 391.184 | 747.384 | 391.184 | 809.087 |
| average | 584.363 | 849.137 | 584.363 | 1010.545 | 584.363 | 767.409 |
| stdev | 654.835 | 621.381 | 654.835 | 1355.310 | 654.835 | 500.795 |
| p (t-test) |  | 0.064 |  | 0.003 |  | 0.247 |
| min | 14.776 | 22.466 | 14.776 | 32.253 | 14.776 | 41.886 |
| max | 5191.176 | 2726.014 | 5191.176 | 7839.221 | 5191.176 | 1568.985 |
| n (Samp) | 246 | 23 | 246 | 35 | 246 | 18 |
| n (Pat) | 159 | 23 | 159 | 35 | 159 | 18 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 446.622 | 601.477 | 446.622 | 565.787 | 446.622 | 828.465 |
| average | 661.802 | 601.477 | 661.802 | 753.335 | 661.802 | 774.947 |
| stdev | 762.897 | 66.826 | 762.897 | 613.424 | 762.897 | 503.594 |
| p (t-test) |  | 0.911 |  | 0.737 |  | 0.697 |
| min | 14.776 | 554.224 | 14.776 | 86.357 | 14.776 | 64.024 |
| max | 7839.221 | 648.731 | 7839.221 | 1915.338 | 7839.221 | 1646.962 |
| n (Samp) | 318 | 2 | 318 | 8 | 318 | 7 |
| n (Pat) | 188 | 2 | 188 | 8 | 188 | 7 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 401.533 | 750.965 | 401.533 | 742.061 | 401.533 | 809.087 |
| average | 570.796 | 869.825 | 570.796 | 1034.799 | 570.796 | 871.272 |
| stdev | 580.161 | 616.779 | 580.161 | 1437.159 | 580.161 | 561.858 |
| p (t-test) |  | 0.020 |  | 0.001 |  | 0.047 |
| min | 14.776 | 22.466 | 14.776 | 32.253 | 14.776 | 41.886 |
| max | 5191.176 | 2726.014 | 5191.176 | 7839.221 | 5191.176 | 1915.338 |
| n (Samp) | 212 | 23 | 212 | 30 | 212 | 16 |
| n (Pat) | 132 | 23 | 132 | 30 | 132 | 16 | sCr or UO

| Time prior AKI stage | AUC | SE | nCohort 1 | nCohort 2 | p |
|---|---|---|---|---|---|
| 0 hours | 0.68 | 0.064 | 246 | 23 | 0.004 |
| 24 hours | 0.65 | 0.053 | 246 | 35 | 0.004 |
| 48 hours | 0.64 | 0.073 | 246 | 18 | 0.058 | sCr only

| Time prior AKI stage | AUC | SE | nCohort 1 | nCohort 2 | p |
|---|---|---|---|---|---|
| 0 hours | 0.61 | 0.213 | 318 | 2 | 0.595 |
| 24 hours | 0.58 | 0.107 | 318 | 8 | 0.443 |
| 48 hours | 0.62 | 0.115 | 318 | 7 | 0.304 |

UO only

| Time prior AKI stage | AUC | SE | nCohort 1 | nCohort 2 | p |
|---|---|---|---|---|---|
| 0 hours | 0.69 | 0.064 | 212 | 23 | 0.004 |
| 24 hours | 0.65 | 0.057 | 212 | 30 | 0.008 |
| 48 hours | 0.68 | 0.076 | 212 | 16 | 0.019 | sCr or UO

| Time prior AKI stage | Cutoff value | sens | spec | Quartile | OR | 95% CI of OR | |
|---|---|---|---|---|---|---|---|
| 0 hours | 471.99234 | 74% | 60% | 1 |  |  |  |
|  | 401.9307 | 83% | 54% | 2 | 1.0 | 0.1 | 7.5 |
|  | 361.16203 | 91% | 47% | 3 | 6.4 | 1.9 | 21.7 |
|  | 634.77395 | 57% | 70% | 4 | 4.3 | 1.2 | 15.7 |
|  | 871.13405 | 30% | 80% |  |  |  |  |
|  | 1274.9436 | 22% | 90% |  |  |  |  |
| 24 hours | 458.31139 | 71% | 59% | 1 |  |  |  |
|  | 309.24101 | 80% | 41% | 2 | 1.5 | 0.6 | 3.7 |
|  | 181.96421 | 91% | 23% | 3 | 3.4 | 1.7 | 7.0 |
|  | 634.77395 | 54% | 70% | 4 | 3.7 | 1.8 | 7.5 |

Fig. 2 - 3

|  | 871.13405 | 34% | 80% |  |  |  |  |
|  | 1274.9436 | 20% | 90% |  |  |  |  |
| 48 hours | 433.14494 | 72% | 56% | 1 |  |  |  |
|  | 174.1918 | 83% | 22% | 2 | 0.2 | 0.0 | 2.9 |
|  | 63.729059 | 94% | 6% | 3 | 1.0 | 0.4 | 2.8 |
|  | 634.77395 | 56% | 70% | 4 | 2.4 | 1.1 | 5.3 |
|  | 871.13405 | 50% | 80% |  |  |  |  |
|  | 1274.9436 | 22% | 90% |  |  |  |  | sCr only

| Time prior AKI stage | Cutoff value | sens | spec | Quartile | OR | 95% CI of OR | |
|---|---|---|---|---|---|---|---|
| 0 hours | 547.65274 | 100% | 58% | 1 |  |  |  |
|  | 547.65274 | 100% | 58% | 2 | na | na | na |
|  | 547.65274 | 100% | 58% | 3 | na | na | na |
|  | 763.54383 | 0% | 70% | 4 | na | na | na |
|  | 994.85278 | 0% | 80% |  |  |  |  |
|  | 1339.5034 | 0% | 90% |  |  |  |  |
| 24 hours | 458.96808 | 75% | 51% | 1 |  |  |  |
|  | 236.40802 | 88% | 28% | 2 | 1.0 | 0.0 | 52.3 |
|  | 85.564359 | 100% | 9% | 3 | 4.2 | 0.3 | 50.6 |
|  | 763.54383 | 38% | 70% | 4 | 2.0 | 0.1 | 39.7 |
|  | 994.85278 | 25% | 80% |  |  |  |  |
|  | 1339.5034 | 25% | 90% |  |  |  |  |
| 48 hours | 606.00549 | 71% | 63% | 1 |  |  |  |
|  | 373.50372 | 86% | 41% | 2 | 1.0 | 0.0 | 52.9 |
|  | 63.729059 | 100% | 6% | 3 | 2.0 | 0.1 | 40.2 |
|  | 763.54383 | 57% | 70% | 4 | 3.0 | 0.2 | 43.5 |
|  | 994.85278 | 14% | 80% |  |  |  |  |
|  | 1339.5034 | 14% | 90% |  |  |  |  |

UO only

| Time prior AKI stage | Cutoff value | sens | spec | Quartile | OR | 95% CI of OR | |
|---|---|---|---|---|---|---|---|
| 0 hours | 471.99234 | 74% | 58% | 1 |  |  |  |
|  | 405.06523 | 83% | 51% | 2 | 1.5 | 0.3 | 8.2 |
|  | 361.16203 | 91% | 43% | 3 | 5.0 | 1.4 | 18.0 |
|  | 664.06712 | 52% | 70% | 4 | 5.0 | 1.4 | 18.0 |
|  | 850.96347 | 35% | 80% |  |  |  |  |
|  | 1209.6432 | 22% | 90% |  |  |  |  |
| 24 hours | 458.31139 | 70% | 56% | 1 |  |  |  |
|  | 387.70579 | 80% | 46% | 2 | 2.1 | 0.7 | 5.9 |
|  | 254.75162 | 90% | 32% | 3 | 3.8 | 1.5 | 9.6 |
|  | 664.06712 | 53% | 70% | 4 | 4.2 | 1.7 | 10.3 |
|  | 850.96347 | 33% | 80% |  |  |  |  |
|  | 1209.6432 | 17% | 90% |  |  |  |  |
| 48 hours | 468.66836 | 75% | 57% | 1 |  |  |  |
|  | 421.70745 | 81% | 53% | 2 | 0.0 | 0.0 | na |
|  | 156.4651 | 94% | 20% | 3 | 1.7 | 0.6 | 5.3 |
|  | 664.06712 | 56% | 70% | 4 | 2.9 | 1.1 | 7.8 |
|  | 850.96347 | 50% | 80% |  |  |  |  |
|  | 1209.6432 | 31% | 90% |  |  |  |  |

Fig. 2 - 4

Interleukin-16 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 8.510 | 9.890 | 8.510 | 11.600 | 8.510 | 14.650 |
| average | 38.048 | 34.959 | 38.048 | 85.756 | 38.048 | 27.446 |
| stdev | 110.313 | 80.369 | 110.313 | 204.858 | 110.313 | 52.785 |
| p (t-test) |  | 0.886 |  | 0.023 |  | 0.685 |
| min | 0.265 | 0.265 | 0.265 | 0.265 | 0.265 | 0.265 |
| max | 1100.000 | 323.000 | 1100.000 | 1010.000 | 1100.000 | 227.000 |
| n (Samp) | 419 | 27 | 419 | 36 | 419 | 18 |
| n (Pat) | 164 | 27 | 164 | 36 | 164 | 18 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 8.665 | 33.900 | 8.665 | 20.050 | 8.665 | 17.900 |
| average | 41.200 | 292.390 | 41.200 | 222.552 | 41.200 | 71.981 |
| stdev | 117.455 | 459.575 | 117.455 | 311.611 | 117.455 | 87.200 |
| p (t-test) |  | 0.000 |  | 0.000 |  | 0.490 |
| min | 0.265 | 5.250 | 0.265 | 0.265 | 0.265 | 0.265 |
| max | 1100.000 | 1080.000 | 1100.000 | 857.000 | 1100.000 | 227.000 |
| n (Samp) | 518 | 5 | 518 | 9 | 518 | 7 |
| n (Pat) | 199 | 5 | 199 | 9 | 199 | 7 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 8.760 | 10.745 | 8.760 | 11.600 | 8.760 | 16.800 |
| average | 41.162 | 24.783 | 41.162 | 66.621 | 41.162 | 26.572 |
| stdev | 110.559 | 57.124 | 110.559 | 195.995 | 110.559 | 54.657 |
| p (t-test) |  | 0.455 |  | 0.262 |  | 0.600 |
| min | 0.265 | 0.265 | 0.265 | 0.265 | 0.265 | 0.265 |
| max | 891.000 | 294.000 | 891.000 | 1010.000 | 891.000 | 229.000 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
| --- | --- | --- | --- | --- | --- |
| 0 hours | 0.52 | 0.058 | 419 | 27 | 0.688 |
| 24 hours | 0.55 | 0.051 | 419 | 36 | 0.330 |
| 48 hours | 0.57 | 0.072 | 419 | 18 | 0.324 | sCr only

| Time prior AKI stage | AUC | SE | nCohort 1 | nCohort 2 | p |
| --- | --- | --- | --- | --- | --- |
| 0 hours | 0.78 | 0.123 | 518 | 5 | 0.025 |
| 24 hours | 0.66 | 0.100 | 518 | 9 | 0.114 |
| 48 hours | 0.70 | 0.111 | 518 | 7 | 0.069 |

UO only

| Time prior AKI stage | AUC | SE | nCohort 1 | nCohort 2 | p |
| --- | --- | --- | --- | --- | --- |
| 0 hours | 0.51 | 0.059 | 352 | 26 | 0.847 |
| 24 hours | 0.54 | 0.056 | 352 | 30 | 0.509 |
| 48 hours | 0.57 | 0.076 | 352 | 16 | 0.347 | sCr or UO

| Time prior AKI stage | Cutoff value | sens | spec | Quartile | OR | 95% CI of OR | |
| --- | --- | --- | --- | --- | --- | --- | --- |
| 0 hours | 5.16 | 70% | 33% | 1 |  |  | |
|  | 0 | 100% | 0% | 2 | 1.0 | 0.5 | 2.0 |
|  | 0 | 100% | 0% | 3 | 1.5 | 0.9 | 2.8 |
|  | 15.8 | 33% | 70% | 4 | 1.0 | 0.5 | 2.0 |
|  | 23.7 | 19% | 80% |  |  |  | |
|  | 81.9 | 7% | 90% |  |  |  | |
| 24 hours | 4.72 | 72% | 32% | 1 |  |  | |
|  | 0 | 100% | 0% | 2 | 3.2 | 1.6 | 6.4 |
|  | 0 | 100% | 0% | 3 | 2.9 | 1.4 | 5.9 |
|  | 15.8 | 39% | 70% | 4 | 2.3 | 1.1 | 4.9 |

Fig. 2 - 5

| | | 23.7 | 19% | 80% | | | | |
|---|---|---|---|---|---|---|---|---|
| | | 81.9 | 19% | 90% | | | | |
| 48 hours | | 10.7 | 72% | 60% | 1 | | | |
| | | 0 | 100% | 0% | 2 | 0.0 | 0.0 | na |
| | | 0 | 100% | 0% | 3 | 1.6 | 0.8 | 3.2 |
| | | 15.8 | 50% | 70% | 4 | 1.0 | 0.4 | 2.3 |
| | | 23.7 | 17% | 80% | | | | |
| | | 81.9 | 6% | 90% | | | | | sCr only

| Time prior AKI stage | Cutoff value | sens | spec | Quartile | OR | 95% CI of OR | |
|---|---|---|---|---|---|---|---|
| 0 hours | 19.6 | 80% | 75% | 1 | | | |
| | 19.6 | 80% | 75% | 2 | na | na | na |
| | 5.2 | 100% | 34% | 3 | na | na | na |
| | 17.4 | 80% | 71% | 4 | na | na | na |
| | 24.7 | 60% | 80% | | | | |
| | 85.9 | 40% | 90% | | | | |
| 24 hours | 4.72 | 78% | 32% | 1 | | | |
| | 0 | 100% | 0% | 2 | 0.5 | 0.0 | 9.6 |
| | 0 | 100% | 0% | 3 | 0.5 | 0.0 | 9.6 |
| | 17.4 | 56% | 71% | 4 | 2.5 | 0.6 | 10.3 |
| | 24.7 | 44% | 80% | | | | |
| | 85.9 | 44% | 90% | | | | |
| 48 hours | 14.1 | 71% | 65% | 1 | | | |
| | 13 | 86% | 63% | 2 | 0.0 | 0.0 | na |
| | 0 | 100% | 0% | 3 | 3.0 | 0.2 | 42.9 |
| | 17.4 | 57% | 71% | 4 | 3.0 | 0.2 | 42.5 |
| | 24.7 | 43% | 80% | | | | |
| | 85.9 | 29% | 90% | | | | |

UO only

| Time prior AKI stage | Cutoff value | sens | spec | Quartile | OR | 95% CI of OR | |
|---|---|---|---|---|---|---|---|
| 0 hours | 5.15 | 73% | 32% | 1 | | | |
| | 0 | 100% | 0% | 2 | 0.8 | 0.4 | 1.7 |
| | 0 | 100% | 0% | 3 | 1.7 | 1.0 | 3.1 |
| | 17.4 | 31% | 70% | 4 | 0.8 | 0.4 | 1.7 |
| | 25.3 | 15% | 80% | | | | |
| | 88.6 | 4% | 90% | | | | |
| 24 hours | 5.27 | 70% | 33% | 1 | | | |
| | 4.07 | 80% | 28% | 2 | 1.6 | 0.8 | 3.2 |
| | 0 | 100% | 0% | 3 | 2.4 | 1.3 | 4.4 |
| | 17.4 | 37% | 70% | 4 | 1.2 | 0.6 | 2.6 |
| | 25.3 | 17% | 80% | | | | |
| | 88.6 | 13% | 90% | | | | |
| 48 hours | 10.7 | 75% | 59% | 1 | | | |
| | 0 | 100% | 0% | 2 | 0.0 | 0.0 | na |
| | 0 | 100% | 0% | 3 | 2.4 | 1.1 | 5.1 |
| | 17.4 | 50% | 70% | 4 | 0.7 | 0.2 | 2.4 |
| | 25.3 | 6% | 80% | | | | |
| | 88.6 | 6% | 90% | | | | |

Fig. 2 - 6

Interleukin-2 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.324 | 0.362 | 0.324 | 0.352 | 0.324 | 0.347 |
| average | 1.190 | 1.248 | 1.190 | 1.139 | 1.190 | 1.206 |
| stdev | 6.550 | 3.498 | 6.550 | 1.984 | 6.550 | 1.968 |
| p (t-test) |  | 0.967 |  | 0.963 |  | 0.992 |
| min | 0.000 | 0.000 | 0.000 | 0.000 | 0.000 | 0.000 |
| max | 96.860 | 17.085 | 96.860 | 9.984 | 96.860 | 7.061 |
| n (Samp) | 247 | 23 | 247 | 35 | 247 | 18 |
| n (Pat) | 159 | 23 | 159 | 35 | 159 | 18 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.335 | 0.392 | 0.335 | 0.171 | 0.335 | 0.475 |
| average | 1.162 | 0.392 | 1.162 | 0.657 | 1.162 | 1.661 |
| stdev | 5.876 | 0.308 | 5.876 | 1.340 | 5.876 | 2.553 |
| p (t-test) |  | 0.853 |  | 0.809 |  | 0.823 |
| min | 0.000 | 0.173 | 0.000 | 0.000 | 0.000 | 0.067 |
| max | 96.860 | 0.610 | 96.860 | 3.946 | 96.860 | 7.061 |
| n (Samp) | 319 | 2 | 319 | 8 | 319 | 7 |
| n (Pat) | 188 | 2 | 188 | 8 | 188 | 7 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.341 | 0.362 | 0.341 | 0.469 | 0.341 | 0.315 |
| average | 1.246 | 1.240 | 1.246 | 1.189 | 1.246 | 0.739 |
| stdev | 6.996 | 3.499 | 6.996 | 2.044 | 6.996 | 1.310 |
| p (t-test) |  | 0.997 |  | 0.965 |  | 0.773 |
| min | 0.000 | 0.000 | 0.000 | 0.000 | 0.000 | 0.000 |
| max | 96.860 | 17.085 | 96.860 | 9.984 | 96.860 | 5.096 |
| n (Samp) | 213 | 23 | 213 | 30 | 213 | 16 |
| n (Pat) | 132 | 23 | 132 | 30 | 132 | 16 | sCr or UO

| Time prior AKI stage | AUC | SE | nCohort 1 | nCohort 2 | p |
|---|---|---|---|---|---|
| 0 hours | 0.57 | 0.065 | 247 | 23 | 0.295 |
| 24 hours | 0.58 | 0.053 | 247 | 35 | 0.131 |
| 48 hours | 0.58 | 0.073 | 247 | 18 | 0.277 | sCr only

| Time prior AKI stage | AUC | SE | nCohort 1 | nCohort 2 | p |
|---|---|---|---|---|---|
| 0 hours | 0.55 | 0.211 | 319 | 2 | 0.803 |
| 24 hours | 0.43 | 0.097 | 319 | 8 | 0.451 |
| 48 hours | 0.64 | 0.114 | 319 | 7 | 0.227 |

UO only

| Time prior AKI stage | AUC | SE | nCohort 1 | nCohort 2 | p |
|---|---|---|---|---|---|
| 0 hours | 0.55 | 0.065 | 213 | 23 | 0.429 |
| 24 hours | 0.61 | 0.058 | 213 | 30 | 0.057 |
| 48 hours | 0.52 | 0.076 | 213 | 16 | 0.815 | sCr or UO

| Time prior AKI stage | Cutoff value | sens | spec | Quartile | OR | 95% CI of OR | |
|---|---|---|---|---|---|---|---|
| 0 hours | 0.2957788 | 74% | 45% | 1 |  |  |  |
|  | 0.1721567 | 83% | 36% | 2 | 2.1 | 0.7 | 5.9 |
|  | 0 | 100% | 0% | 3 | 2.5 | 0.9 | 6.7 |
|  | 0.5221122 | 35% | 70% | 4 | 2.4 | 0.9 | 6.6 |
|  | 0.66824 | 22% | 80% |  |  |  |  |
|  | 1.3590551 | 13% | 90% |  |  |  |  |
| 24 hours | 0.189991 | 71% | 37% | 1 |  |  |  |
|  | 0.1007266 | 80% | 31% | 2 | 2.0 | 1.1 | 3.5 |
|  | 0 | 100% | 0% | 3 | 0.6 | 0.3 | 1.6 |
|  | 0.5221122 | 46% | 70% | 4 | 2.6 | 1.5 | 4.5 |

Fig. 2 - 7

|  | Cutoff value | sens | spec | Quartile | OR | 95% CI of OR | |
|---|---|---|---|---|---|---|---|
|  | 0.66824 | 40% | 80% |  |  |  |  |
|  | 1.3590551 | 20% | 90% |  |  |  |  |
| 48 hours | 0.2893007 | 72% | 45% | 1 |  |  |  |
|  | 0.1721567 | 83% | 36% | 2 | 6.5 | 0.6 | 68.1 |
|  | 0.0642177 | 94% | 28% | 3 | 6.5 | 0.6 | 68.1 |
|  | 0.5221122 | 28% | 70% | 4 | 5.2 | 0.5 | 58.6 |
|  | 0.66824 | 22% | 80% |  |  |  |  |
|  | 1.3590551 | 22% | 90% |  |  |  |  | sCr only

| Time prior AKI stage | Cutoff value | sens | spec | Quartile | OR | 95% CI of OR | |
|---|---|---|---|---|---|---|---|
| 0 hours | 0.1721567 | 100% | 34% | 1 |  |  |  |
|  | 0.1721567 | 100% | 34% | 2 | na | na | na |
|  | 0.1721567 | 100% | 34% | 3 | na | na | na |
|  | 0.5364781 | 50% | 71% | 4 | na | na | na |
|  | 0.7060623 | 0% | 80% |  |  |  |  |
|  | 1.8315249 | 0% | 90% |  |  |  |  |
| 24 hours | 0.1009757 | 75% | 29% | 1 |  |  |  |
|  | 0.0217451 | 88% | 24% | 2 | 1.0 | 0.0 | 52.9 |
|  | 0 | 100% | 0% | 3 | 4.2 | 0.3 | 50.6 |
|  | 0.5364781 | 13% | 71% | 4 | 2.1 | 0.1 | 40.7 |
|  | 0.7060623 | 13% | 80% |  |  |  |  |
|  | 1.8315249 | 13% | 90% |  |  |  |  |
| 48 hours | 0.3346316 | 71% | 50% | 1 |  |  |  |
|  | 0.1824273 | 86% | 35% | 2 | na | na | na |
|  | 0.0642177 | 100% | 26% | 3 | na | na | na |
|  | 0.5364781 | 43% | 71% | 4 | na | na | na |
|  | 0.7060623 | 43% | 80% |  |  |  |  |
|  | 1.8315249 | 29% | 90% |  |  |  |  |

UO only

| Time prior AKI stage | Cutoff value | sens | spec | Quartile | OR | 95% CI of OR | |
|---|---|---|---|---|---|---|---|
| 0 hours | 0.2957788 | 74% | 44% | 1 |  |  |  |
|  | 0.1767872 | 83% | 36% | 2 | 2.9 | 1.1 | 7.7 |
|  | 0 | 100% | 0% | 3 | 2.1 | 0.7 | 6.1 |
|  | 0.5328803 | 30% | 70% | 4 | 2.1 | 0.7 | 6.1 |
|  | 0.6729637 | 22% | 80% |  |  |  |  |
|  | 1.3590551 | 13% | 90% |  |  |  |  |
| 24 hours | 0.2382322 | 70% | 38% | 1 |  |  |  |
|  | 0.189991 | 80% | 36% | 2 | 1.4 | 0.7 | 3.0 |
|  | 0.0054977 | 90% | 25% | 3 | 1.0 | 0.4 | 2.3 |
|  | 0.5328803 | 50% | 70% | 4 | 3.0 | 1.6 | 5.5 |
|  | 0.6729637 | 43% | 80% |  |  |  |  |
|  | 1.3590551 | 20% | 90% |  |  |  |  |
| 48 hours | 0.1734947 | 75% | 35% | 1 |  |  |  |
|  | 0.1721567 | 81% | 35% | 2 | 9.1 | 0.9 | 89.4 |
|  | 0.1007266 | 94% | 30% | 3 | 4.2 | 0.3 | 52.6 |
|  | 0.5328803 | 19% | 70% | 4 | 3.1 | 0.2 | 44.7 |
|  | 0.6729637 | 13% | 80% |  |  |  |  |
|  | 1.3590551 | 13% | 90% |  |  |  |  |

Fig. 2 - 8

Interleukin-12 p40 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 4.969 | 12.424 | 4.969 | 5.527 | 4.969 | 4.430 |
| average | 9.192 | 12.330 | 9.192 | 8.602 | 9.192 | 9.721 |
| stdev | 11.716 | 11.953 | 11.716 | 11.722 | 11.716 | 12.198 |
| p (t-test) |  | 0.221 |  | 0.781 |  | 0.854 |
| min | 0.000 | 0.000 | 0.000 | 0.000 | 0.000 | 0.000 |
| max | 66.881 | 41.936 | 66.881 | 51.256 | 66.881 | 37.732 |
| n (Samp) | 246 | 23 | 246 | 35 | 246 | 18 |
| n (Pat) | 159 | 23 | 159 | 35 | 159 | 18 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 5.790 | 7.194 | 5.790 | 1.290 | 5.790 | 11.189 |
| average | 9.742 | 7.194 | 9.742 | 8.688 | 9.742 | 13.677 |
| stdev | 11.907 | 2.929 | 11.907 | 13.638 | 11.907 | 15.140 |
| p (t-test) |  | 0.763 |  | 0.806 |  | 0.390 |
| min | 0.000 | 5.122 | 0.000 | 0.000 | 0.000 | 0.000 |
| max | 66.881 | 9.265 | 66.881 | 31.752 | 66.881 | 37.732 |
| n (Samp) | 318 | 2 | 318 | 8 | 318 | 7 |
| n (Pat) | 188 | 2 | 188 | 8 | 188 | 7 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 5.412 | 12.424 | 5.412 | 5.678 | 5.412 | 3.090 |
| average | 9.657 | 12.173 | 9.657 | 8.087 | 9.657 | 7.275 |
| stdev | 11.684 | 12.128 | 11.684 | 10.916 | 11.684 | 10.205 |
| p (t-test) |  | 0.329 |  | 0.488 |  | 0.429 |
| min | 0.000 | 0.000 | 0.000 | 0.000 | 0.000 | 0.000 |
| max | 61.635 | 41.936 | 61.635 | 51.256 | 61.635 | 36.364 |
| n (Samp) | 212 | 23 | 212 | 30 | 212 | 16 |
| n (Pat) | 132 | 23 | 132 | 30 | 132 | 16 | sCr or UO

| Time prior AKI stage | AUC | SE | nCohort 1 | nCohort 2 | p |
| --- | --- | --- | --- | --- | --- |
| 0 hours | 0.57 | 0.065 | 246 | 23 | 0.265 |
| 24 hours | 0.47 | 0.051 | 246 | 35 | 0.542 |
| 48 hours | 0.50 | 0.071 | 246 | 18 | 0.958 | sCr only

| Time prior AKI stage | AUC | SE | nCohort 1 | nCohort 2 | p |
| --- | --- | --- | --- | --- | --- |
| 0 hours | 0.54 | 0.210 | 318 | 2 | 0.831 |
| 24 hours | 0.41 | 0.096 | 318 | 8 | 0.354 |
| 48 hours | 0.54 | 0.113 | 318 | 7 | 0.716 |

UO only

| Time prior AKI stage | AUC | SE | nCohort 1 | nCohort 2 | p |
| --- | --- | --- | --- | --- | --- |
| 0 hours | 0.55 | 0.065 | 212 | 23 | 0.459 |
| 24 hours | 0.46 | 0.055 | 212 | 30 | 0.446 |
| 48 hours | 0.43 | 0.071 | 212 | 16 | 0.343 | sCr or UO

| Time prior AKI stage | Cutoff value | sens | spec | Quartile | OR | 95% CI of OR | |
| --- | --- | --- | --- | --- | --- | --- | --- |
| 0 hours | 0 | 100% | 0% | 1 |  |  |  |
|  | 0 | 100% | 0% | 2 | 0.3 | 0.1 | 1.0 |
|  | 0 | 100% | 0% | 3 | 0.8 | 0.4 | 1.7 |
|  | 11.45037 | 52% | 70% | 4 | 1.1 | 0.6 | 2.1 |
|  | 15.294181 | 35% | 80% |  |  |  |  |
|  | 24.020041 | 17% | 90% |  |  |  |  |
| 24 hours | 0 | 100% | 0% | 1 |  |  |  |
|  | 0 | 100% | 0% | 2 | 1.7 | 1.0 | 2.9 |
|  | 0 | 100% | 0% | 3 | 1.3 | 0.8 | 2.4 |
|  | 11.45037 | 20% | 70% | 4 | 1.2 | 0.7 | 2.1 |

Fig. 2 - 9

|  | | 15.294181 | 20% | 80% | | | | |
|---|---|---|---|---|---|---|---|---|
|  | | 24.020041 | 14% | 90% | | | | |
|  | 48 hours | 0.716221 | 72% | 31% | 1 | | | |
|  | | 0 | 100% | 0% | 2 | 0.8 | 0.3 | 2.0 |
|  | | 0 | 100% | 0% | 3 | 0.8 | 0.3 | 2.0 |
|  | | 11.45037 | 28% | 70% | 4 | 1.0 | 0.4 | 2.3 |
|  | | 15.294181 | 22% | 80% | | | | |
|  | | 24.020041 | 11% | 90% | | | | | sCr only

| Time prior AKI stage | Cutoff value | sens | spec | Quartile | OR | 95% CI of OR | |
|---|---|---|---|---|---|---|---|
| 0 hours | 4.8148825 | 100% | 47% | 1 | | | |
| | 4.8148825 | 100% | 47% | 2 | na | na | na |
| | 4.8148825 | 100% | 47% | 3 | na | na | na |
| | 12.423804 | 0% | 70% | 4 | na | na | na |
| | 17.550707 | 0% | 80% | | | | |
| | 25.306177 | 0% | 90% | | | | |
| 24 hours | 0 | 100% | 0% | 1 | | | |
| | 0 | 100% | 0% | 2 | 0.5 | 0.0 | 9.9 |
| | 0 | 100% | 0% | 3 | 0.5 | 0.0 | 9.8 |
| | 12.423804 | 25% | 70% | 4 | 2.1 | 0.5 | 9.5 |
| | 17.550707 | 25% | 80% | | | | |
| | 25.306177 | 25% | 90% | | | | |
| 48 hours | 0 | 100% | 0% | 1 | | | |
| | 0 | 100% | 0% | 2 | 0.0 | 0.0 | na |
| | 0 | 100% | 0% | 3 | 0.3 | 0.0 | 4.7 |
| | 12.423804 | 43% | 70% | 4 | 1.0 | 0.3 | 3.8 |
| | 17.550707 | 43% | 80% | | | | |
| | 25.306177 | 29% | 90% | | | | |

UO only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 0.3 | 0.1 | 1.0 |
| | 0 | 100% | 0% | 3 | 0.8 | 0.4 | 1.6 |
| | 12.058681 | 52% | 70% | 4 | 1.1 | 0.6 | 2.1 |
| | 16.350232 | 35% | 80% | | | | |
| | 25.14651 | 17% | 90% | | | | |
| 24 hours | 1.7242982 | 70% | 34% | 1 | | | |
| | 0 | 100% | 0% | 2 | 2.5 | 1.3 | 4.8 |
| | 0 | 100% | 0% | 3 | 1.7 | 0.8 | 3.4 |
| | 12.058681 | 17% | 70% | 4 | 1.2 | 0.6 | 2.7 |
| | 16.350232 | 17% | 80% | | | | |
| | 25.14651 | 7% | 90% | | | | |
| 48 hours | 0 | 100% | 0% | 1 | | | |
| | 0 | 100% | 0% | 2 | 1.0 | 0.3 | 4.0 |
| | 0 | 100% | 0% | 3 | 1.7 | 0.6 | 5.3 |
| | 12.058681 | 19% | 70% | 4 | 1.7 | 0.6 | 5.3 |
| | 16.350232 | 13% | 80% | | | | |
| | 25.14651 | 6% | 90% | | | | |

Fig. 2 - 10

Matrix metalloproteinase-2 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 21.200 | 24.400 | 21.200 | 24.100 | 21.200 | 22.600 |
| average | 27.778 | 28.301 | 27.778 | 68.594 | 27.778 | 28.755 |
| stdev | 31.632 | 21.083 | 31.632 | 208.990 | 31.632 | 19.398 |
| p (t-test) |  | 0.932 |  | 0.000 |  | 0.897 |
| min | 0.600 | 0.600 | 0.600 | 0.600 | 0.600 | 2.470 |
| max | 371.000 | 98.500 | 371.000 | 1280.000 | 371.000 | 81.000 |
| n (Samp) | 419 | 27 | 419 | 36 | 419 | 18 |
| n (Pat) | 164 | 27 | 164 | 36 | 164 | 18 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 21.600 | 29.100 | 21.600 | 44.600 | 21.600 | 36.900 |
| average | 30.233 | 33.628 | 30.233 | 44.133 | 30.233 | 48.901 |
| stdev | 62.708 | 24.214 | 62.708 | 22.001 | 62.708 | 30.933 |
| p (t-test) |  | 0.904 |  | 0.507 |  | 0.432 |
| min | 0.600 | 6.640 | 0.600 | 11.000 | 0.600 | 8.610 |
| max | 1280.000 | 69.500 | 1280.000 | 71.500 | 1280.000 | 83.700 |
| n (Samp) | 518 | 5 | 518 | 9 | 518 | 7 |
| n (Pat) | 199 | 5 | 199 | 9 | 199 | 7 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 21.600 | 23.750 | 21.600 | 22.000 | 21.600 | 25.850 |
| average | 28.392 | 27.162 | 28.392 | 72.997 | 28.392 | 28.324 |
| stdev | 33.380 | 19.414 | 33.380 | 229.169 | 33.380 | 16.072 |
| p (t-test) |  | 0.853 |  | 0.001 |  | 0.994 |
| min | 0.600 | 0.600 | 0.600 | 0.600 | 0.600 | 2.470 |
| max | 371.000 | 98.500 | 371.000 | 1280.000 | 371.000 | 59.000 |
| n (Samp) | 352 | 26 | 352 | 30 | 352 | 16 |
| n (Pat) | 133 | 26 | 133 | 30 | 133 | 16 | sCr or UO

| Time prior AKI stage | AUC | SE | nCohort 1 | nCohort 2 | p |
| --- | --- | --- | --- | --- | --- |
| 0 hours | 0.56 | 0.059 | 419 | 27 | 0.299 |
| 24 hours | 0.62 | 0.052 | 419 | 36 | 0.016 |
| 48 hours | 0.56 | 0.071 | 419 | 18 | 0.391 | sCr only

| Time prior AKI stage | AUC | SE | nCohort 1 | nCohort 2 | p |
| --- | --- | --- | --- | --- | --- |
| 0 hours | 0.60 | 0.135 | 518 | 5 | 0.439 |
| 24 hours | 0.75 | 0.095 | 518 | 9 | 0.008 |
| 48 hours | 0.73 | 0.109 | 518 | 7 | 0.034 |

UO only

| Time prior AKI stage | AUC | SE | nCohort 1 | nCohort 2 | p |
| --- | --- | --- | --- | --- | --- |
| 0 hours | 0.55 | 0.060 | 352 | 26 | 0.363 |
| 24 hours | 0.59 | 0.057 | 352 | 30 | 0.119 |
| 48 hours | 0.58 | 0.076 | 352 | 16 | 0.325 | sCr or UO

| Time prior AKI stage | Cutoff value | sens | spec | Quartile | OR | 95% CI of OR | |
| --- | --- | --- | --- | --- | --- | --- | --- |
| 0 hours | 20.9 | 70% | 49% | 1 |  |  |  |
|  | 18.1 | 81% | 40% | 2 | 1.3 | 0.5 | 3.1 |
|  | 5.33 | 93% | 6% | 3 | 3.2 | 1.6 | 6.5 |
|  | 27.9 | 30% | 70% | 4 | 1.5 | 0.6 | 3.6 |
|  | 35.1 | 15% | 80% |  |  |  |  |
|  | 51.6 | 15% | 90% |  |  |  |  |
| 24 hours | 21.2 | 72% | 50% | 1 |  |  |  |
|  | 19.1 | 81% | 43% | 2 | 3.1 | 1.3 | 7.8 |
|  | 13.3 | 92% | 26% | 3 | 3.5 | 1.5 | 8.6 |
|  | 27.9 | 42% | 70% | 4 | 5.1 | 2.2 | 11.8 |

Fig. 2 - 11

| | Cutoff value | sens | spec | Quartile | OR | 95% CI of OR | |
|---|---|---|---|---|---|---|---|
| | 35.1 | 33% | 80% | | | | |
| | 51.6 | 25% | 90% | | | | |
| 48 hours | 21.4 | 72% | 50% | 1 | | | |
| | 11.5 | 83% | 19% | 2 | 0.2 | 0.0 | 2.1 |
| | 8.5 | 94% | 11% | 3 | 0.8 | 0.3 | 2.0 |
| | 27.9 | 44% | 70% | 4 | 1.6 | 0.8 | 3.2 |
| | 35.1 | 33% | 80% | | | | |
| | 51.6 | 11% | 90% | | | | | sCr only

| Time prior AKI stage | Cutoff value | sens | spec | Quartile | OR | 95% CI of OR | |
|---|---|---|---|---|---|---|---|
| 0 hours | 19.1 | 80% | 42% | 1 | | | |
| | 19.1 | 80% | 42% | 2 | 1.0 | 0.0 | 51.5 |
| | 6.63 | 100% | 9% | 3 | 1.0 | 0.0 | 51.5 |
| | 28.2 | 60% | 70% | 4 | 2.0 | 0.1 | 39.0 |
| | 35.4 | 40% | 80% | | | | |
| | 53.7 | 20% | 90% | | | | |
| 24 hours | 25.9 | 78% | 65% | 1 | | | |
| | 24 | 89% | 61% | 2 | 0.0 | 0.0 | na |
| | 10.9 | 100% | 16% | 3 | 3.0 | 0.2 | 42.5 |
| | 28.2 | 67% | 70% | 4 | 5.1 | 0.5 | 55.4 |
| | 35.4 | 56% | 80% | | | | |
| | 53.7 | 44% | 90% | | | | |
| 48 hours | 32.1 | 71% | 77% | 1 | | | |
| | 22.5 | 86% | 54% | 2 | 0.0 | 0.0 | na |
| | 8.5 | 100% | 12% | 3 | 1.0 | 0.0 | 51.9 |
| | 28.2 | 71% | 70% | 4 | 5.1 | 0.5 | 55.4 |
| | 35.4 | 57% | 80% | | | | |
| | 53.7 | 43% | 90% | | | | |

UO only

| Time prior AKI stage | Cutoff value | sens | spec | Quartile | OR | 95% CI of OR | |
|---|---|---|---|---|---|---|---|
| 0 hours | 20.4 | 73% | 47% | 1 | | | |
| | 18.2 | 81% | 40% | 2 | 2.0 | 0.7 | 5.7 |
| | 5.14 | 92% | 5% | 3 | 4.4 | 1.9 | 10.5 |
| | 28.3 | 23% | 70% | 4 | 1.7 | 0.6 | 5.0 |
| | 36 | 12% | 80% | | | | |
| | 50.7 | 12% | 90% | | | | |
| 24 hours | 19.9 | 70% | 46% | 1 | | | |
| | 19.1 | 80% | 43% | 2 | 5.4 | 1.6 | 18.3 |
| | 13.6 | 90% | 27% | 3 | 4.9 | 1.4 | 16.8 |
| | 28.3 | 33% | 70% | 4 | 4.8 | 1.4 | 16.6 |
| | 36 | 27% | 80% | | | | |
| | 50.7 | 23% | 90% | | | | |
| 48 hours | 21.1 | 75% | 49% | 1 | | | |
| | 12.3 | 81% | 21% | 2 | 0.5 | 0.1 | 2.2 |
| | 9.57 | 94% | 13% | 3 | 1.0 | 0.4 | 2.8 |
| | 28.3 | 50% | 70% | 4 | 1.5 | 0.6 | 3.6 |
| | 36 | 25% | 80% | | | | |
| | 50.7 | 13% | 90% | | | | |

Fig. 2 - 12

Serum amyloid P-component sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 1.733 | 1.521 | 1.733 | 3.891 | 1.733 | 4.107 |
| average | 4.934 | 3.828 | 4.934 | 12.935 | 4.934 | 8.071 |
| stdev | 8.676 | 5.462 | 8.676 | 26.779 | 8.676 | 10.828 |
| p (t-test) |  | 0.558 |  | 0.000 |  | 0.158 |
| min | 0.038 | 0.025 | 0.038 | 0.129 | 0.038 | 0.269 |
| max | 58.307 | 22.353 | 58.307 | 152.000 | 58.307 | 44.971 |
| n (Samp) | 239 | 22 | 239 | 35 | 239 | 17 |
| n (Pat) | 156 | 22 | 156 | 35 | 156 | 17 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 1.838 | 0.025 | 1.838 | 7.887 | 1.838 | 7.601 |
| average | 5.752 | 3.123 | 5.752 | 8.811 | 5.752 | 10.246 |
| stdev | 12.201 | na | 12.201 | 7.923 | 12.201 | 11.896 |
| p (t-test) |  | na |  | 0.482 |  | 0.336 |
| min | 0.025 | 3.123 | 0.025 | 0.431 | 0.025 | 0.269 |
| max | 152.000 | 3.123 | 152.000 | 22.381 | 152.000 | 34.528 |
| n (Samp) | 310 | 1 | 310 | 8 | 310 | 7 |
| n (Pat) | 185 | 1 | 185 | 8 | 185 | 7 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 1.979 | 1.521 | 1.979 | 3.117 | 1.979 | 5.087 |
| average | 5.639 | 3.979 | 5.639 | 13.447 | 5.639 | 9.831 |
| stdev | 9.025 | 5.358 | 9.025 | 28.777 | 9.025 | 12.096 |
| p (t-test) |  | 0.388 |  | 0.003 |  | 0.102 |
| min | 0.038 | 0.025 | 0.038 | 0.129 | 0.038 | 1.085 |
| max | 58.307 | 22.353 | 58.307 | 152.000 | 58.307 | 44.971 |
| n (Samp) | 207 | 23 | 207 | 30 | 207 | 14 |
| n (Pat) | 130 | 23 | 130 | 30 | 130 | 14 | sCr or UO

| Time prior AKI stage | AUC | SE | nCohort 1 | nCohort 2 | p |
| --- | --- | --- | --- | --- | --- |
| 0 hours | 0.50 | 0.064 | 239 | 22 | 0.995 |
| 24 hours | 0.64 | 0.053 | 239 | 35 | 0.011 |
| 48 hours | 0.67 | 0.074 | 239 | 17 | 0.022 | sCr only

| Time prior AKI stage | AUC | SE | nCohort 1 | nCohort 2 | p |
| --- | --- | --- | --- | --- | --- |
| 0 hours | 0.63 | 0.301 | 310 | 1 | 0.676 |
| 24 hours | 0.66 | 0.107 | 310 | 8 | 0.125 |
| 48 hours | 0.65 | 0.114 | 310 | 7 | 0.174 |

UO only

| Time prior AKI stage | AUC | SE | nCohort 1 | nCohort 2 | p |
| --- | --- | --- | --- | --- | --- |
| 0 hours | 0.49 | 0.063 | 207 | 23 | 0.831 |
| 24 hours | 0.61 | 0.058 | 207 | 30 | 0.069 |
| 48 hours | 0.69 | 0.081 | 207 | 14 | 0.021 | sCr or UO

| Time prior AKI stage | Cutoff value | sens | spec | Quartile | OR | 95% CI of OR | |
| --- | --- | --- | --- | --- | --- | --- | --- |
| 0 hours | 1.0844797 | 73% | 40% | 1 |  |  |  |
|  | 0.6598911 | 82% | 27% | 2 | 4.2 | 1.7 | 10.3 |
|  | 0.617452 | 91% | 26% | 3 | 1.0 | 0.3 | 3.9 |
|  | 3.9445692 | 27% | 70% | 4 | 1.7 | 0.6 | 5.1 |
|  | 6.4927358 | 23% | 80% |  |  |  |  |
|  | 12.688918 | 9% | 91% |  |  |  |  |
| 24 hours | 1.7074782 | 71% | 49% | 1 |  |  |  |
|  | 0.8588182 | 80% | 34% | 2 | 1.2 | 0.6 | 2.3 |
|  | 0.4680993 | 91% | 18% | 3 | 1.0 | 0.5 | 2.0 |
|  | 3.9445692 | 49% | 70% | 4 | 3.1 | 1.9 | 5.2 |

Fig. 2 - 13

|  | 6.4927358 | 46% | 80% |  |  |  |  |
|---|---|---|---|---|---|---|---|
|  | 12.688918 | 23% | 91% |  |  |  |  |
| 48 hours | 3.0914813 | 71% | 64% | 1 |  |  |  |
|  | 1.0852451 | 82% | 40% | 2 | 4.2 | 0.3 | 51.9 |
|  | 1.028192 | 94% | 38% | 3 | 4.2 | 0.3 | 51.9 |
|  | 3.9445692 | 53% | 70% | 4 | 9.0 | 0.9 | 87.2 |
|  | 6.4927358 | 41% | 80% |  |  |  |  |
|  | 12.688918 | 24% | 91% |  |  |  |  | sCr only

| Time prior AKI stage | Cutoff value | sens | spec | Quartile | OR | 95% CI of OR | |
|---|---|---|---|---|---|---|---|
| 0 hours | 3.1116249 | 100% | 63% | 1 |  |  |  |
|  | 3.1116249 | 100% | 63% | 2 | na | na | na |
|  | 3.1116249 | 100% | 63% | 3 | na | na | na |
|  | 4.2002819 | 0% | 70% | 4 | na | na | na |
|  | 7.0241397 | 0% | 80% |  |  |  |  |
|  | 13.552771 | 0% | 90% |  |  |  |  |
| 24 hours | 1.6307525 | 75% | 46% | 1 |  |  |  |
|  | 0.9853183 | 88% | 33% | 2 | 2.0 | 0.1 | 39.8 |
|  | 0.3919172 | 100% | 13% | 3 | 0.0 | 0.0 | na |
|  | 4.2002819 | 63% | 70% | 4 | 5.2 | 0.5 | 57.5 |
|  | 7.0241397 | 50% | 80% |  |  |  |  |
|  | 13.552771 | 25% | 90% |  |  |  |  |
| 48 hours | 2.7653229 | 71% | 60% | 1 |  |  |  |
|  | 1.028192 | 86% | 34% | 2 | 1.0 | 0.0 | 53.0 |
|  | 0.2564023 | 100% | 8% | 3 | 1.0 | 0.0 | 53.0 |
|  | 4.2002819 | 57% | 70% | 4 | 4.1 | 0.3 | 50.1 |
|  | 7.0241397 | 57% | 80% |  |  |  |  |
|  | 13.552771 | 14% | 90% |  |  |  |  |

UO only

| Time prior AKI stage | Cutoff value | sens | spec | Quartile | OR | 95% CI of OR | |
|---|---|---|---|---|---|---|---|
| 0 hours | 1.0844797 | 74% | 37% | 1 |  |  |  |
|  | 0.6598911 | 83% | 25% | 2 | 0.6 | 0.2 | 1.8 |
|  | 0.5885975 | 91% | 24% | 3 | 2.5 | 1.3 | 4.7 |
|  | 5.0110557 | 26% | 70% | 4 | 0.8 | 0.3 | 2.1 |
|  | 8.3049933 | 13% | 80% |  |  |  |  |
|  | 16.375793 | 4% | 90% |  |  |  |  |
| 24 hours | 1.7574663 | 70% | 48% | 1 |  |  |  |
|  | 0.8588182 | 80% | 31% | 2 | 1.5 | 0.7 | 3.1 |
|  | 0.513498 | 90% | 20% | 3 | 1.5 | 0.7 | 3.1 |
|  | 5.0110557 | 40% | 70% | 4 | 2.4 | 1.3 | 4.6 |
|  | 8.3049933 | 37% | 80% |  |  |  |  |
|  | 16.375793 | 20% | 90% |  |  |  |  |
| 48 hours | 3.3281087 | 71% | 62% | 1 |  |  |  |
|  | 1.1230311 | 86% | 37% | 2 | na | na | na |
|  | 1.0852451 | 93% | 37% | 3 | na | na | na |
|  | 5.0110557 | 50% | 70% | 4 | na | na | na |
|  | 8.3049933 | 29% | 80% |  |  |  |  |
|  | 16.375793 | 21% | 90% |  |  |  |  |

Fig. 2 - 14

Matrix metalloproteinase-9 sCr or UO

|        | 0 hr prior to AKI stage | | 24 hr prior to AKI stage | | 48 hr prior to AKI stage | |
|--------|----------|----------|----------|----------|----------|----------|
|        | Cohort 1 | Cohort 2 | Cohort 1 | Cohort 2 | Cohort 1 | Cohort 2 |
| median    | 2919.594   | 10759.715  | 2919.594   | 12341.776  | 2919.594   | 11363.291  |
| average   | 12657.744  | 34384.107  | 12657.744  | 28004.195  | 12657.744  | 28146.981  |
| stdev     | 24357.723  | 49699.726  | 24357.723  | 29887.313  | 24357.723  | 38420.607  |
| p (t-test)|            | 0.000      |            | 0.001      |            | 0.014      |
| min       | 3.588      | 192.720    | 3.588      | 132.776    | 3.588      | 200.747    |
| max       | 159217.283 | 176209.055 | 159217.283 | 109530.934 | 159217.283 | 135985.892 |
| n (Samp)  | 244        | 23         | 244        | 35         | 244        | 18         |
| n (Pat)   | 158        | 23         | 158        | 35         | 158        | 18         | sCr only

|        | 0 hr prior toAKI stage | | 24 hr prior toAKI stage | | 48 hr prior toAKI stage | |
|--------|----------|----------|----------|----------|----------|----------|
|        | Cohort 1 | Cohort 2 | Cohort 1 | Cohort 2 | Cohort 1 | Cohort 2 |
| median    | 4240.182   | 2031.186  | 4240.182   | 5260.972   | 4240.182   | 12438.574  |
| average   | 16510.837  | 2031.186  | 16510.837  | 11325.761  | 16510.837  | 37696.949  |
| stdev     | 29366.734  | 2537.874  | 29366.734  | 19036.200  | 29366.734  | 43094.574  |
| p (t-test)|            | 0.487     |            | 0.620      |            | 0.063      |
| min       | 3.588      | 236.639   | 3.588      | 132.776    | 3.588      | 499.433    |
| max       | 176209.055 | 3825.734  | 176209.055 | 56621.227  | 176209.055 | 112264.995 |
| n (Samp)  | 316        | 2         | 316        | 8          | 316        | 7          |
| n (Pat)   | 187        | 2         | 187        | 8          | 187        | 7          |

UO only

|        | 0 hr prior toAKI stage | | 24 hr prior toAKI stage | | 48 hr prior toAKI stage | |
|--------|----------|----------|----------|----------|----------|----------|
|        | Cohort 1 | Cohort 2 | Cohort 1 | Cohort 2 | Cohort 1 | Cohort 2 |
| median    | 3619.946   | 10759.715  | 3619.946   | 20253.666  | 3619.946   | 8974.200   |
| average   | 13298.584  | 34266.775  | 13298.584  | 30160.313  | 13298.584  | 26828.382  |
| stdev     | 24677.703  | 49778.384  | 24677.703  | 30591.303  | 24677.703  | 39232.221  |
| p (t-test)|            | 0.001      |            | 0.001      |            | 0.045      |
| min       | 3.588      | 115.408    | 3.588      | 133.538    | 3.588      | 200.747    |
| max       | 159217.283 | 176209.055 | 159217.283 | 109530.934 | 159217.283 | 135985.892 |
| n (Samp)  | 211        | 23         | 211        | 30         | 211        | 16         |
| n (Pat)   | 131        | 23         | 131        | 30         | 131        | 16         | sCr or UO

| Time prior AKI stage | AUC  | SE    | nCohort 1 | nCohort 2 | p     |
|----------------------|------|-------|-----------|-----------|-------|
| 0 hours              | 0.70 | 0.063 | 244       | 23        | 0.002 |
| 24 hours             | 0.67 | 0.053 | 244       | 35        | 0.001 |
| 48 hours             | 0.65 | 0.072 | 244       | 18        | 0.035 | sCr only

| Time prior AKI stage | AUC  | SE    | nCohort 1 | nCohort 2 | p     |
|----------------------|------|-------|-----------|-----------|-------|
| 0 hours              | 0.29 | 0.154 | 316       | 2         | 0.174 |
| 24 hours             | 0.44 | 0.099 | 316       | 8         | 0.539 |
| 48 hours             | 0.65 | 0.114 | 316       | 7         | 0.175 |

UO only

| Time prior AKI stage | AUC  | SE    | nCohort 1 | nCohort 2 | p     |
|----------------------|------|-------|-----------|-----------|-------|
| 0 hours              | 0.67 | 0.064 | 211       | 23        | 0.007 |
| 24 hours             | 0.69 | 0.056 | 211       | 30        | 0.001 |
| 48 hours             | 0.63 | 0.077 | 211       | 16        | 0.100 | sCr or UO

| Time prior AKI stage | Cutoff value | sens | spec | Quartile | OR  | 95% CI of OR | |
|----------------------|--------------|------|------|----------|-----|--------------|-----|
| 0 hours  | 6333.2486  | 74% | 65% | 1 |     |     |     |
|          | 3813.5508  | 83% | 56% | 2 | 0.3 | 0.0 | 4.6 |
|          | 252.42408  | 91% | 10% | 3 | 3.3 | 1.3 | 8.3 |
|          | 8081.4656  | 61% | 70% | 4 | 3.7 | 1.5 | 9.2 |
|          | 13914.318  | 43% | 80% |   |     |     |     |
|          | 44000      | 26% | 92% |   |     |     |     |
| 24 hours | 4191.8645  | 71% | 56% | 1 |     |     |     |
|          | 1859.8427  | 80% | 39% | 2 | 1.0 | 0.4 | 2.3 |
|          | 400.98346  | 91% | 16% | 3 | 1.7 | 0.8 | 3.3 |
|          | 8081.4656  | 63% | 70% | 4 | 4.1 | 2.3 | 7.3 |

Fig. 2 - 15

|  | 13914.318 | 49% | 80% |  |  |  |  |
|  | 44000 | 23% | 92% |  |  |  |  |
| 48 hours | 5664.4607 | 72% | 62% | 1 |  |  |  |
|  | 582.72741 | 83% | 20% | 2 | 0.2 | 0.0 | 2.9 |
|  | 307.74357 | 94% | 11% | 3 | 1.0 | 0.4 | 2.8 |
|  | 8081.4656 | 56% | 70% | 4 | 2.4 | 1.1 | 5.2 |
|  | 13914.318 | 39% | 80% |  |  |  |  |
|  | 44000 | 22% | 92% |  |  |  |  | sCr only

| Time prior AKI stage | Cutoff value | sens | spec | Quartile | OR | 95% CI of OR | |
|---|---|---|---|---|---|---|---|
| 0 hours | 228.43976 | 100% | 9% | 1 |  |  |  |
|  | 228.43976 | 100% | 9% | 2 | na | na | na |
|  | 228.43976 | 100% | 9% | 3 | na | na | na |
|  | 11273.561 | 0% | 70% | 4 | na | na | na |
|  | 21431.119 | 0% | 80% |  |  |  |  |
|  | 57264.518 | 0% | 90% |  |  |  |  |
| 24 hours | 400.98346 | 75% | 15% | 1 |  |  |  |
|  | 201.31688 | 88% | 8% | 2 | 3.1 | 0.2 | 44.1 |
|  | 129.86648 | 100% | 6% | 3 | 0.0 | 0.0 | na |
|  | 11273.561 | 25% | 70% | 4 | 4.2 | 0.3 | 50.6 |
|  | 21431.119 | 13% | 80% |  |  |  |  |
|  | 57264.518 | 0% | 90% |  |  |  |  |
| 48 hours | 9943.6746 | 71% | 68% | 1 |  |  |  |
|  | 582.72741 | 86% | 19% | 2 | 0.0 | 0.0 | na |
|  | 493.76972 | 100% | 17% | 3 | 1.0 | 0.1 | 7.4 |
|  | 11273.561 | 57% | 70% | 4 | 1.5 | 0.3 | 8.1 |
|  | 21431.119 | 43% | 80% |  |  |  |  |
|  | 57264.518 | 43% | 90% |  |  |  |  |

UO only

| Time prior AKI stage | Cutoff value | sens | spec | Quartile | OR | 95% CI of OR | |
|---|---|---|---|---|---|---|---|
| 0 hours | 6380.8915 | 74% | 62% | 1 |  |  |  |
|  | 2194.6163 | 83% | 42% | 2 | 0.6 | 0.1 | 3.5 |
|  | 252.42408 | 91% | 9% | 3 | 2.9 | 1.1 | 7.8 |
|  | 9558.2526 | 57% | 70% | 4 | 3.7 | 1.5 | 9.4 |
|  | 15700.544 | 39% | 80% |  |  |  |  |
|  | 44000 | 26% | 92% |  |  |  |  |
| 24 hours | 4633.5168 | 70% | 55% | 1 |  |  |  |
|  | 2068.3695 | 80% | 40% | 2 | 1.3 | 0.5 | 3.3 |
|  | 1142.4862 | 90% | 26% | 3 | 1.3 | 0.5 | 3.3 |
|  | 9558.2526 | 60% | 70% | 4 | 5.0 | 2.5 | 9.9 |
|  | 15700.544 | 53% | 80% |  |  |  |  |
|  | 44000 | 23% | 92% |  |  |  |  |
| 48 hours | 3813.5508 | 75% | 51% | 1 |  |  |  |
|  | 2459.3861 | 81% | 43% | 2 | 0.6 | 0.1 | 3.5 |
|  | 200.74676 | 94% | 8% | 3 | 1.3 | 0.4 | 4.5 |
|  | 9558.2526 | 50% | 70% | 4 | 2.5 | 0.9 | 6.8 |
|  | 15700.544 | 31% | 80% |  |  |  |  |
|  | 44000 | 19% | 92% |  |  |  |  |

Fig. 2 - 16

Clusterin sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 108.761 | 96.960 | 108.761 | 96.960 | 108.761 | 96.960 |
| average | 168.738 | 146.608 | 168.738 | 146.608 | 168.738 | 146.608 |
| stdev | 165.033 | 185.858 | 165.033 | 185.858 | 165.033 | 185.858 |
| p (t-test) |  | 0.611 |  | 0.611 |  | 0.611 |
| min | 7.973 | 5.052 | 7.973 | 5.052 | 7.973 | 5.052 |
| max | 684.578 | 715.260 | 684.578 | 715.260 | 684.578 | 715.260 |
| n (Samp) | 54 | 22 | 54 | 22 | 54 | 22 |
| n (Pat) | 54 | 22 | 54 | 22 | 54 | 22 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 80.501 | 58.315 | 80.501 | 58.315 | 80.501 | 58.315 |
| average | 122.269 | 60.418 | 122.269 | 60.418 | 122.269 | 60.418 |
| stdev | 143.085 | 37.189 | 143.085 | 37.189 | 143.085 | 37.189 |
| p (t-test) |  | 0.407 |  | 0.407 |  | 0.407 |
| min | 5.052 | 23.097 | 5.052 | 23.097 | 5.052 | 23.097 |
| max | 526.949 | 101.944 | 526.949 | 101.944 | 526.949 | 101.944 |
| n (Samp) | 20 | 4 | 20 | 4 | 20 | 4 |
| n (Pat) | 20 | 4 | 20 | 4 | 20 | 4 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 111.123 | 95.181 | 111.123 | 95.181 | 111.123 | 95.181 |
| average | 403.189 | 168.328 | 403.189 | 168.328 | 403.189 | 168.328 |
| stdev | 1515.416 | 206.344 | 1515.416 | 206.344 | 1515.416 | 206.344 |
| p (t-test) |  | 0.529 |  | 0.529 |  | 0.529 |
| min | 9.088 | 37.552 | 9.088 | 37.552 | 9.088 | 37.552 |
| max | 10168.806 | 715.260 | 10168.806 | 715.260 | 10168.806 | 715.260 |
| n (Samp) | 44 | 17 | 44 | 17 | 44 | 17 |
| n (Pat) | 44 | 17 | 44 | 17 | 44 | 17 | sCr or UO

| Time prior AKI stage | AUC | SE | nCohort 1 | nCohort 2 | p |
|---|---|---|---|---|---|
| 0 hours | 0.47 | 0.073 | 54 | 22 | 0.685 |
| 24 hours | 0.47 | 0.073 | 54 | 22 | 0.685 |
| 48 hours | 0.47 | 0.073 | 54 | 22 | 0.685 | sCr only

| Time prior AKI stage | AUC | SE | nCohort 1 | nCohort 2 | p |
|---|---|---|---|---|---|
| 0 hours | 0.40 | 0.151 | 20 | 4 | 0.506 |
| 24 hours | 0.40 | 0.151 | 20 | 4 | 0.506 |
| 48 hours | 0.40 | 0.151 | 20 | 4 | 0.506 |

UO only

| Time prior AKI stage | AUC | SE | nCohort 1 | nCohort 2 | p |
|---|---|---|---|---|---|
| 0 hours | 0.48 | 0.083 | 44 | 17 | 0.795 |
| 24 hours | 0.48 | 0.083 | 44 | 17 | 0.795 |
| 48 hours | 0.48 | 0.083 | 44 | 17 | 0.795 | sCr or UO

| Time prior AKI stage | Cutoff value | sens | spec | Quartile | OR | 95% CI of OR | |
|---|---|---|---|---|---|---|---|
| 0 hours | 69.662131 | 73% | 37% | 1 |  |  |  |
|  | 60.30808 | 82% | 35% | 2 | 6.2 | 1.4 | 28.2 |
|  | 35.699167 | 91% | 26% | 3 | 7.7 | 1.7 | 34.6 |
|  | 250.3383 | 9% | 70% | 4 | 1.6 | 0.2 | 10.4 |
|  | 316.00649 | 9% | 81% |  |  |  |  |
|  | 400 | 9% | 91% |  |  |  |  |
| 24 hours | 69.662131 | 73% | 37% | 1 |  |  |  |
|  | 60.30808 | 82% | 35% | 2 | 6.2 | 1.4 | 28.2 |

Fig. 3 - 1

|  | 35.699167 | 91% | 26% | 3 | 7.7 | 1.7 | 34.6 |
|---|---|---|---|---|---|---|---|
|  | 250.3383 | 9% | 70% | 4 | 1.6 | 0.2 | 10.4 |
|  | 316.00649 | 9% | 81% |  |  |  |  |
|  | 400 | 9% | 91% |  |  |  |  |
| 48 hours | 69.662131 | 73% | 37% | 1 |  |  |  |
|  | 60.30808 | 82% | 35% | 2 | 6.2 | 1.4 | 28.2 |
|  | 35.699167 | 91% | 26% | 3 | 7.7 | 1.7 | 34.6 |
|  | 250.3383 | 9% | 70% | 4 | 1.6 | 0.2 | 10.4 |
|  | 316.00649 | 9% | 81% |  |  |  |  |
|  | 400 | 9% | 91% |  |  |  |  |

UO only

| Time prior AKI stage | Cutoff value | sens | spec | Quartile | OR | 95% CI of OR | |
|---|---|---|---|---|---|---|---|
| 0 hours | 69.662131 | 71% | 34% | 1 |  |  |  |
|  | 62.600557 | 82% | 32% | 2 | 3.5 | 0.6 | 19.3 |
|  | 55.600211 | 94% | 32% | 3 | 10.5 | 2.0 | 55.5 |
|  | 268.89919 | 12% | 70% | 4 | 0.5 | 0.0 | 12.5 |
|  | 359.30566 | 12% | 82% |  |  |  |  |
|  | 400 | 12% | 91% |  |  |  |  |
| 24 hours | 69.662131 | 71% | 34% | 1 |  |  |  |
|  | 62.600557 | 82% | 32% | 2 | 3.5 | 0.6 | 19.3 |
|  | 55.600211 | 94% | 32% | 3 | 10.5 | 2.0 | 55.5 |
|  | 268.89919 | 12% | 70% | 4 | 0.5 | 0.0 | 12.5 |
|  | 359.30566 | 12% | 82% |  |  |  |  |
|  | 400 | 12% | 91% |  |  |  |  |
| 48 hours | 69.662131 | 71% | 34% | 1 |  |  |  |
|  | 62.600557 | 82% | 32% | 2 | 3.5 | 0.6 | 19.3 |
|  | 55.600211 | 94% | 32% | 3 | 10.5 | 2.0 | 55.5 |
|  | 268.89919 | 12% | 70% | 4 | 0.5 | 0.0 | 12.5 |
|  | 359.30566 | 12% | 82% |  |  |  |  |
|  | 400 | 12% | 91% |  |  |  |  |

Fig. 3 - 2

Serum amyloid P-component sCr UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 1.979 | 3.891 | 1.979 | 3.891 | 1.979 | 3.891 |
| average | 6.056 | 10.083 | 6.056 | 10.083 | 6.056 | 10.083 |
| stdev | 9.464 | 14.097 | 9.464 | 14.097 | 9.464 | 14.097 |
| p (t-test) |  | 0.148 |  | 0.148 |  | 0.148 |
| min | 0.038 | 0.731 | 0.038 | 0.731 | 0.038 | 0.731 |
| max | 37.076 | 51.558 | 37.076 | 51.558 | 37.076 | 51.558 |
| n (Samp) | 53 | 23 | 53 | 23 | 53 | 23 |
| n (Pat) | 53 | 23 | 53 | 23 | 53 | 23 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 1.868 | 10.596 | 1.868 | 10.596 | 1.868 | 10.596 |
| average | 7.989 | 12.013 | 7.989 | 12.013 | 7.989 | 12.013 |
| stdev | 14.702 | 7.639 | 14.702 | 7.639 | 14.702 | 7.639 |
| p (t-test) |  | 0.604 |  | 0.604 |  | 0.604 |
| min | 0.038 | 4.481 | 0.038 | 4.481 | 0.038 | 4.481 |
| max | 51.558 | 22.381 | 51.558 | 22.381 | 51.558 | 22.381 |
| n (Samp) | 20 | 4 | 20 | 4 | 20 | 4 |
| n (Pat) | 20 | 4 | 20 | 4 | 20 | 4 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 2.578 | 2.983 | 2.578 | 2.983 | 2.578 | 2.983 |
| average | 7.074 | 5.546 | 7.074 | 5.546 | 7.074 | 5.546 |
| stdev | 10.048 | 7.077 | 10.048 | 7.077 | 10.048 | 7.077 |
| p (t-test) |  | 0.560 |  | 0.560 |  | 0.560 |
| min | 0.038 | 0.731 | 0.038 | 0.731 | 0.038 | 0.731 |
| max | 37.076 | 29.750 | 37.076 | 29.750 | 37.076 | 29.750 |
| n (Samp) | 43 | 18 | 43 | 18 | 43 | 18 |
| n (Pat) | 43 | 18 | 43 | 18 | 43 | 18 | sCr or UO

| Time prior AKI stage | AUC | SE | nCohort 1 | nCohort 2 | p |
| --- | --- | --- | --- | --- | --- |
| 0 hours | 0.67 | 0.070 | 53 | 23 | 0.016 |
| 24 hours | 0.67 | 0.070 | 53 | 23 | 0.016 |
| 48 hours | 0.67 | 0.070 | 53 | 23 | 0.016 | sCr only

| Time prior AKI stage | AUC | SE | nCohort 1 | nCohort 2 | p |
| --- | --- | --- | --- | --- | --- |
| 0 hours | 0.83 | 0.135 | 20 | 4 | 0.016 |
| 24 hours | 0.83 | 0.135 | 20 | 4 | 0.016 |
| 48 hours | 0.83 | 0.135 | 20 | 4 | 0.016 |

UO only

| Time prior AKI stage | AUC | SE | nCohort 1 | nCohort 2 | p |
| --- | --- | --- | --- | --- | --- |
| 0 hours | 0.57 | 0.082 | 43 | 18 | 0.379 |
| 24 hours | 0.57 | 0.082 | 43 | 18 | 0.379 |
| 48 hours | 0.57 | 0.082 | 43 | 18 | 0.379 |

Fig. 3 - 3

Matrix metalloproteinase-9 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 3505.601 | 22269.362 | 3505.601 | 22269.362 | 3505.601 | 22269.362 |
| average | 12914.017 | 37532.158 | 12914.017 | 37532.158 | 12914.017 | 37532.158 |
| stdev | 22424.789 | 38644.771 | 22424.789 | 38644.771 | 22424.789 | 38644.771 |
| p (t-test) |  | 0.001 |  | 0.001 |  | 0.001 |
| min | 55.139 | 104.612 | 55.139 | 104.612 | 55.139 | 104.612 |
| max | 102501.267 | 109530.934 | 102501.267 | 109530.934 | 102501.267 | 109530.934 |
| n (Samp) | 53 | 23 | 53 | 23 | 53 | 23 |
| n (Pat) | 53 | 23 | 53 | 23 | 53 | 23 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 4274.887 | 4935.166 | 4274.887 | 4935.166 | 4274.887 | 4935.166 |
| average | 9968.290 | 17537.123 | 9968.290 | 17537.123 | 9968.290 | 17537.123 |
| stdev | 16421.761 | 28773.904 | 16421.761 | 28773.904 | 16421.761 | 28773.904 |
| p (t-test) |  | 0.470 |  | 0.470 |  | 0.470 |
| min | 111.032 | 104.612 | 111.032 | 104.612 | 111.032 | 104.612 |
| max | 63552.815 | 60173.549 | 63552.815 | 60173.549 | 63552.815 | 60173.549 |
| n (Samp) | 19 | 4 | 19 | 4 | 19 | 4 |
| n (Pat) | 19 | 4 | 19 | 4 | 19 | 4 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 6145.916 | 33134.681 | 6145.916 | 33134.681 | 6145.916 | 33134.681 |
| average | 17708.819 | 38710.302 | 17708.819 | 38710.302 | 17708.819 | 38710.302 |
| stdev | 27866.487 | 37725.444 | 27866.487 | 37725.444 | 27866.487 | 37725.444 |
| p (t-test) |  | 0.018 |  | 0.018 |  | 0.018 |
| min | 55.139 | 127.318 | 55.139 | 127.318 | 55.139 | 127.318 |
| max | 109490.680 | 109530.934 | 109490.680 | 109530.934 | 109490.680 | 109530.934 |
| n (Samp) | 44 | 18 | 44 | 18 | 44 | 18 |
| n (Pat) | 44 | 18 | 44 | 18 | 44 | 18 | sCr or UO

| Time prior AKI stage | AUC | SE | nCohort 1 | nCohort 2 | p |
|---|---|---|---|---|---|
| 0 hours | 0.66 | 0.071 | 53 | 23 | 0.029 |
| 24 hours | 0.66 | 0.071 | 53 | 23 | 0.029 |
| 48 hours | 0.66 | 0.071 | 53 | 23 | 0.029 | sCr only

| Time prior AKI stage | AUC | SE | nCohort 1 | nCohort 2 | p |
|---|---|---|---|---|---|
| 0 hours | 0.43 | 0.156 | 19 | 4 | 0.673 |
| 24 hours | 0.43 | 0.156 | 19 | 4 | 0.673 |
| 48 hours | 0.43 | 0.156 | 19 | 4 | 0.673 |

UO only

| Time prior AKI stage | AUC | SE | nCohort 1 | nCohort 2 | p |
|---|---|---|---|---|---|
| 0 hours | 0.65 | 0.080 | 44 | 18 | 0.061 |
| 24 hours | 0.65 | 0.080 | 44 | 18 | 0.061 |
| 48 hours | 0.65 | 0.080 | 44 | 18 | 0.061 | sCr or UO

| Time prior AKI stage | Cutoff value | sens | spec | Quartile | OR | 95% CI of OR | |
|---|---|---|---|---|---|---|---|
| 0 hours | 4274.8868 | 74% | 53% | 1 |  |  |  |
|  | 414.7431 | 83% | 17% | 2 | 0.4 | 0.1 | 1.4 |
|  | 122.63715 | 91% | 4% | 3 | 0.4 | 0.1 | 1.4 |
|  | 12108.63 | 61% | 72% | 4 | 3.0 | 1.2 | 7.3 |
|  | 13914.318 | 57% | 81% |  |  |  |  |
|  | 37633.202 | 48% | 91% |  |  |  |  |
| 24 hours | 4274.8868 | 74% | 53% | 1 |  |  |  |
|  | 414.7431 | 83% | 17% | 2 | 0.4 | 0.1 | 1.4 |
|  | 122.63715 | 91% | 4% | 3 | 0.4 | 0.1 | 1.4 |
|  | 12108.63 | 61% | 72% | 4 | 3.0 | 1.2 | 7.3 |
|  | 13914.318 | 57% | 81% |  |  |  |  |

Fig. 3 - 4

|  | Cutoff value | sens | spec | Quartile | OR | 95% CI of OR | |
|---|---|---|---|---|---|---|---|
|  | 37633.202 | 48% | 91% |  |  |  |  |
| 48 hours | 4274.8868 | 74% | 53% | 1 |  |  |  |
|  | 414.7431 | 83% | 17% | 2 | 0.4 | 0.1 | 1.4 |
|  | 122.63715 | 91% | 4% | 3 | 0.4 | 0.1 | 1.4 |
|  | 12108.63 | 61% | 72% | 4 | 3.0 | 1.2 | 7.3 |
|  | 13914.318 | 57% | 81% |  |  |  |  |
|  | 37633.202 | 48% | 91% |  |  |  |  | sCr only

| Time prior AKI stage | Cutoff value | sens | spec | Quartile | OR | 95% CI of OR | |
|---|---|---|---|---|---|---|---|
| 0 hours | 201.31688 | 75% | 11% | 1 |  |  |  |
|  | 0 | 100% | 0% | 2 | 1.0 | 0.0 | 110.4 |
|  | 0 | 100% | 0% | 3 | 0.0 | 0.0 | na |
|  | 11273.561 | 25% | 74% | 4 | 3.3 | 0.1 | 179.3 |
|  | 12659.713 | 25% | 84% |  |  |  |  |
|  | 44000 | 25% | 95% |  |  |  |  |
| 24 hours | 201.31688 | 75% | 11% | 1 |  |  |  |
|  | 0 | 100% | 0% | 2 | 1.0 | 0.0 | 110.4 |
|  | 0 | 100% | 0% | 3 | 0.0 | 0.0 | na |
|  | 11273.561 | 25% | 74% | 4 | 3.3 | 0.1 | 179.3 |
|  | 12659.713 | 25% | 84% |  |  |  |  |
|  | 44000 | 25% | 95% |  |  |  |  |
| 48 hours | 201.31688 | 75% | 11% | 1 |  |  |  |
|  | 0 | 100% | 0% | 2 | 1.0 | 0.0 | 110.4 |
|  | 0 | 100% | 0% | 3 | 0.0 | 0.0 | na |
|  | 11273.561 | 25% | 74% | 4 | 3.3 | 0.1 | 179.3 |
|  | 12659.713 | 25% | 84% |  |  |  |  |
|  | 44000 | 25% | 95% |  |  |  |  |

UO only

| Time prior AKI stage | Cutoff value | sens | spec | Quartile | OR | 95% CI of OR | |
|---|---|---|---|---|---|---|---|
| 0 hours | 4882.635 | 72% | 45% | 1 |  |  |  |
|  | 817.28764 | 83% | 20% | 2 | 0.6 | 0.1 | 2.8 |
|  | 190.36647 | 94% | 9% | 3 | 0.4 | 0.1 | 2.6 |
|  | 13914.318 | 61% | 70% | 4 | 3.5 | 1.1 | 11.3 |
|  | 31712.706 | 50% | 82% |  |  |  |  |
|  | 44000 | 33% | 91% |  |  |  |  |
| 24 hours | 4882.635 | 72% | 45% | 1 |  |  |  |
|  | 817.28764 | 83% | 20% | 2 | 0.6 | 0.1 | 2.8 |
|  | 190.36647 | 94% | 9% | 3 | 0.4 | 0.1 | 2.6 |
|  | 13914.318 | 61% | 70% | 4 | 3.5 | 1.1 | 11.3 |
|  | 31712.706 | 50% | 82% |  |  |  |  |
|  | 44000 | 33% | 91% |  |  |  |  |
| 48 hours | 4882.635 | 72% | 45% | 1 |  |  |  |
|  | 817.28764 | 83% | 20% | 2 | 0.6 | 0.1 | 2.8 |
|  | 190.36647 | 94% | 9% | 3 | 0.4 | 0.1 | 2.6 |
|  | 13914.318 | 61% | 70% | 4 | 3.5 | 1.1 | 11.3 |
|  | 31712.706 | 50% | 82% |  |  |  |  |
|  | 44000 | 33% | 91% |  |  |  |  |

Fig. 3 - 5

Fatty acid binding protein, heart sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 117.500 | 922.000 | 117.500 | 1031.000 | 117.500 | 1787.500 |
| average | 455.927 | 3033.788 | 455.927 | 3105.880 | 455.927 | 2692.297 |
| stdev | 1028.417 | 4083.693 | 1028.417 | 4170.880 | 1028.417 | 2926.900 |
| p (t-test) |  | 0.000 |  | 0.000 |  | 0.000 |
| min | 1.880 | 11.000 | 1.880 | 5.180 | 1.880 | 4.070 |
| max | 8087.000 | 14771.000 | 8087.000 | 14771.000 | 8087.000 | 8087.000 |
| n (Samp) | 104 | 17 | 104 | 16 | 104 | 10 |
| n (Pat) | 104 | 17 | 104 | 16 | 104 | 10 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 149.500 | 1050.500 | 149.500 | 1050.500 | 149.500 | 577.000 |
| average | 702.389 | 4277.500 | 702.389 | 4274.898 | 702.389 | 2880.614 |
| stdev | 1678.295 | 5418.522 | 1678.295 | 5420.638 | 1678.295 | 3577.676 |
| p (t-test) |  | 0.000 |  | 0.000 |  | 0.007 |
| min | 1.880 | 11.000 | 1.880 | 5.180 | 1.880 | 4.070 |
| max | 13231.000 | 14771.000 | 13231.000 | 14771.000 | 13231.000 | 8087.000 |
| n (Samp) | 170 | 8 | 170 | 8 | 170 | 5 |
| n (Pat) | 170 | 8 | 170 | 8 | 170 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 118.000 | 922.000 | 118.000 | 1031.000 | 118.000 | 3000.000 |
| average | 554.147 | 2396.582 | 554.147 | 2450.290 | 554.147 | 3026.271 |
| stdev | 1367.982 | 2728.736 | 1367.982 | 2781.185 | 1367.982 | 3123.056 |
| p (t-test) |  | 0.000 |  | 0.000 |  | 0.000 |
| min | 3.520 | 38.600 | 3.520 | 16.300 | 3.520 | 16.300 |
| max | 8087.000 | 8087.000 | 8087.000 | 8087.000 | 8087.000 | 8087.000 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
|---|---|---|---|---|---|
| 0 hours | 0.80 | 0.067 | 104 | 17 | 0.000 |
| 24 hours | 0.77 | 0.072 | 104 | 16 | 0.000 |
| 48 hours | 0.71 | 0.095 | 104 | 10 | 0.026 | sCr only

| Time prior AKI stage | AUC | SE | nCohort 1 | nCohort 2 | p |
|---|---|---|---|---|---|
| 0 hours | 0.79 | 0.097 | 170 | 8 | 0.003 |
| 24 hours | 0.77 | 0.099 | 170 | 8 | 0.005 |
| 48 hours | 0.70 | 0.133 | 170 | 5 | 0.124 |

UO only

| Time prior AKI stage | AUC | SE | nCohort 1 | nCohort 2 | p |
|---|---|---|---|---|---|
| 0 hours | 0.81 | 0.082 | 85 | 11 | 0.000 |
| 24 hours | 0.78 | 0.089 | 85 | 10 | 0.001 |
| 48 hours | 0.75 | 0.109 | 85 | 7 | 0.021 | sCr or UO

| Time prior AKI stage | Cutoff value | sens | spec | Quartile | OR | 95% CI of OR | |
|---|---|---|---|---|---|---|---|
| 0 hours | 582 | 71% | 83% | 1 |  |  |  |
|  | 408 | 82% | 78% | 2 | 2.1 | 0.1 | 45.0 |
|  | 38.2 | 94% | 37% | 3 | 2.1 | 0.1 | 45.0 |
|  | 255 | 82% | 70% | 4 | 18.3 | 1.8 | 181.6 |
|  | 517 | 76% | 81% |  |  |  |  |
|  | 1260 | 35% | 90% |  |  |  |  |
| 24 hours | 566 | 75% | 82% | 1 |  |  |  |
|  | 338 | 81% | 77% | 2 | 0.5 | 0.0 | 10.5 |
|  | 14.5 | 94% | 21% | 3 | 1.0 | 0.1 | 8.2 |
|  | 255 | 81% | 70% | 4 | 8.1 | 2.1 | 30.7 |

Fig. 4 - 1

|  | 517 | 75% | 81% |  |  |  |  |
|---|---|---|---|---|---|---|---|
|  | 1260 | 38% | 90% |  |  |  |  |
| 48 hours | 338 | 70% | 77% | 1 |  |  |  |
|  | 38.2 | 80% | 37% | 2 | 0.5 | 0.0 | 10.2 |
|  | 14.5 | 90% | 21% | 3 | 0.5 | 0.0 | 10.6 |
|  | 255 | 70% | 70% | 4 | 3.4 | 0.8 | 14.7 |
|  | 517 | 60% | 81% |  |  |  |  |
|  | 1260 | 50% | 90% |  |  |  |  | sCr only

| Time prior AKI stage | Cutoff value | sens | spec | Quartile | OR | 95% CI of OR | |
|---|---|---|---|---|---|---|---|
| 0 hours | 582 | 75% | 78% | 1 |  |  |  |
|  | 566 | 88% | 77% | 2 | 0.0 | 0.0 | na |
|  | 10.9 | 100% | 10% | 3 | 1.0 | 0.0 | 55.2 |
|  | 306 | 88% | 70% | 4 | 6.6 | 0.6 | 71.7 |
|  | 718 | 63% | 80% |  |  |  |  |
|  | 1790 | 38% | 90% |  |  |  |  |
| 24 hours | 573 | 75% | 77% | 1 |  |  |  |
|  | 566 | 88% | 77% | 2 | 0.0 | 0.0 | na |
|  | 3.52 | 100% | 2% | 3 | 1.0 | 0.0 | 55.2 |
|  | 306 | 88% | 70% | 4 | 6.6 | 0.6 | 71.7 |
|  | 718 | 63% | 80% |  |  |  |  |
|  | 1790 | 38% | 90% |  |  |  |  |
| 48 hours | 566 | 80% | 77% | 1 |  |  |  |
|  | 566 | 80% | 77% | 2 | 0.0 | 0.0 | na |
|  | 3.52 | 100% | 2% | 3 | 0.0 | 0.0 | na |
|  | 306 | 80% | 70% | 4 | 4.2 | 0.3 | 53.6 |
|  | 718 | 40% | 80% |  |  |  |  |
|  | 1790 | 40% | 90% |  |  |  |  |

UO only

| Time prior AKI stage | Cutoff value | sens | spec | Quartile | OR | 95% CI of OR | |
|---|---|---|---|---|---|---|---|
| 0 hours | 582 | 73% | 85% | 1 |  |  |  |
|  | 408 | 82% | 80% | 2 | na | na | na |
|  | 43.8 | 91% | 39% | 3 | na | na | na |
|  | 271 | 82% | 71% | 4 | na | na | na |
|  | 408 | 82% | 80% |  |  |  |  |
|  | 1360 | 36% | 91% |  |  |  |  |
| 24 hours | 566 | 70% | 84% | 1 |  |  |  |
|  | 338 | 80% | 79% | 2 | 1.0 | 0.0 | 57.4 |
|  | 38.2 | 90% | 38% | 3 | 1.0 | 0.0 | 57.4 |
|  | 271 | 80% | 71% | 4 | 9.1 | 0.8 | 104.4 |
|  | 408 | 70% | 80% |  |  |  |  |
|  | 1360 | 40% | 91% |  |  |  |  |
| 48 hours | 338 | 71% | 79% | 1 |  |  |  |
|  | 38.2 | 86% | 38% | 2 | 1.0 | 0.0 | 60.2 |
|  | 14.5 | 100% | 20% | 3 | 0.0 | 0.0 | na |
|  | 271 | 71% | 71% | 4 | 6.1 | 0.5 | 78.3 |
|  | 408 | 57% | 80% |  |  |  |  |
|  | 1360 | 57% | 91% |  |  |  |  |

Fig. 4 - 2

Hepatocyte growth factor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 360.395 | 1297.169 | 360.395 | 1273.654 | 360.395 | 883.006 |
| average | 479.908 | 1833.085 | 479.908 | 1829.165 | 479.908 | 1210.215 |
| stdev | 456.701 | 2049.583 | 456.701 | 2049.918 | 456.701 | 899.150 |
| p (t-test) |  | 0.000 |  | 0.000 |  | 0.000 |
| min | 27.880 | 86.357 | 27.880 | 86.357 | 27.880 | 86.357 |
| max | 2833.841 | 7839.221 | 2833.841 | 7839.221 | 2833.841 | 2726.014 |
| n (Samp) | 99 | 12 | 99 | 12 | 99 | 8 |
| n (Pat) | 99 | 12 | 99 | 12 | 99 | 8 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 462.730 | 1297.169 | 462.730 | 1297.169 | 462.730 | 1273.654 |
| average | 724.237 | 1247.930 | 724.237 | 1247.930 | 724.237 | 1221.653 |
| stdev | 877.509 | 836.159 | 877.509 | 836.159 | 877.509 | 937.477 |
| p (t-test) |  | 0.153 |  | 0.153 |  | 0.265 |
| min | 27.880 | 86.357 | 27.880 | 86.357 | 27.880 | 86.357 |
| max | 7839.221 | 2252.946 | 7839.221 | 2252.946 | 7839.221 | 2252.946 |
| n (Samp) | 160 | 6 | 160 | 6 | 160 | 4 |
| n (Pat) | 160 | 6 | 160 | 6 | 160 | 4 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 367.333 | 1297.169 | 367.333 | 1273.654 | 367.333 | 883.006 |
| average | 463.070 | 2137.972 | 463.070 | 2132.093 | 463.070 | 1223.736 |
| stdev | 399.975 | 2414.366 | 399.975 | 2415.658 | 399.975 | 813.371 |
| p (t-test) |  | 0.000 |  | 0.000 |  | 0.000 |
| min | 27.880 | 468.837 | 27.880 | 468.837 | 27.880 | 468.837 |
| max | 2258.303 | 7839.221 | 2258.303 | 7839.221 | 2258.303 | 2726.014 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
|---|---|---|---|---|---|
| 0 hours | 0.83 | 0.075 | 99 | 12 | 0.000 |
| 24 hours | 0.83 | 0.075 | 99 | 12 | 0.000 |
| 48 hours | 0.78 | 0.099 | 99 | 8 | 0.005 | sCr only

| Time prior AKI stage | AUC | SE | nCohort 1 | nCohort 2 | p |
|---|---|---|---|---|---|
| 0 hours | 0.71 | 0.121 | 160 | 6 | 0.085 |
| 24 hours | 0.71 | 0.121 | 160 | 6 | 0.085 |
| 48 hours | 0.67 | 0.151 | 160 | 4 | 0.262 |

UO only

| Time prior AKI stage | AUC | SE | nCohort 1 | nCohort 2 | p |
|---|---|---|---|---|---|
| 0 hours | 0.90 | 0.073 | 84 | 8 | 0.000 |
| 24 hours | 0.90 | 0.073 | 84 | 8 | 0.000 |
| 48 hours | 0.87 | 0.095 | 84 | 6 | 0.000 | sCr or UO

| Time prior AKI stage | Cutoff value | sens | spec | Quartile | OR | 95% CI of OR | |
|---|---|---|---|---|---|---|---|
| 0 hours | 830.44724 | 75% | 83% | 1 |  |  |  |
|  | 634.77395 | 83% | 78% | 2 | 0.0 | 0.0 | na |
|  | 468.66836 | 92% | 68% | 3 | 2.0 | 0.1 | 44.0 |
|  | 518.79418 | 83% | 71% | 4 | 12.3 | 1.2 | 130.0 |
|  | 739.74307 | 75% | 81% |  |  |  |  |
|  | 1069.5472 | 50% | 91% |  |  |  |  |
| 24 hours | 830.44724 | 75% | 83% | 1 |  |  |  |
|  | 634.77395 | 83% | 78% | 2 | 0.0 | 0.0 | na |
|  | 468.66836 | 92% | 68% | 3 | 2.0 | 0.1 | 44.0 |
|  | 518.79418 | 83% | 71% | 4 | 12.3 | 1.2 | 130.0 |
|  | 739.74307 | 75% | 81% |  |  |  |  |

Fig. 4 - 3

| Time prior AKI stage | Cutoff value | sens | spec | Quartile | OR | 95% CI of OR | |
|---|---|---|---|---|---|---|---|
| | 1069.5472 | 50% | 91% | | | | |
| 48 hours | 830.44724 | 75% | 83% | 1 | | | |
| | 468.66836 | 88% | 68% | 2 | 0.0 | 0.0 | na |
| | 85.423471 | 100% | 7% | 3 | 1.0 | 0.0 | 56.5 |
| | 518.79418 | 75% | 71% | 4 | 7.1 | 0.6 | 83.5 |
| | 739.74307 | 75% | 81% | | | | |
| | 1069.5472 | 38% | 91% | | | | | sCr only

| Time prior AKI stage | Cutoff value | sens | spec | Quartile | OR | 95% CI of OR | |
|---|---|---|---|---|---|---|---|
| 0 hours | 634.77395 | 83% | 62% | 1 | | | |
| | 634.77395 | 83% | 62% | 2 | 0.0 | 0.0 | na |
| | 85.423471 | 100% | 5% | 3 | 2.1 | 0.1 | 42.9 |
| | 796.84426 | 67% | 70% | 4 | 3.1 | 0.2 | 46.4 |
| | 1015.7457 | 50% | 80% | | | | |
| | 1339.5034 | 50% | 90% | | | | |
| 24 hours | 634.77395 | 83% | 62% | 1 | | | |
| | 634.77395 | 83% | 62% | 2 | 0.0 | 0.0 | na |
| | 85.423471 | 100% | 5% | 3 | 2.1 | 0.1 | 42.9 |
| | 796.84426 | 67% | 70% | 4 | 3.1 | 0.2 | 46.4 |
| | 1015.7457 | 50% | 80% | | | | |
| | 1339.5034 | 50% | 90% | | | | |
| 48 hours | 896.87138 | 75% | 74% | 1 | | | |
| | 85.423471 | 100% | 5% | 2 | 0.0 | 0.0 | na |
| | 85.423471 | 100% | 5% | 3 | 1.0 | 0.0 | 55.6 |
| | 796.84426 | 75% | 70% | 4 | 2.1 | 0.1 | 42.9 |
| | 1015.7457 | 50% | 80% | | | | |
| | 1339.5034 | 50% | 90% | | | | |

Fig. 4 - 4

Interferon gamma sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 10.950 | 20.700 | 10.950 | 20.650 | 10.950 | 16.500 |
| average | 13.139 | 20.476 | 13.139 | 19.220 | 13.139 | 16.941 |
| stdev | 9.279 | 7.995 | 9.279 | 8.981 | 9.279 | 8.908 |
| p (t-test) |  | 0.003 |  | 0.016 |  | 0.217 |
| min | 0.819 | 5.350 | 0.819 | 5.350 | 0.819 | 3.190 |
| max | 45.400 | 32.400 | 45.400 | 32.400 | 45.400 | 29.300 |
| n (Samp) | 104 | 17 | 104 | 16 | 104 | 10 |
| n (Pat) | 104 | 17 | 104 | 16 | 104 | 10 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 12.650 | 21.850 | 12.650 | 21.850 | 12.650 | 20.700 |
| average | 14.148 | 22.406 | 14.148 | 22.406 | 14.148 | 18.758 |
| stdev | 9.443 | 8.528 | 9.443 | 8.528 | 9.443 | 9.006 |
| p (t-test) |  | 0.016 |  | 0.016 |  | 0.283 |
| min | 0.819 | 5.350 | 0.819 | 5.350 | 0.819 | 3.190 |
| max | 51.900 | 32.400 | 51.900 | 32.400 | 51.900 | 26.300 |
| n (Samp) | 170 | 8 | 170 | 8 | 170 | 5 |
| n (Pat) | 170 | 8 | 170 | 8 | 170 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 10.500 | 20.700 | 10.500 | 16.550 | 10.500 | 12.400 |
| average | 12.151 | 19.323 | 12.151 | 17.197 | 12.151 | 17.046 |
| stdev | 8.210 | 6.895 | 8.210 | 8.131 | 8.210 | 8.406 |
| p (t-test) |  | 0.007 |  | 0.069 |  | 0.134 |
| min | 0.819 | 6.850 | 0.819 | 6.850 | 0.819 | 7.320 |
| max | 37.300 | 29.300 | 37.300 | 29.300 | 37.300 | 29.300 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
|---|---|---|---|---|---|
| 0 hours | 0.74 | 0.072 | 104 | 17 | 0.001 |
| 24 hours | 0.70 | 0.077 | 104 | 16 | 0.010 |
| 48 hours | 0.64 | 0.098 | 104 | 10 | 0.154 | sCr only

| Time prior AKI stage | AUC | SE | nCohort 1 | nCohort 2 | p |
|---|---|---|---|---|---|
| 0 hours | 0.76 | 0.101 | 170 | 8 | 0.011 |
| 24 hours | 0.76 | 0.101 | 170 | 8 | 0.011 |
| 48 hours | 0.66 | 0.135 | 170 | 5 | 0.235 |

UO only

| Time prior AKI stage | AUC | SE | nCohort 1 | nCohort 2 | p |
|---|---|---|---|---|---|
| 0 hours | 0.76 | 0.087 | 85 | 11 | 0.003 |
| 24 hours | 0.69 | 0.097 | 85 | 10 | 0.047 |
| 48 hours | 0.69 | 0.115 | 85 | 7 | 0.097 | sCr or UO

| Time prior AKI stage | Cutoff value | sens | spec | Quartile | OR | 95% CI of OR | |
|---|---|---|---|---|---|---|---|
| 0 hours | 17.5 | 71% | 74% | 1 |  |  |  |
|  | 11.9 | 82% | 58% | 2 | 1.0 | 0.0 | 57.7 |
|  | 6.63 | 94% | 34% | 3 | 7.3 | 0.6 | 82.8 |
|  | 16.6 | 71% | 71% | 4 | 11.9 | 1.1 | 122.5 |
|  | 21.9 | 47% | 82% |  |  |  |  |
|  | 26.6 | 18% | 90% |  |  |  |  |
| 24 hours | 11.6 | 75% | 55% | 1 |  |  |  |
|  | 11.2 | 81% | 53% | 2 | 3.2 | 0.2 | 50.6 |
|  | 6.63 | 94% | 34% | 3 | 4.5 | 0.3 | 59.6 |
|  | 16.6 | 63% | 71% | 4 | 10.5 | 1.0 | 111.9 |

Fig. 4 - 5

|  | 21.9 | 44% | 82% |  |  |  |  |
|---|---|---|---|---|---|---|---|
|  | 26.6 | 19% | 90% |  |  |  |  |
| 48 hours | 11.6 | 70% | 55% | 1 |  |  |  |
|  | 10.9 | 80% | 50% | 2 | 2.0 | 0.1 | 43.7 |
|  | 7.15 | 90% | 35% | 3 | 2.1 | 0.1 | 45.6 |
|  | 16.6 | 50% | 71% | 4 | 5.6 | 0.5 | 69.0 |
|  | 21.9 | 40% | 82% |  |  |  |  |
|  | 26.6 | 10% | 90% |  |  |  |  | sCr only

| Time prior AKI stage | Cutoff value | sens | spec | Quartile | OR | 95% CI of OR | |
|---|---|---|---|---|---|---|---|
| 0 hours | 20.5 | 75% | 76% | 1 |  |  |  |
|  | 18.9 | 88% | 72% | 2 | 0.0 | 0.0 | na |
|  | 5.14 | 100% | 18% | 3 | 2.0 | 0.1 | 42.5 |
|  | 18.3 | 88% | 70% | 4 | 5.4 | 0.5 | 62.1 |
|  | 22 | 50% | 80% |  |  |  |  |
|  | 26.4 | 25% | 90% |  |  |  |  |
| 24 hours | 20.5 | 75% | 76% | 1 |  |  |  |
|  | 18.9 | 88% | 72% | 2 | 0.0 | 0.0 | na |
|  | 5.14 | 100% | 18% | 3 | 2.0 | 0.1 | 42.5 |
|  | 18.3 | 88% | 70% | 4 | 5.4 | 0.5 | 62.1 |
|  | 22 | 50% | 80% |  |  |  |  |
|  | 26.4 | 25% | 90% |  |  |  |  |
| 48 hours | 20.5 | 80% | 76% | 1 |  |  |  |
|  | 20.5 | 80% | 76% | 2 | 0.0 | 0.0 | na |
|  | 3.05 | 100% | 8% | 3 | 0.0 | 0.0 | na |
|  | 18.3 | 80% | 70% | 4 | 4.2 | 0.3 | 53.6 |
|  | 22 | 40% | 80% |  |  |  |  |
|  | 26.4 | 0% | 90% |  |  |  |  |

Fig. 4 - 6

Interleukin-16 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 12.800 | 186.000 | 12.800 | 207.500 | 12.800 | 61.050 |
| average | 60.992 | 286.498 | 60.992 | 281.917 | 60.992 | 143.976 |
| stdev | 174.084 | 342.862 | 174.084 | 320.362 | 174.084 | 187.847 |
| p (t-test) |  | 0.000 |  | 0.000 |  | 0.155 |
| min | 0.265 | 0.265 | 0.265 | 0.265 | 0.265 | 0.265 |
| max | 1100.000 | 1080.000 | 1100.000 | 1010.000 | 1100.000 | 599.000 |
| n (Samp) | 104 | 17 | 104 | 16 | 104 | 10 |
| n (Pat) | 104 | 17 | 104 | 16 | 104 | 10 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 14.500 | 245.000 | 14.500 | 245.000 | 14.500 | 186.000 |
| average | 67.841 | 341.363 | 67.841 | 307.613 | 67.841 | 141.540 |
| stdev | 170.105 | 349.303 | 170.105 | 285.158 | 170.105 | 116.885 |
| p (t-test) |  | 0.000 |  | 0.000 |  | 0.338 |
| min | 0.265 | 15.800 | 0.265 | 15.800 | 0.265 | 15.800 |
| max | 1100.000 | 1080.000 | 1100.000 | 857.000 | 1100.000 | 261.000 |
| n (Samp) | 170 | 8 | 170 | 8 | 170 | 5 |
| n (Pat) | 170 | 8 | 170 | 8 | 170 | 5 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 12.700 | 60.400 | 12.700 | 61.050 | 12.700 | 18.100 |
| average | 56.021 | 221.606 | 56.021 | 234.786 | 56.021 | 144.424 |
| stdev | 155.309 | 319.254 | 155.309 | 333.858 | 155.309 | 220.790 |
| p (t-test) |  | 0.005 |  | 0.004 |  | 0.165 |
| min | 0.265 | 0.265 | 0.265 | 0.265 | 0.265 | 0.265 |
| max | 891.000 | 1010.000 | 891.000 | 1010.000 | 891.000 | 599.000 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
| --- | --- | --- | --- | --- | --- |
| 0 hours | 0.81 | 0.066 | 104 | 17 | 0.000 |
| 24 hours | 0.78 | 0.071 | 104 | 16 | 0.000 |
| 48 hours | 0.71 | 0.095 | 104 | 10 | 0.028 | sCr only

| Time prior AKI stage | AUC | SE | nCohort 1 | nCohort 2 | p |
| --- | --- | --- | --- | --- | --- |
| 0 hours | 0.87 | 0.082 | 170 | 8 | 0.000 |
| 24 hours | 0.87 | 0.083 | 170 | 8 | 0.000 |
| 48 hours | 0.77 | 0.125 | 170 | 5 | 0.029 |

UO only

| Time prior AKI stage | AUC | SE | nCohort 1 | nCohort 2 | p |
| --- | --- | --- | --- | --- | --- |
| 0 hours | 0.77 | 0.087 | 85 | 11 | 0.002 |
| 24 hours | 0.72 | 0.095 | 85 | 10 | 0.020 |
| 48 hours | 0.66 | 0.116 | 85 | 7 | 0.161 | sCr or UO

| Time prior AKI stage | Cutoff value | sens | spec | Quartile | OR | 95% CI of OR | |
| --- | --- | --- | --- | --- | --- | --- | --- |
| 0 hours | 36.1 | 71% | 79% | 1 |  |  |  |
|  | 17.6 | 82% | 62% | 2 | 0.0 | 0.0 | na |
|  | 14.6 | 94% | 59% | 3 | 5.8 | 0.5 | 70.5 |
|  | 22.2 | 71% | 70% | 4 | 16.0 | 1.6 | 159.7 |
|  | 45.4 | 65% | 81% |  |  |  |  |
|  | 92.3 | 59% | 90% |  |  |  |  |
| 24 hours | 17.6 | 75% | 62% | 1 |  |  |  |
|  | 17.5 | 81% | 62% | 2 | 1.0 | 0.0 | 57.7 |
|  | 10.5 | 94% | 46% | 3 | 4.5 | 0.3 | 59.6 |
|  | 22.2 | 63% | 70% | 4 | 14.5 | 1.4 | 147.8 |
|  | 45.4 | 63% | 81% |  |  |  |  |

Fig. 4 - 7

| Time prior AKI stage | Cutoff value | sens | spec | Quartile | OR | 95% CI of OR | |
|---|---|---|---|---|---|---|---|
| | 92.3 | 63% | 90% | | | | |
| 48 hours | 17.5 | 70% | 62% | 1 | | | |
| | 14.6 | 80% | 59% | 2 | 1.0 | 0.0 | 56.0 |
| | 10.5 | 90% | 46% | 3 | 3.2 | 0.2 | 51.4 |
| | 22.2 | 50% | 70% | 4 | 5.6 | 0.5 | 69.0 |
| | 45.4 | 50% | 81% | | | | |
| | 92.3 | 50% | 90% | | | | |

UO only

| Time prior AKI stage | Cutoff value | sens | spec | Quartile | OR | 95% CI of OR | |
|---|---|---|---|---|---|---|---|
| 0 hours | 19.8 | 73% | 65% | 1 | | | |
| | 17.6 | 82% | 61% | 2 | 0.0 | 0.0 | na |
| | 17.5 | 91% | 61% | 3 | 3.3 | 0.2 | 53.6 |
| | 22.2 | 64% | 71% | 4 | 9.5 | 0.8 | 108.7 |
| | 36.1 | 64% | 80% | | | | |
| | 73.5 | 45% | 91% | | | | |
| 24 hours | 17.6 | 70% | 61% | 1 | | | |
| | 17.5 | 80% | 61% | 2 | 1.0 | 0.0 | 57.4 |
| | 10.5 | 90% | 47% | 3 | 3.1 | 0.2 | 51.5 |
| | 22.2 | 50% | 71% | 4 | 5.8 | 0.5 | 73.7 |
| | 36.1 | 50% | 80% | | | | |
| | 73.5 | 50% | 91% | | | | |
| 48 hours | 17.5 | 71% | 61% | 1 | | | |
| | 10.5 | 86% | 47% | 2 | 1.0 | 0.0 | 60.2 |
| | 0 | 100% | 0% | 3 | 2.1 | 0.1 | 47.6 |
| | 22.2 | 43% | 71% | 4 | 3.3 | 0.2 | 54.3 |
| | 36.1 | 43% | 80% | | | | |
| | 73.5 | 43% | 91% | | | | |

Fig. 4 - 8

Interleukin-2 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.324 | 0.522 | 0.324 | 0.450 | 0.324 | 0.414 |
| average | 1.664 | 0.945 | 1.664 | 0.851 | 1.664 | 0.458 |
| stdev | 9.767 | 1.414 | 9.767 | 1.423 | 9.767 | 0.323 |
| p (t-test) |  | 0.800 |  | 0.775 |  | 0.729 |
| min | 0.000 | 0.000 | 0.000 | 0.000 | 0.000 | 0.000 |
| max | 96.860 | 5.260 | 96.860 | 5.260 | 96.860 | 1.141 |
| n (Samp) | 99 | 12 | 99 | 12 | 99 | 8 |
| n (Pat) | 99 | 12 | 99 | 12 | 99 | 8 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.410 | 0.501 | 0.410 | 0.365 | 0.410 | 0.501 |
| average | 1.711 | 0.573 | 1.711 | 0.493 | 1.711 | 0.511 |
| stdev | 8.128 | 0.441 | 8.128 | 0.469 | 8.128 | 0.190 |
| p (t-test) |  | 0.733 |  | 0.715 |  | 0.769 |
| min | 0.000 | 0.107 | 0.000 | 0.107 | 0.000 | 0.301 |
| max | 96.860 | 1.383 | 96.860 | 1.383 | 96.860 | 0.742 |
| n (Samp) | 160 | 6 | 160 | 6 | 160 | 4 |
| n (Pat) | 160 | 6 | 160 | 6 | 160 | 4 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.324 | 0.623 | 0.324 | 0.623 | 0.324 | 0.435 |
| average | 1.922 | 1.232 | 1.922 | 1.152 | 1.922 | 0.489 |
| stdev | 10.604 | 1.685 | 10.604 | 1.692 | 10.604 | 0.374 |
| p (t-test) |  | 0.855 |  | 0.839 |  | 0.743 |
| min | 0.000 | 0.000 | 0.000 | 0.000 | 0.000 | 0.000 |
| max | 96.860 | 5.260 | 96.860 | 5.260 | 96.860 | 1.141 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
|---|---|---|---|---|---|
| 0 hours | 0.65 | 0.090 | 99 | 12 | 0.093 |
| 24 hours | 0.61 | 0.091 | 99 | 12 | 0.214 |
| 48 hours | 0.58 | 0.110 | 99 | 8 | 0.444 | sCr only

| Time prior AKI stage | AUC | SE | nCohort 1 | nCohort 2 | p |
|---|---|---|---|---|---|
| 0 hours | 0.56 | 0.124 | 160 | 6 | 0.631 |
| 24 hours | 0.49 | 0.120 | 160 | 6 | 0.958 |
| 48 hours | 0.56 | 0.151 | 160 | 4 | 0.671 |

UO only

| Time prior AKI stage | AUC | SE | nCohort 1 | nCohort 2 | p |
|---|---|---|---|---|---|
| 0 hours | 0.70 | 0.107 | 84 | 8 | 0.059 |
| 24 hours | 0.69 | 0.108 | 84 | 8 | 0.077 |
| 48 hours | 0.61 | 0.126 | 84 | 6 | 0.392 | sCr or UO

| Time prior AKI stage | Cutoff value | sens | spec | Quartile | OR | 95% CI of OR | |
|---|---|---|---|---|---|---|---|
| 0 hours | 0.3502873 | 75% | 55% | 1 |  |  |  |
|  | 0.2275537 | 83% | 43% | 2 | 2.0 | 0.1 | 44.0 |
|  | 0.1007266 | 92% | 36% | 3 | 4.3 | 0.3 | 58.8 |
|  | 0.4943534 | 50% | 71% | 4 | 5.7 | 0.5 | 69.7 |
|  | 0.7994405 | 25% | 81% |  |  |  |  |
|  | 2.092275 | 8% | 91% |  |  |  |  |
| 24 hours | 0.2275537 | 75% | 43% | 1 |  |  |  |
|  | 0.1603607 | 83% | 41% | 2 | 3.1 | 0.2 | 49.6 |
|  | 0.1007266 | 92% | 36% | 3 | 4.3 | 0.3 | 58.8 |
|  | 0.4943534 | 42% | 71% | 4 | 4.3 | 0.3 | 58.8 |
|  | 0.7994405 | 17% | 81% |  |  |  |  |

Fig. 4 - 9

|  |  | 2.092275 | 8% | 91% |  |  |  |  |
| --- | --- | --- | --- | --- | --- | --- | --- | --- |
| 48 hours |  | 0.3502873 | 75% | 55% | 1 |  |  |  |
|  |  | 0.2275537 | 88% | 43% | 2 | 1.0 | 0.0 | 56.5 |
|  |  | 0 | 100% | 0% | 3 | 4.3 | 0.3 | 59.3 |
|  |  | 0.4943534 | 25% | 71% | 4 | 2.0 | 0.1 | 44.3 |
|  |  | 0.7994405 | 13% | 81% |  |  |  |  |
|  |  | 2.092275 | 0% | 91% |  |  |  |  | sCr only

| Time prior AKI stage | Cutoff value | sens | spec | Quartile | OR | 95% CI of OR | |
| --- | --- | --- | --- | --- | --- | --- | --- |
| 0 hours | 0.2957788 | 83% | 34% | 1 |  |  |  |
|  | 0.2957788 | 83% | 34% | 2 | na | na | na |
|  | 0.1007266 | 100% | 28% | 3 | na | na | na |
|  | 0.6304922 | 33% | 70% | 4 | na | na | na |
|  | 0.8830422 | 17% | 80% |  |  |  |  |
|  | 2.2250583 | 0% | 90% |  |  |  |  |
| 24 hours | 0.1603607 | 83% | 31% | 1 |  |  |  |
|  | 0.1603607 | 83% | 31% | 2 | 2.1 | 0.1 | 43.9 |
|  | 0.1007266 | 100% | 28% | 3 | 3.2 | 0.2 | 47.5 |
|  | 0.6304922 | 17% | 70% | 4 | 0.0 | 0.0 | na |
|  | 0.8830422 | 17% | 80% |  |  |  |  |
|  | 2.2250583 | 0% | 90% |  |  |  |  |
| 48 hours | 0.4241216 | 75% | 52% | 1 |  |  |  |
|  | 0.2957788 | 100% | 34% | 2 | na | na | na |
|  | 0.2957788 | 100% | 34% | 3 | na | na | na |
|  | 0.6304922 | 25% | 70% | 4 | na | na | na |
|  | 0.8830422 | 0% | 80% |  |  |  |  |
|  | 2.2250583 | 0% | 90% |  |  |  |  |

UO only

| Time prior AKI stage | Cutoff value | sens | spec | Quartile | OR | 95% CI of OR | |
| --- | --- | --- | --- | --- | --- | --- | --- |
| 0 hours | 0.4617212 | 75% | 69% | 1 |  |  |  |
|  | 0.3502873 | 88% | 57% | 2 | 0.0 | 0.0 | na |
|  | 0 | 100% | 0% | 3 | 4.6 | 0.3 | 65.0 |
|  | 0.4896804 | 63% | 70% | 4 | 3.3 | 0.2 | 54.3 |
|  | 0.8413233 | 38% | 81% |  |  |  |  |
|  | 2.7380733 | 13% | 90% |  |  |  |  |
| 24 hours | 0.4617212 | 75% | 69% | 1 |  |  |  |
|  | 0.3502873 | 88% | 57% | 2 | na | na | na |
|  | 0 | 100% | 0% | 3 | na | na | na |
|  | 0.4896804 | 63% | 70% | 4 | na | na | na |
|  | 0.8413233 | 25% | 81% |  |  |  |  |
|  | 2.7380733 | 13% | 90% |  |  |  |  |
| 48 hours | 0.3502873 | 83% | 57% | 1 |  |  |  |
|  | 0.3502873 | 83% | 57% | 2 | 0.0 | 0.0 | na |
|  | 0 | 100% | 0% | 3 | 3.3 | 0.2 | 55.1 |
|  | 0.4896804 | 33% | 70% | 4 | 2.0 | 0.1 | 45.6 |
|  | 0.8413233 | 17% | 81% |  |  |  |  |
|  | 2.7380733 | 0% | 90% |  |  |  |  |

Fig. 4 - 10

Interleukin-12 p40 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 6.940 | 4.762 | 6.940 | 3.096 | 6.940 | 3.096 |
| average | 10.369 | 9.575 | 10.369 | 8.958 | 10.369 | 11.752 |
| stdev | 13.459 | 14.343 | 13.459 | 14.602 | 13.459 | 17.367 |
| p (t-test) |  | 0.848 |  | 0.735 |  | 0.785 |
| min | 0.000 | 0.000 | 0.000 | 0.000 | 0.000 | 0.000 |
| max | 66.881 | 49.268 | 66.881 | 49.268 | 66.881 | 49.268 |
| n (Samp) | 99 | 12 | 99 | 12 | 99 | 8 |
| n (Pat) | 99 | 12 | 99 | 12 | 99 | 8 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 8.396 | 6.658 | 8.396 | 4.246 | 8.396 | 13.383 |
| average | 11.419 | 14.892 | 11.419 | 13.658 | 11.419 | 19.008 |
| stdev | 13.224 | 18.858 | 13.224 | 19.671 | 13.224 | 22.903 |
| p (t-test) |  | 0.535 |  | 0.690 |  | 0.267 |
| min | 0.000 | 0.000 | 0.000 | 0.000 | 0.000 | 0.000 |
| max | 66.881 | 49.268 | 66.881 | 49.268 | 66.881 | 49.268 |
| n (Samp) | 160 | 6 | 160 | 6 | 160 | 4 |
| n (Pat) | 160 | 6 | 160 | 6 | 160 | 4 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 7.005 | 2.218 | 7.005 | 2.218 | 7.005 | 2.218 |
| average | 10.395 | 9.352 | 10.395 | 9.352 | 10.395 | 11.208 |
| stdev | 12.676 | 16.827 | 12.676 | 16.827 | 12.676 | 19.343 |
| p (t-test) |  | 0.830 |  | 0.830 |  | 0.884 |
| min | 0.000 | 0.000 | 0.000 | 0.000 | 0.000 | 0.000 |
| max | 61.635 | 49.268 | 61.635 | 49.268 | 61.635 | 49.268 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
| --- | --- | --- | --- | --- | --- |
| 0 hours | 0.47 | 0.087 | 99 | 12 | 0.731 |
| 24 hours | 0.44 | 0.085 | 99 | 12 | 0.470 |
| 48 hours | 0.50 | 0.106 | 99 | 8 | 0.972 | sCr only

| Time prior AKI stage | AUC | SE | nCohort 1 | nCohort 2 | p |
| --- | --- | --- | --- | --- | --- |
| 0 hours | 0.53 | 0.122 | 160 | 6 | 0.808 |
| 24 hours | 0.47 | 0.118 | 160 | 6 | 0.801 |
| 48 hours | 0.57 | 0.151 | 160 | 4 | 0.649 |

UO only

| Time prior AKI stage | AUC | SE | nCohort 1 | nCohort 2 | p |
| --- | --- | --- | --- | --- | --- |
| 0 hours | 0.41 | 0.100 | 84 | 8 | 0.372 |
| 24 hours | 0.41 | 0.100 | 84 | 8 | 0.372 |
| 48 hours | 0.44 | 0.117 | 84 | 6 | 0.587 | sCr or UO

| Time prior AKI stage | Cutoff value | sens | spec | Quartile | OR | 95% CI of OR | |
| --- | --- | --- | --- | --- | --- | --- | --- |
| 0 hours | 0.2877802 | 75% | 30% | 1 |  |  |  |
|  | 0 | 100% | 0% | 2 | 1.6 | 0.3 | 9.3 |
|  | 0 | 100% | 0% | 3 | 2.2 | 0.4 | 11.0 |
|  | 14.053599 | 17% | 71% | 4 | 1.6 | 0.3 | 9.7 |
|  | 18.778128 | 17% | 81% |  |  |  |  |
|  | 26.148501 | 8% | 91% |  |  |  |  |
| 24 hours | 0 | 100% | 0% | 1 |  |  |  |
|  | 0 | 100% | 0% | 2 | 1.6 | 0.3 | 9.3 |
|  | 0 | 100% | 0% | 3 | 1.6 | 0.3 | 9.3 |
|  | 14.053599 | 17% | 71% | 4 | 2.3 | 0.4 | 11.5 |
|  | 18.778128 | 17% | 81% |  |  |  |  |

Fig. 4 - 11

| Time prior AKI stage | Cutoff value | sens | spec | Quartile | OR | 95% CI of OR | |
|---|---|---|---|---|---|---|---|
| | 26.148501 | 8% | 91% | | | | |
| 48 hours | 0.2877802 | 75% | 30% | 1 | | | |
| | 0 | 100% | 0% | 2 | 0.5 | 0.0 | 10.6 |
| | 0 | 100% | 0% | 3 | 1.6 | 0.3 | 9.4 |
| | 14.053599 | 25% | 71% | 4 | 1.0 | 0.1 | 8.7 |
| | 18.778128 | 25% | 81% | | | | |
| | 26.148501 | 13% | 91% | | | | | sCr only

| Time prior AKI stage | Cutoff value | sens | spec | Quartile | OR | 95% CI of OR | |
|---|---|---|---|---|---|---|---|
| 0 hours | 2.5686249 | 83% | 32% | 1 | | | |
| | 2.5686249 | 83% | 32% | 2 | 3.1 | 0.2 | 46.4 |
| | 0 | 100% | 0% | 3 | 0.0 | 0.0 | na |
| | 14.524637 | 33% | 70% | 4 | 2.0 | 0.1 | 41.7 |
| | 18.806933 | 33% | 80% | | | | |
| | 27.054283 | 17% | 90% | | | | |
| 24 hours | 0 | 100% | 0% | 1 | | | |
| | 0 | 100% | 0% | 2 | 0.0 | 0.0 | na |
| | 0 | 100% | 0% | 3 | 1.0 | 0.1 | 7.8 |
| | 14.524637 | 33% | 70% | 4 | 1.0 | 0.1 | 8.0 |
| | 18.806933 | 33% | 80% | | | | |
| | 27.054283 | 17% | 90% | | | | |
| 48 hours | 2.5686249 | 75% | 32% | 1 | | | |
| | 0 | 100% | 0% | 2 | 1.0 | 0.0 | 55.6 |
| | 0 | 100% | 0% | 3 | 0.0 | 0.0 | na |
| | 14.524637 | 50% | 70% | 4 | 2.1 | 0.1 | 42.9 |
| | 18.806933 | 50% | 80% | | | | |
| | 27.054283 | 25% | 90% | | | | |

UO only

| Time prior AKI stage | Cutoff value | sens | spec | Quartile | OR | 95% CI of OR | |
|---|---|---|---|---|---|---|---|
| 0 hours | 0 | 100% | 0% | 1 | | | |
| | 0 | 100% | 0% | 2 | 2.1 | 0.1 | 47.6 |
| | 0 | 100% | 0% | 3 | 4.6 | 0.3 | 65.0 |
| | 14.053599 | 13% | 70% | 4 | 1.0 | 0.0 | 60.2 |
| | 18.778128 | 13% | 81% | | | | |
| | 24.423486 | 13% | 90% | | | | |
| 24 hours | 0 | 100% | 0% | 1 | | | |
| | 0 | 100% | 0% | 2 | 2.1 | 0.1 | 47.6 |
| | 0 | 100% | 0% | 3 | 4.6 | 0.3 | 65.0 |
| | 14.053599 | 13% | 70% | 4 | 1.0 | 0.0 | 60.2 |
| | 18.778128 | 13% | 81% | | | | |
| | 24.423486 | 13% | 90% | | | | |
| 48 hours | 0 | 100% | 0% | 1 | | | |
| | 0 | 100% | 0% | 2 | 1.0 | 0.0 | 63.4 |
| | 0 | 100% | 0% | 3 | 2.1 | 0.1 | 47.6 |
| | 14.053599 | 17% | 70% | 4 | 2.2 | 0.1 | 50.2 |
| | 18.778128 | 17% | 81% | | | | |
| | 24.423486 | 17% | 90% | | | | |

Fig. 4 - 12

Matrix metalloproteinase-2 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 27.450 | 55.600 | 27.450 | 57.300 | 27.450 | 33.250 |
| average | 34.955 | 125.176 | 34.955 | 128.300 | 34.955 | 47.050 |
| stdev | 32.704 | 299.597 | 32.704 | 308.608 | 32.704 | 35.697 |
| p (t-test) |  | 0.003 |  | 0.003 |  | 0.270 |
| min | 0.600 | 11.000 | 0.600 | 11.000 | 0.600 | 11.000 |
| max | 293.000 | 1280.000 | 293.000 | 1280.000 | 293.000 | 116.000 |
| n (Samp) | 104 | 17 | 104 | 16 | 104 | 10 |
| n (Pat) | 104 | 17 | 104 | 16 | 104 | 10 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 28.000 | 76.250 | 28.000 | 76.250 | 28.000 | 81.900 |
| average | 44.722 | 76.250 | 44.722 | 76.250 | 44.722 | 74.720 |
| stdev | 102.888 | 36.398 | 102.888 | 36.398 | 102.888 | 38.522 |
| p (t-test) |  | 0.390 |  | 0.390 |  | 0.517 |
| min | 0.600 | 11.000 | 0.600 | 11.000 | 0.600 | 11.000 |
| max | 1280.000 | 129.000 | 1280.000 | 129.000 | 1280.000 | 116.000 |
| n (Samp) | 170 | 8 | 170 | 8 | 170 | 5 |
| n (Pat) | 170 | 8 | 170 | 8 | 170 | 5 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 28.000 | 32.700 | 28.000 | 33.250 | 28.000 | 32.700 |
| average | 36.566 | 157.173 | 36.566 | 165.370 | 36.566 | 37.500 |
| stdev | 35.106 | 373.944 | 35.106 | 392.435 | 35.106 | 24.576 |
| p (t-test) |  | 0.004 |  | 0.003 |  | 0.945 |
| min | 0.600 | 19.000 | 0.600 | 19.200 | 0.600 | 12.400 |
| max | 293.000 | 1280.000 | 293.000 | 1280.000 | 293.000 | 81.900 |
| n (Samp) | 85 | 11 | 85 | 10 | 85 | 7 |
| n (Pat) | 85 | 11 | 85 | 10 | 85 | 7 | sCr or UO

| Time prior AKI stage | AUC | SE | nCohort 1 | nCohort 2 | p |
| --- | --- | --- | --- | --- | --- |
| 0 hours | 0.68 | 0.076 | 104 | 17 | 0.019 |
| 24 hours | 0.68 | 0.078 | 104 | 16 | 0.020 |
| 48 hours | 0.58 | 0.099 | 104 | 10 | 0.421 | sCr only

| Time prior AKI stage | AUC | SE | nCohort 1 | nCohort 2 | p |
| --- | --- | --- | --- | --- | --- |
| 0 hours | 0.81 | 0.093 | 170 | 8 | 0.001 |
| 24 hours | 0.81 | 0.093 | 170 | 8 | 0.001 |
| 48 hours | 0.76 | 0.126 | 170 | 5 | 0.038 |

UO only

| Time prior AKI stage | AUC | SE | nCohort 1 | nCohort 2 | p |
| --- | --- | --- | --- | --- | --- |
| 0 hours | 0.61 | 0.095 | 85 | 11 | 0.269 |
| 24 hours | 0.60 | 0.100 | 85 | 10 | 0.304 |
| 48 hours | 0.53 | 0.116 | 85 | 7 | 0.816 | sCr or UO

| Time prior AKI stage | Cutoff value | sens | spec | Quartile | OR | 95% CI of OR | |
| --- | --- | --- | --- | --- | --- | --- | --- |
| 0 hours | 31.2 | 71% | 63% | 1 |  |  |  |
|  | 20.6 | 82% | 29% | 2 | 0.6 | 0.1 | 3.8 |
|  | 18.5 | 94% | 21% | 3 | 1.0 | 0.2 | 4.3 |
|  | 34.5 | 53% | 70% | 4 | 3.7 | 1.3 | 10.3 |
|  | 42.7 | 53% | 81% |  |  |  |  |
|  | 61.1 | 41% | 90% |  |  |  |  |
| 24 hours | 22 | 75% | 34% | 1 |  |  |  |
|  | 20.6 | 81% | 29% | 2 | 0.6 | 0.1 | 3.8 |
|  | 18.5 | 94% | 21% | 3 | 0.6 | 0.1 | 3.8 |
|  | 34.5 | 56% | 70% | 4 | 3.9 | 1.4 | 10.9 |
|  | 42.7 | 56% | 81% |  |  |  |  |

Fig. 4 - 13

| | | | | | | | |
|---|---|---|---|---|---|---|---|
| | 61.1 | 44% | 90% | | | | |
| 48 hours | 22 | 70% | 34% | 1 | | | |
| | 20 | 80% | 25% | 2 | 1.0 | 0.1 | 7.9 |
| | 11 | 90% | 4% | 3 | 1.0 | 0.1 | 8.3 |
| | 34.5 | 40% | 70% | 4 | 2.1 | 0.4 | 10.6 |
| | 42.7 | 40% | 81% | | | | |
| | 61.1 | 30% | 90% | | | | | sCr only

| Time prior AKI stage | Cutoff value | sens | spec | Quartile | OR | 95% CI of OR | |
|---|---|---|---|---|---|---|---|
| 0 hours | 63.1 | 75% | 91% | 1 | | | |
| | 53.4 | 88% | 84% | 2 | 0.0 | 0.0 | na |
| | 9.49 | 100% | 2% | 3 | 0.0 | 0.0 | na |
| | 37.6 | 88% | 70% | 4 | 7.9 | 0.8 | 82.0 |
| | 45.9 | 88% | 80% | | | | |
| | 62.8 | 75% | 90% | | | | |
| 24 hours | 63.1 | 75% | 91% | 1 | | | |
| | 53.4 | 88% | 84% | 2 | 0.0 | 0.0 | na |
| | 9.49 | 100% | 2% | 3 | 0.0 | 0.0 | na |
| | 37.6 | 88% | 70% | 4 | 7.9 | 0.8 | 82.0 |
| | 45.9 | 88% | 80% | | | | |
| | 62.8 | 75% | 90% | | | | |
| 48 hours | 77.3 | 80% | 94% | 1 | | | |
| | 77.3 | 80% | 94% | 2 | 0.0 | 0.0 | na |
| | 9.49 | 100% | 2% | 3 | 0.0 | 0.0 | na |
| | 37.6 | 80% | 70% | 4 | 4.2 | 0.3 | 53.6 |
| | 45.9 | 80% | 80% | | | | |
| | 62.8 | 80% | 90% | | | | |

UO only

| Time prior AKI stage | Cutoff value | sens | spec | Quartile | OR | 95% CI of OR | |
|---|---|---|---|---|---|---|---|
| 0 hours | 22 | 73% | 29% | 1 | | | |
| | 20.6 | 82% | 25% | 2 | 0.3 | 0.0 | 5.0 |
| | 19 | 91% | 18% | 3 | 1.0 | 0.2 | 4.5 |
| | 35.1 | 36% | 71% | 4 | 1.4 | 0.4 | 5.3 |
| | 42.7 | 36% | 80% | | | | |
| | 61.1 | 27% | 91% | | | | |
| 24 hours | 22 | 70% | 29% | 1 | | | |
| | 20.6 | 80% | 25% | 2 | 1.0 | 0.1 | 8.1 |
| | 19.4 | 90% | 21% | 3 | 1.0 | 0.1 | 8.1 |
| | 35.1 | 40% | 71% | 4 | 2.1 | 0.4 | 11.1 |
| | 42.7 | 40% | 80% | | | | |
| | 61.1 | 30% | 91% | | | | |
| 48 hours | 22 | 71% | 29% | 1 | | | |
| | 19.4 | 86% | 21% | 2 | 0.5 | 0.0 | 10.8 |
| | 0.6 | 100% | 1% | 3 | 1.0 | 0.1 | 8.6 |
| | 35.1 | 29% | 71% | 4 | 1.0 | 0.1 | 8.6 |
| | 42.7 | 29% | 80% | | | | |
| | 61.1 | 14% | 91% | | | | |

Fig. 4 - 14

Midkine sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 0.079 | 0.677 | 0.079 | 0.279 | 0.079 | 0.273 |
| average | 0.354 | 1.061 | 0.354 | 0.713 | 0.354 | 0.374 |
| stdev | 1.120 | 1.185 | 1.120 | 1.061 | 1.120 | 0.307 |
| p (t-test) |  | 0.036 |  | 0.274 |  | 0.957 |
| min | 0.000 | 0.058 | 0.000 | 0.058 | 0.000 | 0.058 |
| max | 8.902 | 4.142 | 8.902 | 4.142 | 8.902 | 0.923 |
| n (Samp) | 67 | 14 | 67 | 14 | 67 | 9 |
| n (Pat) | 67 | 14 | 67 | 14 | 67 | 9 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 0.132 | 0.558 | 0.132 | 0.279 | 0.132 | 0.285 |
| average | 0.351 | 0.992 | 0.351 | 0.869 | 0.351 | 0.462 |
| stdev | 0.966 | 1.327 | 0.966 | 1.384 | 0.966 | 0.375 |
| p (t-test) |  | 0.079 |  | 0.156 |  | 0.797 |
| min | 0.000 | 0.073 | 0.000 | 0.062 | 0.000 | 0.073 |
| max | 8.902 | 4.142 | 8.902 | 4.142 | 8.902 | 1.010 |
| n (Samp) | 116 | 8 | 116 | 8 | 116 | 5 |
| n (Pat) | 116 | 8 | 116 | 8 | 116 | 5 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 0.078 | 0.960 | 0.078 | 0.478 | 0.078 | 0.258 |
| average | 0.404 | 1.060 | 0.404 | 0.574 | 0.404 | 0.390 |
| stdev | 1.251 | 0.967 | 1.251 | 0.447 | 1.251 | 0.337 |
| p (t-test) |  | 0.163 |  | 0.708 |  | 0.978 |
| min | 0.000 | 0.058 | 0.000 | 0.058 | 0.000 | 0.058 |
| max | 8.902 | 3.139 | 8.902 | 1.238 | 8.902 | 0.923 |
| n (Samp) | 51 | 8 | 51 | 8 | 51 | 6 |
| n (Pat) | 51 | 8 | 51 | 8 | 51 | 6 | sCr or UO

| Time prior AKI stage | AUC | SE | nCohort 1 | nCohort 2 | p |
|---|---|---|---|---|---|
| 0 hours | 0.83 | 0.070 | 67 | 14 | 0.000 |
| 24 hours | 0.73 | 0.081 | 67 | 14 | 0.004 |
| 48 hours | 0.71 | 0.102 | 67 | 9 | 0.043 | sCr only

| Time prior AKI stage | AUC | SE | nCohort 1 | nCohort 2 | p |
|---|---|---|---|---|---|
| 0 hours | 0.80 | 0.096 | 116 | 8 | 0.002 |
| 24 hours | 0.69 | 0.107 | 116 | 8 | 0.084 |
| 48 hours | 0.72 | 0.131 | 116 | 5 | 0.088 |

UO only

| Time prior AKI stage | AUC | SE | nCohort 1 | nCohort 2 | p |
|---|---|---|---|---|---|
| 0 hours | 0.83 | 0.092 | 51 | 8 | 0.000 |
| 24 hours | 0.75 | 0.105 | 51 | 8 | 0.017 |
| 48 hours | 0.68 | 0.126 | 51 | 6 | 0.147 |

Fig. 4 - 15

Serum amyloid P-component sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 1.543 | 12.744 | 1.543 | 12.744 | 1.543 | 9.597 |
| average | 5.522 | 25.254 | 5.522 | 25.254 | 5.522 | 9.203 |
| stdev | 10.915 | 41.036 | 10.915 | 41.036 | 10.915 | 7.157 |
| p (t-test) |  | 0.000 |  | 0.000 |  | 0.352 |
| min | 0.093 | 0.431 | 0.093 | 0.431 | 0.093 | 0.431 |
| max | 58.307 | 152.000 | 58.307 | 152.000 | 58.307 | 22.353 |
| n (Samp) | 96 | 12 | 96 | 12 | 96 | 8 |
| n (Pat) | 96 | 12 | 96 | 12 | 96 | 8 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 2.591 | 14.400 | 2.591 | 14.400 | 2.591 | 12.744 |
| average | 7.376 | 16.430 | 7.376 | 16.430 | 7.376 | 15.112 |
| stdev | 15.365 | 11.373 | 15.365 | 11.373 | 15.365 | 14.188 |
| p (t-test) |  | 0.156 |  | 0.156 |  | 0.321 |
| min | 0.093 | 0.431 | 0.093 | 0.431 | 0.093 | 0.431 |
| max | 152.000 | 34.528 | 152.000 | 34.528 | 152.000 | 34.528 |
| n (Samp) | 157 | 6 | 157 | 6 | 157 | 4 |
| n (Pat) | 157 | 6 | 157 | 6 | 157 | 4 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 1.585 | 12.398 | 1.585 | 12.398 | 1.585 | 9.597 |
| average | 5.882 | 31.429 | 5.882 | 31.429 | 5.882 | 10.025 |
| stdev | 11.052 | 49.792 | 11.052 | 49.792 | 11.052 | 7.249 |
| p (t-test) |  | 0.000 |  | 0.000 |  | 0.370 |
| min | 0.093 | 2.799 | 0.093 | 2.799 | 0.093 | 2.799 |
| max | 58.307 | 152.000 | 58.307 | 152.000 | 58.307 | 22.353 |
| n (Samp) | 82 | 8 | 82 | 8 | 82 | 6 |
| n (Pat) | 82 | 8 | 82 | 8 | 82 | 6 | sCr or UO

| Time prior AKI stage | AUC | SE | nCohort 1 | nCohort 2 | p |
| --- | --- | --- | --- | --- | --- |
| 0 hours | 0.82 | 0.077 | 96 | 12 | 0.000 |
| 24 hours | 0.82 | 0.077 | 96 | 12 | 0.000 |
| 48 hours | 0.74 | 0.103 | 96 | 8 | 0.018 | sCr only

| Time prior AKI stage | AUC | SE | nCohort 1 | nCohort 2 | p |
| --- | --- | --- | --- | --- | --- |
| 0 hours | 0.76 | 0.116 | 157 | 6 | 0.028 |
| 24 hours | 0.76 | 0.116 | 157 | 6 | 0.028 |
| 48 hours | 0.69 | 0.149 | 157 | 4 | 0.206 |

UO only

| Time prior AKI stage | AUC | SE | nCohort 1 | nCohort 2 | p |
| --- | --- | --- | --- | --- | --- |
| 0 hours | 0.86 | 0.086 | 82 | 8 | 0.000 |
| 24 hours | 0.86 | 0.086 | 82 | 8 | 0.000 |
| 48 hours | 0.81 | 0.110 | 82 | 6 | 0.005 | sCr or UO

| Time prior AKI stage | Cutoff value | sens | spec | Quartile | OR | 95% CI of OR | |
| --- | --- | --- | --- | --- | --- | --- | --- |
| 0 hours | 11.50007 | 75% | 89% | 1 |  |  |  |
|  | 3.3281087 | 83% | 73% | 2 | 0.0 | 0.0 | na |
|  | 2.7653229 | 92% | 66% | 3 | 2.1 | 0.1 | 45.9 |
|  | 3.26012 | 83% | 71% | 4 | 13.0 | 1.2 | 138.0 |
|  | 6.0497473 | 75% | 80% |  |  |  |  |
|  | 13.046066 | 42% | 91% |  |  |  |  |
| 24 hours | 11.50007 | 75% | 89% | 1 |  |  |  |
|  | 3.3281087 | 83% | 73% | 2 | 0.0 | 0.0 | na |
|  | 2.7653229 | 92% | 66% | 3 | 2.1 | 0.1 | 45.9 |
|  | 3.26012 | 83% | 71% | 4 | 13.0 | 1.2 | 138.0 |
|  | 6.0497473 | 75% | 80% |  |  |  |  |

Fig. 4 - 16

|  | | 13.046066 | 42% | 91% | | | | |
|---|---|---|---|---|---|---|---|---|
| 48 hours | | 3.3281087 | 75% | 73% | 1 | | | |
| | | 2.7653229 | 88% | 66% | 2 | 0.0 | 0.0 | na |
| | | 0.3460298 | 100% | 13% | 3 | 2.1 | 0.1 | 46.2 |
| | | 3.26012 | 75% | 71% | 4 | 6.0 | 0.5 | 74.3 |
| | | 6.0497473 | 63% | 80% | | | | |
| | | 13.046066 | 13% | 91% | | | | | sCr only

| Time prior AKI stage | Cutoff value | sens | spec | Quartile | OR | 95% CI of OR | |
|---|---|---|---|---|---|---|---|
| 0 hours | 12.354421 | 83% | 84% | 1 | | | |
| | 12.354421 | 83% | 84% | 2 | 0.0 | 0.0 | na |
| | 0.3715084 | 100% | 10% | 3 | 0.0 | 0.0 | na |
| | 5.8831817 | 83% | 70% | 4 | 5.4 | 0.5 | 63.2 |
| | 10.004281 | 83% | 81% | | | | |
| | 20.878347 | 33% | 90% | | | | |
| 24 hours | 12.354421 | 83% | 84% | 1 | | | |
| | 12.354421 | 83% | 84% | 2 | 0.0 | 0.0 | na |
| | 0.3715084 | 100% | 10% | 3 | 0.0 | 0.0 | na |
| | 5.8831817 | 83% | 70% | 4 | 5.4 | 0.5 | 63.2 |
| | 10.004281 | 83% | 81% | | | | |
| | 20.878347 | 33% | 90% | | | | |
| 48 hours | 12.354421 | 75% | 84% | 1 | | | |
| | 0.3715084 | 100% | 10% | 2 | 0.0 | 0.0 | na |
| | 0.3715084 | 100% | 10% | 3 | 0.0 | 0.0 | na |
| | 5.8831817 | 75% | 70% | 4 | 3.1 | 0.2 | 46.5 |
| | 10.004281 | 75% | 81% | | | | |
| | 20.878347 | 25% | 90% | | | | |

Fig. 4 - 17

Matrix metalloproteinase-9 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 2548.413 | 11219.932 | 2548.413 | 11219.932 | 2548.413 | 28219.287 |
| average | 12780.174 | 30494.072 | 12780.174 | 30381.575 | 12780.174 | 42212.294 |
| stdev | 27271.206 | 39052.282 | 27271.206 | 39145.007 | 27271.206 | 43754.117 |
| p (t-test) |  | 0.046 |  | 0.047 |  | 0.006 |
| min | 32.788 | 413.469 | 32.788 | 221.527 | 32.788 | 331.428 |
| max | 159217.283 | 112264.995 | 159217.283 | 112264.995 | 159217.283 | 112264.995 |
| n (Samp) | 98 | 12 | 98 | 12 | 98 | 8 |
| n (Pat) | 98 | 12 | 98 | 12 | 98 | 8 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 5297.651 | 11219.932 | 5297.651 | 11219.932 | 5297.651 | 11219.932 |
| average | 20060.467 | 19955.002 | 20060.467 | 19730.008 | 20060.467 | 26298.712 |
| stdev | 35159.374 | 31036.604 | 35159.374 | 31200.983 | 35159.374 | 37720.689 |
| p (t-test) |  | 0.994 |  | 0.982 |  | 0.727 |
| min | 32.788 | 413.469 | 32.788 | 221.527 | 32.788 | 413.469 |
| max | 176209.055 | 82341.516 | 176209.055 | 82341.516 | 176209.055 | 82341.516 |
| n (Samp) | 159 | 6 | 159 | 6 | 159 | 4 |
| n (Pat) | 159 | 6 | 159 | 6 | 159 | 4 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 3489.739 | 27000.645 | 3489.739 | 27000.645 | 3489.739 | 61123.989 |
| average | 14156.222 | 42317.708 | 14156.222 | 42317.708 | 14156.222 | 54141.052 |
| stdev | 29193.825 | 43560.839 | 29193.825 | 43560.839 | 29193.825 | 44527.680 |
| p (t-test) |  | 0.015 |  | 0.015 |  | 0.002 |
| min | 32.788 | 1903.662 | 32.788 | 1903.662 | 32.788 | 331.428 |
| max | 159217.283 | 112264.995 | 159217.283 | 112264.995 | 159217.283 | 112264.995 |
| n (Samp) | 83 | 8 | 83 | 8 | 83 | 6 |
| n (Pat) | 83 | 8 | 83 | 8 | 83 | 6 | sCr or UO

| Time prior AKI stage | AUC | SE | nCohort 1 | nCohort 2 | p |
|---|---|---|---|---|---|
| 0 hours | 0.69 | 0.088 | 98 | 12 | 0.029 |
| 24 hours | 0.67 | 0.090 | 98 | 12 | 0.061 |
| 48 hours | 0.70 | 0.107 | 98 | 8 | 0.065 | sCr only

| Time prior AKI stage | AUC | SE | nCohort 1 | nCohort 2 | p |
|---|---|---|---|---|---|
| 0 hours | 0.57 | 0.124 | 159 | 6 | 0.583 |
| 24 hours | 0.53 | 0.122 | 159 | 6 | 0.810 |
| 48 hours | 0.60 | 0.152 | 159 | 4 | 0.501 |

UO only

| Time prior AKI stage | AUC | SE | nCohort 1 | nCohort 2 | p |
|---|---|---|---|---|---|
| 0 hours | 0.75 | 0.103 | 83 | 8 | 0.017 |
| 24 hours | 0.75 | 0.103 | 83 | 8 | 0.017 |
| 48 hours | 0.75 | 0.118 | 83 | 6 | 0.032 | sCr or UO

| Time prior AKI stage | Cutoff value | sens | spec | Quartile | OR | 95% CI of OR | |
|---|---|---|---|---|---|---|---|
| 0 hours | 2026.199 | 75% | 45% | 1 |  |  |  |
|  | 1859.8427 | 83% | 42% | 2 | 3.1 | 0.2 | 49.6 |
|  | 1482.9443 | 92% | 38% | 3 | 1.0 | 0.0 | 58.6 |
|  | 6948.9906 | 67% | 70% | 4 | 8.7 | 0.8 | 96.4 |
|  | 10936.729 | 50% | 81% |  |  |  |  |
|  | 44000 | 25% | 91% |  |  |  |  |
| 24 hours | 2026.199 | 75% | 45% | 1 |  |  |  |
|  | 1859.8427 | 83% | 42% | 2 | 1.0 | 0.1 | 8.0 |
|  | 397.66566 | 92% | 14% | 3 | 0.5 | 0.0 | 10.6 |

Fig. 4 - 18

|  | Cutoff value | sens | spec | Quartile | OR | 95% CI of OR | |
|---|---|---|---|---|---|---|---|
|  | 6948.9906 | 67% | 70% | 4 | 4.2 | 1.0 | 17.4 |
|  | 10936.729 | 50% | 81% |  |  |  |  |
|  | 44000 | 25% | 91% |  |  |  |  |
| 48 hours | 7647.3802 | 75% | 71% | 1 |  |  |  |
|  | 397.66566 | 88% | 14% | 2 | 0.0 | 0.0 | na |
|  | 307.74357 | 100% | 11% | 3 | 0.5 | 0.0 | 10.7 |
|  | 6948.9906 | 75% | 70% | 4 | 2.7 | 0.6 | 12.8 |
|  | 10936.729 | 63% | 81% |  |  |  |  |
|  | 44000 | 38% | 91% |  |  |  |  | sCr only

| Time prior AKI stage | Cutoff value | sens | spec | Quartile | OR | 95% CI of OR | |
|---|---|---|---|---|---|---|---|
| 0 hours | 1482.9443 | 83% | 28% | 1 |  |  |  |
|  | 1482.9443 | 83% | 28% | 2 | 1.0 | 0.0 | 55.6 |
|  | 397.66566 | 100% | 11% | 3 | 3.2 | 0.2 | 47.6 |
|  | 12108.63 | 50% | 70% | 4 | 1.0 | 0.0 | 54.2 |
|  | 25535.993 | 17% | 81% |  |  |  |  |
|  | 70809.57 | 17% | 91% |  |  |  |  |
| 24 hours | 397.66566 | 83% | 11% | 1 |  |  |  |
|  | 397.66566 | 83% | 11% | 2 | 0.0 | 0.0 | na |
|  | 200.74676 | 100% | 5% | 3 | 1.5 | 0.3 | 8.7 |
|  | 12108.63 | 50% | 70% | 4 | 0.5 | 0.0 | 9.9 |
|  | 25535.993 | 17% | 81% |  |  |  |  |
|  | 70809.57 | 17% | 91% |  |  |  |  |
| 48 hours | 9616.4598 | 75% | 67% | 1 |  |  |  |
|  | 397.66566 | 100% | 11% | 2 | 0.0 | 0.0 | na |
|  | 397.66566 | 100% | 11% | 3 | 2.0 | 0.1 | 41.8 |
|  | 12108.63 | 50% | 70% | 4 | 1.0 | 0.0 | 54.3 |
|  | 25535.993 | 25% | 81% |  |  |  |  |
|  | 70809.57 | 25% | 91% |  |  |  |  |

UO only

| Time prior AKI stage | Cutoff value | sens | spec | Quartile | OR | 95% CI of OR | |
|---|---|---|---|---|---|---|---|
| 0 hours | 7647.3802 | 75% | 69% | 1 |  |  |  |
|  | 2026.199 | 88% | 40% | 2 | na | na | na |
|  | 1859.8427 | 100% | 35% | 3 | na | na | na |
|  | 8042.5801 | 63% | 71% | 4 | na | na | na |
|  | 12774.377 | 50% | 81% |  |  |  |  |
|  | 46014.881 | 38% | 90% |  |  |  |  |
| 24 hours | 7647.3802 | 75% | 69% | 1 |  |  |  |
|  | 2026.199 | 88% | 40% | 2 | na | na | na |
|  | 1859.8427 | 100% | 35% | 3 | na | na | na |
|  | 8042.5801 | 63% | 71% | 4 | na | na | na |
|  | 12774.377 | 50% | 81% |  |  |  |  |
|  | 46014.881 | 38% | 90% |  |  |  |  |
| 48 hours | 7647.3802 | 83% | 69% | 1 |  |  |  |
|  | 7647.3802 | 83% | 69% | 2 | 0.0 | 0.0 | na |
|  | 307.74357 | 100% | 6% | 3 | 1.0 | 0.0 | 60.7 |
|  | 8042.5801 | 67% | 71% | 4 | 4.4 | 0.3 | 62.4 |
|  | 12774.377 | 67% | 81% |  |  |  |  |
|  | 46014.881 | 50% | 90% |  |  |  |  |

Fig. 4 - 19

Clusterin sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 105471.555 | 102144.952 | 105471.555 | 91734.716 | 105471.555 | 102457.166 |
| average | 103548.936 | 103840.742 | 103548.936 | 96143.377 | 103548.936 | 91184.420 |
| stdev | 32624.306 | 41323.685 | 32624.306 | 41761.748 | 32624.306 | 28741.302 |
| p (t-test) |  | 0.962 |  | 0.218 |  | 0.084 |
| min | 25053.295 | 31439.276 | 25053.295 | 22142.935 | 25053.295 | 29219.208 |
| max | 190261.364 | 244623.417 | 190261.364 | 227787.431 | 190261.364 | 120000.000 |
| n (Samp) | 105 | 48 | 105 | 55 | 105 | 25 |
| n (Pat) | 99 | 48 | 99 | 55 | 99 | 25 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 97216.331 | 120000.000 | 97216.331 | 116067.381 | 97216.331 | 110644.560 |
| average | 96957.849 | 112773.425 | 96957.849 | 114732.527 | 96957.849 | 96615.398 |
| stdev | 35978.921 | 43172.705 | 35978.921 | 50750.963 | 35978.921 | 28342.475 |
| p (t-test) |  | 0.094 |  | 0.041 |  | 0.974 |
| min | 369.562 | 53297.264 | 369.562 | 22142.935 | 369.562 | 49149.536 |
| max | 244623.417 | 201365.565 | 244623.417 | 227787.431 | 244623.417 | 120000.000 |
| n (Samp) | 242 | 16 | 242 | 20 | 242 | 12 |
| n (Pat) | 161 | 16 | 161 | 20 | 161 | 12 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 101952.773 | 95932.951 | 101952.773 | 88962.457 | 101952.773 | 97090.578 |
| average | 102438.494 | 99158.898 | 102438.494 | 89026.491 | 102438.494 | 86412.967 |
| stdev | 34600.331 | 38738.041 | 34600.331 | 31350.984 | 34600.331 | 29538.579 |
| p (t-test) |  | 0.628 |  | 0.030 |  | 0.051 |
| min | 25053.295 | 31439.276 | 25053.295 | 22142.935 | 25053.295 | 29219.208 |
| max | 201365.565 | 244623.417 | 201365.565 | 155818.229 | 201365.565 | 120000.000 |
| n (Samp) | 96 | 40 | 96 | 44 | 96 | 21 |
| n (Pat) | 84 | 40 | 84 | 44 | 84 | 21 | sCr or UO

| Time prior AKI stage | AUC | SE | nCohort 1 | nCohort 2 | p |
|---|---|---|---|---|---|
| 0 hours | 0.50 | 0.050 | 105 | 48 | 0.984 |
| 24 hours | 0.43 | 0.047 | 105 | 55 | 0.153 |
| 48 hours | 0.41 | 0.061 | 105 | 25 | 0.135 | sCr only

| Time prior AKI stage | AUC | SE | nCohort 1 | nCohort 2 | p |
|---|---|---|---|---|---|
| 0 hours | 0.61 | 0.077 | 242 | 16 | 0.148 |
| 24 hours | 0.61 | 0.069 | 242 | 20 | 0.118 |
| 48 hours | 0.52 | 0.086 | 242 | 12 | 0.844 |

UO only

| Time prior AKI stage | AUC | SE | nCohort 1 | nCohort 2 | p |
|---|---|---|---|---|---|
| 0 hours | 0.48 | 0.054 | 96 | 40 | 0.740 |
| 24 hours | 0.41 | 0.050 | 96 | 44 | 0.062 |
| 48 hours | 0.39 | 0.064 | 96 | 21 | 0.074 | sCr or UO

| Time prior AKI stage | Cutoff value | sens | spec | Quartile | OR | 95% CI of OR | |
|---|---|---|---|---|---|---|---|
| 0 hours | 79084.922 | 71% | 28% | 1 |  |  |  |
|  | 63492.875 | 81% | 9% | 2 | 0.8 | 0.5 | 1.3 |
|  | 53297.264 | 92% | 4% | 3 | 0.9 | 0.6 | 1.5 |
|  | 120000 | 27% | 80% | 4 | 0.9 | 0.6 | 1.5 |
|  | 120000 | 27% | 80% |  |  |  |  |
|  | 149406.14 | 8% | 90% |  |  |  |  |
| 24 hours | 78565.883 | 71% | 27% | 1 |  |  |  |
|  | 56870.171 | 80% | 6% | 2 | 0.5 | 0.3 | 0.9 |
|  | 46178.387 | 91% | 3% | 3 | 1.4 | 0.9 | 2.1 |
|  | 120000 | 15% | 80% | 4 | 1.1 | 0.7 | 1.7 |
|  | 120000 | 15% | 80% |  |  |  |  |

Fig. 5 - 1

|  | Cutoff value | sens | spec | Quartile | OR | 95% CI of OR | |
|---|---|---|---|---|---|---|---|
|  | 149406.14 | 7% | 90% |  |  |  |  |
| 48 hours | 68407.421 | 72% | 14% | 1 |  |  |  |
|  | 61419.254 | 80% | 9% | 2 | 3.3 | 1.2 | 9.5 |
|  | 50234.038 | 92% | 4% | 3 | 2.2 | 0.7 | 6.8 |
|  | 120000 | 0% | 80% | 4 | 3.3 | 1.2 | 9.5 |
|  | 120000 | 0% | 80% |  |  |  |  |
|  | 149406.14 | 0% | 90% |  |  |  |  | sCr only

| Time prior AKI stage | Cutoff value | sens | spec | Quartile | OR | 95% CI of OR | |
|---|---|---|---|---|---|---|---|
| 0 hours | 85005.727 | 75% | 39% | 1 |  |  |  |
|  | 78071.147 | 81% | 31% | 2 | 1.3 | 0.4 | 4.5 |
|  | 56870.171 | 94% | 13% | 3 | 0.3 | 0.0 | 4.7 |
|  | 119702.71 | 56% | 70% | 4 | 2.9 | 1.1 | 7.5 |
|  | 120000 | 38% | 83% |  |  |  |  |
|  | 138096.84 | 25% | 90% |  |  |  |  |
| 24 hours | 90505.879 | 70% | 44% | 1 |  |  |  |
|  | 78628.309 | 80% | 32% | 2 | 1.7 | 0.6 | 5.1 |
|  | 61244.828 | 90% | 16% | 3 | 1.4 | 0.4 | 4.5 |
|  | 119702.71 | 50% | 70% | 4 | 2.9 | 1.1 | 7.5 |
|  | 120000 | 30% | 83% |  |  |  |  |
|  | 138096.84 | 25% | 90% |  |  |  |  |
| 48 hours | 66314.972 | 75% | 20% | 1 |  |  |  |
|  | 62815.705 | 83% | 17% | 2 | 0.0 | 0.0 | na |
|  | 60213.292 | 92% | 15% | 3 | 2.1 | 1.0 | 4.8 |
|  | 119702.71 | 42% | 70% | 4 | 0.0 | 0.0 | na |
|  | 120000 | 0% | 83% |  |  |  |  |
|  | 138096.84 | 0% | 90% |  |  |  |  |

UO only

| Time prior AKI stage | Cutoff value | sens | spec | Quartile | OR | 95% CI of OR | |
|---|---|---|---|---|---|---|---|
| 0 hours | 79009.201 | 70% | 30% | 1 |  |  |  |
|  | 63492.875 | 80% | 11% | 2 | 0.5 | 0.3 | 0.9 |
|  | 54290.639 | 90% | 6% | 3 | 0.7 | 0.4 | 1.1 |
|  | 120000 | 25% | 81% | 4 | 1.0 | 0.6 | 1.7 |
|  | 120000 | 25% | 81% |  |  |  |  |
|  | 154350.07 | 3% | 91% |  |  |  |  |
| 24 hours | 78282.6 | 70% | 28% | 1 |  |  |  |
|  | 56025.435 | 82% | 7% | 2 | 1.2 | 0.6 | 2.2 |
|  | 46178.387 | 91% | 3% | 3 | 2.5 | 1.5 | 4.4 |
|  | 120000 | 9% | 81% | 4 | 1.8 | 1.0 | 3.1 |
|  | 120000 | 9% | 81% |  |  |  |  |
|  | 154350.07 | 2% | 91% |  |  |  |  |
| 48 hours | 61419.254 | 71% | 11% | 1 |  |  |  |
|  | 56870.171 | 81% | 8% | 2 | 2.9 | 1.0 | 8.6 |
|  | 53297.264 | 90% | 6% | 3 | 1.0 | 0.2 | 4.4 |
|  | 120000 | 0% | 81% | 4 | 3.4 | 1.2 | 9.9 |
|  | 120000 | 0% | 81% |  |  |  |  |
|  | 154350.07 | 0% | 91% |  |  |  |  |

Fig. 5 - 2

Fatty acid binding protein, heart sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 6.830 | 12.500 | 6.830 | 13.200 | 6.830 | 15.250 |
| average | 25.474 | 46.679 | 25.474 | 83.953 | 25.474 | 37.778 |
| stdev | 70.615 | 93.933 | 70.615 | 223.292 | 70.615 | 54.745 |
| p (t-test) |  | 0.057 |  | 0.000 |  | 0.389 |
| min | 0.030 | 0.030 | 0.030 | 0.030 | 0.030 | 0.030 |
| max | 713.000 | 623.000 | 713.000 | 1477.000 | 713.000 | 208.000 |
| n (Samp) | 257 | 56 | 257 | 61 | 257 | 26 |
| n (Pat) | 112 | 56 | 112 | 61 | 112 | 26 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 8.660 | 17.900 | 8.660 | 29.950 | 8.660 | 16.250 |
| average | 39.723 | 144.530 | 39.723 | 149.598 | 39.723 | 42.209 |
| stdev | 109.437 | 295.256 | 109.437 | 323.693 | 109.437 | 48.671 |
| p (t-test) |  | 0.000 |  | 0.000 |  | 0.933 |
| min | 0.030 | 0.030 | 0.030 | 0.030 | 0.030 | 0.293 |
| max | 944.000 | 1260.000 | 944.000 | 1477.000 | 944.000 | 140.000 |
| n (Samp) | 459 | 23 | 459 | 26 | 459 | 14 |
| n (Pat) | 180 | 23 | 180 | 26 | 180 | 14 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 7.850 | 13.000 | 7.850 | 13.200 | 7.850 | 18.900 |
| average | 25.943 | 46.542 | 25.943 | 61.579 | 25.943 | 52.266 |
| stdev | 63.034 | 96.379 | 63.034 | 136.551 | 63.034 | 79.748 |
| p (t-test) |  | 0.062 |  | 0.005 |  | 0.065 |
| min | 0.030 | 0.030 | 0.030 | 0.030 | 0.030 | 0.030 |
| max | 713.000 | 623.000 | 713.000 | 944.000 | 713.000 | 324.000 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
|---|---|---|---|---|---|
| 0 hours | 0.61 | 0.043 | 257 | 56 | 0.010 |
| 24 hours | 0.65 | 0.041 | 257 | 61 | 0.000 |
| 48 hours | 0.61 | 0.061 | 257 | 26 | 0.086 | sCr only

| Time prior AKI stage | AUC | SE | nCohort 1 | nCohort 2 | p |
|---|---|---|---|---|---|
| 0 hours | 0.66 | 0.063 | 459 | 23 | 0.012 |
| 24 hours | 0.67 | 0.060 | 459 | 26 | 0.005 |
| 48 hours | 0.61 | 0.081 | 459 | 14 | 0.176 |

UO only

| Time prior AKI stage | AUC | SE | nCohort 1 | nCohort 2 | p |
|---|---|---|---|---|---|
| 0 hours | 0.62 | 0.046 | 213 | 51 | 0.007 |
| 24 hours | 0.65 | 0.044 | 213 | 53 | 0.001 |
| 48 hours | 0.64 | 0.065 | 213 | 23 | 0.028 | sCr or UO

| Time prior AKI stage | Cutoff value | sens | spec | Quartile | OR | 95% CI of OR | |
|---|---|---|---|---|---|---|---|
| 0 hours | 5.55 | 71% | 45% | 1 |  |  |  |
|  | 3.52 | 80% | 34% | 2 | 1.0 | 0.6 | 1.6 |
|  | 1.04 | 91% | 12% | 3 | 1.5 | 1.0 | 2.2 |
|  | 13.6 | 43% | 70% | 4 | 2.6 | 1.9 | 3.7 |
|  | 26.3 | 32% | 80% |  |  |  |  |
|  | 58.6 | 23% | 90% |  |  |  |  |
| 24 hours | 7.96 | 70% | 53% | 1 |  |  |  |
|  | 5.44 | 80% | 44% | 2 | 1.7 | 1.1 | 2.7 |
|  | 1.83 | 90% | 21% | 3 | 1.9 | 1.2 | 3.0 |
|  | 13.6 | 48% | 70% | 4 | 4.3 | 2.9 | 6.3 |

Fig. 5 - 3

|  | Cutoff value | sens | spec | Quartile | OR | 95% CI of OR | |
|---|---|---|---|---|---|---|---|
|  | 26.3 | 43% | 80% |  |  |  |  |
|  | 58.6 | 26% | 90% |  |  |  |  |
| 48 hours | 5.88 | 73% | 46% | 1 |  |  |  |
|  | 3.66 | 81% | 35% | 2 | 1.0 | 0.4 | 2.3 |
|  | 0.429 | 92% | 5% | 3 | 1.2 | 0.6 | 2.6 |
|  | 13.6 | 54% | 70% | 4 | 2.1 | 1.1 | 4.1 |
|  | 26.3 | 31% | 80% |  |  |  |  |
|  | 58.6 | 19% | 90% |  |  |  |  | sCr only

| Time prior AKI stage | Cutoff value | sens | spec | Quartile | OR | 95% CI of OR | |
|---|---|---|---|---|---|---|---|
| 0 hours | 7.45 | 74% | 46% | 1 |  |  |  |
|  | 6.63 | 83% | 42% | 2 | 3.1 | 0.8 | 11.8 |
|  | 3.42 | 91% | 28% | 3 | 2.0 | 0.5 | 9.1 |
|  | 19.7 | 48% | 70% | 4 | 5.9 | 1.8 | 19.4 |
|  | 36.1 | 43% | 80% |  |  |  |  |
|  | 87.8 | 30% | 90% |  |  |  |  |
| 24 hours | 8.92 | 73% | 51% | 1 |  |  |  |
|  | 7.51 | 81% | 46% | 2 | 1.3 | 0.4 | 4.4 |
|  | 1.66 | 92% | 16% | 3 | 2.1 | 0.7 | 5.7 |
|  | 19.7 | 58% | 70% | 4 | 4.7 | 2.0 | 10.9 |
|  | 36.1 | 42% | 80% |  |  |  |  |
|  | 87.8 | 27% | 90% |  |  |  |  |
| 48 hours | 6.31 | 71% | 41% | 1 |  |  |  |
|  | 5.07 | 86% | 35% | 2 | 1.5 | 0.3 | 8.0 |
|  | 0.429 | 93% | 5% | 3 | 1.5 | 0.3 | 8.0 |
|  | 19.7 | 43% | 70% | 4 | 3.1 | 0.8 | 11.8 |
|  | 36.1 | 43% | 80% |  |  |  |  |
|  | 87.8 | 21% | 90% |  |  |  |  |

UO only

| Time prior AKI stage | Cutoff value | sens | spec | Quartile | OR | 95% CI of OR | |
|---|---|---|---|---|---|---|---|
| 0 hours | 6.19 | 71% | 46% | 1 |  |  |  |
|  | 4.08 | 80% | 36% | 2 | 1.7 | 1.0 | 2.9 |
|  | 1.93 | 90% | 23% | 3 | 2.5 | 1.5 | 4.0 |
|  | 15 | 47% | 70% | 4 | 3.2 | 2.0 | 5.0 |
|  | 30.8 | 29% | 80% |  |  |  |  |
|  | 67.1 | 20% | 90% |  |  |  |  |
| 24 hours | 7.19 | 72% | 49% | 1 |  |  |  |
|  | 5.44 | 81% | 44% | 2 | 3.5 | 1.9 | 6.4 |
|  | 2.97 | 91% | 31% | 3 | 2.4 | 1.3 | 4.6 |
|  | 15 | 47% | 70% | 4 | 6.0 | 3.4 | 10.4 |
|  | 30.8 | 42% | 80% |  |  |  |  |
|  | 67.1 | 26% | 90% |  |  |  |  |
| 48 hours | 5.88 | 74% | 45% | 1 |  |  |  |
|  | 3.66 | 83% | 34% | 2 | 1.7 | 0.6 | 5.3 |
|  | 1.52 | 91% | 20% | 3 | 2.1 | 0.7 | 6.1 |
|  | 15 | 57% | 70% | 4 | 3.4 | 1.3 | 8.6 |
|  | 30.8 | 39% | 80% |  |  |  |  |
|  | 67.1 | 22% | 90% |  |  |  |  |

Fig. 5 - 4

Hepatocyte growth factor sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 633.080 | 777.891 | 633.080 | 1043.203 | 633.080 | 982.405 |
| average | 1537.665 | 1916.231 | 1537.665 | 1856.655 | 1537.665 | 2517.712 |
| stdev | 1801.833 | 2773.891 | 1801.833 | 2160.458 | 1801.833 | 4008.988 |
| p (t-test) |  | 0.314 |  | 0.323 |  | 0.066 |
| min | 51.808 | 142.681 | 51.808 | 132.334 | 51.808 | 180.668 |
| max | 7752.950 | 15931.424 | 7752.950 | 11707.161 | 7752.950 | 14423.806 |
| n (Samp) | 105 | 48 | 105 | 55 | 105 | 25 |
| n (Pat) | 99 | 48 | 99 | 55 | 99 | 25 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 837.929 | 810.686 | 837.929 | 1257.747 | 837.929 | 1182.948 |
| average | 1761.680 | 2116.616 | 1761.680 | 2492.148 | 1761.680 | 2514.827 |
| stdev | 2472.544 | 3776.134 | 2472.544 | 3145.736 | 2472.544 | 3955.216 |
| p (t-test) |  | 0.593 |  | 0.215 |  | 0.320 |
| min | 51.808 | 142.681 | 51.808 | 209.588 | 51.808 | 184.185 |
| max | 25326.471 | 15931.424 | 25326.471 | 11707.161 | 25326.471 | 14423.806 |
| n (Samp) | 242 | 16 | 242 | 20 | 242 | 12 |
| n (Pat) | 161 | 16 | 161 | 20 | 161 | 12 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 628.920 | 930.828 | 628.920 | 1115.761 | 628.920 | 982.405 |
| average | 2015.721 | 3046.173 | 2015.721 | 1636.249 | 2015.721 | 2226.069 |
| stdev | 3211.472 | 8296.541 | 3211.472 | 1590.315 | 3211.472 | 3394.072 |
| p (t-test) |  | 0.297 |  | 0.459 |  | 0.788 |
| min | 51.808 | 184.185 | 51.808 | 132.334 | 51.808 | 180.668 |
| max | 17531.948 | 52712.475 | 17531.948 | 6754.272 | 17531.948 | 12135.776 |
| n (Samp) | 96 | 40 | 96 | 44 | 96 | 21 |
| n (Pat) | 84 | 40 | 84 | 44 | 84 | 21 | sCr or UO

| Time prior AKI stage | AUC | SE | nCohort 1 | nCohort 2 | p |
|---|---|---|---|---|---|
| 0 hours | 0.56 | 0.051 | 105 | 48 | 0.242 |
| 24 hours | 0.59 | 0.048 | 105 | 55 | 0.062 |
| 48 hours | 0.55 | 0.065 | 105 | 25 | 0.417 | sCr only

| Time prior AKI stage | AUC | SE | nCohort 1 | nCohort 2 | p |
|---|---|---|---|---|---|
| 0 hours | 0.54 | 0.076 | 242 | 16 | 0.620 |
| 24 hours | 0.59 | 0.069 | 242 | 20 | 0.174 |
| 48 hours | 0.57 | 0.088 | 242 | 12 | 0.423 |

UO only

| Time prior AKI stage | AUC | SE | nCohort 1 | nCohort 2 | p |
|---|---|---|---|---|---|
| 0 hours | 0.56 | 0.055 | 96 | 40 | 0.310 |
| 24 hours | 0.57 | 0.053 | 96 | 44 | 0.210 |
| 48 hours | 0.53 | 0.071 | 96 | 21 | 0.633 | sCr or UO

| Time prior AKI stage | Cutoff value | sens | spec | Quartile | OR | 95% CI of OR | |
|---|---|---|---|---|---|---|---|
| 0 hours | 548.24211 | 71% | 42% | 1 |  |  |  |
|  | 449.35994 | 81% | 33% | 2 | 2.9 | 1.7 | 5.1 |
|  | 270.54522 | 92% | 17% | 3 | 2.3 | 1.3 | 4.1 |
|  | 1450.5401 | 31% | 70% | 4 | 2.2 | 1.3 | 3.9 |
|  | 2393.3103 | 19% | 80% |  |  |  |  |
|  | 4662.0537 | 13% | 90% |  |  |  |  |
| 24 hours | 615.05921 | 71% | 48% | 1 |  |  |  |
|  | 462.27088 | 80% | 34% | 2 | 1.5 | 0.9 | 2.5 |
|  | 331.38504 | 91% | 22% | 3 | 3.4 | 2.1 | 5.5 |
|  | 1450.5401 | 36% | 70% | 4 | 1.9 | 1.1 | 3.0 |
|  | 2393.3103 | 20% | 80% |  |  |  |  |

Fig. 5 - 5

|  | | | | | | | |
|---|---|---|---|---|---|---|---|
|  | 4662.0537 | 11% | 90% | | | | |
| 48 hours | 419.42929 | 72% | 29% | 1 | | | |
|  | 411.80033 | 80% | 29% | 2 | 1.6 | 0.6 | 4.1 |
|  | 258.71872 | 92% | 16% | 3 | 2.7 | 1.2 | 6.5 |
|  | 1450.5401 | 36% | 70% | 4 | 1.6 | 0.6 | 4.1 |
|  | 2393.3103 | 24% | 80% | | | | |
|  | 4662.0537 | 16% | 90% | | | | | sCr only

| Time prior AKI stage | Cutoff value | sens | spec | Quartile | OR | 95% CI of OR | |
|---|---|---|---|---|---|---|---|
| 0 hours | 593.51109 | 75% | 39% | 1 | | | |
|  | 576.16729 | 81% | 37% | 2 | 3.2 | 0.8 | 12.4 |
|  | 258.71872 | 94% | 11% | 3 | 1.0 | 0.1 | 7.6 |
|  | 1651.3048 | 38% | 70% | 4 | 3.2 | 0.8 | 12.4 |
|  | 2526.8808 | 6% | 80% | | | | |
|  | 4719.486 | 6% | 90% | | | | |
| 24 hours | 662.69965 | 70% | 44% | 1 | | | |
|  | 607.42531 | 80% | 40% | 2 | 3.7 | 1.0 | 14.1 |
|  | 450.46649 | 90% | 27% | 3 | 2.6 | 0.6 | 11.0 |
|  | 1651.3048 | 40% | 70% | 4 | 3.2 | 0.8 | 12.4 |
|  | 2526.8808 | 25% | 80% | | | | |
|  | 4719.486 | 15% | 90% | | | | |
| 48 hours | 895.36951 | 75% | 52% | 1 | | | |
|  | 540.29622 | 83% | 35% | 2 | 0.5 | 0.0 | 9.8 |
|  | 258.71872 | 92% | 11% | 3 | 3.2 | 0.8 | 12.7 |
|  | 1651.3048 | 25% | 70% | 4 | 1.5 | 0.3 | 8.2 |
|  | 2526.8808 | 25% | 80% | | | | |
|  | 4719.486 | 17% | 90% | | | | |

UO only

| Time prior AKI stage | Cutoff value | sens | spec | Quartile | OR | 95% CI of OR | |
|---|---|---|---|---|---|---|---|
| 0 hours | 523.58816 | 70% | 41% | 1 | | | |
|  | 449.35994 | 80% | 30% | 2 | 2.5 | 1.3 | 4.9 |
|  | 298.34033 | 90% | 18% | 3 | 2.9 | 1.5 | 5.5 |
|  | 1863.8946 | 30% | 71% | 4 | 1.7 | 0.8 | 3.4 |
|  | 3401.6543 | 23% | 80% | | | | |
|  | 4731.8509 | 15% | 91% | | | | |
| 24 hours | 624.8267 | 70% | 50% | 1 | | | |
|  | 411.80033 | 82% | 28% | 2 | 0.8 | 0.4 | 1.6 |
|  | 298.34033 | 91% | 18% | 3 | 4.0 | 2.3 | 6.9 |
|  | 1863.8946 | 30% | 71% | 4 | 1.4 | 0.7 | 2.4 |
|  | 3401.6543 | 14% | 80% | | | | |
|  | 4731.8509 | 7% | 91% | | | | |
| 48 hours | 419.42929 | 71% | 28% | 1 | | | |
|  | 411.80033 | 81% | 28% | 2 | 2.3 | 0.7 | 7.1 |
|  | 270.54522 | 90% | 17% | 3 | 2.8 | 0.9 | 8.3 |
|  | 1863.8946 | 29% | 71% | 4 | 1.7 | 0.5 | 5.7 |
|  | 3401.6543 | 14% | 80% | | | | |
|  | 4731.8509 | 14% | 91% | | | | |

Fig. 5 - 6

Interferon gamma sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 3.710 | 2.570 | 3.710 | 4.270 | 3.710 | 7.050 |
| average | 8.075 | 5.871 | 8.075 | 8.311 | 8.075 | 10.774 |
| stdev | 10.808 | 7.366 | 10.808 | 9.175 | 10.808 | 11.447 |
| p (t-test) |  | 0.147 |  | 0.875 |  | 0.229 |
| min | 0.046 | 0.046 | 0.046 | 0.046 | 0.046 | 0.046 |
| max | 80.000 | 27.200 | 80.000 | 32.200 | 80.000 | 40.400 |
| n (Samp) | 257 | 56 | 257 | 61 | 257 | 26 |
| n (Pat) | 112 | 56 | 112 | 61 | 112 | 26 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 3.620 | 4.680 | 3.620 | 5.715 | 3.620 | 7.050 |
| average | 8.202 | 6.150 | 8.202 | 8.860 | 8.202 | 10.416 |
| stdev | 10.578 | 6.804 | 10.578 | 8.119 | 10.578 | 12.065 |
| p (t-test) |  | 0.358 |  | 0.755 |  | 0.443 |
| min | 0.046 | 0.046 | 0.046 | 0.046 | 0.046 | 0.046 |
| max | 80.000 | 25.300 | 80.000 | 29.900 | 80.000 | 40.400 |
| n (Samp) | 459 | 23 | 459 | 26 | 459 | 14 |
| n (Pat) | 180 | 23 | 180 | 26 | 180 | 14 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 4.100 | 2.950 | 4.100 | 3.160 | 4.100 | 6.180 |
| average | 7.470 | 6.314 | 7.470 | 8.421 | 7.470 | 9.540 |
| stdev | 9.253 | 7.666 | 9.253 | 9.063 | 9.253 | 10.138 |
| p (t-test) |  | 0.409 |  | 0.502 |  | 0.314 |
| min | 0.046 | 0.046 | 0.046 | 0.046 | 0.046 | 0.046 |
| max | 48.700 | 27.200 | 48.700 | 32.200 | 48.700 | 32.600 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
|---|---|---|---|---|---|
| 0 hours | 0.42 | 0.040 | 257 | 56 | 0.038 |
| 24 hours | 0.51 | 0.041 | 257 | 61 | 0.781 |
| 48 hours | 0.57 | 0.061 | 257 | 26 | 0.250 | sCr only

| Time prior AKI stage | AUC | SE | nCohort 1 | nCohort 2 | p |
|---|---|---|---|---|---|
| 0 hours | 0.46 | 0.060 | 459 | 23 | 0.552 |
| 24 hours | 0.59 | 0.060 | 459 | 26 | 0.152 |
| 48 hours | 0.56 | 0.081 | 459 | 14 | 0.439 |

UO only

| Time prior AKI stage | AUC | SE | nCohort 1 | nCohort 2 | p |
|---|---|---|---|---|---|
| 0 hours | 0.45 | 0.044 | 213 | 51 | 0.235 |
| 24 hours | 0.52 | 0.045 | 213 | 53 | 0.656 |
| 48 hours | 0.57 | 0.065 | 213 | 23 | 0.305 | sCr or UO

| Time prior AKI stage | Cutoff value | sens | spec | Quartile | OR | 95% CI of OR | |
|---|---|---|---|---|---|---|---|
| 0 hours | 1.62 | 75% | 18% | 1 |  |  |  |
|  | 1.09 | 80% | 11% | 2 | 0.8 | 0.5 | 1.2 |
|  | 0 | 100% | 0% | 3 | 1.0 | 0.7 | 1.5 |
|  | 7.25 | 25% | 70% | 4 | 2.2 | 1.6 | 3.0 |
|  | 12.4 | 16% | 80% |  |  |  |  |
|  | 22.5 | 5% | 90% |  |  |  |  |
| 24 hours | 2.35 | 70% | 28% | 1 |  |  |  |
|  | 1.62 | 80% | 18% | 2 | 0.8 | 0.6 | 1.2 |
|  | 0.917 | 92% | 11% | 3 | 0.7 | 0.5 | 1.0 |
|  | 7.25 | 36% | 70% | 4 | 1.2 | 0.9 | 1.6 |

Fig. 5 - 7

|  | Cutoff value | sens | spec | Quartile | OR | 95% CI of OR |  |
|---|---|---|---|---|---|---|---|
|  | 12.4 | 23% | 80% |  |  |  |  |
|  | 22.5 | 13% | 90% |  |  |  |  |
| 48 hours | 1.94 | 73% | 24% | 1 |  |  |  |
|  | 1.7 | 81% | 21% | 2 | 0.2 | 0.1 | 0.8 |
|  | 1.09 | 92% | 11% | 3 | 0.7 | 0.4 | 1.3 |
|  | 7.25 | 50% | 70% | 4 | 1.3 | 0.8 | 2.1 |
|  | 12.4 | 31% | 80% |  |  |  |  |
|  | 22.5 | 15% | 90% |  |  |  |  | sCr only

| Time prior AKI stage | Cutoff value | sens | spec | Quartile | OR | 95% CI of OR |  |
|---|---|---|---|---|---|---|---|
| 0 hours | 1.49 | 74% | 19% | 1 |  |  |  |
|  | 0 | 100% | 0% | 2 | 2.1 | 1.0 | 4.5 |
|  | 0 | 100% | 0% | 3 | 1.0 | 0.4 | 2.8 |
|  | 8.78 | 26% | 70% | 4 | 1.8 | 0.8 | 4.0 |
|  | 13.9 | 17% | 80% |  |  |  |  |
|  | 24.2 | 4% | 90% |  |  |  |  |
| 24 hours | 3.67 | 73% | 51% | 1 |  |  |  |
|  | 1.79 | 81% | 28% | 2 | 0.6 | 0.2 | 1.7 |
|  | 0.982 | 92% | 13% | 3 | 2.3 | 1.3 | 4.2 |
|  | 8.78 | 38% | 70% | 4 | 1.4 | 0.7 | 2.9 |
|  | 13.9 | 27% | 80% |  |  |  |  |
|  | 24.2 | 8% | 90% |  |  |  |  |
| 48 hours | 2.95 | 71% | 41% | 1 |  |  |  |
|  | 0.982 | 86% | 13% | 2 | 0.7 | 0.1 | 3.5 |
|  | 0 | 100% | 0% | 3 | 1.3 | 0.4 | 4.4 |
|  | 8.78 | 43% | 70% | 4 | 1.7 | 0.6 | 4.9 |
|  | 13.9 | 21% | 80% |  |  |  |  |
|  | 24.2 | 14% | 90% |  |  |  |  |

UO only

| Time prior AKI stage | Cutoff value | sens | spec | Quartile | OR | 95% CI of OR |  |
|---|---|---|---|---|---|---|---|
| 0 hours | 1.7 | 71% | 22% | 1 |  |  |  |
|  | 1.58 | 80% | 21% | 2 | 0.8 | 0.5 | 1.3 |
|  | 0.917 | 90% | 13% | 3 | 1.3 | 0.9 | 2.0 |
|  | 7.66 | 25% | 70% | 4 | 1.7 | 1.2 | 2.5 |
|  | 11.7 | 18% | 80% |  |  |  |  |
|  | 21.2 | 8% | 90% |  |  |  |  |
| 24 hours | 2.28 | 72% | 31% | 1 |  |  |  |
|  | 1.58 | 81% | 21% | 2 | 1.1 | 0.7 | 1.6 |
|  | 0.951 | 91% | 14% | 3 | 0.5 | 0.3 | 0.8 |
|  | 7.66 | 42% | 70% | 4 | 1.6 | 1.2 | 2.2 |
|  | 11.7 | 28% | 80% |  |  |  |  |
|  | 21.2 | 11% | 90% |  |  |  |  |
| 48 hours | 1.94 | 74% | 27% | 1 |  |  |  |
|  | 1.49 | 87% | 19% | 2 | 0.8 | 0.3 | 2.0 |
|  | 1.07 | 91% | 14% | 3 | 1.5 | 0.7 | 3.1 |
|  | 7.66 | 43% | 70% | 4 | 1.5 | 0.7 | 3.1 |
|  | 11.7 | 26% | 80% |  |  |  |  |
|  | 21.2 | 13% | 90% |  |  |  |  |

Fig. 5 - 8

Interleukin-16 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 466.000 | 480.500 | 466.000 | 538.000 | 466.000 | 428.000 |
| average | 569.981 | 605.232 | 569.981 | 638.836 | 569.981 | 538.231 |
| stdev | 732.345 | 443.554 | 732.345 | 394.017 | 732.345 | 331.617 |
| p (t-test) |  | 0.729 |  | 0.478 |  | 0.827 |
| min | 161.000 | 165.000 | 161.000 | 217.000 | 161.000 | 231.000 |
| max | 11500.000 | 3110.000 | 11500.000 | 2030.000 | 11500.000 | 1530.000 |
| n (Samp) | 257 | 56 | 257 | 61 | 257 | 26 |
| n (Pat) | 112 | 56 | 112 | 61 | 112 | 26 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 464.000 | 549.000 | 464.000 | 598.500 | 464.000 | 529.000 |
| average | 557.318 | 1378.087 | 557.318 | 710.115 | 557.318 | 658.143 |
| stdev | 588.467 | 3381.637 | 588.467 | 399.424 | 588.467 | 321.392 |
| p (t-test) |  | 0.000 |  | 0.192 |  | 0.524 |
| min | 153.000 | 165.000 | 153.000 | 302.000 | 153.000 | 310.000 |
| max | 11500.000 | 16800.000 | 11500.000 | 1930.000 | 11500.000 | 1220.000 |
| n (Samp) | 459 | 23 | 459 | 26 | 459 | 14 |
| n (Pat) | 180 | 23 | 180 | 26 | 180 | 14 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 466.000 | 479.000 | 466.000 | 505.000 | 466.000 | 445.000 |
| average | 536.075 | 602.039 | 536.075 | 607.245 | 536.075 | 535.696 |
| stdev | 257.240 | 439.479 | 257.240 | 362.716 | 257.240 | 322.038 |
| p (t-test) |  | 0.161 |  | 0.100 |  | 0.995 |
| min | 172.000 | 249.000 | 172.000 | 217.000 | 172.000 | 231.000 |
| max | 1550.000 | 3110.000 | 1550.000 | 2030.000 | 1550.000 | 1530.000 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
|---|---|---|---|---|---|
| 0 hours | 0.53 | 0.043 | 257 | 56 | 0.446 |
| 24 hours | 0.56 | 0.042 | 257 | 61 | 0.143 |
| 48 hours | 0.47 | 0.058 | 257 | 26 | 0.561 | sCr only

| Time prior AKI stage | AUC | SE | nCohort 1 | nCohort 2 | p |
|---|---|---|---|---|---|
| 0 hours | 0.63 | 0.064 | 459 | 23 | 0.035 |
| 24 hours | 0.65 | 0.060 | 459 | 26 | 0.013 |
| 48 hours | 0.62 | 0.081 | 459 | 14 | 0.149 |

UO only

| Time prior AKI stage | AUC | SE | nCohort 1 | nCohort 2 | p |
|---|---|---|---|---|---|
| 0 hours | 0.53 | 0.046 | 213 | 51 | 0.465 |
| 24 hours | 0.53 | 0.045 | 213 | 53 | 0.469 |
| 48 hours | 0.47 | 0.062 | 213 | 23 | 0.623 | sCr or UO

| Time prior AKI stage | Cutoff value | sens | spec | Quartile | OR | 95% CI of OR | |
|---|---|---|---|---|---|---|---|
| 0 hours | 375 | 71% | 29% | 1 |  |  |  |
|  | 345 | 80% | 23% | 2 | 1.1 | 0.8 | 1.6 |
|  | 295 | 91% | 15% | 3 | 0.8 | 0.6 | 1.2 |
|  | 592 | 36% | 70% | 4 | 1.5 | 1.1 | 2.0 |
|  | 666 | 29% | 80% |  |  |  |  |
|  | 914 | 14% | 90% |  |  |  |  |
| 24 hours | 383 | 70% | 32% | 1 |  |  |  |
|  | 334 | 80% | 20% | 2 | 0.7 | 0.5 | 1.0 |
|  | 288 | 90% | 14% | 3 | 1.2 | 0.9 | 1.6 |
|  | 592 | 38% | 70% | 4 | 1.2 | 0.9 | 1.7 |
|  | 666 | 30% | 80% |  |  |  |  |

Fig. 5 - 9

|  |  | 914 | 21% | 90% |  |  |  |  |
|---|---|---|---|---|---|---|---|---|
| 48 hours |  | 364 | 73% | 26% | 1 |  |  |  |
|  |  | 332 | 81% | 20% | 2 | 1.4 | 0.7 | 3.0 |
|  |  | 306 | 92% | 16% | 3 | 1.4 | 0.7 | 3.0 |
|  |  | 592 | 23% | 70% | 4 | 1.5 | 0.7 | 3.1 |
|  |  | 666 | 15% | 80% |  |  |  |  |
|  |  | 914 | 12% | 90% |  |  |  |  | sCr only

| Time prior AKI stage | Cutoff value | sens | spec | Quartile | OR | 95% CI of OR | |
|---|---|---|---|---|---|---|---|
| 0 hours | 433 | 74% | 43% | 1 |  |  |  |
|  | 377 | 83% | 30% | 2 | 3.6 | 1.0 | 13.2 |
|  | 361 | 91% | 26% | 3 | 2.0 | 0.5 | 9.1 |
|  | 585 | 43% | 70% | 4 | 5.3 | 1.6 | 17.8 |
|  | 671 | 39% | 80% |  |  |  |  |
|  | 914 | 30% | 90% |  |  |  |  |
| 24 hours | 512 | 73% | 59% | 1 |  |  |  |
|  | 361 | 81% | 26% | 2 | 0.7 | 0.2 | 2.4 |
|  | 329 | 92% | 19% | 3 | 1.8 | 0.8 | 4.0 |
|  | 585 | 54% | 70% | 4 | 3.2 | 1.6 | 6.3 |
|  | 671 | 38% | 80% |  |  |  |  |
|  | 914 | 27% | 90% |  |  |  |  |
| 48 hours | 410 | 71% | 39% | 1 |  |  |  |
|  | 371 | 86% | 29% | 2 | 4.1 | 0.3 | 49.2 |
|  | 364 | 93% | 27% | 3 | 4.1 | 0.3 | 49.2 |
|  | 585 | 43% | 70% | 4 | 5.1 | 0.5 | 55.8 |
|  | 671 | 36% | 80% |  |  |  |  |
|  | 914 | 29% | 90% |  |  |  |  |

UO only

| Time prior AKI stage | Cutoff value | sens | spec | Quartile | OR | 95% CI of OR | |
|---|---|---|---|---|---|---|---|
| 0 hours | 414 | 71% | 40% | 1 |  |  |  |
|  | 345 | 80% | 21% | 2 | 1.1 | 0.7 | 1.6 |
|  | 299 | 90% | 15% | 3 | 0.9 | 0.6 | 1.4 |
|  | 613 | 33% | 70% | 4 | 1.3 | 0.9 | 1.9 |
|  | 683 | 27% | 80% |  |  |  |  |
|  | 915 | 12% | 90% |  |  |  |  |
| 24 hours | 375 | 72% | 27% | 1 |  |  |  |
|  | 332 | 81% | 18% | 2 | 0.7 | 0.4 | 1.0 |
|  | 272 | 91% | 11% | 3 | 1.1 | 0.8 | 1.5 |
|  | 613 | 30% | 70% | 4 | 1.0 | 0.7 | 1.4 |
|  | 683 | 26% | 80% |  |  |  |  |
|  | 915 | 19% | 90% |  |  |  |  |
| 48 hours | 336 | 74% | 19% | 1 |  |  |  |
|  | 311 | 83% | 16% | 2 | 0.8 | 0.4 | 1.8 |
|  | 292 | 91% | 15% | 3 | 0.8 | 0.4 | 1.8 |
|  | 613 | 26% | 70% | 4 | 1.2 | 0.6 | 2.4 |
|  | 683 | 17% | 80% |  |  |  |  |
|  | 915 | 9% | 90% |  |  |  |  |

Fig. 5 - 10

Interleukin-2 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.502 | 0.585 | 0.502 | 0.594 | 0.502 | 0.586 |
| average | 0.735 | 0.771 | 0.735 | 1.057 | 0.735 | 0.751 |
| stdev | 0.952 | 0.600 | 0.952 | 1.385 | 0.952 | 0.561 |
| p (t-test) |  | 0.810 |  | 0.086 |  | 0.938 |
| min | 0.000 | 0.021 | 0.000 | 0.157 | 0.000 | 0.138 |
| max | 7.239 | 2.839 | 7.239 | 8.727 | 7.239 | 2.654 |
| n (Samp) | 105 | 48 | 105 | 55 | 105 | 25 |
| n (Pat) | 99 | 48 | 99 | 55 | 99 | 25 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 0.533 | 0.575 | 0.533 | 0.712 | 0.533 | 0.649 |
| average | 0.887 | 0.631 | 0.887 | 0.860 | 0.887 | 0.610 |
| stdev | 1.535 | 0.488 | 1.535 | 0.593 | 1.535 | 0.342 |
| p (t-test) |  | 0.508 |  | 0.938 |  | 0.533 |
| min | 0.000 | 0.021 | 0.000 | 0.237 | 0.000 | 0.138 |
| max | 19.127 | 2.173 | 19.127 | 2.538 | 19.127 | 1.164 |
| n (Samp) | 242 | 16 | 242 | 20 | 242 | 12 |
| n (Pat) | 161 | 16 | 161 | 20 | 161 | 12 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 0.542 | 0.586 | 0.542 | 0.586 | 0.542 | 0.586 |
| average | 0.824 | 0.781 | 0.824 | 1.128 | 0.824 | 0.879 |
| stdev | 1.008 | 0.590 | 1.008 | 1.526 | 1.008 | 0.675 |
| p (t-test) |  | 0.800 |  | 0.164 |  | 0.812 |
| min | 0.045 | 0.143 | 0.045 | 0.157 | 0.045 | 0.210 |
| max | 7.239 | 2.839 | 7.239 | 8.727 | 7.239 | 2.654 |
| n (Samp) | 96 | 40 | 96 | 44 | 96 | 21 |
| n (Pat) | 84 | 40 | 84 | 44 | 84 | 21 | sCr or UO

| Time prior AKI stage | AUC | SE | nCohort 1 | nCohort 2 | p |
| --- | --- | --- | --- | --- | --- |
| 0 hours | 0.58 | 0.051 | 105 | 48 | 0.126 |
| 24 hours | 0.61 | 0.048 | 105 | 55 | 0.024 |
| 48 hours | 0.58 | 0.066 | 105 | 25 | 0.235 | sCr only

| Time prior AKI stage | AUC | SE | nCohort 1 | nCohort 2 | p |
| --- | --- | --- | --- | --- | --- |
| 0 hours | 0.50 | 0.075 | 242 | 16 | 0.966 |
| 24 hours | 0.59 | 0.069 | 242 | 20 | 0.187 |
| 48 hours | 0.51 | 0.086 | 242 | 12 | 0.946 |

UO only

| Time prior AKI stage | AUC | SE | nCohort 1 | nCohort 2 | p |
| --- | --- | --- | --- | --- | --- |
| 0 hours | 0.54 | 0.055 | 96 | 40 | 0.417 |
| 24 hours | 0.56 | 0.053 | 96 | 44 | 0.236 |
| 48 hours | 0.57 | 0.071 | 96 | 21 | 0.318 | sCr or UO

| Time prior AKI stage | Cutoff value | sens | spec | Quartile | OR | 95% CI of OR | |
| --- | --- | --- | --- | --- | --- | --- | --- |
| 0 hours | 0.441742 | 71% | 44% | 1 |  |  |  |
|  | 0.3227725 | 81% | 28% | 2 | 1.3 | 0.8 | 2.2 |
|  | 0.2225612 | 92% | 16% | 3 | 1.5 | 0.9 | 2.5 |
|  | 0.6608587 | 40% | 70% | 4 | 2.2 | 1.4 | 3.7 |
|  | 0.8141932 | 29% | 80% |  |  |  |  |
|  | 1.4175697 | 17% | 90% |  |  |  |  |
| 24 hours | 0.4058343 | 71% | 38% | 1 |  |  |  |
|  | 0.3397476 | 80% | 30% | 2 | 1.4 | 0.9 | 2.3 |
|  | 0.2727072 | 91% | 22% | 3 | 1.4 | 0.9 | 2.3 |
|  | 0.6608587 | 45% | 70% | 4 | 2.7 | 1.7 | 4.3 |
|  | 0.8141932 | 36% | 80% |  |  |  |  |

Fig. 5 - 11

|  |  | 1.4175697 | 18% | 90% |  |  |  |  |
|---|---|---|---|---|---|---|---|---|
| 48 hours |  | 0.441742 | 72% | 44% | 1 |  |  |  |
|  |  | 0.4007328 | 80% | 37% | 2 | 1.2 | 0.5 | 2.8 |
|  |  | 0.1974446 | 92% | 12% | 3 | 1.0 | 0.4 | 2.5 |
|  |  | 0.6608587 | 44% | 70% | 4 | 2.0 | 0.9 | 4.3 |
|  |  | 0.8141932 | 36% | 80% |  |  |  |  |
|  |  | 1.4175697 | 8% | 90% |  |  |  |  | sCr only

| Time prior AKI stage | Cutoff value | sens | spec | Quartile | OR | 95% CI of OR | |
|---|---|---|---|---|---|---|---|
| 0 hours | 0.3778117 | 75% | 33% | 1 |  |  |  |
|  | 0.3600263 | 81% | 29% | 2 | 2.6 | 0.6 | 10.9 |
|  | 0.1258636 | 94% | 5% | 3 | 3.8 | 1.0 | 14.3 |
|  | 0.766354 | 19% | 70% | 4 | 1.0 | 0.1 | 7.4 |
|  | 1.0624848 | 13% | 80% |  |  |  |  |
|  | 1.8023893 | 6% | 90% |  |  |  |  |
| 24 hours | 0.4673005 | 70% | 43% | 1 |  |  |  |
|  | 0.3902944 | 80% | 34% | 2 | 1.0 | 0.3 | 2.8 |
|  | 0.2920348 | 90% | 21% | 3 | 0.7 | 0.2 | 2.5 |
|  | 0.766354 | 50% | 70% | 4 | 2.4 | 1.1 | 5.2 |
|  | 1.0624848 | 25% | 80% |  |  |  |  |
|  | 1.8023893 | 10% | 90% |  |  |  |  |
| 48 hours | 0.2697168 | 75% | 17% | 1 |  |  |  |
|  | 0.2487421 | 83% | 14% | 2 | 0.0 | 0.0 | na |
|  | 0.1572836 | 92% | 7% | 3 | 1.3 | 0.5 | 3.3 |
|  | 0.766354 | 42% | 70% | 4 | 0.7 | 0.2 | 2.4 |
|  | 1.0624848 | 8% | 80% |  |  |  |  |
|  | 1.8023893 | 0% | 90% |  |  |  |  |

UO only

| Time prior AKI stage | Cutoff value | sens | spec | Quartile | OR | 95% CI of OR | |
|---|---|---|---|---|---|---|---|
| 0 hours | 0.4469507 | 70% | 42% | 1 |  |  |  |
|  | 0.3397476 | 80% | 27% | 2 | 1.4 | 0.7 | 2.5 |
|  | 0.2894797 | 90% | 21% | 3 | 1.8 | 1.0 | 3.1 |
|  | 0.78861 | 33% | 71% | 4 | 1.4 | 0.7 | 2.5 |
|  | 0.9678962 | 25% | 80% |  |  |  |  |
|  | 1.5351742 | 15% | 91% |  |  |  |  |
| 24 hours | 0.3872229 | 70% | 32% | 1 |  |  |  |
|  | 0.3271002 | 82% | 25% | 2 | 1.3 | 0.8 | 2.3 |
|  | 0.2665305 | 91% | 16% | 3 | 1.2 | 0.7 | 2.0 |
|  | 0.78861 | 41% | 71% | 4 | 1.9 | 1.1 | 3.3 |
|  | 0.9678962 | 30% | 80% |  |  |  |  |
|  | 1.5351742 | 18% | 91% |  |  |  |  |
| 48 hours | 0.4469507 | 71% | 42% | 1 |  |  |  |
|  | 0.4209348 | 81% | 36% | 2 | 2.8 | 0.9 | 8.3 |
|  | 0.278692 | 90% | 17% | 3 | 1.4 | 0.4 | 5.1 |
|  | 0.78861 | 33% | 71% | 4 | 2.6 | 0.9 | 7.9 |
|  | 0.9678962 | 33% | 80% |  |  |  |  |
|  | 1.5351742 | 19% | 91% |  |  |  |  |

Fig. 5 - 12

Interleukin-12 p40 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 33.113 | 26.461 | 33.113 | 20.388 | 33.113 | 26.282 |
| average | 44.441 | 28.178 | 44.441 | 33.913 | 44.441 | 34.108 |
| stdev | 45.103 | 19.402 | 45.103 | 35.548 | 45.103 | 33.576 |
| p (t-test) |  | 0.018 |  | 0.135 |  | 0.284 |
| min | 0.000 | 0.000 | 0.000 | 0.000 | 0.000 | 0.000 |
| max | 230.675 | 74.271 | 230.675 | 199.554 | 230.675 | 163.969 |
| n (Samp) | 105 | 48 | 105 | 55 | 105 | 25 |
| n (Pat) | 99 | 48 | 99 | 55 | 99 | 25 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 28.168 | 40.846 | 28.168 | 16.783 | 28.168 | 39.569 |
| average | 35.854 | 42.961 | 35.854 | 31.632 | 35.854 | 44.630 |
| stdev | 35.190 | 22.328 | 35.190 | 44.969 | 35.190 | 42.545 |
| p (t-test) |  | 0.426 |  | 0.615 |  | 0.405 |
| min | 0.000 | 9.137 | 0.000 | 0.000 | 0.000 | 0.000 |
| max | 230.675 | 89.352 | 230.675 | 199.554 | 230.675 | 163.969 |
| n (Samp) | 242 | 16 | 242 | 20 | 242 | 12 |
| n (Pat) | 161 | 16 | 161 | 20 | 161 | 12 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 32.732 | 20.996 | 32.732 | 27.081 | 32.732 | 26.282 |
| average | 41.130 | 25.635 | 41.130 | 38.284 | 41.130 | 35.752 |
| stdev | 40.396 | 19.095 | 40.396 | 37.534 | 40.396 | 35.676 |
| p (t-test) |  | 0.022 |  | 0.693 |  | 0.574 |
| min | 0.000 | 0.000 | 0.000 | 0.000 | 0.000 | 0.000 |
| max | 230.675 | 74.271 | 230.675 | 199.554 | 230.675 | 163.969 |
| n (Samp) | 96 | 40 | 96 | 44 | 96 | 21 |
| n (Pat) | 84 | 40 | 84 | 44 | 84 | 21 | sCr or UO

| Time prior AKI stage | AUC | SE | nCohort 1 | nCohort 2 | p |
|---|---|---|---|---|---|
| 0 hours | 0.42 | 0.049 | 105 | 48 | 0.082 |
| 24 hours | 0.42 | 0.047 | 105 | 55 | 0.076 |
| 48 hours | 0.44 | 0.062 | 105 | 25 | 0.326 | sCr only

| Time prior AKI stage | AUC | SE | nCohort 1 | nCohort 2 | p |
|---|---|---|---|---|---|
| 0 hours | 0.64 | 0.077 | 242 | 16 | 0.066 |
| 24 hours | 0.40 | 0.062 | 242 | 20 | 0.099 |
| 48 hours | 0.59 | 0.088 | 242 | 12 | 0.289 |

UO only

| Time prior AKI stage | AUC | SE | nCohort 1 | nCohort 2 | p |
|---|---|---|---|---|---|
| 0 hours | 0.39 | 0.051 | 96 | 40 | 0.025 |
| 24 hours | 0.48 | 0.052 | 96 | 44 | 0.643 |
| 48 hours | 0.46 | 0.068 | 96 | 21 | 0.515 | sCr or UO

| Time prior AKI stage | Cutoff value | sens | spec | Quartile | OR | 95% CI of OR | |
|---|---|---|---|---|---|---|---|
| 0 hours | 15.666709 | 71% | 24% | 1 |  |  |  |
|  | 9.4129279 | 81% | 14% | 2 | 1.0 | 0.6 | 1.8 |
|  | 3.3229148 | 92% | 9% | 3 | 2.4 | 1.5 | 4.0 |
|  | 43.818211 | 19% | 70% | 4 | 1.9 | 1.2 | 3.2 |
|  | 64.573125 | 6% | 80% |  |  |  |  |
|  | 103.64968 | 0% | 90% |  |  |  |  |
| 24 hours | 16.126739 | 71% | 25% | 1 |  |  |  |
|  | 11.758032 | 80% | 17% | 2 | 0.4 | 0.2 | 0.7 |
|  | 1.2982033 | 91% | 8% | 3 | 1.7 | 1.1 | 2.5 |
|  | 43.818211 | 27% | 70% | 4 | 1.1 | 0.7 | 1.7 |
|  | 64.573125 | 15% | 80% |  |  |  |  |

Fig. 5 - 13

|  | 103.64968 | 7% | 90% |  |  |  |  |
|---|---|---|---|---|---|---|---|
| 48 hours | 18.199316 | 72% | 30% | 1 |  |  |  |
|  | 13.847063 | 80% | 22% | 2 | 0.8 | 0.3 | 2.2 |
|  | 0 | 100% | 0% | 3 | 2.1 | 1.0 | 4.5 |
|  | 43.818211 | 24% | 70% | 4 | 1.6 | 0.7 | 3.6 |
|  | 64.573125 | 8% | 80% |  |  |  |  |
|  | 103.64968 | 4% | 90% |  |  |  |  | sCr only

| Time prior AKI stage | Cutoff value | sens | spec | Quartile | OR | 95% CI of OR | |
|---|---|---|---|---|---|---|---|
| 0 hours | 26.774518 | 75% | 48% | 1 |  |  |  |
|  | 24.36913 | 81% | 45% | 2 | 4.1 | 0.3 | 51.0 |
|  | 16.717185 | 94% | 29% | 3 | 6.5 | 0.6 | 68.4 |
|  | 39.823651 | 56% | 70% | 4 | 5.3 | 0.5 | 58.8 |
|  | 49.184951 | 31% | 80% |  |  |  |  |
|  | 74.125859 | 13% | 90% |  |  |  |  |
| 24 hours | 9.6041633 | 70% | 17% | 1 |  |  |  |
|  | 5.1253412 | 80% | 12% | 2 | 0.4 | 0.1 | 1.6 |
|  | 1.846505 | 90% | 9% | 3 | 0.8 | 0.3 | 2.0 |
|  | 39.823651 | 25% | 70% | 4 | 2.0 | 1.0 | 3.9 |
|  | 49.184951 | 25% | 80% |  |  |  |  |
|  | 74.125859 | 5% | 90% |  |  |  |  |
| 48 hours | 22.206909 | 75% | 43% | 1 |  |  |  |
|  | 21.27953 | 83% | 41% | 2 | 1.0 | 0.1 | 7.4 |
|  | 1.846505 | 92% | 9% | 3 | 2.1 | 0.4 | 9.6 |
|  | 39.823651 | 50% | 70% | 4 | 2.0 | 0.4 | 9.4 |
|  | 49.184951 | 33% | 80% |  |  |  |  |
|  | 74.125859 | 8% | 90% |  |  |  |  |

UO only

| Time prior AKI stage | Cutoff value | sens | spec | Quartile | OR | 95% CI of OR | |
|---|---|---|---|---|---|---|---|
| 0 hours | 15.286756 | 70% | 23% | 1 |  |  |  |
|  | 9.4129279 | 80% | 18% | 2 | 1.2 | 0.6 | 2.3 |
|  | 3.3229148 | 90% | 8% | 3 | 2.4 | 1.3 | 4.3 |
|  | 43.818211 | 18% | 71% | 4 | 2.1 | 1.1 | 3.9 |
|  | 55.173538 | 8% | 80% |  |  |  |  |
|  | 89.565615 | 0% | 91% |  |  |  |  |
| 24 hours | 17.960094 | 70% | 30% | 1 |  |  |  |
|  | 15.666709 | 82% | 24% | 2 | 0.3 | 0.1 | 0.6 |
|  | 5.1253412 | 91% | 9% | 3 | 1.3 | 0.8 | 2.0 |
|  | 43.818211 | 32% | 71% | 4 | 0.8 | 0.5 | 1.3 |
|  | 55.173538 | 23% | 80% |  |  |  |  |
|  | 89.565615 | 9% | 91% |  |  |  |  |
| 48 hours | 18.11806 | 71% | 31% | 1 |  |  |  |
|  | 13.847063 | 81% | 22% | 2 | 0.8 | 0.3 | 2.3 |
|  | 8.1183826 | 90% | 13% | 3 | 1.3 | 0.5 | 3.2 |
|  | 43.818211 | 29% | 71% | 4 | 1.3 | 0.5 | 3.2 |
|  | 55.173538 | 14% | 80% |  |  |  |  |
|  | 89.565615 | 5% | 91% |  |  |  |  |

Fig. 5 - 14

Matrix metalloproteinase-2 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 2410.000 | 2695.000 | 2410.000 | 2730.000 | 2410.000 | 2755.000 |
| average | 2499.735 | 2820.714 | 2499.735 | 2717.230 | 2499.735 | 2848.077 |
| stdev | 889.134 | 940.104 | 889.134 | 1056.121 | 889.134 | 863.806 |
| p (t-test) |  | 0.016 |  | 0.099 |  | 0.057 |
| min | 618.000 | 1520.000 | 618.000 | 1190.000 | 618.000 | 1440.000 |
| max | 5710.000 | 5520.000 | 5710.000 | 5621.000 | 5710.000 | 5080.000 |
| n (Samp) | 257 | 56 | 257 | 61 | 257 | 26 |
| n (Pat) | 112 | 56 | 112 | 61 | 112 | 26 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 2490.000 | 2590.000 | 2490.000 | 2610.000 | 2490.000 | 2920.000 |
| average | 2629.743 | 2796.957 | 2629.743 | 2822.346 | 2629.743 | 3013.571 |
| stdev | 974.304 | 1054.611 | 974.304 | 1302.561 | 974.304 | 1038.028 |
| p (t-test) |  | 0.424 |  | 0.337 |  | 0.148 |
| min | 618.000 | 1720.000 | 618.000 | 1350.000 | 618.000 | 1690.000 |
| max | 6370.000 | 5130.000 | 6370.000 | 5621.000 | 6370.000 | 5030.000 |
| n (Samp) | 459 | 23 | 459 | 26 | 459 | 14 |
| n (Pat) | 180 | 23 | 180 | 26 | 180 | 14 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 2460.000 | 2870.000 | 2460.000 | 2820.000 | 2460.000 | 2850.000 |
| average | 2510.056 | 2977.451 | 2510.056 | 2765.094 | 2510.056 | 2976.087 |
| stdev | 893.199 | 994.601 | 893.199 | 944.296 | 893.199 | 879.048 |
| p (t-test) |  | 0.001 |  | 0.067 |  | 0.018 |
| min | 618.000 | 1520.000 | 618.000 | 1190.000 | 618.000 | 1440.000 |
| max | 5710.000 | 5870.000 | 5710.000 | 5270.000 | 5710.000 | 5080.000 |
| n (Samp) | 213 | 51 | 213 | 53 | 213 | 23 |
| n (Pat) | 89 | 51 | 89 | 53 | 89 | 23 | sCr or UO

| Time prior AKI stage | AUC | SE | nCohort 1 | nCohort 2 | p |
| --- | --- | --- | --- | --- | --- |
| 0 hours | 0.60 | 0.043 | 257 | 56 | 0.028 |
| 24 hours | 0.55 | 0.042 | 257 | 61 | 0.226 |
| 48 hours | 0.62 | 0.061 | 257 | 26 | 0.054 | sCr only

| Time prior AKI stage | AUC | SE | nCohort 1 | nCohort 2 | p |
| --- | --- | --- | --- | --- | --- |
| 0 hours | 0.53 | 0.063 | 459 | 23 | 0.619 |
| 24 hours | 0.52 | 0.059 | 459 | 26 | 0.790 |
| 48 hours | 0.61 | 0.081 | 459 | 14 | 0.192 |

UO only

| Time prior AKI stage | AUC | SE | nCohort 1 | nCohort 2 | p |
| --- | --- | --- | --- | --- | --- |
| 0 hours | 0.63 | 0.045 | 213 | 51 | 0.003 |
| 24 hours | 0.58 | 0.045 | 213 | 53 | 0.087 |
| 48 hours | 0.66 | 0.065 | 213 | 23 | 0.015 | sCr or UO

| Time prior AKI stage | Cutoff value | sens | spec | Quartile | OR | 95% CI of OR | |
| --- | --- | --- | --- | --- | --- | --- | --- |
| 0 hours | 2080 | 71% | 34% | 1 |  |  |  |
|  | 1960 | 80% | 28% | 2 | 1.7 | 1.1 | 2.5 |
|  | 1740 | 93% | 21% | 3 | 1.4 | 0.9 | 2.2 |
|  | 2890 | 45% | 70% | 4 | 2.8 | 1.9 | 4.0 |
|  | 3150 | 32% | 80% |  |  |  |  |
|  | 3660 | 18% | 90% |  |  |  |  |
| 24 hours | 1940 | 70% | 28% | 1 |  |  |  |
|  | 1760 | 80% | 21% | 2 | 0.6 | 0.4 | 0.9 |
|  | 1480 | 90% | 12% | 3 | 0.8 | 0.6 | 1.1 |
|  | 2890 | 43% | 70% | 4 | 1.4 | 1.1 | 1.9 |
|  | 3150 | 30% | 80% |  |  |  |  |

Fig. 5 - 15

|  | | 3660 | 15% | 90% | | | | |
|---|---|---|---|---|---|---|---|---|
| 48 hours | | 2370 | 73% | 49% | 1 | | | |
| | | 2210 | 81% | 42% | 2 | 2.1 | 0.7 | 5.8 |
| | | 1810 | 92% | 22% | 3 | 2.8 | 1.1 | 7.4 |
| | | 2890 | 38% | 70% | 4 | 3.2 | 1.3 | 8.2 |
| | | 3150 | 31% | 80% | | | | |
| | | 3660 | 12% | 90% | | | | | sCr only

| Time prior AKI stage | Cutoff value | sens | spec | Quartile | OR | 95% CI of OR | |
|---|---|---|---|---|---|---|---|
| 0 hours | 1880 | 74% | 22% | 1 | | | |
| | 1780 | 83% | 18% | 2 | 0.6 | 0.2 | 1.2 |
| | 1740 | 91% | 17% | 3 | 0.6 | 0.2 | 1.2 |
| | 2970 | 39% | 70% | 4 | 1.1 | 0.7 | 2.0 |
| | 3320 | 26% | 80% | | | | |
| | 3880 | 17% | 90% | | | | |
| 24 hours | 1740 | 73% | 17% | 1 | | | |
| | 1710 | 81% | 16% | 2 | 0.3 | 0.1 | 0.7 |
| | 1370 | 92% | 7% | 3 | 0.2 | 0.1 | 0.6 |
| | 2970 | 42% | 70% | 4 | 1.1 | 0.7 | 1.7 |
| | 3320 | 31% | 80% | | | | |
| | 3880 | 19% | 90% | | | | |
| 48 hours | 2370 | 71% | 45% | 1 | | | |
| | 1970 | 86% | 26% | 2 | 2.0 | 0.5 | 9.2 |
| | 1810 | 93% | 19% | 3 | 1.0 | 0.1 | 7.3 |
| | 2970 | 50% | 70% | 4 | 3.1 | 0.8 | 11.8 |
| | 3320 | 43% | 80% | | | | |
| | 3880 | 14% | 90% | | | | |

UO only

| Time prior AKI stage | Cutoff value | sens | spec | Quartile | OR | 95% CI of OR | |
|---|---|---|---|---|---|---|---|
| 0 hours | 2290 | 71% | 44% | 1 | | | |
| | 2080 | 80% | 31% | 2 | 2.1 | 1.3 | 3.4 |
| | 1940 | 90% | 26% | 3 | 1.9 | 1.1 | 3.1 |
| | 2910 | 49% | 70% | 4 | 3.4 | 2.2 | 5.4 |
| | 3150 | 35% | 80% | | | | |
| | 3540 | 25% | 90% | | | | |
| 24 hours | 2130 | 72% | 35% | 1 | | | |
| | 1860 | 81% | 23% | 2 | 0.8 | 0.5 | 1.2 |
| | 1700 | 91% | 18% | 3 | 1.1 | 0.7 | 1.6 |
| | 2910 | 43% | 70% | 4 | 1.7 | 1.2 | 2.3 |
| | 3150 | 28% | 80% | | | | |
| | 3540 | 13% | 90% | | | | |
| 48 hours | 2470 | 74% | 53% | 1 | | | |
| | 2220 | 83% | 40% | 2 | 2.1 | 0.4 | 9.7 |
| | 2130 | 91% | 35% | 3 | 3.8 | 1.0 | 14.5 |
| | 2910 | 48% | 70% | 4 | 5.8 | 1.7 | 20.3 |
| | 3150 | 39% | 80% | | | | |
| | 3540 | 22% | 90% | | | | |

Fig. 5 - 16

Midkine sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 5.146 | 4.121 | 5.146 | 2.690 | 5.146 | 0.002 |
| average | 17.661 | 12.486 | 17.661 | 2.690 | 17.661 | 4.680 |
| stdev | 21.849 | 15.424 | 21.849 | 2.877 | 21.849 | na |
| p (t-test) |  | 0.422 |  | 0.341 |  | na |
| min | 0.002 | 0.326 | 0.002 | 0.656 | 0.002 | 4.680 |
| max | 72.865 | 48.646 | 72.865 | 4.725 | 72.865 | 4.680 |
| n (Samp) | 57 | 13 | 57 | 2 | 57 | 1 |
| n (Pat) | 37 | 13 | 37 | 2 | 37 | 1 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 4.019 | 11.724 | 4.019 | 5.802 | 4.019 | 30.690 |
| average | 15.715 | 18.765 | 15.715 | 14.762 | 15.715 | 30.690 |
| stdev | 20.369 | 19.678 | 20.369 | 21.340 | 20.369 | 35.804 |
| p (t-test) |  | 0.723 |  | 0.927 |  | 0.312 |
| min | 0.002 | 0.604 | 0.002 | 0.889 | 0.002 | 5.373 |
| max | 72.865 | 50.413 | 72.865 | 46.556 | 72.865 | 56.007 |
| n (Samp) | 89 | 6 | 89 | 4 | 89 | 2 |
| n (Pat) | 61 | 6 | 61 | 4 | 61 | 2 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 8.186 | 3.724 | 8.186 | 20.336 | 8.186 | 0.002 |
| average | 19.917 | 11.085 | 19.917 | 20.336 | 19.917 | 4.680 |
| stdev | 23.138 | 14.963 | 23.138 | 27.832 | 23.138 | na |
| p (t-test) |  | 0.188 |  | 0.980 |  | na |
| min | 0.002 | 0.326 | 0.002 | 0.656 | 0.002 | 4.680 |
| max | 72.865 | 48.646 | 72.865 | 40.017 | 72.865 | 4.680 |
| n (Samp) | 42 | 14 | 42 | 2 | 42 | 1 |
| n (Pat) | 27 | 14 | 27 | 2 | 27 | 1 | sCr or UO

| Time prior AKI stage | AUC | SE | nCohort 1 | nCohort 2 | p |
|---|---|---|---|---|---|
| 0 hours | 0.46 | 0.087 | 57 | 13 | 0.615 |
| 24 hours | 0.27 | 0.153 | 57 | 2 | 0.135 |
| 48 hours | 0.47 | 0.288 | 57 | 1 | 0.927 | sCr only

| Time prior AKI stage | AUC | SE | nCohort 1 | nCohort 2 | p |
|---|---|---|---|---|---|
| 0 hours | 0.60 | 0.126 | 89 | 6 | 0.423 |
| 24 hours | 0.55 | 0.152 | 89 | 4 | 0.753 |
| 48 hours | 0.74 | 0.204 | 89 | 2 | 0.236 |

UO only

| Time prior AKI stage | AUC | SE | nCohort 1 | nCohort 2 | p |
|---|---|---|---|---|---|
| 0 hours | 0.44 | 0.087 | 42 | 14 | 0.470 |
| 24 hours | 0.44 | 0.202 | 42 | 2 | 0.768 |
| 48 hours | 0.43 | 0.278 | 42 | 1 | 0.798 | sCr or UO

| Time prior AKI stage | Cutoff value | sens | spec | Quartile | OR | 95% CI of OR | |
|---|---|---|---|---|---|---|---|
| 0 hours | 1.8154762 | 77% | 37% | 1 |  |  |  |
|  | 0.6001451 | 85% | 7% | 2 | 1.1 | 0.2 | 5.2 |
|  | 0.41705 | 92% | 4% | 3 | 1.4 | 0.3 | 5.9 |
|  | 24.521014 | 23% | 70% | 4 | 1.1 | 0.2 | 5.2 |
|  | 38.15427 | 8% | 81% |  |  |  |  |
|  | 58.20643 | 0% | 91% |  |  |  |  |
| 24 hours | 0.6001451 | 100% | 7% | 1 |  |  |  |
|  | 0.6001451 | 100% | 7% | 2 | na | na | na |
|  | 0.6001451 | 100% | 7% | 3 | na | na | na |
|  | 24.521014 | 0% | 70% | 4 | na | na | na |
|  | 38.15427 | 0% | 81% |  |  |  |  |

Fig. 5 - 17

|  |  | 58.20643 | 0% | 91% |  |  |  |  |
|---|---|---|---|---|---|---|---|---|
| 48 hours |  | 3.8837139 | 100% | 47% | 1 |  |  |  |
|  |  | 3.8837139 | 100% | 47% | 2 | na | na | na |
|  |  | 3.8837139 | 100% | 47% | 3 | na | na | na |
|  |  | 24.521014 | 0% | 70% | 4 | na | na | na |
|  |  | 38.15427 | 0% | 81% |  |  |  |  |
|  |  | 58.20643 | 0% | 91% |  |  |  |  | sCr only

| Time prior AKI stage | Cutoff value | sens | spec | Quartile | OR | 95% CI of OR | |
|---|---|---|---|---|---|---|---|
| 0 hours | 4.120827 | 83% | 52% | 1 |  |  |  |
|  | 4.120827 | 83% | 52% | 2 | 0.0 | 0.0 | na |
|  | 0.6001451 | 100% | 13% | 3 | 3.1 | 0.2 | 51.5 |
|  | 23.377627 | 33% | 71% | 4 | 2.0 | 0.1 | 45.2 |
|  | 37.817259 | 17% | 81% |  |  |  |  |
|  | 50.930626 | 0% | 91% |  |  |  |  |
| 24 hours | 4.679988 | 75% | 53% | 1 |  |  |  |
|  | 0.8763587 | 100% | 22% | 2 | 0.0 | 0.0 | na |
|  | 0.8763587 | 100% | 22% | 3 | 2.1 | 0.1 | 47.6 |
|  | 23.377627 | 25% | 71% | 4 | 1.0 | 0.0 | 57.4 |
|  | 37.817259 | 25% | 81% |  |  |  |  |
|  | 50.930626 | 0% | 91% |  |  |  |  |
| 48 hours | 5.2959736 | 100% | 56% | 1 |  |  |  |
|  | 5.2959736 | 100% | 56% | 2 | na | na | na |
|  | 5.2959736 | 100% | 56% | 3 | na | na | na |
|  | 23.377627 | 50% | 71% | 4 | na | na | na |
|  | 37.817259 | 50% | 81% |  |  |  |  |
|  | 50.930626 | 50% | 91% |  |  |  |  |

UO only

| Time prior AKI stage | Cutoff value | sens | spec | Quartile | OR | 95% CI of OR | |
|---|---|---|---|---|---|---|---|
| 0 hours | 2.1084701 | 71% | 36% | 1 |  |  |  |
|  | 1.7559524 | 86% | 33% | 2 | 2.4 | 0.4 | 15.0 |
|  | 0.41705 | 93% | 5% | 3 | 4.5 | 0.8 | 25.0 |
|  | 25.482094 | 21% | 71% | 4 | 1.0 | 0.1 | 9.8 |
|  | 40.35533 | 7% | 81% |  |  |  |  |
|  | 58.544839 | 0% | 90% |  |  |  |  |
| 24 hours | 0.647909 | 100% | 10% | 1 |  |  |  |
|  | 0.647909 | 100% | 10% | 2 | 0.0 | 0.0 | na |
|  | 0.647909 | 100% | 10% | 3 | 0.0 | 0.0 | na |
|  | 25.482094 | 50% | 71% | 4 | 1.0 | 0.0 | 74.6 |
|  | 40.35533 | 0% | 81% |  |  |  |  |
|  | 58.544839 | 0% | 90% |  |  |  |  |
| 48 hours | 3.7035281 | 100% | 43% | 1 |  |  |  |
|  | 3.7035281 | 100% | 43% | 2 | na | na | na |
|  | 3.7035281 | 100% | 43% | 3 | na | na | na |
|  | 25.482094 | 0% | 71% | 4 | na | na | na |
|  | 40.35533 | 0% | 81% |  |  |  |  |
|  | 58.544839 | 0% | 90% |  |  |  |  |

Fig. 5 - 18

Serum amyloid P-component sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 4777.794 | 5269.103 | 4777.794 | 5335.126 | 4777.794 | 5911.409 |
| average | 5429.356 | 5900.293 | 5429.356 | 5634.925 | 5429.356 | 5864.357 |
| stdev | 2598.916 | 2923.675 | 2598.916 | 2733.024 | 2598.916 | 1615.939 |
| p (t-test) |  | 0.319 |  | 0.641 |  | 0.425 |
| min | 96.224 | 1726.916 | 96.224 | 915.589 | 96.224 | 2435.350 |
| max | 16315.493 | 16576.982 | 16315.493 | 15099.189 | 16315.493 | 9313.335 |
| n (Samp) | 105 | 48 | 105 | 55 | 105 | 25 |
| n (Pat) | 99 | 48 | 99 | 55 | 99 | 25 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 4901.022 | 4965.322 | 4901.022 | 5479.072 | 4901.022 | 7025.322 |
| average | 5410.216 | 5730.188 | 5410.216 | 6527.434 | 5410.216 | 6721.597 |
| stdev | 2594.166 | 2543.963 | 2594.166 | 3060.956 | 2594.166 | 1258.388 |
| p (t-test) |  | 0.633 |  | 0.069 |  | 0.083 |
| min | 96.224 | 2712.995 | 96.224 | 1775.429 | 96.224 | 4897.196 |
| max | 16576.982 | 11731.227 | 16576.982 | 15099.189 | 16576.982 | 9313.335 |
| n (Samp) | 242 | 16 | 242 | 20 | 242 | 12 |
| n (Pat) | 161 | 16 | 161 | 20 | 161 | 12 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 5129.158 | 5619.867 | 5129.158 | 4951.655 | 5129.158 | 5489.238 |
| average | 5466.850 | 6142.521 | 5466.850 | 5295.765 | 5466.850 | 5308.809 |
| stdev | 2241.215 | 3084.026 | 2241.215 | 2476.546 | 2241.215 | 1442.404 |
| p (t-test) |  | 0.156 |  | 0.686 |  | 0.758 |
| min | 1580.497 | 1726.916 | 1580.497 | 915.589 | 1580.497 | 2435.350 |
| max | 16315.493 | 16576.982 | 16315.493 | 11719.795 | 16315.493 | 7635.468 |
| n (Samp) | 96 | 40 | 96 | 44 | 96 | 21 |
| n (Pat) | 84 | 40 | 84 | 44 | 84 | 21 | sCr or UO

| Time prior AKI stage | AUC | SE | nCohort 1 | nCohort 2 | p |
|---|---|---|---|---|---|
| 0 hours | 0.55 | 0.051 | 105 | 48 | 0.299 |
| 24 hours | 0.53 | 0.048 | 105 | 55 | 0.539 |
| 48 hours | 0.61 | 0.065 | 105 | 25 | 0.086 | sCr only

| Time prior AKI stage | AUC | SE | nCohort 1 | nCohort 2 | p |
|---|---|---|---|---|---|
| 0 hours | 0.54 | 0.076 | 242 | 16 | 0.625 |
| 24 hours | 0.62 | 0.069 | 242 | 20 | 0.085 |
| 48 hours | 0.74 | 0.084 | 242 | 12 | 0.005 |

UO only

| Time prior AKI stage | AUC | SE | nCohort 1 | nCohort 2 | p |
|---|---|---|---|---|---|
| 0 hours | 0.56 | 0.055 | 96 | 40 | 0.271 |
| 24 hours | 0.48 | 0.052 | 96 | 44 | 0.688 |
| 48 hours | 0.52 | 0.070 | 96 | 21 | 0.824 | sCr or UO

| Time prior AKI stage | Cutoff value | sens | spec | Quartile | OR | 95% CI of OR | |
|---|---|---|---|---|---|---|---|
| 0 hours | 4189.319 | 71% | 34% | 1 |  |  |  |
|  | 3804.4829 | 81% | 26% | 2 | 0.7 | 0.4 | 1.1 |
|  | 2574.8577 | 92% | 7% | 3 | 1.3 | 0.8 | 2.1 |
|  | 6201.8056 | 35% | 70% | 4 | 1.7 | 1.1 | 2.7 |
|  | 6895.0273 | 33% | 80% |  |  |  |  |
|  | 8454.6109 | 8% | 90% |  |  |  |  |
| 24 hours | 4055.2483 | 71% | 31% | 1 |  |  |  |
|  | 3704.7846 | 80% | 25% | 2 | 1.0 | 0.6 | 1.6 |
|  | 2272.6685 | 91% | 5% | 3 | 1.6 | 1.0 | 2.4 |
|  | 6201.8056 | 31% | 70% | 4 | 1.4 | 0.9 | 2.2 |
|  | 6895.0273 | 25% | 80% |  |  |  |  |

Fig. 5 - 19

|  | 8454.6109 | 18% | 90% |  |  |  |  |
|---|---|---|---|---|---|---|---|
| 48 hours | 5360.051 | 72% | 60% | 1 |  |  |  |
|  | 4394.6994 | 80% | 40% | 2 | 1.3 | 0.4 | 4.8 |
|  | 3804.4829 | 92% | 26% | 3 | 4.4 | 1.6 | 12.0 |
|  | 6201.8056 | 48% | 70% | 4 | 3.1 | 1.1 | 8.8 |
|  | 6895.0273 | 32% | 80% |  |  |  |  |
|  | 8454.6109 | 4% | 90% |  |  |  |  | sCr only

| Time prior AKI stage | Cutoff value | sens | spec | Quartile | OR | 95% CI of OR | |
|---|---|---|---|---|---|---|---|
| 0 hours | 4189.319 | 75% | 35% | 1 |  |  |  |
|  | 3439.4811 | 81% | 18% | 2 | 1.0 | 0.3 | 2.8 |
|  | 2870.5973 | 94% | 13% | 3 | 0.5 | 0.1 | 2.2 |
|  | 6201.8056 | 38% | 70% | 4 | 1.5 | 0.6 | 3.7 |
|  | 7006.5873 | 38% | 80% |  |  |  |  |
|  | 8367.1538 | 19% | 90% |  |  |  |  |
| 24 hours | 5324.4963 | 70% | 57% | 1 |  |  |  |
|  | 4189.319 | 80% | 35% | 2 | 2.0 | 0.4 | 9.4 |
|  | 3956.1005 | 90% | 28% | 3 | 3.8 | 1.0 | 14.3 |
|  | 6201.8056 | 35% | 70% | 4 | 3.7 | 1.0 | 14.1 |
|  | 7006.5873 | 35% | 80% |  |  |  |  |
|  | 8367.1538 | 25% | 90% |  |  |  |  |
| 48 hours | 5653.03 | 75% | 62% | 1 |  |  |  |
|  | 5427.0131 | 83% | 58% | 2 | na | na | na |
|  | 5296.6572 | 92% | 57% | 3 | na | na | na |
|  | 6201.8056 | 67% | 70% | 4 | na | na | na |
|  | 7006.5873 | 50% | 80% |  |  |  |  |
|  | 8367.1538 | 8% | 90% |  |  |  |  |

UO only

| Time prior AKI stage | Cutoff value | sens | spec | Quartile | OR | 95% CI of OR | |
|---|---|---|---|---|---|---|---|
| 0 hours | 4394.6994 | 70% | 35% | 1 |  |  |  |
|  | 3811.5919 | 80% | 21% | 2 | 0.7 | 0.4 | 1.3 |
|  | 3425.1197 | 90% | 15% | 3 | 0.6 | 0.3 | 1.2 |
|  | 6201.8056 | 40% | 71% | 4 | 1.9 | 1.1 | 3.2 |
|  | 6895.0273 | 38% | 80% |  |  |  |  |
|  | 8435.3903 | 10% | 91% |  |  |  |  |
| 24 hours | 3970.7915 | 70% | 25% | 1 |  |  |  |
|  | 2870.5973 | 82% | 10% | 2 | 1.1 | 0.7 | 2.0 |
|  | 2272.6685 | 91% | 4% | 3 | 1.1 | 0.7 | 2.0 |
|  | 6201.8056 | 27% | 71% | 4 | 1.3 | 0.8 | 2.2 |
|  | 6895.0273 | 20% | 80% |  |  |  |  |
|  | 8435.3903 | 16% | 91% |  |  |  |  |
| 48 hours | 4394.6994 | 71% | 35% | 1 |  |  |  |
|  | 3912.6934 | 81% | 23% | 2 | 0.6 | 0.2 | 1.8 |
|  | 3425.1197 | 90% | 15% | 3 | 1.8 | 0.8 | 4.1 |
|  | 6201.8056 | 33% | 71% | 4 | 1.0 | 0.4 | 2.5 |
|  | 6895.0273 | 14% | 80% |  |  |  |  |
|  | 8435.3903 | 0% | 91% |  |  |  |  |

Fig. 5 - 20

Fatty acid binding protein, heart sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 7.870 | 28.350 | 7.870 | 23.500 | 7.870 | 25.850 |
| average | 29.799 | 86.504 | 29.799 | 157.776 | 29.799 | 83.122 |
| stdev | 78.132 | 183.922 | 78.132 | 343.908 | 78.132 | 128.747 |
| p (t-test) |  | 0.001 |  | 0.000 |  | 0.006 |
| min | 0.030 | 1.440 | 0.030 | 0.030 | 0.030 | 1.440 |
| max | 944.000 | 809.000 | 944.000 | 1477.000 | 944.000 | 463.000 |
| n (Samp) | 434 | 28 | 434 | 36 | 434 | 18 |
| n (Pat) | 173 | 28 | 173 | 36 | 173 | 18 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 8.920 | 91.250 | 8.920 | 48.250 | 8.920 | 84.700 |
| average | 38.900 | 208.083 | 38.900 | 363.564 | 38.900 | 181.943 |
| stdev | 103.113 | 301.551 | 103.113 | 564.084 | 103.113 | 233.374 |
| p (t-test) |  | 0.000 |  | 0.000 |  | 0.000 |
| min | 0.030 | 17.900 | 0.030 | 4.660 | 0.030 | 13.500 |
| max | 944.000 | 809.000 | 944.000 | 1477.000 | 944.000 | 572.000 |
| n (Samp) | 542 | 6 | 542 | 10 | 542 | 7 |
| n (Pat) | 208 | 6 | 208 | 10 | 208 | 7 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 8.445 | 26.600 | 8.445 | 36.350 | 8.445 | 25.850 |
| average | 30.058 | 57.893 | 30.058 | 93.107 | 30.058 | 63.806 |
| stdev | 76.890 | 119.253 | 76.890 | 178.545 | 76.890 | 91.809 |
| p (t-test) |  | 0.084 |  | 0.000 |  | 0.089 |
| min | 0.030 | 1.440 | 0.030 | 0.030 | 0.030 | 1.440 |
| max | 944.000 | 623.000 | 944.000 | 944.000 | 944.000 | 324.000 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
|---|---|---|---|---|---|
| 0 hours | 0.72 | 0.056 | 434 | 28 | 0.000 |
| 24 hours | 0.70 | 0.050 | 434 | 36 | 0.000 |
| 48 hours | 0.69 | 0.071 | 434 | 18 | 0.009 | sCr only

| Time prior AKI stage | AUC | SE | nCohort 1 | nCohort 2 | p |
|---|---|---|---|---|---|
| 0 hours | 0.87 | 0.094 | 542 | 6 | 0.000 |
| 24 hours | 0.73 | 0.091 | 542 | 10 | 0.010 |
| 48 hours | 0.83 | 0.095 | 542 | 7 | 0.000 |

UO only

| Time prior AKI stage | AUC | SE | nCohort 1 | nCohort 2 | p |
|---|---|---|---|---|---|
| 0 hours | 0.69 | 0.058 | 356 | 27 | 0.001 |
| 24 hours | 0.69 | 0.054 | 356 | 32 | 0.000 |
| 48 hours | 0.66 | 0.076 | 356 | 16 | 0.034 | sCr or UO

| Time prior AKI stage | Cutoff value | sens | spec | Quartile | OR | 95% CI of OR | |
|---|---|---|---|---|---|---|---|
| 0 hours | 11.5 | 71% | 62% | 1 |  |  |  |
|  | 10 | 82% | 59% | 2 | 1.5 | 0.3 | 8.0 |
|  | 3.37 | 93% | 28% | 3 | 4.2 | 1.2 | 14.9 |
|  | 16.1 | 64% | 70% | 4 | 8.4 | 2.7 | 26.4 |
|  | 33.4 | 39% | 80% |  |  |  |  |
|  | 71.6 | 25% | 90% |  |  |  |  |
| 24 hours | 11 | 72% | 62% | 1 |  |  |  |
|  | 8.42 | 81% | 52% | 2 | 0.2 | 0.0 | 1.6 |
|  | 1.93 | 94% | 20% | 3 | 2.1 | 1.2 | 3.6 |
|  | 16.1 | 61% | 70% | 4 | 3.1 | 1.9 | 5.0 |

Fig. 6 - 1

|  | 33.4 | 47% | 80% |  |  |  |  |
|  | 71.6 | 33% | 90% |  |  |  |  |
| 48 hours | 13.3 | 72% | 67% | 1 |  |  |  |
|  | 2.99 | 83% | 26% | 2 | 0.3 | 0.0 | 4.6 |
|  | 1.83 | 94% | 19% | 3 | 1.7 | 0.6 | 5.0 |
|  | 16.1 | 61% | 70% | 4 | 3.2 | 1.3 | 7.9 |
|  | 33.4 | 44% | 80% |  |  |  |  |
|  | 71.6 | 28% | 90% |  |  |  |  |

UO only

| Time prior AKI stage | Cutoff value | sens | spec | Quartile | OR | 95% CI of OR | |
|---|---|---|---|---|---|---|---|
| 0 hours | 11.5 | 70% | 60% | 1 |  |  |  |
|  | 9.97 | 81% | 57% | 2 | 1.5 | 0.3 | 8.0 |
|  | 3.25 | 93% | 26% | 3 | 4.8 | 1.4 | 16.6 |
|  | 17.5 | 63% | 70% | 4 | 7.3 | 2.2 | 23.6 |
|  | 33.9 | 37% | 80% |  |  |  |  |
|  | 76.8 | 15% | 90% |  |  |  |  |
| 24 hours | 13.3 | 72% | 65% | 1 |  |  |  |
|  | 5.18 | 81% | 37% | 2 | 0.2 | 0.0 | 1.6 |
|  | 1.93 | 94% | 19% | 3 | 1.4 | 0.7 | 2.5 |
|  | 17.5 | 66% | 70% | 4 | 3.2 | 2.0 | 5.3 |
|  | 33.9 | 50% | 80% |  |  |  |  |
|  | 76.8 | 34% | 90% |  |  |  |  |
| 48 hours | 9.97 | 75% | 57% | 1 |  |  |  |
|  | 2.99 | 81% | 25% | 2 | 0.0 | 0.0 | na |
|  | 1.81 | 94% | 18% | 3 | 1.3 | 0.5 | 3.2 |
|  | 17.5 | 63% | 70% | 4 | 1.8 | 0.8 | 4.1 |
|  | 33.9 | 44% | 80% |  |  |  |  |
|  | 76.8 | 25% | 90% |  |  |  |  |

Fig. 6 - 2

Hepatocyte growth factor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 785.857 | 800.061 | 785.857 | 959.117 | 785.857 | 1140.990 |
| average | 1837.846 | 4370.706 | 1837.846 | 1873.697 | 1837.846 | 1421.852 |
| stdev | 2549.628 | 11864.960 | 2549.628 | 2004.545 | 2549.628 | 1536.897 |
| p (t-test) |  | 0.009 |  | 0.943 |  | 0.520 |
| min | 51.808 | 312.956 | 51.808 | 225.202 | 51.808 | 180.668 |
| max | 17531.948 | 52712.475 | 17531.948 | 7301.432 | 17531.948 | 6754.272 |
| n (Samp) | 230 | 19 | 230 | 28 | 230 | 16 |
| n (Pat) | 158 | 19 | 158 | 28 | 158 | 16 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 847.303 | 27453.357 | 847.303 | 1517.974 | 847.303 | 960.960 |
| average | 1869.522 | 27453.357 | 1869.522 | 3111.683 | 1869.522 | 1219.269 |
| stdev | 2768.460 | 35721.787 | 2768.460 | 3452.908 | 2768.460 | 647.369 |
| p (t-test) |  | 0.000 |  | 0.244 |  | 0.601 |
| min | 51.808 | 2194.240 | 51.808 | 452.950 | 51.808 | 591.579 |
| max | 25326.471 | 52712.475 | 25326.471 | 8813.508 | 25326.471 | 2260.899 |
| n (Samp) | 295 | 2 | 295 | 7 | 295 | 5 |
| n (Pat) | 187 | 2 | 187 | 7 | 187 | 5 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 748.776 | 752.858 | 748.776 | 1136.803 | 748.776 | 1319.719 |
| average | 1846.731 | 1608.159 | 1846.731 | 3739.396 | 1846.731 | 1576.384 |
| stdev | 2650.927 | 1941.760 | 2650.927 | 10136.948 | 2650.927 | 1634.436 |
| p (t-test) |  | 0.703 |  | 0.033 |  | 0.707 |
| min | 51.808 | 312.956 | 51.808 | 225.202 | 51.808 | 180.668 |
| max | 17531.948 | 7852.366 | 17531.948 | 52712.475 | 17531.948 | 6754.272 |
| n (Samp) | 198 | 19 | 198 | 26 | 198 | 14 |
| n (Pat) | 132 | 19 | 132 | 26 | 132 | 14 | sCr or UO

| Time prior AKI stage | AUC | SE | nCohort 1 | nCohort 2 | p |
| --- | --- | --- | --- | --- | --- |
| 0 hours | 0.57 | 0.071 | 230 | 19 | 0.357 |
| 24 hours | 0.56 | 0.059 | 230 | 28 | 0.308 |
| 48 hours | 0.53 | 0.076 | 230 | 16 | 0.676 | sCr only

| Time prior AKI stage | AUC | SE | nCohort 1 | nCohort 2 | p |
| --- | --- | --- | --- | --- | --- |
| 0 hours | 0.88 | 0.159 | 295 | 2 | 0.017 |
| 24 hours | 0.65 | 0.114 | 295 | 7 | 0.178 |
| 48 hours | 0.57 | 0.134 | 295 | 5 | 0.619 |

UO only

| Time prior AKI stage | AUC | SE | nCohort 1 | nCohort 2 | p |
| --- | --- | --- | --- | --- | --- |
| 0 hours | 0.54 | 0.071 | 198 | 19 | 0.555 |
| 24 hours | 0.58 | 0.062 | 198 | 26 | 0.176 |
| 48 hours | 0.55 | 0.082 | 198 | 14 | 0.517 | sCr or UO

| Time prior AKI stage | Cutoff value | sens | spec | Quartile | OR | 95% CI of OR | |
| --- | --- | --- | --- | --- | --- | --- | --- |
| 0 hours | 575.20844 | 74% | 38% | 1 |  |  |  |
|  | 513.85383 | 84% | 34% | 2 | 3.8 | 1.0 | 14.4 |
|  | 358.54972 | 95% | 19% | 3 | 3.2 | 0.8 | 12.7 |
|  | 1863.8946 | 37% | 70% | 4 | 2.0 | 0.4 | 9.4 |
|  | 2715.1627 | 21% | 80% |  |  |  |  |
|  | 4719.486 | 16% | 90% |  |  |  |  |
| 24 hours | 660.41281 | 71% | 47% | 1 |  |  |  |
|  | 468.6146 | 82% | 30% | 2 | 1.8 | 0.8 | 4.2 |
|  | 309.45606 | 93% | 16% | 3 | 2.5 | 1.1 | 5.3 |
|  | 1863.8946 | 32% | 70% | 4 | 2.1 | 0.9 | 4.7 |
|  | 2715.1627 | 18% | 80% |  |  |  |  |

Fig. 6 - 3

|  | 4719.486 | 14% | 90% |  |  |  |  |
|---|---|---|---|---|---|---|---|
| 48 hours | 611.77344 | 75% | 43% | 1 |  |  |  |
|  | 591.03997 | 81% | 40% | 2 | 1.0 | 0.2 | 3.9 |
|  | 298.34033 | 94% | 15% | 3 | 3.3 | 1.3 | 8.6 |
|  | 1863.8946 | 19% | 70% | 4 | 0.3 | 0.0 | 4.6 |
|  | 2715.1627 | 6% | 80% |  |  |  |  |
|  | 4719.486 | 6% | 90% |  |  |  |  |

UO only

| Time prior AKI stage | Cutoff value | sens | spec | Quartile | OR | 95% CI of OR | |
|---|---|---|---|---|---|---|---|
| 0 hours | 575.20844 | 74% | 39% | 1 |  |  |  |
|  | 513.85383 | 84% | 35% | 2 | 3.9 | 1.0 | 14.8 |
|  | 358.54972 | 95% | 20% | 3 | 3.3 | 0.8 | 13.0 |
|  | 1823.3743 | 26% | 70% | 4 | 2.0 | 0.4 | 9.6 |
|  | 2715.1627 | 16% | 80% |  |  |  |  |
|  | 4719.486 | 11% | 90% |  |  |  |  |
| 24 hours | 649.07174 | 73% | 48% | 1 |  |  |  |
|  | 474.87493 | 81% | 31% | 2 | 1.3 | 0.5 | 3.3 |
|  | 307.96674 | 92% | 17% | 3 | 2.2 | 1.0 | 4.9 |
|  | 1823.3743 | 35% | 70% | 4 | 2.5 | 1.1 | 5.5 |
|  | 2715.1627 | 19% | 80% |  |  |  |  |
|  | 4719.486 | 15% | 90% |  |  |  |  |
| 48 hours | 709.80187 | 71% | 49% | 1 |  |  |  |
|  | 401.51729 | 86% | 22% | 2 | 0.7 | 0.1 | 3.6 |
|  | 298.34033 | 93% | 16% | 3 | 2.1 | 0.7 | 6.1 |
|  | 1823.3743 | 29% | 70% | 4 | 1.0 | 0.3 | 4.0 |
|  | 2715.1627 | 7% | 80% |  |  |  |  |
|  | 4719.486 | 7% | 90% |  |  |  |  |

Fig. 6 - 4

Interleukin-16 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 465.500 | 618.000 | 465.500 | 559.500 | 465.500 | 528.000 |
| average | 546.730 | 1220.893 | 546.730 | 729.083 | 546.730 | 671.611 |
| stdev | 582.350 | 3070.443 | 582.350 | 561.517 | 582.350 | 447.400 |
| p (t-test) |  | 0.000 |  | 0.071 |  | 0.369 |
| min | 161.000 | 153.000 | 161.000 | 190.000 | 161.000 | 263.000 |
| max | 11500.000 | 16800.000 | 11500.000 | 3110.000 | 11500.000 | 1630.000 |
| n (Samp) | 434 | 28 | 434 | 36 | 434 | 18 |
| n (Pat) | 173 | 28 | 173 | 36 | 173 | 18 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 466.000 | 911.000 | 466.000 | 823.000 | 466.000 | 1040.000 |
| average | 559.373 | 3556.167 | 559.373 | 804.700 | 559.373 | 1010.000 |
| stdev | 553.796 | 6496.693 | 553.796 | 354.016 | 553.796 | 493.955 |
| p (t-test) |  | 0.000 |  | 0.164 |  | 0.033 |
| min | 153.000 | 567.000 | 153.000 | 302.000 | 153.000 | 365.000 |
| max | 11500.000 | 16800.000 | 11500.000 | 1280.000 | 11500.000 | 1630.000 |
| n (Samp) | 542 | 6 | 542 | 10 | 542 | 7 |
| n (Pat) | 208 | 6 | 208 | 10 | 208 | 7 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 465.500 | 554.000 | 465.500 | 554.000 | 465.500 | 570.000 |
| average | 527.596 | 627.074 | 527.596 | 701.563 | 527.596 | 1595.563 |
| stdev | 246.463 | 328.308 | 246.463 | 573.322 | 246.463 | 4066.286 |
| p (t-test) |  | 0.049 |  | 0.001 |  | 0.000 |
| min | 172.000 | 153.000 | 172.000 | 190.000 | 172.000 | 263.000 |
| max | 1630.000 | 1600.000 | 1630.000 | 3110.000 | 1630.000 | 16800.000 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
| --- | --- | --- | --- | --- | --- |
| 0 hours | 0.63 | 0.058 | 434 | 28 | 0.029 |
| 24 hours | 0.61 | 0.052 | 434 | 36 | 0.041 |
| 48 hours | 0.55 | 0.071 | 434 | 18 | 0.452 | sCr only

| Time prior AKI stage | AUC | SE | nCohort 1 | nCohort 2 | p |
| --- | --- | --- | --- | --- | --- |
| 0 hours | 0.87 | 0.093 | 542 | 6 | 0.000 |
| 24 hours | 0.72 | 0.092 | 542 | 10 | 0.015 |
| 48 hours | 0.77 | 0.105 | 542 | 7 | 0.009 |

UO only

| Time prior AKI stage | AUC | SE | nCohort 1 | nCohort 2 | p |
| --- | --- | --- | --- | --- | --- |
| 0 hours | 0.59 | 0.059 | 356 | 27 | 0.141 |
| 24 hours | 0.58 | 0.055 | 356 | 32 | 0.132 |
| 48 hours | 0.56 | 0.076 | 356 | 16 | 0.421 | sCr or UO

| Time prior AKI stage | Cutoff value | sens | spec | Quartile | OR | 95% CI of OR | |
| --- | --- | --- | --- | --- | --- | --- | --- |
| 0 hours | 438 | 71% | 44% | 1 |  |  |  |
|  | 346 | 82% | 22% | 2 | 0.5 | 0.2 | 1.3 |
|  | 261 | 93% | 8% | 3 | 0.8 | 0.4 | 1.8 |
|  | 579 | 54% | 70% | 4 | 2.5 | 1.5 | 4.1 |
|  | 655 | 46% | 80% |  |  |  |  |
|  | 829 | 29% | 90% |  |  |  |  |
| 24 hours | 399 | 72% | 35% | 1 |  |  |  |
|  | 360 | 81% | 25% | 2 | 0.6 | 0.3 | 1.2 |
|  | 295 | 92% | 13% | 3 | 1.0 | 0.6 | 1.7 |
|  | 579 | 47% | 70% | 4 | 2.0 | 1.3 | 3.0 |
|  | 655 | 39% | 80% |  |  |  |  |

Fig. 6 - 5

|  | 829 | 28% | 90% |  |  |  |  |
|---|---|---|---|---|---|---|---|
| 48 hours | 364 | 72% | 25% | 1 |  |  |  |
|  | 327 | 83% | 18% | 2 | 0.6 | 0.2 | 1.7 |
|  | 310 | 94% | 15% | 3 | 0.8 | 0.3 | 2.0 |
|  | 579 | 39% | 70% | 4 | 1.2 | 0.6 | 2.6 |
|  | 655 | 33% | 80% |  |  |  |  |
|  | 829 | 22% | 90% |  |  |  |  | sCr only

| Time prior AKI stage | Cutoff value | sens | spec | Quartile | OR | 95% CI of OR | |
|---|---|---|---|---|---|---|---|
| 0 hours | 655 | 83% | 78% | 1 |  |  |  |
|  | 655 | 83% | 78% | 2 | na | na | na |
|  | 566 | 100% | 67% | 3 | na | na | na |
|  | 592 | 83% | 70% | 4 | na | na | na |
|  | 683 | 67% | 80% |  |  |  |  |
|  | 914 | 50% | 90% |  |  |  |  |
| 24 hours | 589 | 70% | 70% | 1 |  |  |  |
|  | 525 | 80% | 61% | 2 | 0.0 | 0.0 | na |
|  | 362 | 90% | 25% | 3 | 1.0 | 0.1 | 7.3 |
|  | 592 | 60% | 70% | 4 | 3.1 | 0.8 | 11.8 |
|  | 683 | 50% | 80% |  |  |  |  |
|  | 914 | 50% | 90% |  |  |  |  |
| 48 hours | 996 | 71% | 93% | 1 |  |  |  |
|  | 404 | 86% | 37% | 2 | na | na | na |
|  | 364 | 100% | 25% | 3 | na | na | na |
|  | 592 | 71% | 70% | 4 | na | na | na |
|  | 683 | 71% | 80% |  |  |  |  |
|  | 914 | 71% | 90% |  |  |  |  |

UO only

| Time prior AKI stage | Cutoff value | sens | spec | Quartile | OR | 95% CI of OR | |
|---|---|---|---|---|---|---|---|
| 0 hours | 416 | 70% | 39% | 1 |  |  |  |
|  | 346 | 81% | 21% | 2 | 0.6 | 0.3 | 1.5 |
|  | 261 | 93% | 7% | 3 | 0.8 | 0.4 | 1.7 |
|  | 592 | 44% | 70% | 4 | 2.1 | 1.2 | 3.6 |
|  | 673 | 37% | 80% |  |  |  |  |
|  | 883 | 26% | 90% |  |  |  |  |
| 24 hours | 399 | 72% | 35% | 1 |  |  |  |
|  | 360 | 81% | 24% | 2 | 0.7 | 0.3 | 1.4 |
|  | 295 | 91% | 13% | 3 | 1.3 | 0.8 | 2.3 |
|  | 592 | 38% | 70% | 4 | 1.6 | 1.0 | 2.7 |
|  | 673 | 34% | 80% |  |  |  |  |
|  | 883 | 19% | 90% |  |  |  |  |
| 48 hours | 333 | 75% | 18% | 1 |  |  |  |
|  | 327 | 81% | 17% | 2 | 0.2 | 0.0 | 2.1 |
|  | 307 | 94% | 15% | 3 | 1.0 | 0.4 | 2.3 |
|  | 592 | 31% | 70% | 4 | 1.0 | 0.4 | 2.3 |
|  | 673 | 31% | 80% |  |  |  |  |
|  | 883 | 19% | 90% |  |  |  |  |

Fig. 6 - 6

Interleukin-2 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.507 | 0.567 | 0.507 | 0.718 | 0.507 | 0.576 |
| average | 0.862 | 0.660 | 0.862 | 1.097 | 0.862 | 0.824 |
| stdev | 1.545 | 0.433 | 1.545 | 1.050 | 1.545 | 0.671 |
| p (t-test) |  | 0.570 |  | 0.435 |  | 0.921 |
| min | 0.000 | 0.125 | 0.000 | 0.209 | 0.000 | 0.167 |
| max | 19.127 | 1.719 | 19.127 | 5.074 | 19.127 | 2.654 |
| n (Samp) | 230 | 19 | 230 | 28 | 230 | 16 |
| n (Pat) | 158 | 19 | 158 | 28 | 158 | 16 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.537 | 0.565 | 0.537 | 0.541 | 0.537 | 0.575 |
| average | 0.871 | 0.565 | 0.871 | 0.976 | 0.871 | 0.488 |
| stdev | 1.419 | 0.092 | 1.419 | 0.819 | 1.419 | 0.270 |
| p (t-test) |  | 0.761 |  | 0.845 |  | 0.547 |
| min | 0.000 | 0.500 | 0.000 | 0.294 | 0.000 | 0.167 |
| max | 19.127 | 0.630 | 19.127 | 2.538 | 19.127 | 0.844 |
| n (Samp) | 295 | 2 | 295 | 7 | 295 | 5 |
| n (Pat) | 187 | 2 | 187 | 7 | 187 | 5 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.535 | 0.567 | 0.535 | 0.718 | 0.535 | 0.609 |
| average | 0.934 | 0.633 | 0.934 | 1.109 | 0.934 | 0.895 |
| stdev | 1.650 | 0.458 | 1.650 | 1.081 | 1.650 | 0.679 |
| p (t-test) |  | 0.431 |  | 0.599 |  | 0.930 |
| min | 0.000 | 0.000 | 0.000 | 0.209 | 0.000 | 0.207 |
| max | 19.127 | 1.719 | 19.127 | 5.074 | 19.127 | 2.654 |
| n (Samp) | 198 | 19 | 198 | 26 | 198 | 14 |
| n (Pat) | 132 | 19 | 132 | 26 | 132 | 14 | sCr or UO

| Time prior AKI stage | AUC | SE | nCohort 1 | nCohort 2 | p |
| --- | --- | --- | --- | --- | --- |
| 0 hours | 0.51 | 0.070 | 230 | 19 | 0.843 |
| 24 hours | 0.63 | 0.059 | 230 | 28 | 0.023 |
| 48 hours | 0.55 | 0.077 | 230 | 16 | 0.494 | sCr only

| Time prior AKI stage | AUC | SE | nCohort 1 | nCohort 2 | p |
| --- | --- | --- | --- | --- | --- |
| 0 hours | 0.53 | 0.209 | 295 | 2 | 0.874 |
| 24 hours | 0.58 | 0.114 | 295 | 7 | 0.507 |
| 48 hours | 0.42 | 0.121 | 295 | 5 | 0.485 |

UO only

| Time prior AKI stage | AUC | SE | nCohort 1 | nCohort 2 | p |
| --- | --- | --- | --- | --- | --- |
| 0 hours | 0.46 | 0.068 | 198 | 19 | 0.606 |
| 24 hours | 0.61 | 0.062 | 198 | 26 | 0.069 |
| 48 hours | 0.58 | 0.082 | 198 | 14 | 0.323 | sCr or UO

| Time prior AKI stage | Cutoff value | sens | spec | Quartile | OR | 95% CI of OR | |
| --- | --- | --- | --- | --- | --- | --- | --- |
| 0 hours | 0.3397476 | 74% | 27% | 1 |  |  |  |
|  | 0.2818205 | 84% | 20% | 2 | 0.6 | 0.2 | 1.8 |
|  | 0.1689911 | 95% | 8% | 3 | 1.2 | 0.6 | 2.7 |
|  | 0.7604118 | 32% | 70% | 4 | 1.0 | 0.4 | 2.3 |
|  | 0.9730253 | 21% | 80% |  |  |  |  |
|  | 1.6431131 | 5% | 90% |  |  |  |  |
| 24 hours | 0.536801 | 71% | 53% | 1 |  |  |  |
|  | 0.3872229 | 82% | 33% | 2 | 1.7 | 0.6 | 5.1 |
|  | 0.2920348 | 93% | 21% | 3 | 3.3 | 1.3 | 8.5 |
|  | 0.7604118 | 50% | 70% | 4 | 4.1 | 1.7 | 10.2 |
|  | 0.9730253 | 36% | 80% |  |  |  |  |

Fig. 6 - 7

|  | | 1.6431131 | 18% | 90% | | | | |
|---|---|---|---|---|---|---|---|---|
| | 48 hours | 0.3701848 | 75% | 31% | 1 | | | |
| | | 0.3498805 | 81% | 28% | 2 | 1.3 | 0.4 | 4.5 |
| | | 0.1974446 | 94% | 9% | 3 | 1.0 | 0.3 | 4.0 |
| | | 0.7604118 | 38% | 70% | 4 | 2.1 | 0.7 | 5.9 |
| | | 0.9730253 | 31% | 80% | | | | |
| | | 1.6431131 | 13% | 90% | | | | | sCr only

| Time prior AKI stage | Cutoff value | sens | spec | Quartile | OR | 95% CI of OR | |
|---|---|---|---|---|---|---|---|
| 0 hours | 0.4991843 | 100% | 46% | 1 | | | |
| | 0.4991843 | 100% | 46% | 2 | na | na | na |
| | 0.4991843 | 100% | 46% | 3 | na | na | na |
| | 0.798842 | 0% | 70% | 4 | na | na | na |
| | 1.0624848 | 0% | 80% | | | | |
| | 1.8023893 | 0% | 91% | | | | |
| 24 hours | 0.4625933 | 71% | 41% | 1 | | | |
| | 0.3397476 | 86% | 25% | 2 | 2.0 | 0.1 | 39.9 |
| | 0.2920348 | 100% | 20% | 3 | 1.0 | 0.0 | 53.1 |
| | 0.798842 | 43% | 70% | 4 | 3.0 | 0.2 | 43.8 |
| | 1.0624848 | 43% | 80% | | | | |
| | 1.8023893 | 14% | 91% | | | | |
| 48 hours | 0.2697168 | 80% | 16% | 1 | | | |
| | 0.2697168 | 80% | 16% | 2 | na | na | na |
| | 0.1572836 | 100% | 6% | 3 | na | na | na |
| | 0.798842 | 20% | 70% | 4 | na | na | na |
| | 1.0624848 | 0% | 80% | | | | |
| | 1.8023893 | 0% | 91% | | | | |

UO only

| Time prior AKI stage | Cutoff value | sens | spec | Quartile | OR | 95% CI of OR | |
|---|---|---|---|---|---|---|---|
| 0 hours | 0.2894797 | 74% | 18% | 1 | | | |
| | 0.2369188 | 84% | 9% | 2 | 1.3 | 0.6 | 2.8 |
| | 0.1018729 | 95% | 2% | 3 | 0.4 | 0.1 | 1.6 |
| | 0.8014655 | 32% | 70% | 4 | 1.3 | 0.6 | 2.8 |
| | 1.0624848 | 21% | 80% | | | | |
| | 1.9083031 | 0% | 90% | | | | |
| 24 hours | 0.4991843 | 73% | 46% | 1 | | | |
| | 0.3872229 | 81% | 30% | 2 | 1.3 | 0.5 | 3.3 |
| | 0.3448618 | 92% | 26% | 3 | 2.2 | 1.0 | 4.9 |
| | 0.8014655 | 46% | 70% | 4 | 2.5 | 1.1 | 5.5 |
| | 1.0624848 | 35% | 80% | | | | |
| | 1.9083031 | 15% | 90% | | | | |
| 48 hours | 0.5018027 | 71% | 47% | 1 | | | |
| | 0.3701848 | 86% | 28% | 2 | 4.2 | 0.3 | 53.2 |
| | 0.3498805 | 93% | 26% | 3 | 4.2 | 0.3 | 53.2 |
| | 0.8014655 | 36% | 70% | 4 | 5.4 | 0.5 | 61.6 |
| | 1.0624848 | 36% | 80% | | | | |
| | 1.9083031 | 7% | 90% | | | | |

Fig. 6 - 8

Interleukin-12 p40 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 29.421 | 24.796 | 29.421 | 20.981 | 29.421 | 28.057 |
| average | 37.589 | 32.490 | 37.589 | 26.235 | 37.589 | 39.505 |
| stdev | 37.641 | 22.888 | 37.641 | 22.375 | 37.641 | 31.171 |
| p (t-test) |  | 0.562 |  | 0.120 |  | 0.843 |
| min | 0.000 | 2.416 | 0.000 | 0.000 | 0.000 | 0.000 |
| max | 230.675 | 74.865 | 230.675 | 79.271 | 230.675 | 107.372 |
| n (Samp) | 230 | 19 | 230 | 28 | 230 | 16 |
| n (Pat) | 158 | 19 | 158 | 28 | 158 | 16 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 29.143 | 16.864 | 29.143 | 10.418 | 29.143 | 21.542 |
| average | 37.181 | 16.864 | 37.181 | 16.871 | 37.181 | 30.226 |
| stdev | 35.168 | 0.098 | 35.168 | 18.872 | 35.168 | 36.405 |
| p (t-test) |  | 0.415 |  | 0.129 |  | 0.661 |
| min | 0.000 | 16.795 | 0.000 | 0.000 | 0.000 | 0.000 |
| max | 230.675 | 16.933 | 230.675 | 54.997 | 230.675 | 87.251 |
| n (Samp) | 295 | 2 | 295 | 7 | 295 | 5 |
| n (Pat) | 187 | 2 | 187 | 7 | 187 | 5 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 29.340 | 27.679 | 29.340 | 20.881 | 29.340 | 28.057 |
| average | 37.224 | 36.534 | 37.224 | 26.338 | 37.224 | 38.587 |
| stdev | 36.469 | 26.001 | 36.469 | 21.695 | 36.469 | 28.968 |
| p (t-test) |  | 0.936 |  | 0.139 |  | 0.891 |
| min | 0.000 | 2.416 | 0.000 | 0.000 | 0.000 | 9.604 |
| max | 230.675 | 90.638 | 230.675 | 79.271 | 230.675 | 107.372 |
| n (Samp) | 198 | 19 | 198 | 26 | 198 | 14 |
| n (Pat) | 132 | 19 | 132 | 26 | 132 | 14 | sCr or UO

| Time prior AKI stage | AUC | SE | nCohort 1 | nCohort 2 | p |
| --- | --- | --- | --- | --- | --- |
| 0 hours | 0.49 | 0.069 | 230 | 19 | 0.910 |
| 24 hours | 0.41 | 0.054 | 230 | 28 | 0.094 |
| 48 hours | 0.53 | 0.076 | 230 | 16 | 0.654 | sCr only

| Time prior AKI stage | AUC | SE | nCohort 1 | nCohort 2 | p |
| --- | --- | --- | --- | --- | --- |
| 0 hours | 0.28 | 0.149 | 295 | 2 | 0.136 |
| 24 hours | 0.27 | 0.080 | 295 | 7 | 0.005 |
| 48 hours | 0.41 | 0.120 | 295 | 5 | 0.457 |

UO only

| Time prior AKI stage | AUC | SE | nCohort 1 | nCohort 2 | p |
| --- | --- | --- | --- | --- | --- |
| 0 hours | 0.53 | 0.070 | 198 | 19 | 0.673 |
| 24 hours | 0.41 | 0.056 | 198 | 26 | 0.107 |
| 48 hours | 0.53 | 0.081 | 198 | 14 | 0.669 | sCr or UO

| Time prior AKI stage | Cutoff value | sens | spec | Quartile | OR | 95% CI of OR | |
| --- | --- | --- | --- | --- | --- | --- | --- |
| 0 hours | 16.782721 | 74% | 28% | 1 |  |  |  |
|  | 13.217232 | 84% | 22% | 2 | 0.0 | 0.0 | na |
|  | 6.8184348 | 95% | 13% | 3 | 1.2 | 0.7 | 2.2 |
|  | 40.115254 | 37% | 70% | 4 | 0.6 | 0.2 | 1.3 |
|  | 50.721949 | 26% | 80% |  |  |  |  |
|  | 73.080875 | 11% | 90% |  |  |  |  |
| 24 hours | 11.758032 | 71% | 19% | 1 |  |  |  |
|  | 3.3229148 | 82% | 10% | 2 | 0.7 | 0.3 | 1.6 |
|  | 1.846505 | 93% | 9% | 3 | 1.4 | 0.7 | 2.6 |
|  | 40.115254 | 25% | 70% | 4 | 1.8 | 1.0 | 3.3 |
|  | 50.721949 | 18% | 80% |  |  |  |  |

Fig. 6 - 9

|  | 73.080875 | 4% | 90% |  |  |  |  |
| --- | --- | --- | --- | --- | --- | --- | --- |
| 48 hours | 20.314692 | 75% | 38% | 1 |  |  |  |
|  | 15.666709 | 81% | 26% | 2 | 2.1 | 0.7 | 5.9 |
|  | 9.4129279 | 94% | 16% | 3 | 0.7 | 0.1 | 3.6 |
|  | 40.115254 | 38% | 70% | 4 | 1.7 | 0.6 | 5.2 |
|  | 50.721949 | 31% | 80% |  |  |  |  |
|  | 73.080875 | 19% | 90% |  |  |  |  | sCr only

| Time prior AKI stage | Cutoff value | sens | spec | Quartile | OR | 95% CI of OR | |
| --- | --- | --- | --- | --- | --- | --- | --- |
| 0 hours | 16.782721 | 100% | 28% | 1 |  |  |  |
|  | 16.782721 | 100% | 28% | 2 | na | na | na |
|  | 16.782721 | 100% | 28% | 3 | na | na | na |
|  | 42.898246 | 0% | 70% | 4 | na | na | na |
|  | 52.907928 | 0% | 80% |  |  |  |  |
|  | 74.125859 | 0% | 90% |  |  |  |  |
| 24 hours | 6.5431504 | 71% | 11% | 1 |  |  |  |
|  | 2.4162018 | 86% | 8% | 2 | 0.0 | 0.0 | na |
|  | 0 | 100% | 0% | 3 | 2.0 | 0.1 | 40.4 |
|  | 42.898246 | 14% | 70% | 4 | 4.2 | 0.3 | 51.7 |
|  | 52.907928 | 14% | 80% |  |  |  |  |
|  | 74.125859 | 0% | 90% |  |  |  |  |
| 48 hours | 0 | 100% | 0% | 1 |  |  |  |
|  | 0 | 100% | 0% | 2 | 1.0 | 0.0 | 53.1 |
|  | 0 | 100% | 0% | 3 | 1.0 | 0.0 | 53.1 |
|  | 42.898246 | 20% | 70% | 4 | 2.0 | 0.1 | 40.5 |
|  | 52.907928 | 20% | 80% |  |  |  |  |
|  | 74.125859 | 20% | 90% |  |  |  |  |

UO only

| Time prior AKI stage | Cutoff value | sens | spec | Quartile | OR | 95% CI of OR | |
| --- | --- | --- | --- | --- | --- | --- | --- |
| 0 hours | 18.286402 | 74% | 32% | 1 |  |  |  |
|  | 13.217232 | 84% | 21% | 2 | 1.9 | 0.8 | 4.4 |
|  | 6.8184348 | 95% | 14% | 3 | 0.5 | 0.1 | 2.3 |
|  | 41.97433 | 42% | 70% | 4 | 1.5 | 0.6 | 3.7 |
|  | 51.841969 | 32% | 80% |  |  |  |  |
|  | 73.080875 | 16% | 90% |  |  |  |  |
| 24 hours | 11.758032 | 73% | 19% | 1 |  |  |  |
|  | 9.4129279 | 81% | 18% | 2 | 0.8 | 0.3 | 2.0 |
|  | 1.8746115 | 92% | 10% | 3 | 1.7 | 0.8 | 3.5 |
|  | 41.97433 | 23% | 70% | 4 | 2.0 | 1.0 | 3.9 |
|  | 51.841969 | 15% | 80% |  |  |  |  |
|  | 73.080875 | 4% | 90% |  |  |  |  |
| 48 hours | 20.314692 | 71% | 38% | 1 |  |  |  |
|  | 15.666709 | 86% | 25% | 2 | 1.4 | 0.4 | 4.6 |
|  | 13.847063 | 93% | 23% | 3 | 1.0 | 0.3 | 4.0 |
|  | 41.97433 | 36% | 70% | 4 | 1.4 | 0.4 | 4.6 |
|  | 51.841969 | 29% | 80% |  |  |  |  |
|  | 73.080875 | 14% | 90% |  |  |  |  |

Fig. 6 - 10

Matrix metalloproteinase-2 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 2515.000 | 2640.000 | 2515.000 | 2340.000 | 2515.000 | 2540.000 |
| average | 2612.539 | 2935.000 | 2612.539 | 2711.694 | 2612.539 | 2774.444 |
| stdev | 922.086 | 1107.993 | 922.086 | 1126.460 | 922.086 | 943.025 |
| p (t-test) |  | 0.077 |  | 0.543 |  | 0.466 |
| min | 618.000 | 1610.000 | 618.000 | 1330.000 | 618.000 | 1440.000 |
| max | 5710.000 | 5870.000 | 5710.000 | 5621.000 | 5710.000 | 4820.000 |
| n (Samp) | 434 | 28 | 434 | 36 | 434 | 18 |
| n (Pat) | 173 | 28 | 173 | 36 | 173 | 18 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 2470.000 | 3045.000 | 2470.000 | 2990.000 | 2470.000 | 3530.000 |
| average | 2615.170 | 3256.667 | 2615.170 | 3126.100 | 2615.170 | 3432.857 |
| stdev | 943.514 | 1581.463 | 943.514 | 1398.175 | 943.514 | 1051.043 |
| p (t-test) |  | 0.101 |  | 0.093 |  | 0.023 |
| min | 618.000 | 1740.000 | 618.000 | 1350.000 | 618.000 | 2280.000 |
| max | 6370.000 | 5870.000 | 6370.000 | 5621.000 | 6370.000 | 5130.000 |
| n (Samp) | 542 | 6 | 542 | 10 | 542 | 7 |
| n (Pat) | 208 | 6 | 208 | 10 | 208 | 7 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 2570.000 | 2650.000 | 2570.000 | 2300.000 | 2570.000 | 2215.000 |
| average | 2648.292 | 3062.593 | 2648.292 | 2668.750 | 2648.292 | 2575.625 |
| stdev | 943.214 | 1252.111 | 943.214 | 1106.974 | 943.214 | 932.280 |
| p (t-test) |  | 0.033 |  | 0.908 |  | 0.763 |
| min | 618.000 | 1610.000 | 618.000 | 1330.000 | 618.000 | 1440.000 |
| max | 5710.000 | 7300.000 | 5710.000 | 5870.000 | 5710.000 | 4820.000 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
|---|---|---|---|---|---|
| 0 hours | 0.57 | 0.058 | 434 | 28 | 0.217 |
| 24 hours | 0.50 | 0.050 | 434 | 36 | 0.942 |
| 48 hours | 0.54 | 0.071 | 434 | 18 | 0.582 | sCr only

| Time prior AKI stage | AUC | SE | nCohort 1 | nCohort 2 | p |
|---|---|---|---|---|---|
| 0 hours | 0.61 | 0.123 | 542 | 6 | 0.369 |
| 24 hours | 0.61 | 0.096 | 542 | 10 | 0.238 |
| 48 hours | 0.73 | 0.109 | 542 | 7 | 0.036 |

UO only

| Time prior AKI stage | AUC | SE | nCohort 1 | nCohort 2 | p |
|---|---|---|---|---|---|
| 0 hours | 0.59 | 0.059 | 356 | 27 | 0.149 |
| 24 hours | 0.47 | 0.052 | 356 | 32 | 0.593 |
| 48 hours | 0.45 | 0.071 | 356 | 16 | 0.494 | sCr or UO

| Time prior AKI stage | Cutoff value | sens | spec | Quartile | OR | 95% CI of OR | |
|---|---|---|---|---|---|---|---|
| 0 hours | 2250 | 71% | 38% | 1 |  |  |  |
|  | 2080 | 82% | 31% | 2 | 1.6 | 0.8 | 3.2 |
|  | 1650 | 93% | 13% | 3 | 1.2 | 0.6 | 2.6 |
|  | 3010 | 36% | 70% | 4 | 1.9 | 1.0 | 3.5 |
|  | 3280 | 32% | 80% |  |  |  |  |
|  | 3750 | 29% | 90% |  |  |  |  |
| 24 hours | 1950 | 72% | 25% | 1 |  |  |  |
|  | 1800 | 81% | 20% | 2 | 0.3 | 0.1 | 0.6 |
|  | 1480 | 92% | 9% | 3 | 1.2 | 0.8 | 1.7 |
|  | 3010 | 31% | 70% | 4 | 0.8 | 0.5 | 1.2 |
|  | 3280 | 31% | 80% |  |  |  |  |

Fig. 6 - 11

| | | 3750 | 17% | 90% | | | | |
|---|---|---|---|---|---|---|---|---|
| 48 hours | | 2160 | 72% | 34% | 1 | | | |
| | | 2010 | 83% | 28% | 2 | 2.1 | 0.7 | 5.7 |
| | | 1810 | 94% | 20% | 3 | 1.3 | 0.4 | 4.4 |
| | | 3010 | 28% | 70% | 4 | 1.7 | 0.6 | 5.0 |
| | | 3280 | 28% | 80% | | | | |
| | | 3750 | 17% | 90% | | | | | sCr only

| Time prior AKI stage | Cutoff value | sens | spec | Quartile | OR | 95% CI of OR | |
|---|---|---|---|---|---|---|---|
| 0 hours | 1760 | 83% | 18% | 1 | | | |
| | 1760 | 83% | 18% | 2 | 0.0 | 0.0 | na |
| | 1730 | 100% | 17% | 3 | 0.5 | 0.0 | 9.7 |
| | 2970 | 50% | 70% | 4 | 1.5 | 0.3 | 8.0 |
| | 3280 | 50% | 80% | | | | |
| | 3830 | 33% | 90% | | | | |
| 24 hours | 2460 | 70% | 50% | 1 | | | |
| | 2300 | 80% | 42% | 2 | 1.0 | 0.1 | 7.3 |
| | 1350 | 90% | 6% | 3 | 1.0 | 0.1 | 7.3 |
| | 2970 | 50% | 70% | 4 | 2.0 | 0.5 | 9.1 |
| | 3280 | 40% | 80% | | | | |
| | 3830 | 20% | 90% | | | | |
| 48 hours | 2760 | 71% | 61% | 1 | | | |
| | 2300 | 86% | 42% | 2 | na | na | na |
| | 2260 | 100% | 40% | 3 | na | na | na |
| | 2970 | 57% | 70% | 4 | na | na | na |
| | 3280 | 57% | 80% | | | | |
| | 3830 | 43% | 90% | | | | |

UO only

| Time prior AKI stage | Cutoff value | sens | spec | Quartile | OR | 95% CI of OR | |
|---|---|---|---|---|---|---|---|
| 0 hours | 2310 | 74% | 40% | 1 | | | |
| | 2200 | 81% | 34% | 2 | 3.2 | 1.3 | 7.9 |
| | 1650 | 93% | 14% | 3 | 2.0 | 0.7 | 5.7 |
| | 3050 | 37% | 71% | 4 | 3.2 | 1.3 | 7.9 |
| | 3320 | 33% | 80% | | | | |
| | 3840 | 22% | 90% | | | | |
| 24 hours | 1950 | 72% | 22% | 1 | | | |
| | 1800 | 81% | 19% | 2 | 0.3 | 0.1 | 0.8 |
| | 1490 | 91% | 10% | 3 | 1.1 | 0.7 | 1.8 |
| | 3050 | 31% | 71% | 4 | 1.1 | 0.7 | 1.8 |
| | 3320 | 28% | 80% | | | | |
| | 3840 | 16% | 90% | | | | |
| 48 hours | 2010 | 75% | 25% | 1 | | | |
| | 1930 | 81% | 22% | 2 | 1.0 | 0.3 | 3.9 |
| | 1730 | 94% | 17% | 3 | 2.1 | 0.7 | 5.8 |
| | 3050 | 19% | 71% | 4 | 1.3 | 0.4 | 4.4 |
| | 3320 | 19% | 80% | | | | |
| | 3840 | 13% | 90% | | | | |

Fig. 6 - 12

Serum amyloid P-component sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 5009.291 | 5666.298 | 5009.291 | 4768.194 | 5009.291 | 5020.099 |
| average | 5491.353 | 5692.800 | 5491.353 | 5252.102 | 5491.353 | 5150.099 |
| stdev | 2562.610 | 1959.462 | 2562.610 | 3108.044 | 2562.610 | 2101.379 |
| p (t-test) |  | 0.738 |  | 0.649 |  | 0.603 |
| min | 96.224 | 2111.440 | 96.224 | 915.589 | 96.224 | 2116.488 |
| max | 16315.493 | 9440.651 | 16315.493 | 16576.982 | 16315.493 | 9029.353 |
| n (Samp) | 230 | 19 | 230 | 28 | 230 | 16 |
| n (Pat) | 158 | 19 | 158 | 28 | 158 | 16 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 5008.293 | 3974.530 | 5008.293 | 5878.713 | 5008.293 | 5316.421 |
| average | 5467.355 | 3974.530 | 5467.355 | 6043.664 | 5467.355 | 5836.461 |
| stdev | 2601.621 | 529.617 | 2601.621 | 2681.917 | 2601.621 | 1562.309 |
| p (t-test) |  | 0.419 |  | 0.563 |  | 0.752 |
| min | 96.224 | 3600.034 | 96.224 | 1775.429 | 96.224 | 3970.792 |
| max | 16576.982 | 4349.026 | 16576.982 | 10815.095 | 16576.982 | 7618.702 |
| n (Samp) | 295 | 2 | 295 | 7 | 295 | 5 |
| n (Pat) | 187 | 2 | 187 | 7 | 187 | 5 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 5093.263 | 5666.298 | 5093.263 | 4667.156 | 5093.263 | 4287.587 |
| average | 5457.133 | 5735.132 | 5457.133 | 5344.247 | 5457.133 | 4916.368 |
| stdev | 2341.787 | 1920.012 | 2341.787 | 3189.378 | 2341.787 | 2147.724 |
| p (t-test) |  | 0.617 |  | 0.826 |  | 0.402 |
| min | 1161.809 | 2111.440 | 1161.809 | 915.589 | 1161.809 | 2116.488 |
| max | 16315.493 | 9440.651 | 16315.493 | 16576.982 | 16315.493 | 9029.353 |
| n (Samp) | 198 | 19 | 198 | 26 | 198 | 14 |
| n (Pat) | 132 | 19 | 132 | 26 | 132 | 14 | sCr or UO

| Time prior AKI stage | AUC | SE | nCohort 1 | nCohort 2 | p |
| --- | --- | --- | --- | --- | --- |
| 0 hours | 0.56 | 0.071 | 230 | 19 | 0.410 |
| 24 hours | 0.46 | 0.056 | 230 | 28 | 0.471 |
| 48 hours | 0.48 | 0.074 | 230 | 16 | 0.764 | sCr only

| Time prior AKI stage | AUC | SE | nCohort 1 | nCohort 2 | p |
| --- | --- | --- | --- | --- | --- |
| 0 hours | 0.28 | 0.150 | 295 | 2 | 0.146 |
| 24 hours | 0.60 | 0.115 | 295 | 7 | 0.367 |
| 48 hours | 0.59 | 0.135 | 295 | 5 | 0.500 |

UO only

| Time prior AKI stage | AUC | SE | nCohort 1 | nCohort 2 | p |
| --- | --- | --- | --- | --- | --- |
| 0 hours | 0.56 | 0.071 | 198 | 19 | 0.366 |
| 24 hours | 0.45 | 0.059 | 198 | 26 | 0.422 |
| 48 hours | 0.43 | 0.076 | 198 | 14 | 0.376 | sCr or UO

| Time prior AKI stage | Cutoff value | sens | spec | Quartile | OR | 95% CI of OR | |
| --- | --- | --- | --- | --- | --- | --- | --- |
| 0 hours | 4336.5188 | 74% | 36% | 1 |  |  |  |
|  | 3644.9233 | 84% | 19% | 2 | 0.6 | 0.2 | 1.8 |
|  | 3161.183 | 95% | 14% | 3 | 0.6 | 0.2 | 1.8 |
|  | 6163.242 | 42% | 70% | 4 | 1.7 | 0.8 | 3.4 |
|  | 6919.0319 | 42% | 80% |  |  |  |  |
|  | 8435.3903 | 5% | 90% |  |  |  |  |
| 24 hours | 3956.1005 | 71% | 27% | 1 |  |  |  |
|  | 2777.9862 | 82% | 9% | 2 | 1.0 | 0.5 | 2.1 |
|  | 1819.2755 | 93% | 3% | 3 | 1.4 | 0.7 | 2.6 |
|  | 6163.242 | 25% | 70% | 4 | 1.4 | 0.7 | 2.7 |
|  | 6919.0319 | 21% | 80% |  |  |  |  |

Fig. 6 - 13

|  |  | 8435.3903 | 11% | 90% |  |  |  |  |
|---|---|---|---|---|---|---|---|---|
| 48 hours |  | 3766.3572 | 75% | 21% | 1 |  |  |  |
|  |  | 3558.3957 | 81% | 18% | 2 | 0.6 | 0.2 | 1.8 |
|  |  | 2300.6963 | 94% | 5% | 3 | 0.6 | 0.2 | 1.8 |
|  |  | 6163.242 | 38% | 70% | 4 | 1.0 | 0.4 | 2.4 |
|  |  | 6919.0319 | 31% | 80% |  |  |  |  |
|  |  | 8435.3903 | 6% | 90% |  |  |  |  | sCr only

| Time prior AKI stage | Cutoff value | sens | spec | Quartile | OR | 95% CI of OR ||
|---|---|---|---|---|---|---|---|
| 0 hours | 3570.863 | 100% | 20% | 1 |  |  |  |
|  | 3570.863 | 100% | 20% | 2 | na | na | na |
|  | 3570.863 | 100% | 20% | 3 | na | na | na |
|  | 6211.9302 | 0% | 70% | 4 | na | na | na |
|  | 7205.7873 | 0% | 80% |  |  |  |  |
|  | 8594.5677 | 0% | 90% |  |  |  |  |
| 24 hours | 5373.5983 | 71% | 57% | 1 |  |  |  |
|  | 5324.4963 | 86% | 55% | 2 | 0.0 | 0.0 | na |
|  | 1726.9163 | 100% | 2% | 3 | 4.2 | 0.3 | 51.0 |
|  | 6211.9302 | 29% | 70% | 4 | 2.0 | 0.1 | 39.9 |
|  | 7205.7873 | 14% | 80% |  |  |  |  |
|  | 8594.5677 | 14% | 90% |  |  |  |  |
| 48 hours | 4979.4707 | 80% | 49% | 1 |  |  |  |
|  | 4979.4707 | 80% | 49% | 2 | na | na | na |
|  | 3956.1005 | 100% | 27% | 3 | na | na | na |
|  | 6211.9302 | 40% | 70% | 4 | na | na | na |
|  | 7205.7873 | 40% | 80% |  |  |  |  |
|  | 8594.5677 | 0% | 90% |  |  |  |  |

UO only

| Time prior AKI stage | Cutoff value | sens | spec | Quartile | OR | 95% CI of OR ||
|---|---|---|---|---|---|---|---|
| 0 hours | 4378.7135 | 74% | 35% | 1 |  |  |  |
|  | 3877.5439 | 84% | 21% | 2 | 1.0 | 0.3 | 2.9 |
|  | 3161.183 | 95% | 14% | 3 | 0.7 | 0.2 | 2.5 |
|  | 6157.9343 | 42% | 70% | 4 | 2.1 | 0.9 | 4.8 |
|  | 6895.0273 | 42% | 80% |  |  |  |  |
|  | 8250.4495 | 5% | 90% |  |  |  |  |
| 24 hours | 3675.773 | 73% | 17% | 1 |  |  |  |
|  | 2984.665 | 81% | 12% | 2 | 0.4 | 0.1 | 1.1 |
|  | 1891.309 | 92% | 4% | 3 | 1.2 | 0.6 | 2.1 |
|  | 6157.9343 | 31% | 70% | 4 | 1.2 | 0.6 | 2.1 |
|  | 6895.0273 | 27% | 80% |  |  |  |  |
|  | 8250.4495 | 15% | 90% |  |  |  |  |
| 48 hours | 3766.3572 | 71% | 18% | 1 |  |  |  |
|  | 2425.2241 | 86% | 6% | 2 | 0.5 | 0.1 | 2.3 |
|  | 2300.6963 | 93% | 5% | 3 | 0.7 | 0.2 | 2.5 |
|  | 6157.9343 | 36% | 70% | 4 | 1.3 | 0.5 | 3.3 |
|  | 6895.0273 | 29% | 80% |  |  |  |  |
|  | 8250.4495 | 7% | 90% |  |  |  |  |

Fig. 6 - 14

Matrix metalloproteinase-9 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 280.000 | 408.500 | 280.000 | 428.500 | 280.000 | 397.000 |
| average | 485.877 | 792.929 | 485.877 | 490.119 | 485.877 | 655.789 |
| stdev | 805.767 | 1466.404 | 805.767 | 402.427 | 805.767 | 1078.232 |
| p (t-test) |  | 0.067 |  | 0.975 |  | 0.388 |
| min | 20.000 | 39.900 | 20.000 | 69.800 | 20.000 | 36.200 |
| max | 8903.000 | 7705.000 | 8903.000 | 2020.000 | 8903.000 | 4830.000 |
| n (Samp) | 434 | 28 | 434 | 36 | 434 | 18 |
| n (Pat) | 173 | 28 | 173 | 36 | 173 | 18 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 300.500 | 540.500 | 300.500 | 502.500 | 300.500 | 676.000 |
| average | 510.765 | 1938.333 | 510.765 | 598.000 | 510.765 | 663.000 |
| stdev | 782.318 | 2911.673 | 782.318 | 447.251 | 782.318 | 230.372 |
| p (t-test) |  | 0.000 |  | 0.725 |  | 0.607 |
| min | 20.000 | 307.000 | 20.000 | 161.000 | 20.000 | 335.000 |
| max | 8903.000 | 7705.000 | 8903.000 | 1540.000 | 8903.000 | 1020.000 |
| n (Samp) | 542 | 6 | 542 | 10 | 542 | 7 |
| n (Pat) | 208 | 6 | 208 | 10 | 208 | 7 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 272.000 | 435.000 | 272.000 | 378.000 | 272.000 | 330.000 |
| average | 433.651 | 817.963 | 433.651 | 510.603 | 433.651 | 1075.825 |
| stdev | 599.233 | 1489.393 | 599.233 | 491.118 | 599.233 | 2104.250 |
| p (t-test) |  | 0.006 |  | 0.481 |  | 0.001 |
| min | 20.000 | 39.900 | 20.000 | 69.800 | 20.000 | 36.200 |
| max | 7705.000 | 7705.000 | 7705.000 | 2240.000 | 7705.000 | 7705.000 |
| n (Samp) | 356 | 27 | 356 | 32 | 356 | 16 |
| n (Pat) | 138 | 27 | 138 | 32 | 138 | 16 | sCr or UO

| Time prior AKI stage | AUC | SE | nCohort 1 | nCohort 2 | p |
| --- | --- | --- | --- | --- | --- |
| 0 hours | 0.60 | 0.058 | 434 | 28 | 0.080 |
| 24 hours | 0.59 | 0.052 | 434 | 36 | 0.081 |
| 48 hours | 0.57 | 0.072 | 434 | 18 | 0.299 | sCr only

| Time prior AKI stage | AUC | SE | nCohort 1 | nCohort 2 | p |
| --- | --- | --- | --- | --- | --- |
| 0 hours | 0.75 | 0.116 | 542 | 6 | 0.031 |
| 24 hours | 0.65 | 0.095 | 542 | 10 | 0.124 |
| 48 hours | 0.76 | 0.107 | 542 | 7 | 0.017 |

UO only

| Time prior AKI stage | AUC | SE | nCohort 1 | nCohort 2 | p |
| --- | --- | --- | --- | --- | --- |
| 0 hours | 0.62 | 0.059 | 356 | 27 | 0.041 |
| 24 hours | 0.59 | 0.055 | 356 | 32 | 0.095 |
| 48 hours | 0.56 | 0.076 | 356 | 16 | 0.408 | sCr or UO

| Time prior AKI stage | Cutoff value | sens | spec | Quartile | OR | 95% CI of OR | |
| --- | --- | --- | --- | --- | --- | --- | --- |
| 0 hours | 306 | 71% | 55% | 1 |  |  |  |
|  | 158 | 82% | 30% | 2 | 1.0 | 0.4 | 2.7 |
|  | 52 | 93% | 4% | 3 | 2.4 | 1.1 | 5.0 |
|  | 461 | 39% | 70% | 4 | 2.9 | 1.4 | 5.9 |
|  | 647 | 25% | 80% |  |  |  |  |
|  | 1020 | 11% | 90% |  |  |  |  |
| 24 hours | 244 | 75% | 45% | 1 |  |  |  |
|  | 194 | 81% | 38% | 2 | 1.3 | 0.7 | 2.5 |
|  | 98.6 | 92% | 15% | 3 | 1.9 | 1.1 | 3.3 |
|  | 461 | 44% | 70% | 4 | 1.9 | 1.1 | 3.3 |
|  | 647 | 25% | 80% |  |  |  |  |

Fig. 6 - 15

| | | 1020 | 6% | 90% | | | | |
|---|---|---|---|---|---|---|---|---|
| 48 hours | | 206 | 72% | 39% | 1 | | | |
| | | 173 | 83% | 32% | 2 | 1.3 | 0.4 | 4.4 |
| | | 120 | 94% | 19% | 3 | 1.7 | 0.6 | 5.0 |
| | | 461 | 39% | 70% | 4 | 2.1 | 0.7 | 5.7 |
| | | 647 | 28% | 80% | | | | |
| | | 1020 | 6% | 90% | | | | |

UO only

| Time prior AKI stage | Cutoff value | sens | spec | Quartile | OR | 95% CI of OR | |
|---|---|---|---|---|---|---|---|
| 0 hours | 317 | 70% | 57% | 1 | | | |
| | 156 | 81% | 29% | 2 | 1.0 | 0.4 | 2.8 |
| | 52 | 93% | 4% | 3 | 1.8 | 0.8 | 4.0 |
| | 424 | 52% | 70% | 4 | 3.3 | 1.6 | 6.5 |
| | 582 | 33% | 80% | | | | |
| | 906 | 11% | 90% | | | | |
| 24 hours | 247 | 72% | 46% | 1 | | | |
| | 194 | 81% | 38% | 2 | 1.2 | 0.6 | 2.3 |
| | 98.6 | 91% | 14% | 3 | 1.4 | 0.7 | 2.5 |
| | 424 | 44% | 70% | 4 | 1.9 | 1.1 | 3.4 |
| | 582 | 25% | 80% | | | | |
| | 906 | 6% | 90% | | | | |
| 48 hours | 194 | 75% | 38% | 1 | | | |
| | 173 | 81% | 32% | 2 | 1.3 | 0.4 | 4.4 |
| | 120 | 94% | 18% | 3 | 1.3 | 0.4 | 4.4 |
| | 424 | 44% | 70% | 4 | 1.7 | 0.6 | 5.1 |
| | 582 | 25% | 80% | | | | |
| | 906 | 13% | 90% | | | | |

Fig. 6 - 16

Clusterin sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 108848.034 | 84699.814 | 108848.034 | 84699.814 | 108848.034 | 84699.814 |
| average | 106505.593 | 83381.434 | 106505.593 | 83381.434 | 106505.593 | 83381.434 |
| stdev | 39394.888 | 51247.025 | 39394.888 | 51247.025 | 39394.888 | 51247.025 |
| p (t-test) |  | 0.056 |  | 0.056 |  | 0.056 |
| min | 31439.276 | 369.562 | 31439.276 | 369.562 | 31439.276 | 369.562 |
| max | 201365.565 | 244623.417 | 201365.565 | 244623.417 | 201365.565 | 244623.417 |
| n (Samp) | 52 | 17 | 52 | 17 | 52 | 17 |
| n (Pat) | 52 | 17 | 52 | 17 | 52 | 17 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 114689.518 | 90003.239 | 114689.518 | 90003.239 | 114689.518 | 90003.239 |
| average | 111966.570 | 90003.239 | 111966.570 | 90003.239 | 111966.570 | 90003.239 |
| stdev | 38887.769 | 42421.826 | 38887.769 | 42421.826 | 38887.769 | 42421.826 |
| p (t-test) |  | 0.459 |  | 0.459 |  | 0.459 |
| min | 53297.264 | 60006.479 | 53297.264 | 60006.479 | 53297.264 | 60006.479 |
| max | 201365.565 | 120000.000 | 201365.565 | 120000.000 | 201365.565 | 120000.000 |
| n (Samp) | 19 | 2 | 19 | 2 | 19 | 2 |
| n (Pat) | 19 | 2 | 19 | 2 | 19 | 2 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 106794.363 | 69283.724 | 106794.363 | 69283.724 | 106794.363 | 69283.724 |
| average | 104013.855 | 79523.052 | 104013.855 | 79523.052 | 104013.855 | 79523.052 |
| stdev | 37433.727 | 55357.877 | 37433.727 | 55357.877 | 37433.727 | 55357.877 |
| p (t-test) |  | 0.068 |  | 0.068 |  | 0.068 |
| min | 31439.276 | 369.562 | 31439.276 | 369.562 | 31439.276 | 369.562 |
| max | 197636.915 | 244623.417 | 197636.915 | 244623.417 | 197636.915 | 244623.417 |
| n (Samp) | 41 | 14 | 41 | 14 | 41 | 14 |
| n (Pat) | 41 | 14 | 41 | 14 | 41 | 14 | sCr or UO

| Time prior AKI stage | AUC | SE | nCohort 1 | nCohort 2 | p |
| --- | --- | --- | --- | --- | --- |
| 0 hours | 0.31 | 0.069 | 52 | 17 | 0.007 |
| 24 hours | 0.31 | 0.069 | 52 | 17 | 0.007 |
| 48 hours | 0.31 | 0.069 | 52 | 17 | 0.007 | sCr only

| Time prior AKI stage | AUC | SE | nCohort 1 | nCohort 2 | p |
| --- | --- | --- | --- | --- | --- |
| 0 hours | 0.36 | 0.192 | 19 | 2 | 0.451 |
| 24 hours | 0.36 | 0.192 | 19 | 2 | 0.451 |
| 48 hours | 0.36 | 0.192 | 19 | 2 | 0.451 |

UO only

| Time prior AKI stage | AUC | SE | nCohort 1 | nCohort 2 | p |
| --- | --- | --- | --- | --- | --- |
| 0 hours | 0.28 | 0.073 | 41 | 14 | 0.003 |
| 24 hours | 0.28 | 0.073 | 41 | 14 | 0.003 |
| 48 hours | 0.28 | 0.073 | 41 | 14 | 0.003 | sCr or UO

| Time prior AKI stage | Cutoff value | sens | spec | Quartile | OR | 95% CI of OR | |
| --- | --- | --- | --- | --- | --- | --- | --- |
| 0 hours | 58284.001 | 71% | 12% | 1 |  |  |  |
|  | 54502.153 | 82% | 12% | 2 | 9.3 | 0.7 | 122.4 |
|  | 369.56176 | 94% | 0% | 3 | 3.6 | 0.2 | 64.2 |
|  | 120554.14 | 6% | 71% | 4 | 11.9 | 0.9 | 152.6 |
|  | 137689.21 | 6% | 81% |  |  |  |  |
|  | 156761.93 | 6% | 90% |  |  |  |  |
| 24 hours | 58284.001 | 71% | 12% | 1 |  |  |  |
|  | 54502.153 | 82% | 12% | 2 | 9.3 | 0.7 | 122.4 |
|  | 369.56176 | 94% | 0% | 3 | 3.6 | 0.2 | 64.2 |
|  | 120554.14 | 6% | 71% | 4 | 11.9 | 0.9 | 152.6 |
|  | 137689.21 | 6% | 81% |  |  |  |  |

Fig. 7 - 1

| Time prior AKI stage | Cutoff value | sens | spec | Quartile | OR | 95% CI of OR | |
|---|---|---|---|---|---|---|---|
| | 156761.93 | 6% | 90% | | | | |
| 48 hours | 58284.001 | 71% | 12% | 1 | | | |
| | 54502.153 | 82% | 12% | 2 | 9.3 | 0.7 | 122.4 |
| | 369.56176 | 94% | 0% | 3 | 3.6 | 0.2 | 64.2 |
| | 120554.14 | 6% | 71% | 4 | 11.9 | 0.9 | 152.6 |
| | 137689.21 | 6% | 81% | | | | |
| | 156761.93 | 6% | 90% | | | | |

UO only

| Time prior AKI stage | Cutoff value | sens | spec | Quartile | OR | 95% CI of OR | |
|---|---|---|---|---|---|---|---|
| 0 hours | 58284.001 | 71% | 12% | 1 | | | |
| | 47727.274 | 86% | 7% | 2 | 3.5 | 0.2 | 67.2 |
| | 369.56176 | 93% | 0% | 3 | 3.5 | 0.2 | 67.2 |
| | 120554.14 | 7% | 71% | 4 | 15.2 | 1.0 | 229.6 |
| | 127576.59 | 7% | 80% | | | | |
| | 143211.86 | 7% | 90% | | | | |
| 24 hours | 58284.001 | 71% | 12% | 1 | | | |
| | 47727.274 | 86% | 7% | 2 | 3.5 | 0.2 | 67.2 |
| | 369.56176 | 93% | 0% | 3 | 3.5 | 0.2 | 67.2 |
| | 120554.14 | 7% | 71% | 4 | 15.2 | 1.0 | 229.6 |
| | 127576.59 | 7% | 80% | | | | |
| | 143211.86 | 7% | 90% | | | | |
| 48 hours | 58284.001 | 71% | 12% | 1 | | | |
| | 47727.274 | 86% | 7% | 2 | 3.5 | 0.2 | 67.2 |
| | 369.56176 | 93% | 0% | 3 | 3.5 | 0.2 | 67.2 |
| | 120554.14 | 7% | 71% | 4 | 15.2 | 1.0 | 229.6 |
| | 127576.59 | 7% | 80% | | | | |
| | 143211.86 | 7% | 90% | | | | |

Fig. 7 - 2

Serum amyloid P-component sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 5025.127 | 4154.461 | 5025.127 | 4154.461 | 5025.127 | 4154.461 |
| average | 5554.467 | 5079.717 | 5554.467 | 5079.717 | 5554.467 | 5079.717 |
| stdev | 2849.319 | 3357.607 | 2849.319 | 3357.607 | 2849.319 | 3357.607 |
| p (t-test) |  | 0.570 |  | 0.570 |  | 0.570 |
| min | 1726.916 | 1867.819 | 1726.916 | 1867.819 | 1726.916 | 1867.819 |
| max | 16242.949 | 16576.982 | 16242.949 | 16576.982 | 16242.949 | 16576.982 |
| n (Samp) | 52 | 17 | 52 | 17 | 52 | 17 |
| n (Pat) | 52 | 17 | 52 | 17 | 52 | 17 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 4745.512 | 7217.428 | 4745.512 | 7217.428 | 4745.512 | 7217.428 |
| average | 5378.006 | 7217.428 | 5378.006 | 7217.428 | 5378.006 | 7217.428 |
| stdev | 2476.478 | 102.721 | 2476.478 | 102.721 | 2476.478 | 102.721 |
| p (t-test) |  | 0.318 |  | 0.318 |  | 0.318 |
| min | 2295.394 | 7144.793 | 2295.394 | 7144.793 | 2295.394 | 7144.793 |
| max | 11731.227 | 7290.063 | 11731.227 | 7290.063 | 11731.227 | 7290.063 |
| n (Samp) | 19 | 2 | 19 | 2 | 19 | 2 |
| n (Pat) | 19 | 2 | 19 | 2 | 19 | 2 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 5041.961 | 4190.305 | 5041.961 | 4190.305 | 5041.961 | 4190.305 |
| average | 5753.104 | 5179.572 | 5753.104 | 5179.572 | 5753.104 | 5179.572 |
| stdev | 3106.048 | 3569.540 | 3106.048 | 3569.540 | 3106.048 | 3569.540 |
| p (t-test) |  | 0.568 |  | 0.568 |  | 0.568 |
| min | 1726.916 | 1867.819 | 1726.916 | 1867.819 | 1726.916 | 1867.819 |
| max | 16242.949 | 16576.982 | 16242.949 | 16576.982 | 16242.949 | 16576.982 |
| n (Samp) | 41 | 14 | 41 | 14 | 41 | 14 |
| n (Pat) | 41 | 14 | 41 | 14 | 41 | 14 | sCr or UO

| Time prior AKI stage | AUC | SE | nCohort 1 | nCohort 2 | p |
| --- | --- | --- | --- | --- | --- |
| 0 hours | 0.40 | 0.077 | 52 | 17 | 0.210 |
| 24 hours | 0.40 | 0.077 | 52 | 17 | 0.210 |
| 48 hours | 0.40 | 0.077 | 52 | 17 | 0.210 | sCr only

| Time prior AKI stage | AUC | SE | nCohort 1 | nCohort 2 | p |
| --- | --- | --- | --- | --- | --- |
| 0 hours | 0.79 | 0.200 | 19 | 2 | 0.147 |
| 24 hours | 0.79 | 0.200 | 19 | 2 | 0.147 |
| 48 hours | 0.79 | 0.200 | 19 | 2 | 0.147 |

UO only

| Time prior AKI stage | AUC | SE | nCohort 1 | nCohort 2 | p |
| --- | --- | --- | --- | --- | --- |
| 0 hours | 0.39 | 0.085 | 41 | 14 | 0.209 |
| 24 hours | 0.39 | 0.085 | 41 | 14 | 0.209 |
| 48 hours | 0.39 | 0.085 | 41 | 14 | 0.209 | sCr or UO

| Time prior AKI stage | Cutoff value | sens | spec | Quartile | OR | 95% CI of OR | |
| --- | --- | --- | --- | --- | --- | --- | --- |
| 0 hours | 3570.863 | 71% | 17% | 1 |  |  |  |
|  | 2815.0629 | 82% | 13% | 2 | 1.5 | 0.4 | 6.4 |
|  | 1891.309 | 94% | 6% | 3 | 1.5 | 0.4 | 6.4 |
|  | 6076.4492 | 18% | 71% | 4 | 2.7 | 0.8 | 9.9 |
|  | 7262.678 | 18% | 81% |  |  |  |  |
|  | 8399.8565 | 6% | 90% |  |  |  |  |
| 24 hours | 3570.863 | 71% | 17% | 1 |  |  |  |
|  | 2815.0629 | 82% | 13% | 2 | 1.5 | 0.4 | 6.4 |
|  | 1891.309 | 94% | 6% | 3 | 1.5 | 0.4 | 6.4 |
|  | 6076.4492 | 18% | 71% | 4 | 2.7 | 0.8 | 9.9 |
|  | 7262.678 | 18% | 81% |  |  |  |  |

Fig. 7 - 3

| | | 8399.8565 | 6% | 90% | | | | |
|---|---|---|---|---|---|---|---|---|
| 48 hours | | 3570.863 | 71% | 17% | 1 | | | |
| | | 2815.0629 | 82% | 13% | 2 | 1.5 | 0.4 | 6.4 |
| | | 1891.309 | 94% | 6% | 3 | 1.5 | 0.4 | 6.4 |
| | | 6076.4492 | 18% | 71% | 4 | 2.7 | 0.8 | 9.9 |
| | | 7262.678 | 18% | 81% | | | | |
| | | 8399.8565 | 6% | 90% | | | | |

UO only

| Time prior AKI stage | Cutoff value | sens | spec | Quartile | OR | 95% CI of OR | |
|---|---|---|---|---|---|---|---|
| 0 hours | 3600.0341 | 71% | 15% | 1 | | | |
| | 2815.0629 | 86% | 15% | 2 | 1.6 | 0.2 | 11.8 |
| | 2591.9192 | 93% | 15% | 3 | 2.4 | 0.4 | 15.0 |
| | 6424.9768 | 14% | 71% | 4 | 3.8 | 0.6 | 22.2 |
| | 7645.7332 | 7% | 80% | | | | |
| | 8399.8565 | 7% | 90% | | | | |
| 24 hours | 3600.0341 | 71% | 15% | 1 | | | |
| | 2815.0629 | 86% | 15% | 2 | 1.6 | 0.2 | 11.8 |
| | 2591.9192 | 93% | 15% | 3 | 2.4 | 0.4 | 15.0 |
| | 6424.9768 | 14% | 71% | 4 | 3.8 | 0.6 | 22.2 |
| | 7645.7332 | 7% | 80% | | | | |
| | 8399.8565 | 7% | 90% | | | | |
| 48 hours | 3600.0341 | 71% | 15% | 1 | | | |
| | 2815.0629 | 86% | 15% | 2 | 1.6 | 0.2 | 11.8 |
| | 2591.9192 | 93% | 15% | 3 | 2.4 | 0.4 | 15.0 |
| | 6424.9768 | 14% | 71% | 4 | 3.8 | 0.6 | 22.2 |
| | 7645.7332 | 7% | 80% | | | | |
| | 8399.8565 | 7% | 90% | | | | |

Fig. 7 - 4

Matrix metalloproteinase-9 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 252.000 | 532.000 | 252.000 | 532.000 | 252.000 | 532.000 |
| average | 404.304 | 627.205 | 404.304 | 627.205 | 404.304 | 627.205 |
| stdev | 437.057 | 494.325 | 437.057 | 494.325 | 437.057 | 494.325 |
| p (t-test) |  | 0.058 |  | 0.058 |  | 0.058 |
| min | 26.300 | 36.200 | 26.300 | 36.200 | 26.300 | 36.200 |
| max | 2320.000 | 2020.000 | 2320.000 | 2020.000 | 2320.000 | 2020.000 |
| n (Samp) | 56 | 21 | 56 | 21 | 56 | 21 |
| n (Pat) | 56 | 21 | 56 | 21 | 56 | 21 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 216.000 | 545.000 | 216.000 | 545.000 | 216.000 | 545.000 |
| average | 263.900 | 459.600 | 263.900 | 459.600 | 263.900 | 459.600 |
| stdev | 152.928 | 235.652 | 152.928 | 235.652 | 152.928 | 235.652 |
| p (t-test) |  | 0.029 |  | 0.029 |  | 0.029 |
| min | 26.300 | 119.000 | 26.300 | 119.000 | 26.300 | 119.000 |
| max | 619.000 | 663.000 | 619.000 | 663.000 | 619.000 | 663.000 |
| n (Samp) | 21 | 5 | 21 | 5 | 21 | 5 |
| n (Pat) | 21 | 5 | 21 | 5 | 21 | 5 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 284.500 | 532.000 | 284.500 | 532.000 | 284.500 | 532.000 |
| average | 458.241 | 660.135 | 458.241 | 660.135 | 458.241 | 660.135 |
| stdev | 469.494 | 537.946 | 469.494 | 537.946 | 469.494 | 537.946 |
| p (t-test) |  | 0.150 |  | 0.150 |  | 0.150 |
| min | 29.500 | 36.200 | 29.500 | 36.200 | 29.500 | 36.200 |
| max | 2320.000 | 2020.000 | 2320.000 | 2020.000 | 2320.000 | 2020.000 |
| n (Samp) | 46 | 17 | 46 | 17 | 46 | 17 |
| n (Pat) | 46 | 17 | 46 | 17 | 46 | 17 | sCr or UO

| Time prior AKI stage | AUC | SE | nCohort 1 | nCohort 2 | p |
| --- | --- | --- | --- | --- | --- |
| 0 hours | 0.67 | 0.073 | 56 | 21 | 0.018 |
| 24 hours | 0.67 | 0.073 | 56 | 21 | 0.018 |
| 48 hours | 0.67 | 0.073 | 56 | 21 | 0.018 | sCr only

| Time prior AKI stage | AUC | SE | nCohort 1 | nCohort 2 | p |
| --- | --- | --- | --- | --- | --- |
| 0 hours | 0.74 | 0.137 | 21 | 5 | 0.077 |
| 24 hours | 0.74 | 0.137 | 21 | 5 | 0.077 |
| 48 hours | 0.74 | 0.137 | 21 | 5 | 0.077 |

UO only

| Time prior AKI stage | AUC | SE | nCohort 1 | nCohort 2 | p |
| --- | --- | --- | --- | --- | --- |
| 0 hours | 0.63 | 0.082 | 46 | 17 | 0.102 |
| 24 hours | 0.63 | 0.082 | 46 | 17 | 0.102 |
| 48 hours | 0.63 | 0.082 | 46 | 17 | 0.102 | sCr or UO

| Time prior AKI stage | Cutoff value | sens | spec | Quartile | OR | 95% CI of OR | |
| --- | --- | --- | --- | --- | --- | --- | --- |
| 0 hours | 304 | 71% | 66% | 1 |  |  |  |
|  | 213 | 81% | 45% | 2 | 1.0 | 0.2 | 4.7 |
|  | 94.6 | 90% | 16% | 3 | 2.5 | 0.7 | 8.6 |
|  | 416 | 67% | 71% | 4 | 4.4 | 1.4 | 14.1 |
|  | 664 | 43% | 80% |  |  |  |  |
|  | 1010 | 14% | 91% |  |  |  |  |
| 24 hours | 304 | 71% | 66% | 1 |  |  |  |
|  | 213 | 81% | 45% | 2 | 1.0 | 0.2 | 4.7 |
|  | 94.6 | 90% | 16% | 3 | 2.5 | 0.7 | 8.6 |
|  | 416 | 67% | 71% | 4 | 4.4 | 1.4 | 14.1 |
|  | 664 | 43% | 80% |  |  |  |  |

Fig. 7 - 5

|  |  | 1010 | 14% | 91% |  |  |  |  |
|---|---|---|---|---|---|---|---|---|
| 48 hours |  | 304 | 71% | 66% | 1 |  |  |  |
|  |  | 213 | 81% | 45% | 2 | 1.0 | 0.2 | 4.7 |
|  |  | 94.6 | 90% | 16% | 3 | 2.5 | 0.7 | 8.6 |
|  |  | 416 | 67% | 71% | 4 | 4.4 | 1.4 | 14.1 |
|  |  | 664 | 43% | 80% |  |  |  |  |
|  |  | 1010 | 14% | 91% |  |  |  |  | sCr only

| Time prior AKI stage | Cutoff value | sens | spec | Quartile | OR | 95% CI of OR | |
|---|---|---|---|---|---|---|---|
| 0 hours | 303 | 80% | 67% | 1 |  |  |  |
|  | 303 | 80% | 67% | 2 | 0.0 | 0.0 | na |
|  | 107 | 100% | 14% | 3 | 1.0 | 0.0 | 110.4 |
|  | 322 | 60% | 71% | 4 | 3.8 | 0.1 | 123.6 |
|  | 336 | 60% | 81% |  |  |  |  |
|  | 420 | 60% | 90% |  |  |  |  |
| 24 hours | 303 | 80% | 67% | 1 |  |  |  |
|  | 303 | 80% | 67% | 2 | 0.0 | 0.0 | na |
|  | 107 | 100% | 14% | 3 | 1.0 | 0.0 | 110.4 |
|  | 322 | 60% | 71% | 4 | 3.8 | 0.1 | 123.6 |
|  | 336 | 60% | 81% |  |  |  |  |
|  | 420 | 60% | 90% |  |  |  |  |
| 48 hours | 303 | 80% | 67% | 1 |  |  |  |
|  | 303 | 80% | 67% | 2 | 0.0 | 0.0 | na |
|  | 107 | 100% | 14% | 3 | 1.0 | 0.0 | 110.4 |
|  | 322 | 60% | 71% | 4 | 3.8 | 0.1 | 123.6 |
|  | 336 | 60% | 81% |  |  |  |  |
|  | 420 | 60% | 90% |  |  |  |  |

UO only

| Time prior AKI stage | Cutoff value | sens | spec | Quartile | OR | 95% CI of OR | |
|---|---|---|---|---|---|---|---|
| 0 hours | 324 | 71% | 63% | 1 |  |  |  |
|  | 167 | 82% | 33% | 2 | 0.6 | 0.1 | 4.0 |
|  | 85.5 | 94% | 11% | 3 | 1.8 | 0.5 | 7.3 |
|  | 647 | 47% | 72% | 4 | 3.1 | 0.8 | 11.6 |
|  | 720 | 47% | 80% |  |  |  |  |
|  | 1270 | 12% | 91% |  |  |  |  |
| 24 hours | 324 | 71% | 63% | 1 |  |  |  |
|  | 167 | 82% | 33% | 2 | 0.6 | 0.1 | 4.0 |
|  | 85.5 | 94% | 11% | 3 | 1.8 | 0.5 | 7.3 |
|  | 647 | 47% | 72% | 4 | 3.1 | 0.8 | 11.6 |
|  | 720 | 47% | 80% |  |  |  |  |
|  | 1270 | 12% | 91% |  |  |  |  |
| 48 hours | 324 | 71% | 63% | 1 |  |  |  |
|  | 167 | 82% | 33% | 2 | 0.6 | 0.1 | 4.0 |
|  | 85.5 | 94% | 11% | 3 | 1.8 | 0.5 | 7.3 |
|  | 647 | 47% | 72% | 4 | 3.1 | 0.8 | 11.6 |
|  | 720 | 47% | 80% |  |  |  |  |
|  | 1270 | 12% | 91% |  |  |  |  |

Fig. 7 - 6

Fatty acid binding protein, heart sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 11.450 | 157.000 | 11.450 | 146.000 | 11.450 | 147.000 |
| average | 43.685 | 408.925 | 43.685 | 337.735 | 43.685 | 209.933 |
| stdev | 102.008 | 479.936 | 102.008 | 472.555 | 102.008 | 250.366 |
| p (t-test) |  | 0.000 |  | 0.000 |  | 0.000 |
| min | 0.030 | 1.930 | 0.030 | 1.930 | 0.030 | 1.930 |
| max | 713.000 | 1477.000 | 713.000 | 1477.000 | 713.000 | 809.000 |
| n (Samp) | 112 | 17 | 112 | 17 | 112 | 10 |
| n (Pat) | 112 | 17 | 112 | 17 | 112 | 10 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 13.550 | 477.500 | 13.550 | 477.500 | 13.550 | 146.000 |
| average | 65.916 | 590.541 | 65.916 | 580.674 | 65.916 | 300.926 |
| stdev | 152.960 | 600.838 | 152.960 | 610.933 | 152.960 | 333.377 |
| p (t-test) |  | 0.000 |  | 0.000 |  | 0.001 |
| min | 0.030 | 1.930 | 0.030 | 1.930 | 0.030 | 1.930 |
| max | 944.000 | 1477.000 | 944.000 | 1477.000 | 944.000 | 809.000 |
| n (Samp) | 180 | 8 | 180 | 8 | 180 | 5 |
| n (Pat) | 180 | 8 | 180 | 8 | 180 | 5 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 12.600 | 204.000 | 12.600 | 157.000 | 12.600 | 148.000 |
| average | 43.377 | 360.582 | 43.377 | 257.736 | 43.377 | 212.629 |
| stdev | 90.955 | 360.607 | 90.955 | 314.733 | 90.955 | 274.682 |
| p (t-test) |  | 0.000 |  | 0.000 |  | 0.000 |
| min | 0.030 | 24.700 | 0.030 | 24.700 | 0.030 | 24.700 |
| max | 713.000 | 944.000 | 713.000 | 944.000 | 713.000 | 809.000 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
|---|---|---|---|---|---|
| 0 hours | 0.86 | 0.059 | 112 | 17 | 0.000 |
| 24 hours | 0.81 | 0.066 | 112 | 17 | 0.000 |
| 48 hours | 0.81 | 0.084 | 112 | 10 | 0.000 | sCr only

| Time prior AKI stage | AUC | SE | nCohort 1 | nCohort 2 | p |
|---|---|---|---|---|---|
| 0 hours | 0.79 | 0.096 | 180 | 8 | 0.002 |
| 24 hours | 0.72 | 0.104 | 180 | 8 | 0.037 |
| 48 hours | 0.76 | 0.127 | 180 | 5 | 0.043 |

UO only

| Time prior AKI stage | AUC | SE | nCohort 1 | nCohort 2 | p |
|---|---|---|---|---|---|
| 0 hours | 0.90 | 0.062 | 89 | 11 | 0.000 |
| 24 hours | 0.88 | 0.067 | 89 | 11 | 0.000 |
| 48 hours | 0.86 | 0.091 | 89 | 7 | 0.000 | sCr or UO

| Time prior AKI stage | Cutoff value | sens | spec | Quartile | OR | 95% CI of OR | |
|---|---|---|---|---|---|---|---|
| 0 hours | 77.7 | 71% | 88% | 1 |  |  |  |
|  | 34.9 | 82% | 75% | 2 | 0.0 | 0.0 | na |
|  | 17.8 | 94% | 60% | 3 | 3.2 | 0.2 | 49.9 |
|  | 31.2 | 82% | 71% | 4 | 20.2 | 2.1 | 195.4 |
|  | 53.5 | 76% | 80% |  |  |  |  |
|  | 94.1 | 65% | 90% |  |  |  |  |
| 24 hours | 53.5 | 71% | 80% | 1 |  |  |  |
|  | 24.4 | 82% | 67% | 2 | 1.0 | 0.0 | 57.2 |
|  | 4.31 | 94% | 29% | 3 | 4.4 | 0.3 | 58.6 |
|  | 31.2 | 76% | 71% | 4 | 15.5 | 1.6 | 153.1 |

Fig. 8 - 1

|  | 53.5 | 71% | 80% |  |  |  |  |
|  | 94.1 | 59% | 90% |  |  |  |  |
| 48 hours | 53.5 | 70% | 80% | 1 |  |  |  |
|  | 34.9 | 80% | 75% | 2 | 0.0 | 0.0 | na |
|  | 24.4 | 90% | 67% | 3 | 2.1 | 0.1 | 45.0 |
|  | 31.2 | 80% | 71% | 4 | 8.5 | 0.8 | 92.2 |
|  | 53.5 | 70% | 80% |  |  |  |  |
|  | 94.1 | 60% | 90% |  |  |  |  | sCr only

| Time prior AKI stage | Cutoff value | sens | spec | Quartile | OR | 95% CI of OR | |
| --- | --- | --- | --- | --- | --- | --- | --- |
| 0 hours | 80.9 | 75% | 83% | 1 |  |  |  |
|  | 17.8 | 88% | 54% | 2 | 0.0 | 0.0 | na |
|  | 1.84 | 100% | 9% | 3 | 1.0 | 0.0 | 54.9 |
|  | 40.2 | 75% | 70% | 4 | 6.7 | 0.6 | 72.5 |
|  | 70.4 | 75% | 80% |  |  |  |  |
|  | 143 | 63% | 90% |  |  |  |  |
| 24 hours | 16.4 | 75% | 52% | 1 |  |  |  |
|  | 4.52 | 88% | 24% | 2 | 0.0 | 0.0 | na |
|  | 1.84 | 100% | 9% | 3 | 0.5 | 0.0 | 10.1 |
|  | 40.2 | 63% | 70% | 4 | 2.7 | 0.6 | 11.6 |
|  | 70.4 | 63% | 80% |  |  |  |  |
|  | 143 | 63% | 90% |  |  |  |  |
| 48 hours | 80.9 | 80% | 83% | 1 |  |  |  |
|  | 80.9 | 80% | 83% | 2 | 0.0 | 0.0 | na |
|  | 1.84 | 100% | 9% | 3 | 0.0 | 0.0 | na |
|  | 40.2 | 80% | 70% | 4 | 4.2 | 0.3 | 53.0 |
|  | 70.4 | 80% | 80% |  |  |  |  |
|  | 143 | 60% | 90% |  |  |  |  |

Fig. 8 - 2

Hepatocyte growth factor sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 680.387 | 4037.748 | 680.387 | 1889.437 | 680.387 | 994.934 |
| average | 1568.697 | 7749.618 | 1568.697 | 3054.082 | 1568.697 | 2751.743 |
| stdev | 1805.239 | 15137.567 | 1805.239 | 2761.856 | 1805.239 | 2469.215 |
| p (t-test) |  | 0.000 |  | 0.021 |  | 0.105 |
| min | 51.808 | 601.481 | 51.808 | 406.000 | 51.808 | 406.000 |
| max | 7752.950 | 52712.475 | 7752.950 | 8813.508 | 7752.950 | 5912.184 |
| n (Samp) | 99 | 11 | 99 | 10 | 99 | 7 |
| n (Pat) | 99 | 11 | 99 | 10 | 99 | 7 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 904.843 | 1517.974 | 904.843 | 1239.467 | 904.843 | 960.960 |
| average | 1972.450 | 12014.181 | 1972.450 | 1839.607 | 1972.450 | 1347.811 |
| stdev | 2780.569 | 22788.548 | 2780.569 | 1509.169 | 2780.569 | 793.822 |
| p (t-test) |  | 0.000 |  | 0.924 |  | 0.699 |
| min | 51.808 | 821.575 | 51.808 | 821.575 | 51.808 | 821.575 |
| max | 25326.471 | 52712.475 | 25326.471 | 4057.920 | 25326.471 | 2260.899 |
| n (Samp) | 161 | 5 | 161 | 4 | 161 | 3 |
| n (Pat) | 161 | 5 | 161 | 4 | 161 | 3 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 628.920 | 4047.834 | 628.920 | 3149.323 | 628.920 | 2880.853 |
| average | 1664.488 | 3774.222 | 1664.488 | 3525.159 | 1664.488 | 3073.437 |
| stdev | 2459.709 | 2842.020 | 2459.709 | 2916.250 | 2459.709 | 2539.120 |
| p (t-test) |  | 0.024 |  | 0.047 |  | 0.180 |
| min | 51.808 | 601.481 | 51.808 | 406.000 | 51.808 | 406.000 |
| max | 17531.948 | 8813.508 | 17531.948 | 8813.508 | 17531.948 | 5912.184 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
| --- | --- | --- | --- | --- | --- |
| 0 hours | 0.77 | 0.086 | 99 | 11 | 0.001 |
| 24 hours | 0.72 | 0.094 | 99 | 10 | 0.017 |
| 48 hours | 0.70 | 0.114 | 99 | 7 | 0.087 | sCr only

| Time prior AKI stage | AUC | SE | nCohort 1 | nCohort 2 | p |
| --- | --- | --- | --- | --- | --- |
| 0 hours | 0.69 | 0.133 | 161 | 5 | 0.145 |
| 24 hours | 0.62 | 0.152 | 161 | 4 | 0.437 |
| 48 hours | 0.57 | 0.174 | 161 | 3 | 0.690 |

UO only

| Time prior AKI stage | AUC | SE | nCohort 1 | nCohort 2 | p |
| --- | --- | --- | --- | --- | --- |
| 0 hours | 0.79 | 0.098 | 84 | 8 | 0.003 |
| 24 hours | 0.75 | 0.102 | 84 | 8 | 0.013 |
| 48 hours | 0.73 | 0.121 | 84 | 6 | 0.061 | sCr or UO

| Time prior AKI stage | Cutoff value | sens | spec | Quartile | OR | 95% CI of OR | |
| --- | --- | --- | --- | --- | --- | --- | --- |
| 0 hours | 1034.9179 | 73% | 62% | 1 |  |  |  |
|  | 856.25091 | 82% | 60% | 2 | na | na | na |
|  | 814.68335 | 91% | 57% | 3 | na | na | na |
|  | 1665.8905 | 55% | 71% | 4 | na | na | na |
|  | 2569.5825 | 55% | 81% |  |  |  |  |
|  | 4662.0537 | 36% | 91% |  |  |  |  |
| 24 hours | 1034.9179 | 70% | 62% | 1 |  |  |  |
|  | 856.25091 | 80% | 60% | 2 | 0.0 | 0.0 | na |
|  | 814.68335 | 90% | 57% | 3 | 4.5 | 0.3 | 61.5 |
|  | 1665.8905 | 50% | 71% | 4 | 5.7 | 0.5 | 69.7 |
|  | 2569.5825 | 40% | 81% |  |  |  |  |

Fig. 8 - 3

|  | 4662.0537 | 30% | 91% |  |  |  |  |
|---|---|---|---|---|---|---|---|
| 48 hours | 856.25091 | 71% | 60% | 1 |  |  |  |
|  | 814.68335 | 86% | 57% | 2 | na | na | na |
|  | 398.32477 | 100% | 26% | 3 | na | na | na |
|  | 1665.8905 | 43% | 71% | 4 | na | na | na |
|  | 2569.5825 | 43% | 81% |  |  |  |  |
|  | 4662.0537 | 43% | 91% |  |  |  |  |

UO only

| Time prior AKI stage | Cutoff value | sens | spec | Quartile | OR | 95% CI of OR | |
|---|---|---|---|---|---|---|---|
| 0 hours | 1034.9179 | 75% | 64% | 1 |  |  |  |
|  | 832.22559 | 88% | 63% | 2 | na | na | na |
|  | 591.03997 | 100% | 44% | 3 | na | na | na |
|  | 1449.1471 | 63% | 70% | 4 | na | na | na |
|  | 3331.9938 | 63% | 81% |  |  |  |  |
|  | 4625.6742 | 38% | 90% |  |  |  |  |
| 24 hours | 1034.9179 | 75% | 64% | 1 |  |  |  |
|  | 832.22559 | 88% | 63% | 2 | 0.0 | 0.0 | na |
|  | 401.51729 | 100% | 26% | 3 | 3.3 | 0.2 | 54.3 |
|  | 1449.1471 | 63% | 70% | 4 | 4.6 | 0.3 | 65.0 |
|  | 3331.9938 | 50% | 81% |  |  |  |  |
|  | 4625.6742 | 38% | 90% |  |  |  |  |
| 48 hours | 832.22559 | 83% | 63% | 1 |  |  |  |
|  | 832.22559 | 83% | 63% | 2 | na | na | na |
|  | 401.51729 | 100% | 26% | 3 | na | na | na |
|  | 1449.1471 | 50% | 70% | 4 | na | na | na |
|  | 3331.9938 | 50% | 81% |  |  |  |  |
|  | 4625.6742 | 50% | 90% |  |  |  |  |

Fig. 8 - 4

Interferon gamma sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 4.105 | 9.870 | 4.105 | 8.440 | 4.105 | 4.420 |
| average | 9.379 | 12.182 | 9.379 | 10.766 | 9.379 | 8.370 |
| stdev | 13.003 | 8.529 | 13.003 | 9.056 | 13.003 | 9.876 |
| p (t-test) |  | 0.392 |  | 0.672 |  | 0.812 |
| min | 0.046 | 1.580 | 0.046 | 1.580 | 0.046 | 1.580 |
| max | 80.000 | 32.100 | 80.000 | 32.100 | 80.000 | 32.100 |
| n (Samp) | 112 | 17 | 112 | 17 | 112 | 10 |
| n (Pat) | 112 | 17 | 112 | 17 | 112 | 10 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 4.185 | 8.185 | 4.185 | 8.185 | 4.185 | 4.270 |
| average | 9.915 | 10.565 | 9.915 | 10.170 | 9.915 | 4.832 |
| stdev | 12.683 | 7.987 | 12.683 | 8.321 | 12.683 | 3.443 |
| p (t-test) |  | 0.886 |  | 0.955 |  | 0.373 |
| min | 0.046 | 1.580 | 0.046 | 1.580 | 0.046 | 1.580 |
| max | 80.000 | 24.300 | 80.000 | 24.300 | 80.000 | 9.870 |
| n (Samp) | 180 | 8 | 180 | 8 | 180 | 5 |
| n (Pat) | 180 | 8 | 180 | 8 | 180 | 5 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 4.100 | 9.870 | 4.100 | 8.440 | 4.100 | 6.500 |
| average | 8.775 | 12.632 | 8.775 | 10.731 | 8.775 | 10.844 |
| stdev | 11.476 | 8.555 | 11.476 | 9.186 | 11.476 | 11.036 |
| p (t-test) |  | 0.284 |  | 0.588 |  | 0.646 |
| min | 0.046 | 1.830 | 0.046 | 1.830 | 0.046 | 1.830 |
| max | 48.700 | 32.100 | 48.700 | 32.100 | 48.700 | 32.100 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
| --- | --- | --- | --- | --- | --- |
| 0 hours | 0.67 | 0.076 | 112 | 17 | 0.022 |
| 24 hours | 0.62 | 0.077 | 112 | 17 | 0.134 |
| 48 hours | 0.53 | 0.097 | 112 | 10 | 0.730 | sCr only

| Time prior AKI stage | AUC | SE | nCohort 1 | nCohort 2 | p |
| --- | --- | --- | --- | --- | --- |
| 0 hours | 0.61 | 0.108 | 180 | 8 | 0.303 |
| 24 hours | 0.59 | 0.108 | 180 | 8 | 0.423 |
| 48 hours | 0.46 | 0.127 | 180 | 5 | 0.723 |

UO only

| Time prior AKI stage | AUC | SE | nCohort 1 | nCohort 2 | p |
| --- | --- | --- | --- | --- | --- |
| 0 hours | 0.72 | 0.091 | 89 | 11 | 0.017 |
| 24 hours | 0.65 | 0.094 | 89 | 11 | 0.120 |
| 48 hours | 0.63 | 0.117 | 89 | 7 | 0.279 | sCr or UO

| Time prior AKI stage | Cutoff value | sens | spec | Quartile | OR | 95% CI of OR | |
| --- | --- | --- | --- | --- | --- | --- | --- |
| 0 hours | 6.43 | 71% | 65% | 1 |  |  |  |
|  | 4.27 | 82% | 55% | 2 | 0.5 | 0.0 | 10.4 |
|  | 1.78 | 94% | 26% | 3 | 4.2 | 1.0 | 17.1 |
|  | 8.23 | 65% | 71% | 4 | 4.0 | 1.0 | 16.4 |
|  | 15.4 | 35% | 80% |  |  |  |  |
|  | 28.1 | 6% | 90% |  |  |  |  |
| 24 hours | 4.26 | 71% | 54% | 1 |  |  |  |
|  | 2.72 | 82% | 35% | 2 | 0.6 | 0.1 | 3.8 |
|  | 1.78 | 94% | 26% | 3 | 2.2 | 0.7 | 6.9 |
|  | 8.23 | 53% | 71% | 4 | 2.1 | 0.7 | 6.6 |

Fig. 8 - 5

|  | 15.4 | 29% | 80% |  |  |  |  |
|  | 28.1 | 6% | 90% |  |  |  |  |
| 48 hours | 2.96 | 70% | 38% | 1 |  |  |  |
|  | 1.83 | 80% | 26% | 2 | 3.1 | 0.2 | 48.6 |
|  | 1.78 | 90% | 26% | 3 | 4.5 | 0.3 | 59.6 |
|  | 8.23 | 30% | 71% | 4 | 2.0 | 0.1 | 43.3 |
|  | 15.4 | 20% | 80% |  |  |  |  |
|  | 28.1 | 10% | 90% |  |  |  |  | sCr only

| Time prior AKI stage | Cutoff value | sens | spec | Quartile | OR | 95% CI of OR | |
| --- | --- | --- | --- | --- | --- | --- | --- |
| 0 hours | 6.25 | 75% | 61% | 1 |  |  |  |
|  | 2.96 | 88% | 38% | 2 | 1.0 | 0.0 | 54.9 |
|  | 1.54 | 100% | 17% | 3 | 4.3 | 0.3 | 54.2 |
|  | 9.87 | 38% | 70% | 4 | 2.0 | 0.1 | 42.2 |
|  | 17.7 | 25% | 80% |  |  |  |  |
|  | 29.7 | 0% | 90% |  |  |  |  |
| 24 hours | 4.26 | 75% | 52% | 1 |  |  |  |
|  | 1.83 | 88% | 26% | 2 | 1.0 | 0.0 | 54.9 |
|  | 1.54 | 100% | 17% | 3 | 4.3 | 0.3 | 54.2 |
|  | 9.87 | 38% | 70% | 4 | 2.0 | 0.1 | 42.2 |
|  | 17.7 | 25% | 80% |  |  |  |  |
|  | 29.7 | 0% | 90% |  |  |  |  |
| 48 hours | 1.83 | 80% | 26% | 1 |  |  |  |
|  | 1.83 | 80% | 26% | 2 | na | na | na |
|  | 1.54 | 100% | 17% | 3 | na | na | na |
|  | 9.87 | 0% | 70% | 4 | na | na | na |
|  | 17.7 | 0% | 80% |  |  |  |  |
|  | 29.7 | 0% | 90% |  |  |  |  |

UO only

| Time prior AKI stage | Cutoff value | sens | spec | Quartile | OR | 95% CI of OR | |
| --- | --- | --- | --- | --- | --- | --- | --- |
| 0 hours | 8.23 | 73% | 70% | 1 |  |  |  |
|  | 6.43 | 82% | 67% | 2 | 0.0 | 0.0 | na |
|  | 4.26 | 91% | 56% | 3 | 6.0 | 0.5 | 75.4 |
|  | 8.88 | 55% | 71% | 4 | 6.0 | 0.5 | 75.4 |
|  | 14.6 | 36% | 81% |  |  |  |  |
|  | 28.1 | 9% | 91% |  |  |  |  |
| 24 hours | 4.26 | 73% | 56% | 1 |  |  |  |
|  | 2.96 | 82% | 39% | 2 | 2.1 | 0.1 | 46.6 |
|  | 2.72 | 91% | 36% | 3 | 4.6 | 0.3 | 63.1 |
|  | 8.88 | 45% | 71% | 4 | 4.6 | 0.3 | 63.1 |
|  | 14.6 | 27% | 81% |  |  |  |  |
|  | 28.1 | 9% | 91% |  |  |  |  |
| 48 hours | 4.26 | 71% | 56% | 1 |  |  |  |
|  | 2.96 | 86% | 39% | 2 | na | na | na |
|  | 1.79 | 100% | 26% | 3 | na | na | na |
|  | 8.88 | 29% | 71% | 4 | na | na | na |
|  | 14.6 | 29% | 81% |  |  |  |  |
|  | 28.1 | 14% | 91% |  |  |  |  |

Fig. 8 - 6

Interleukin-16 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 532.000 | 1060.000 | 532.000 | 1000.000 | 532.000 | 881.000 |
| average | 692.429 | 1147.647 | 692.429 | 982.529 | 692.429 | 861.000 |
| stdev | 1070.969 | 857.072 | 1070.969 | 567.592 | 1070.969 | 448.785 |
| p (t-test) |  | 0.097 |  | 0.277 |  | 0.623 |
| min | 178.000 | 332.000 | 178.000 | 332.000 | 178.000 | 332.000 |
| max | 11500.000 | 3940.000 | 11500.000 | 2230.000 | 11500.000 | 1560.000 |
| n (Samp) | 112 | 17 | 112 | 17 | 112 | 10 |
| n (Pat) | 112 | 17 | 112 | 17 | 112 | 10 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 533.000 | 1030.000 | 533.000 | 841.000 | 533.000 | 1000.000 |
| average | 677.567 | 938.875 | 677.567 | 863.750 | 677.567 | 930.800 |
| stdev | 884.793 | 377.777 | 884.793 | 401.997 | 884.793 | 459.185 |
| p (t-test) |  | 0.407 |  | 0.555 |  | 0.525 |
| min | 178.000 | 332.000 | 178.000 | 332.000 | 178.000 | 332.000 |
| max | 11500.000 | 1560.000 | 11500.000 | 1560.000 | 11500.000 | 1560.000 |
| n (Samp) | 180 | 8 | 180 | 8 | 180 | 5 |
| n (Pat) | 180 | 8 | 180 | 8 | 180 | 5 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 533.000 | 1080.000 | 533.000 | 1080.000 | 533.000 | 1080.000 |
| average | 600.112 | 1279.909 | 600.112 | 1079.364 | 600.112 | 862.286 |
| stdev | 285.110 | 1011.900 | 285.110 | 617.830 | 285.110 | 410.726 |
| p (t-test) |  | 0.000 |  | 0.000 |  | 0.026 |
| min | 178.000 | 361.000 | 178.000 | 361.000 | 178.000 | 335.000 |
| max | 1550.000 | 3940.000 | 1550.000 | 2230.000 | 1550.000 | 1380.000 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
| --- | --- | --- | --- | --- | --- |
| 0 hours | 0.75 | 0.071 | 112 | 17 | 0.000 |
| 24 hours | 0.71 | 0.074 | 112 | 17 | 0.006 |
| 48 hours | 0.65 | 0.098 | 112 | 10 | 0.117 | sCr only

| Time prior AKI stage | AUC | SE | nCohort 1 | nCohort 2 | p |
| --- | --- | --- | --- | --- | --- |
| 0 hours | 0.76 | 0.100 | 180 | 8 | 0.009 |
| 24 hours | 0.70 | 0.106 | 180 | 8 | 0.059 |
| 48 hours | 0.72 | 0.131 | 180 | 5 | 0.091 |

UO only

| Time prior AKI stage | AUC | SE | nCohort 1 | nCohort 2 | p |
| --- | --- | --- | --- | --- | --- |
| 0 hours | 0.77 | 0.086 | 89 | 11 | 0.002 |
| 24 hours | 0.74 | 0.089 | 89 | 11 | 0.007 |
| 48 hours | 0.67 | 0.116 | 89 | 7 | 0.132 | sCr or UO

| Time prior AKI stage | Cutoff value | sens | spec | Quartile | OR | 95% CI of OR | |
| --- | --- | --- | --- | --- | --- | --- | --- |
| 0 hours | 723 | 71% | 79% | 1 |  |  |  |
|  | 546 | 82% | 54% | 2 | 1.0 | 0.1 | 8.1 |
|  | 360 | 94% | 16% | 3 | 1.0 | 0.1 | 8.1 |
|  | 651 | 71% | 71% | 4 | 7.5 | 2.0 | 27.9 |
|  | 733 | 65% | 80% |  |  |  |  |
|  | 1040 | 53% | 90% |  |  |  |  |
| 24 hours | 551 | 71% | 54% | 1 |  |  |  |
|  | 515 | 82% | 48% | 2 | 1.0 | 0.1 | 8.1 |
|  | 360 | 94% | 16% | 3 | 2.1 | 0.4 | 10.7 |
|  | 651 | 59% | 71% | 4 | 5.6 | 1.5 | 21.6 |
|  | 733 | 53% | 80% |  |  |  |  |

Fig. 8 - 7

| | | 1040 | 47% | 90% | | | | |
|---|---|---|---|---|---|---|---|---|
| | 48 hours | 546 | 70% | 54% | 1 | | | |
| | | 426 | 80% | 29% | 2 | 0.5 | 0.0 | 10.1 |
| | | 332 | 90% | 13% | 3 | 1.0 | 0.1 | 8.2 |
| | | 651 | 60% | 71% | 4 | 2.7 | 0.6 | 12.3 |
| | | 733 | 50% | 80% | | | | |
| | | 1040 | 50% | 90% | | | | | sCr only

| Time prior AKI stage | Cutoff value | sens | spec | Quartile | OR | 95% CI of OR | |
|---|---|---|---|---|---|---|---|
| 0 hours | 769 | 75% | 82% | 1 | | | |
| | 566 | 88% | 56% | 2 | 0.0 | 0.0 | na |
| | 327 | 100% | 10% | 3 | 1.0 | 0.0 | 54.9 |
| | 655 | 75% | 70% | 4 | 6.7 | 0.6 | 72.5 |
| | 733 | 75% | 80% | | | | |
| | 1040 | 50% | 90% | | | | |
| 24 hours | 587 | 75% | 59% | 1 | | | |
| | 525 | 88% | 47% | 2 | 1.0 | 0.0 | 54.9 |
| | 327 | 100% | 10% | 3 | 2.0 | 0.1 | 42.2 |
| | 655 | 63% | 70% | 4 | 4.3 | 0.3 | 54.2 |
| | 733 | 50% | 80% | | | | |
| | 1040 | 38% | 90% | | | | |
| 48 hours | 679 | 80% | 73% | 1 | | | |
| | 679 | 80% | 73% | 2 | 0.0 | 0.0 | na |
| | 327 | 100% | 10% | 3 | 1.0 | 0.0 | 55.0 |
| | 655 | 80% | 70% | 4 | 3.1 | 0.2 | 45.7 |
| | 733 | 60% | 80% | | | | |
| | 1040 | 40% | 90% | | | | |

UO only

| Time prior AKI stage | Cutoff value | sens | spec | Quartile | OR | 95% CI of OR | |
|---|---|---|---|---|---|---|---|
| 0 hours | 723 | 73% | 79% | 1 | | | |
| | 546 | 82% | 53% | 2 | 2.1 | 0.1 | 46.6 |
| | 426 | 91% | 29% | 3 | 1.0 | 0.0 | 59.3 |
| | 666 | 73% | 71% | 4 | 9.3 | 0.8 | 106.1 |
| | 763 | 64% | 81% | | | | |
| | 1020 | 55% | 91% | | | | |
| 24 hours | 551 | 73% | 53% | 1 | | | |
| | 546 | 82% | 53% | 2 | 2.1 | 0.1 | 46.6 |
| | 426 | 91% | 29% | 3 | 1.0 | 0.0 | 59.3 |
| | 666 | 64% | 71% | 4 | 9.3 | 0.8 | 106.1 |
| | 763 | 64% | 81% | | | | |
| | 1020 | 55% | 91% | | | | |
| 48 hours | 546 | 71% | 53% | 1 | | | |
| | 426 | 86% | 29% | 2 | 1.0 | 0.0 | 59.8 |
| | 319 | 100% | 12% | 3 | 1.0 | 0.0 | 59.8 |
| | 666 | 57% | 71% | 4 | 4.6 | 0.3 | 64.0 |
| | 763 | 57% | 81% | | | | |
| | 1020 | 57% | 91% | | | | |

Fig. 8 - 8

Interleukin-2 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 0.508 | 1.225 | 0.508 | 1.238 | 0.508 | 1.250 |
| average | 0.751 | 1.641 | 0.751 | 1.738 | 0.751 | 1.835 |
| stdev | 0.977 | 1.339 | 0.977 | 1.369 | 0.977 | 1.579 |
| p (t-test) |  | 0.007 |  | 0.004 |  | 0.008 |
| min | 0.000 | 0.575 | 0.000 | 0.575 | 0.000 | 0.605 |
| max | 7.239 | 5.074 | 7.239 | 5.074 | 7.239 | 5.074 |
| n (Samp) | 99 | 11 | 99 | 10 | 99 | 7 |
| n (Pat) | 99 | 11 | 99 | 10 | 99 | 7 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 0.589 | 1.250 | 0.589 | 1.341 | 0.589 | 1.250 |
| average | 1.046 | 1.289 | 1.046 | 1.449 | 1.046 | 1.085 |
| stdev | 1.838 | 0.790 | 1.838 | 0.814 | 1.838 | 0.451 |
| p (t-test) |  | 0.769 |  | 0.663 |  | 0.970 |
| min | 0.000 | 0.575 | 0.000 | 0.575 | 0.000 | 0.575 |
| max | 19.127 | 2.538 | 19.127 | 2.538 | 19.127 | 1.431 |
| n (Samp) | 161 | 5 | 161 | 4 | 161 | 3 |
| n (Pat) | 161 | 5 | 161 | 4 | 161 | 3 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 0.542 | 1.184 | 0.542 | 1.173 | 0.542 | 1.186 |
| average | 0.851 | 1.679 | 0.851 | 1.676 | 0.851 | 1.902 |
| stdev | 1.069 | 1.516 | 1.069 | 1.517 | 1.069 | 1.719 |
| p (t-test) |  | 0.047 |  | 0.047 |  | 0.028 |
| min | 0.045 | 0.575 | 0.045 | 0.575 | 0.045 | 0.605 |
| max | 7.239 | 5.074 | 7.239 | 5.074 | 7.239 | 5.074 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
| --- | --- | --- | --- | --- | --- |
| 0 hours | 0.84 | 0.076 | 99 | 11 | 0.000 |
| 24 hours | 0.85 | 0.077 | 99 | 10 | 0.000 |
| 48 hours | 0.85 | 0.093 | 99 | 7 | 0.000 | sCr only

| Time prior AKI stage | AUC | SE | nCohort 1 | nCohort 2 | p |
| --- | --- | --- | --- | --- | --- |
| 0 hours | 0.73 | 0.131 | 161 | 5 | 0.083 |
| 24 hours | 0.76 | 0.141 | 161 | 4 | 0.065 |
| 48 hours | 0.71 | 0.170 | 161 | 3 | 0.212 |

UO only

| Time prior AKI stage | AUC | SE | nCohort 1 | nCohort 2 | p |
| --- | --- | --- | --- | --- | --- |
| 0 hours | 0.81 | 0.096 | 84 | 8 | 0.001 |
| 24 hours | 0.81 | 0.096 | 84 | 8 | 0.001 |
| 48 hours | 0.81 | 0.109 | 84 | 6 | 0.004 |

Fig. 8 - 9

Interleukin-12 p40 sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 33.113 | 18.459 | 33.113 | 11.088 | 33.113 | 11.758 |
| average | 45.270 | 28.085 | 45.270 | 22.882 | 45.270 | 27.059 |
| stdev | 45.927 | 27.038 | 45.927 | 27.869 | 45.927 | 32.021 |
| p (t-test) |  | 0.227 |  | 0.134 |  | 0.306 |
| min | 0.000 | 3.180 | 0.000 | 0.000 | 0.000 | 3.180 |
| max | 230.675 | 83.149 | 230.675 | 83.149 | 230.675 | 83.149 |
| n (Samp) | 99 | 11 | 99 | 10 | 99 | 7 |
| n (Pat) | 99 | 11 | 99 | 10 | 99 | 7 | sCr only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 32.159 | 19.123 | 32.159 | 33.795 | 32.159 | 3.180 |
| average | 41.702 | 30.442 | 41.702 | 33.272 | 41.702 | 21.833 |
| stdev | 39.600 | 27.399 | 39.600 | 30.782 | 39.600 | 35.097 |
| p (t-test) |  | 0.529 |  | 0.673 |  | 0.390 |
| min | 0.000 | 3.180 | 0.000 | 3.180 | 0.000 | 0.000 |
| max | 230.675 | 62.318 | 230.675 | 62.318 | 230.675 | 62.318 |
| n (Samp) | 161 | 5 | 161 | 4 | 161 | 3 |
| n (Pat) | 161 | 5 | 161 | 4 | 161 | 3 |

UO only

|  | 0 hr prior toAKI stage | | 24 hr prior toAKI stage | | 48 hr prior toAKI stage | |
| --- | --- | --- | --- | --- | --- | --- |
|  | Cohort 1 | Cohort 2 | Cohort 1 | Cohort 2 | Cohort 1 | Cohort 2 |
| median | 32.732 | 23.725 | 32.732 | 13.201 | 32.732 | 13.201 |
| average | 42.660 | 34.526 | 42.660 | 26.903 | 42.660 | 31.039 |
| stdev | 42.380 | 29.194 | 42.380 | 30.042 | 42.380 | 33.126 |
| p (t-test) |  | 0.598 |  | 0.308 |  | 0.513 |
| min | 0.000 | 4.527 | 0.000 | 0.000 | 0.000 | 4.527 |
| max | 230.675 | 83.149 | 230.675 | 83.149 | 230.675 | 83.149 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
| --- | --- | --- | --- | --- | --- |
| 0 hours | 0.36 | 0.081 | 99 | 11 | 0.096 |
| 24 hours | 0.29 | 0.075 | 99 | 10 | 0.005 |
| 48 hours | 0.33 | 0.094 | 99 | 7 | 0.072 | sCr only

| Time prior AKI stage | AUC | SE | nCohort 1 | nCohort 2 | p |
| --- | --- | --- | --- | --- | --- |
| 0 hours | 0.42 | 0.123 | 161 | 5 | 0.521 |
| 24 hours | 0.46 | 0.142 | 161 | 4 | 0.759 |
| 48 hours | 0.30 | 0.130 | 161 | 3 | 0.127 |

UO only

| Time prior AKI stage | AUC | SE | nCohort 1 | nCohort 2 | p |
| --- | --- | --- | --- | --- | --- |
| 0 hours | 0.46 | 0.104 | 84 | 8 | 0.690 |
| 24 hours | 0.35 | 0.093 | 84 | 8 | 0.117 |
| 48 hours | 0.39 | 0.112 | 84 | 6 | 0.347 | sCr or UO

| Time prior AKI stage | Cutoff value | sens | spec | Quartile | OR | 95% CI of OR | |
| --- | --- | --- | --- | --- | --- | --- | --- |
| 0 hours | 9.8385095 | 73% | 14% | 1 |  |  |  |
|  | 9.4129279 | 82% | 14% | 2 | 0.0 | 0.0 | na |
|  | 3.3229148 | 91% | 8% | 3 | 1.0 | 0.2 | 4.3 |
|  | 43.818211 | 27% | 71% | 4 | 1.9 | 0.6 | 6.4 |
|  | 65.137251 | 9% | 81% |  |  |  |  |
|  | 108.38454 | 0% | 91% |  |  |  |  |
| 24 hours | 9.4129279 | 70% | 14% | 1 |  |  |  |
|  | 3.3229148 | 80% | 8% | 2 | 0.0 | 0.0 | na |
|  | 1.2982033 | 90% | 7% | 3 | 1.0 | 0.1 | 8.6 |
|  | 43.818211 | 20% | 71% | 4 | 3.7 | 0.8 | 16.2 |
|  | 65.137251 | 10% | 81% |  |  |  |  |

Fig. 8 - 10

|  | 108.38454 | 0% | 91% |  |  |  |  |
|---|---|---|---|---|---|---|---|
| 48 hours | 9.4129279 | 71% | 14% | 1 |  |  |  |
|  | 3.3229148 | 86% | 8% | 2 | 0.0 | 0.0 | na |
|  | 1.2982033 | 100% | 7% | 3 | 0.0 | 0.0 | na |
|  | 43.818211 | 29% | 71% | 4 | 3.0 | 0.6 | 13.9 |
|  | 65.137251 | 14% | 81% |  |  |  |  |
|  | 108.38454 | 0% | 91% |  |  |  |  | sCr only

| Time prior AKI stage | Cutoff value | sens | spec | Quartile | OR | 95% CI of OR | |
|---|---|---|---|---|---|---|---|
| 0 hours | 9.6041633 | 80% | 14% | 1 |  |  |  |
|  | 9.6041633 | 80% | 14% | 2 | 0.0 | 0.0 | na |
|  | 1.846505 | 100% | 7% | 3 | 0.5 | 0.0 | 10.2 |
|  | 44.321401 | 40% | 70% | 4 | 1.0 | 0.1 | 8.0 |
|  | 55.567948 | 40% | 80% |  |  |  |  |
|  | 89.565615 | 0% | 90% |  |  |  |  |
| 24 hours | 9.6041633 | 75% | 14% | 1 |  |  |  |
|  | 1.846505 | 100% | 7% | 2 | 0.0 | 0.0 | na |
|  | 1.846505 | 100% | 7% | 3 | 0.0 | 0.0 | na |
|  | 44.321401 | 50% | 70% | 4 | 1.0 | 0.1 | 8.0 |
|  | 55.567948 | 50% | 80% |  |  |  |  |
|  | 89.565615 | 0% | 90% |  |  |  |  |
| 48 hours | 0 | 100% | 0% | 1 |  |  |  |
|  | 0 | 100% | 0% | 2 | 0.0 | 0.0 | na |
|  | 0 | 100% | 0% | 3 | 0.0 | 0.0 | na |
|  | 44.321401 | 33% | 70% | 4 | 2.1 | 0.1 | 42.9 |
|  | 55.567948 | 33% | 80% |  |  |  |  |
|  | 89.565615 | 0% | 90% |  |  |  |  |

UO only

| Time prior AKI stage | Cutoff value | sens | spec | Quartile | OR | 95% CI of OR | |
|---|---|---|---|---|---|---|---|
| 0 hours | 11.290059 | 75% | 19% | 1 |  |  |  |
|  | 9.4129279 | 88% | 18% | 2 | 0.0 | 0.0 | na |
|  | 3.3229148 | 100% | 8% | 3 | 0.6 | 0.1 | 3.9 |
|  | 44.429066 | 38% | 70% | 4 | 1.0 | 0.2 | 4.5 |
|  | 61.565682 | 25% | 81% |  |  |  |  |
|  | 97.366099 | 0% | 90% |  |  |  |  |
| 24 hours | 9.4129279 | 75% | 18% | 1 |  |  |  |
|  | 3.3229148 | 88% | 8% | 2 | 0.0 | 0.0 | na |
|  | 0 | 100% | 0% | 3 | 1.0 | 0.1 | 8.6 |
|  | 44.429066 | 25% | 70% | 4 | 2.2 | 0.4 | 11.7 |
|  | 61.565682 | 25% | 81% |  |  |  |  |
|  | 97.366099 | 0% | 90% |  |  |  |  |
| 48 hours | 9.4129279 | 83% | 18% | 1 |  |  |  |
|  | 9.4129279 | 83% | 18% | 2 | 0.0 | 0.0 | na |
|  | 3.3229148 | 100% | 8% | 3 | 0.5 | 0.0 | 10.8 |
|  | 44.429066 | 33% | 70% | 4 | 1.7 | 0.3 | 10.3 |
|  | 61.565682 | 33% | 81% |  |  |  |  |
|  | 97.366099 | 0% | 90% |  |  |  |  |

Fig. 8 - 11

Matrix metalloproteinase-2 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 2850.000 | 3740.000 | 2850.000 | 3460.000 | 2850.000 | 3650.000 |
| average | 2926.071 | 3797.647 | 2926.071 | 3435.294 | 2926.071 | 3441.000 |
| stdev | 930.041 | 1332.078 | 930.041 | 1396.733 | 930.041 | 1411.102 |
| p (t-test) |  | 0.001 |  | 0.053 |  | 0.112 |
| min | 1410.000 | 1890.000 | 1410.000 | 1350.000 | 1410.000 | 1360.000 |
| max | 5710.000 | 5870.000 | 5710.000 | 5630.000 | 5710.000 | 5380.000 |
| n (Samp) | 112 | 17 | 112 | 17 | 112 | 10 |
| n (Pat) | 112 | 17 | 112 | 17 | 112 | 10 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 2885.000 | 3610.000 | 2895.000 | 2895.000 | 2885.000 | 2280.000 |
| average | 2987.000 | 3761.250 | 2987.000 | 3146.250 | 2987.000 | 3100.000 |
| stdev | 979.445 | 1517.803 | 979.445 | 1495.965 | 979.445 | 1681.800 |
| p (t-test) |  | 0.034 |  | 0.661 |  | 0.803 |
| min | 1070.000 | 1890.000 | 1070.000 | 1350.000 | 1070.000 | 1360.000 |
| max | 6370.000 | 5870.000 | 6370.000 | 5380.000 | 6370.000 | 5380.000 |
| n (Samp) | 180 | 8 | 180 | 8 | 180 | 5 |
| n (Pat) | 180 | 8 | 180 | 8 | 180 | 5 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 2910.000 | 3840.000 | 2910.000 | 3840.000 | 2910.000 | 3840.000 |
| average | 2957.528 | 3939.091 | 2957.528 | 3826.364 | 2957.528 | 3795.714 |
| stdev | 938.245 | 1209.913 | 938.245 | 1303.137 | 938.245 | 1307.196 |
| p (t-test) |  | 0.002 |  | 0.007 |  | 0.030 |
| min | 1410.000 | 2110.000 | 1410.000 | 2110.000 | 1410.000 | 2110.000 |
| max | 5710.000 | 5630.000 | 5710.000 | 5630.000 | 5710.000 | 5380.000 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
|---|---|---|---|---|---|
| 0 hours | 0.69 | 0.075 | 112 | 17 | 0.011 |
| 24 hours | 0.60 | 0.077 | 112 | 17 | 0.215 |
| 48 hours | 0.60 | 0.098 | 112 | 10 | 0.305 | sCr only

| Time prior AKI stage | AUC | SE | nCohort 1 | nCohort 2 | p |
|---|---|---|---|---|---|
| 0 hours | 0.64 | 0.108 | 180 | 8 | 0.195 |
| 24 hours | 0.50 | 0.105 | 180 | 8 | 0.992 |
| 48 hours | 0.46 | 0.128 | 180 | 5 | 0.771 |

UO only

| Time prior AKI stage | AUC | SE | nCohort 1 | nCohort 2 | p |
|---|---|---|---|---|---|
| 0 hours | 0.75 | 0.089 | 89 | 11 | 0.006 |
| 24 hours | 0.70 | 0.092 | 89 | 11 | 0.029 |
| 48 hours | 0.70 | 0.114 | 89 | 7 | 0.084 | sCr or UO

| Time prior AKI stage | Cutoff value | sens | spec | Quartile | OR | 95% CI of OR | |
|---|---|---|---|---|---|---|---|
| 0 hours | 3100 | 71% | 64% | 1 |  |  |  |
|  | 2130 | 88% | 21% | 2 | 0.2 | 0.0 | 3.0 |
|  | 2100 | 94% | 21% | 3 | 0.7 | 0.2 | 2.6 |
|  | 3270 | 65% | 71% | 4 | 2.6 | 1.1 | 6.2 |
|  | 3660 | 53% | 80% |  |  |  |  |
|  | 4030 | 41% | 90% |  |  |  |  |
| 24 hours | 2260 | 71% | 27% | 1 |  |  |  |
|  | 2130 | 82% | 21% | 2 | 0.4 | 0.1 | 1.6 |
|  | 1730 | 94% | 9% | 3 | 0.4 | 0.1 | 1.6 |
|  | 3270 | 53% | 71% | 4 | 1.7 | 0.8 | 3.8 |
|  | 3660 | 47% | 80% |  |  |  |  |

Fig. 8 - 12

| | | 4030 | 35% | 90% | | | | |
|---|---|---|---|---|---|---|---|---|
| 48 hours | | 2130 | 80% | 21% | 1 | | | |
| | | 2130 | 80% | 21% | 2 | 0.0 | 0.0 | na |
| | | 2100 | 90% | 21% | 3 | 0.2 | 0.0 | 3.0 |
| | | 3270 | 60% | 71% | 4 | 1.3 | 0.4 | 3.5 |
| | | 3660 | 50% | 80% | | | | |
| | | 4030 | 40% | 90% | | | | | sCr only

| Time prior AKI stage | Cutoff value | sens | spec | Quartile | OR | 95% CI of OR | |
|---|---|---|---|---|---|---|---|
| 0 hours | 2580 | 75% | 38% | 1 | | | |
| | 2130 | 88% | 18% | 2 | 0.5 | 0.0 | 10.1 |
| | 1850 | 100% | 10% | 3 | 0.5 | 0.0 | 10.1 |
| | 3340 | 63% | 70% | 4 | 2.1 | 0.4 | 10.0 |
| | 3710 | 50% | 80% | | | | |
| | 4290 | 38% | 90% | | | | |
| 24 hours | 2130 | 75% | 18% | 1 | | | |
| | 1730 | 88% | 8% | 2 | 0.3 | 0.0 | 4.7 |
| | 1290 | 100% | 2% | 3 | 0.3 | 0.0 | 4.7 |
| | 3340 | 50% | 70% | 4 | 1.0 | 0.2 | 4.0 |
| | 3710 | 38% | 80% | | | | |
| | 4290 | 25% | 90% | | | | |
| 48 hours | 2130 | 80% | 18% | 1 | | | |
| | 2130 | 80% | 18% | 2 | 0.0 | 0.0 | na |
| | 1290 | 100% | 2% | 3 | 0.5 | 0.0 | 10.3 |
| | 3340 | 40% | 70% | 4 | 1.0 | 0.1 | 7.9 |
| | 3710 | 40% | 80% | | | | |
| | 4290 | 40% | 90% | | | | |

UO only

| Time prior AKI stage | Cutoff value | sens | spec | Quartile | OR | 95% CI of OR | |
|---|---|---|---|---|---|---|---|
| 0 hours | 3440 | 73% | 76% | 1 | | | |
| | 3100 | 82% | 62% | 2 | 0.0 | 0.0 | na |
| | 2110 | 91% | 20% | 3 | 1.6 | 0.3 | 9.6 |
| | 3230 | 73% | 71% | 4 | 3.6 | 0.8 | 16.2 |
| | 3660 | 55% | 81% | | | | |
| | 4220 | 45% | 91% | | | | |
| 24 hours | 3100 | 73% | 62% | 1 | | | |
| | 2260 | 82% | 27% | 2 | 0.5 | 0.0 | 10.7 |
| | 2110 | 91% | 20% | 3 | 1.0 | 0.1 | 8.4 |
| | 3230 | 64% | 71% | 4 | 3.6 | 0.8 | 16.2 |
| | 3660 | 55% | 81% | | | | |
| | 4220 | 45% | 91% | | | | |
| 48 hours | 3440 | 71% | 76% | 1 | | | |
| | 2110 | 86% | 20% | 2 | 0.0 | 0.0 | na |
| | 2100 | 100% | 20% | 3 | 0.5 | 0.0 | 10.8 |
| | 3230 | 71% | 71% | 4 | 2.2 | 0.4 | 11.5 |
| | 3660 | 57% | 81% | | | | |
| | 4220 | 43% | 91% | | | | |

Fig. 8 - 13

Midkine sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 6.599 | 21.914 | 6.599 | 33.926 | 6.599 | 4.169 |
| average | 20.838 | 25.691 | 20.838 | 27.379 | 20.838 | 19.131 |
| stdev | 23.837 | 23.326 | 23.837 | 24.489 | 23.837 | 25.917 |
| p (t-test) |  | 0.569 |  | 0.511 |  | 0.873 |
| min | 0.417 | 0.904 | 0.417 | 0.889 | 0.417 | 0.889 |
| max | 72.865 | 56.007 | 72.865 | 56.007 | 72.865 | 56.007 |
| n (Samp) | 37 | 10 | 37 | 7 | 37 | 6 |
| n (Pat) | 37 | 10 | 37 | 7 | 37 | 6 | sCr only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 4.680 | 6.094 | 4.680 | 4.725 | 4.680 | 3.891 |
| average | 17.629 | 16.930 | 17.629 | 13.185 | 17.629 | 3.891 |
| stdev | 21.611 | 18.023 | 21.611 | 18.063 | 21.611 | 4.225 |
| p (t-test) |  | 0.944 |  | 0.728 |  | 0.376 |
| min | 0.002 | 0.904 | 0.002 | 0.904 | 0.002 | 0.904 |
| max | 72.865 | 39.002 | 72.865 | 33.926 | 72.865 | 6.879 |
| n (Samp) | 61 | 5 | 61 | 3 | 61 | 2 |
| n (Pat) | 61 | 5 | 61 | 3 | 61 | 2 |

UO only

|  | 0 hr prior toAKI stage | | 24 hr prior toAKI stage | | 48 hr prior toAKI stage | |
|---|---|---|---|---|---|---|
|  | Cohort 1 | Cohort 2 | Cohort 1 | Cohort 2 | Cohort 1 | Cohort 2 |
| median | 13.546 | 50.413 | 13.546 | 47.601 | 13.546 | 25.053 |
| average | 24.117 | 34.452 | 24.117 | 38.025 | 24.117 | 26.750 |
| stdev | 25.221 | 26.599 | 25.221 | 25.087 | 25.221 | 29.686 |
| p (t-test) |  | 0.410 |  | 0.312 |  | 0.850 |
| min | 0.417 | 1.287 | 0.417 | 0.889 | 0.417 | 0.889 |
| max | 72.865 | 56.007 | 72.865 | 56.007 | 72.865 | 56.007 |
| n (Samp) | 27 | 5 | 27 | 4 | 27 | 4 |
| n (Pat) | 27 | 5 | 27 | 4 | 27 | 4 | sCr or UO

| Time prior AKI stage | AUC | SE | nCohort 1 | nCohort 2 | p |
|---|---|---|---|---|---|
| 0 hours | 0.58 | 0.105 | 37 | 10 | 0.457 |
| 24 hours | 0.56 | 0.122 | 37 | 7 | 0.625 |
| 48 hours | 0.45 | 0.125 | 37 | 6 | 0.719 | sCr only

| Time prior AKI stage | AUC | SE | nCohort 1 | nCohort 2 | p |
|---|---|---|---|---|---|
| 0 hours | 0.56 | 0.138 | 61 | 5 | 0.679 |
| 24 hours | 0.49 | 0.171 | 61 | 3 | 0.962 |
| 48 hours | 0.37 | 0.183 | 61 | 2 | 0.474 |

UO only

| Time prior AKI stage | AUC | SE | nCohort 1 | nCohort 2 | p |
|---|---|---|---|---|---|
| 0 hours | 0.60 | 0.145 | 27 | 5 | 0.492 |
| 24 hours | 0.61 | 0.160 | 27 | 4 | 0.489 |
| 48 hours | 0.49 | 0.156 | 27 | 4 | 0.953 | sCr or UO

| Time prior AKI stage | Cutoff value | sens | spec | Quartile | OR | 95% CI of OR | |
|---|---|---|---|---|---|---|---|
| 0 hours | 5.2959736 | 70% | 49% | 1 |  |  |  |
|  | 3.8837139 | 80% | 46% | 2 | 0.9 | 0.1 | 9.7 |
|  | 0.9035326 | 90% | 16% | 3 | 1.5 | 0.2 | 11.9 |
|  | 29.610829 | 50% | 70% | 4 | 1.5 | 0.2 | 11.9 |
|  | 49.407783 | 30% | 81% |  |  |  |  |
|  | 63.085399 | 0% | 92% |  |  |  |  |
| 24 hours | 3.8837139 | 71% | 46% | 1 |  |  |  |
|  | 0.8890913 | 86% | 16% | 2 | 0.5 | 0.0 | 12.9 |
|  | 0.8763587 | 100% | 16% | 3 | 0.5 | 0.0 | 12.9 |
|  | 29.610829 | 57% | 70% | 4 | 1.7 | 0.2 | 13.7 |
|  | 49.407783 | 14% | 81% |  |  |  |  |

Fig. 8 - 14

|  | 63.085399 | 0% | 92% |  |  |  |  |
|---|---|---|---|---|---|---|---|
| 48 hours | 0.8890913 | 83% | 16% | 1 |  |  |  |
|  | 0.8890913 | 83% | 16% | 2 | 0.5 | 0.0 | 12.9 |
|  | 0.8763587 | 100% | 16% | 3 | 0.5 | 0.0 | 12.9 |
|  | 29.610829 | 33% | 70% | 4 | 1.1 | 0.1 | 12.7 |
|  | 49.407783 | 17% | 81% |  |  |  |  |
|  | 63.085399 | 0% | 92% |  |  |  |  | sCr only

| Time prior AKI stage | Cutoff value | sens | spec | Quartile | OR | 95% CI of OR | |
|---|---|---|---|---|---|---|---|
| 0 hours | 4.679988 | 80% | 51% | 1 |  |  |  |
|  | 4.679988 | 80% | 51% | 2 | 0.9 | 0.0 | 60.9 |
|  | 0.8763587 | 100% | 20% | 3 | 1.0 | 0.0 | 65.5 |
|  | 24.521014 | 40% | 70% | 4 | 2.0 | 0.1 | 49.1 |
|  | 40.35533 | 0% | 82% |  |  |  |  |
|  | 54.65313 | 0% | 90% |  |  |  |  |
| 24 hours | 0.8763587 | 100% | 20% | 1 |  |  |  |
|  | 0.8763587 | 100% | 20% | 2 | 1.0 | 0.0 | 65.5 |
|  | 0.8763587 | 100% | 20% | 3 | 0.0 | 0.0 | na |
|  | 24.521014 | 33% | 70% | 4 | 1.0 | 0.0 | 65.5 |
|  | 40.35533 | 0% | 82% |  |  |  |  |
|  | 54.65313 | 0% | 90% |  |  |  |  |
| 48 hours | 0.8763587 | 100% | 20% | 1 |  |  |  |
|  | 0.8763587 | 100% | 20% | 2 | na | na | na |
|  | 0.8763587 | 100% | 20% | 3 | na | na | na |
|  | 24.521014 | 0% | 70% | 4 | na | na | na |
|  | 40.35533 | 0% | 82% |  |  |  |  |
|  | 54.65313 | 0% | 90% |  |  |  |  |

UO only

| Time prior AKI stage | Cutoff value | sens | spec | Quartile | OR | 95% CI of OR | |
|---|---|---|---|---|---|---|---|
| 0 hours | 9.7721354 | 80% | 48% | 1 |  |  |  |
|  | 9.7721354 | 80% | 48% | 2 | 1.0 | 0.0 | 88.2 |
|  | 0.8763587 | 100% | 19% | 3 | 1.0 | 0.0 | 88.2 |
|  | 31.133672 | 60% | 70% | 4 | 2.3 | 0.1 | 81.0 |
|  | 56.514382 | 0% | 81% |  |  |  |  |
|  | 64.187328 | 0% | 93% |  |  |  |  |
| 24 hours | 40.35533 | 75% | 74% | 1 |  |  |  |
|  | 0.8763587 | 100% | 19% | 2 | 0.0 | 0.0 | na |
|  | 0.8763587 | 100% | 19% | 3 | 2.0 | 0.1 | 72.7 |
|  | 31.133672 | 75% | 70% | 4 | 0.9 | 0.0 | 79.2 |
|  | 56.514382 | 0% | 81% |  |  |  |  |
|  | 64.187328 | 0% | 93% |  |  |  |  |
| 48 hours | 1.3827646 | 75% | 26% | 1 |  |  |  |
|  | 0.8763587 | 100% | 19% | 2 | 1.0 | 0.0 | 88.2 |
|  | 0.8763587 | 100% | 19% | 3 | 1.0 | 0.0 | 88.2 |
|  | 31.133672 | 50% | 70% | 4 | 1.2 | 0.0 | 107.9 |
|  | 56.514382 | 0% | 81% |  |  |  |  |
|  | 64.187328 | 0% | 93% |  |  |  |  |

Fig. 8 - 15

Serum amyloid P-component sCr or UO

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 4758.594 | 7144.793 | 4758.594 | 6494.385 | 4758.594 | 7105.260 |
| average | 5442.318 | 6631.266 | 5442.318 | 6510.234 | 5442.318 | 7057.266 |
| stdev | 2648.446 | 2799.175 | 2648.446 | 2861.268 | 2648.446 | 1597.203 |
| p (t-test) |  | 0.163 |  | 0.230 |  | 0.115 |
| min | 96.224 | 915.589 | 96.224 | 915.589 | 96.224 | 5335.126 |
| max | 16315.493 | 10815.095 | 16315.493 | 10815.095 | 16315.493 | 9395.400 |
| n (Samp) | 99 | 11 | 99 | 10 | 99 | 7 |
| n (Pat) | 99 | 11 | 99 | 10 | 99 | 7 | sCr only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 4979.471 | 7144.793 | 4979.471 | 7988.651 | 4979.471 | 5335.126 |
| average | 5596.394 | 7145.511 | 5596.394 | 8031.881 | 5596.394 | 6046.142 |
| stdev | 2845.854 | 2835.477 | 2845.854 | 2341.417 | 2845.854 | 2507.635 |
| p (t-test) |  | 0.232 |  | 0.092 |  | 0.786 |
| min | 96.224 | 3600.034 | 96.224 | 5335.126 | 96.224 | 3970.792 |
| max | 16576.982 | 10815.095 | 16576.982 | 10815.095 | 16576.982 | 8832.509 |
| n (Samp) | 161 | 5 | 161 | 4 | 161 | 3 |
| n (Pat) | 161 | 5 | 161 | 4 | 161 | 3 |

UO only

|  | 0 hr prior to AKI stage | | 24 hr prior to AKI stage | | 48 hr prior to AKI stage | |
| --- | --- | --- | --- | --- | --- | --- |
|  | Cohort 1 | Cohort 2 | Cohort 1 | Cohort 2 | Cohort 1 | Cohort 2 |
| median | 5129.158 | 7223.623 | 5129.158 | 6494.385 | 5129.158 | 7203.857 |
| average | 5501.565 | 6649.209 | 5501.565 | 6119.015 | 5501.565 | 7344.290 |
| stdev | 2324.764 | 2672.037 | 2324.764 | 2739.775 | 2324.764 | 1539.239 |
| p (t-test) |  | 0.191 |  | 0.481 |  | 0.060 |
| min | 1580.497 | 915.589 | 1580.497 | 915.589 | 1580.497 | 5546.607 |
| max | 16315.493 | 9395.400 | 16315.493 | 9395.400 | 16315.493 | 9395.400 |
| n (Samp) | 84 | 8 | 84 | 8 | 84 | 6 |
| n (Pat) | 84 | 8 | 84 | 8 | 84 | 6 | sCr or UO

| Time prior AKI stage | AUC | SE | nCohort 1 | nCohort 2 | p |
| --- | --- | --- | --- | --- | --- |
| 0 hours | 0.67 | 0.093 | 99 | 11 | 0.067 |
| 24 hours | 0.66 | 0.098 | 99 | 10 | 0.102 |
| 48 hours | 0.76 | 0.108 | 99 | 7 | 0.016 | sCr only

| Time prior AKI stage | AUC | SE | nCohort 1 | nCohort 2 | p |
| --- | --- | --- | --- | --- | --- |
| 0 hours | 0.68 | 0.134 | 161 | 5 | 0.183 |
| 24 hours | 0.80 | 0.134 | 161 | 4 | 0.025 |
| 48 hours | 0.59 | 0.175 | 161 | 3 | 0.619 |

UO only

| Time prior AKI stage | AUC | SE | nCohort 1 | nCohort 2 | p |
| --- | --- | --- | --- | --- | --- |
| 0 hours | 0.70 | 0.107 | 84 | 8 | 0.064 |
| 24 hours | 0.62 | 0.110 | 84 | 8 | 0.277 |
| 48 hours | 0.78 | 0.113 | 84 | 6 | 0.012 | sCr or UO

| Time prior AKI stage | Cutoff value | sens | spec | Quartile | OR | 95% CI of OR | |
| --- | --- | --- | --- | --- | --- | --- | --- |
| 0 hours | 5499.6001 | 73% | 62% | 1 |  |  |  |
|  | 5324.4963 | 82% | 59% | 2 | 0.0 | 0.0 | na |
|  | 3439.4811 | 91% | 20% | 3 | 1.6 | 0.3 | 9.4 |
|  | 6336.0501 | 55% | 71% | 4 | 3.4 | 0.8 | 14.9 |
|  | 6925.5816 | 55% | 81% |  |  |  |  |
|  | 8769.955 | 27% | 91% |  |  |  |  |
| 24 hours | 5499.6001 | 70% | 62% | 1 |  |  |  |
|  | 5324.4963 | 80% | 59% | 2 | 1.0 | 0.0 | 58.6 |
|  | 3943.9292 | 90% | 29% | 3 | 3.3 | 0.2 | 51.9 |
|  | 6336.0501 | 50% | 71% | 4 | 5.7 | 0.5 | 69.7 |
|  | 6925.5816 | 50% | 81% |  |  |  |  |

Fig. 8 - 16

| | 8769.955 | 30% | 91% | | | | |
|---|---|---|---|---|---|---|---|
| 48 hours | 5724.4425 | 71% | 65% | 1 | | | |
| | 5499.6001 | 86% | 62% | 2 | na | na | na |
| | 5324.4963 | 100% | 59% | 3 | na | na | na |
| | 6336.0501 | 57% | 71% | 4 | na | na | na |
| | 6925.5816 | 57% | 81% | | | | |
| | 8769.955 | 29% | 91% | | | | | sCr only

| Time prior AKI stage | Cutoff value | sens | spec | Quartile | OR | 95% CI of OR | |
|---|---|---|---|---|---|---|---|
| 0 hours | 5324.4963 | 80% | 55% | 1 | | | |
| | 5324.4963 | 80% | 55% | 2 | 0.0 | 0.0 | na |
| | 3439.4811 | 100% | 19% | 3 | 1.0 | 0.0 | 55.6 |
| | 6424.9768 | 60% | 70% | 4 | 3.1 | 0.2 | 46.4 |
| | 7622.1289 | 40% | 80% | | | | |
| | 8594.5677 | 40% | 90% | | | | |
| 24 hours | 7073.5661 | 75% | 77% | 1 | | | |
| | 5324.4963 | 100% | 55% | 2 | na | na | na |
| | 5324.4963 | 100% | 55% | 3 | na | na | na |
| | 6424.9768 | 75% | 70% | 4 | na | na | na |
| | 7622.1289 | 50% | 80% | | | | |
| | 8594.5677 | 50% | 90% | | | | |
| 48 hours | 3956.1005 | 100% | 29% | 1 | | | |
| | 3956.1005 | 100% | 29% | 2 | na | na | na |
| | 3956.1005 | 100% | 29% | 3 | na | na | na |
| | 6424.9768 | 33% | 70% | 4 | na | na | na |
| | 7622.1289 | 33% | 80% | | | | |
| | 8594.5677 | 33% | 90% | | | | |

UO only

| Time prior AKI stage | Cutoff value | sens | spec | Quartile | OR | 95% CI of OR | |
|---|---|---|---|---|---|---|---|
| 0 hours | 5724.4425 | 75% | 63% | 1 | | | |
| | 5499.6001 | 88% | 57% | 2 | 0.0 | 0.0 | na |
| | 0 | 100% | 0% | 3 | 2.1 | 0.1 | 47.6 |
| | 6336.0501 | 63% | 70% | 4 | 6.1 | 0.5 | 78.3 |
| | 6925.5816 | 63% | 81% | | | | |
| | 8769.955 | 25% | 90% | | | | |
| 24 hours | 5499.6001 | 75% | 57% | 1 | | | |
| | 3943.9292 | 88% | 25% | 2 | 0.0 | 0.0 | na |
| | 0 | 100% | 0% | 3 | 1.0 | 0.1 | 8.6 |
| | 6336.0501 | 50% | 70% | 4 | 2.2 | 0.4 | 11.7 |
| | 6925.5816 | 50% | 81% | | | | |
| | 8769.955 | 25% | 90% | | | | |
| 48 hours | 5724.4425 | 83% | 63% | 1 | | | |
| | 5724.4425 | 83% | 63% | 2 | na | na | na |
| | 5499.6001 | 100% | 57% | 3 | na | na | na |
| | 6336.0501 | 67% | 70% | 4 | na | na | na |
| | 6925.5816 | 67% | 81% | | | | |
| | 8769.955 | 33% | 90% | | | | |

Fig. 8 - 17

Matrix metalloproteinase-9 sCr or UO

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 398.000 | 694.000 | 398.000 | 653.000 | 398.000 | 638.000 |
| average | 684.421 | 1406.824 | 684.421 | 933.647 | 684.421 | 848.400 |
| stdev | 1184.299 | 1741.414 | 1184.299 | 685.773 | 1184.299 | 576.178 |
| p (t-test) |  | 0.030 |  | 0.400 |  | 0.666 |
| min | 33.200 | 315.000 | 33.200 | 315.000 | 33.200 | 315.000 |
| max | 8903.000 | 7705.000 | 8903.000 | 2270.000 | 8903.000 | 1990.000 |
| n (Samp) | 112 | 17 | 112 | 17 | 112 | 10 |
| n (Pat) | 112 | 17 | 112 | 17 | 112 | 10 | sCr only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 424.500 | 778.500 | 424.500 | 692.500 | 424.500 | 694.000 |
| average | 762.806 | 1029.500 | 762.806 | 1003.250 | 762.806 | 1132.200 |
| stdev | 1189.773 | 560.743 | 1189.773 | 574.400 | 1189.773 | 668.691 |
| p (t-test) |  | 0.530 |  | 0.571 |  | 0.491 |
| min | 33.200 | 460.000 | 33.200 | 460.000 | 33.200 | 566.000 |
| max | 8903.000 | 1990.000 | 8903.000 | 1990.000 | 8903.000 | 1990.000 |
| n (Samp) | 180 | 8 | 180 | 8 | 180 | 5 |
| n (Pat) | 180 | 8 | 180 | 8 | 180 | 5 |

UO only

|  | 0 hr prior to AKI stage | | 24 hr prior to AKI stage | | 48 hr prior to AKI stage | |
|---|---|---|---|---|---|---|
|  | Cohort 1 | Cohort 2 | Cohort 1 | Cohort 2 | Cohort 1 | Cohort 2 |
| median | 376.000 | 691.000 | 376.000 | 585.000 | 376.000 | 585.000 |
| average | 517.840 | 1551.364 | 517.840 | 839.182 | 517.840 | 601.143 |
| stdev | 544.989 | 2144.086 | 544.989 | 720.722 | 544.989 | 263.688 |
| p (t-test) |  | 0.000 |  | 0.078 |  | 0.691 |
| min | 33.200 | 315.000 | 33.200 | 315.000 | 33.200 | 315.000 |
| max | 3830.000 | 7705.000 | 3830.000 | 2270.000 | 3830.000 | 1020.000 |
| n (Samp) | 89 | 11 | 89 | 11 | 89 | 7 |
| n (Pat) | 89 | 11 | 89 | 11 | 89 | 7 | sCr or UO

| Time prior AKI stage | AUC | SE | nCohort 1 | nCohort 2 | p |
|---|---|---|---|---|---|
| 0 hours | 0.77 | 0.069 | 112 | 17 | 0.000 |
| 24 hours | 0.71 | 0.074 | 112 | 17 | 0.005 |
| 48 hours | 0.70 | 0.096 | 112 | 10 | 0.038 | sCr only

| Time prior AKI stage | AUC | SE | nCohort 1 | nCohort 2 | p |
|---|---|---|---|---|---|
| 0 hours | 0.75 | 0.101 | 180 | 8 | 0.012 |
| 24 hours | 0.74 | 0.102 | 180 | 8 | 0.018 |
| 48 hours | 0.77 | 0.125 | 180 | 5 | 0.029 |

UO only

| Time prior AKI stage | AUC | SE | nCohort 1 | nCohort 2 | p |
|---|---|---|---|---|---|
| 0 hours | 0.78 | 0.085 | 89 | 11 | 0.001 |
| 24 hours | 0.69 | 0.093 | 89 | 11 | 0.043 |
| 48 hours | 0.66 | 0.116 | 89 | 7 | 0.169 |

Fig. 8 - 18

SEQUENCE LISTING

```
<160> NUMBER OF SEQ ID NOS: 11

<210> SEQ ID NO 1
<211> LENGTH: 449
<212> TYPE: PRT
<213> ORGANISM: Homo sapiens

<400> SEQUENCE: 1

Met Met Lys Thr Leu Leu Phe Val Gly Leu Leu Thr Trp Glu
1               5                   10                  15

Ser Gly Gln Val Leu Gly Asp Gln Thr Val Ser Asp Asn Glu Leu Gln
                20                  25                  30

Glu Met Ser Asn Gln Gly Ser Lys Tyr Val Asn Lys Glu Ile Gln Asn
            35                  40                  45

Ala Val Asn Gly Val Lys Gln Ile Lys Thr Leu Ile Glu Lys Thr Asn
        50                  55                  60

Glu Glu Arg Lys Thr Leu Leu Ser Asn Leu Glu Glu Ala Lys Lys Lys
65                  70                  75                  80

Lys Glu Asp Ala Leu Asn Glu Thr Arg Glu Ser Glu Thr Lys Leu Lys
                85                  90                  95

Glu Leu Pro Gly Val Cys Asn Glu Thr Met Met Ala Leu Trp Glu Glu
            100                 105                 110

Cys Lys Pro Cys Leu Lys Gln Thr Cys Met Lys Phe Tyr Ala Arg Val
        115                 120                 125

Cys Arg Ser Gly Ser Gly Leu Val Gly Arg Gln Leu Glu Glu Phe Leu
    130                 135                 140

Asn Gln Ser Ser Pro Phe Tyr Phe Trp Met Asn Gly Asp Arg Ile Asp
145                 150                 155                 160

Ser Leu Leu Glu Asn Asp Arg Gln Gln Thr His Met Leu Asp Val Met
                165                 170                 175

Gln Asp His Phe Ser Arg Ala Ser Ser Ile Ile Asp Glu Leu Phe Gln
            180                 185                 190

Asp Arg Phe Phe Thr Arg Glu Pro Gln Asp Thr Tyr His Tyr Leu Pro
        195                 200                 205

Phe Ser Leu Pro His Arg Arg Pro His Phe Phe Pro Lys Ser Arg
    210                 215                 220

Ile Val Arg Ser Leu Met Pro Phe Ser Pro Tyr Glu Pro Leu Asn Phe
225                 230                 235                 240

His Ala Met Phe Gln Pro Phe Leu Glu Met Ile His Glu Ala Gln Gln
                245                 250                 255

Ala Met Asp Ile His Phe His Ser Pro Ala Phe Gln His Pro Pro Thr
            260                 265                 270

Glu Phe Ile Arg Glu Gly Asp Asp Arg Thr Val Cys Arg Glu Ile
        275                 280                 285

Arg His Asn Ser Thr Gly Cys Leu Arg Met Lys Asp Gln Cys Asp Lys
    290                 295                 300
```

```
Cys Arg Glu Ile Leu Ser Val Asp Cys Ser Thr Asn Asn Pro Ser Gln
305                 310                 315                 320

Ala Lys Leu Arg Arg Glu Leu Asp Glu Ser Leu Gln Val Ala Glu Arg
            325                 330                 335

Leu Thr Arg Lys Tyr Asn Glu Leu Leu Lys Ser Tyr Gln Trp Lys Met
            340                 345                 350

Leu Asn Thr Ser Ser Leu Leu Glu Gln Leu Asn Glu Gln Phe Asn Trp
            355                 360                 365

Val Ser Arg Leu Ala Asn Leu Thr Gln Gly Glu Asp Gln Tyr Tyr Leu
        370                 375                 380

Arg Val Thr Thr Val Ala Ser His Thr Ser Asp Ser Asp Val Pro Ser
385                 390                 395                 400

Gly Val Thr Glu Val Val Lys Leu Phe Asp Ser Asp Pro Ile Thr
            405                 410                 415

Val Thr Val Pro Val Glu Val Ser Arg Lys Asn Pro Lys Phe Met Glu
            420                 425                 430

Thr Val Ala Glu Lys Ala Leu Gln Glu Tyr Arg Lys Lys His Arg Glu
            435                 440                 445

Glu

<210> SEQ ID NO 2
<211> LENGTH: 133
<212> TYPE: PRT
<213> ORGANISM: Homo sapiens

<400> SEQUENCE: 2

Met Val Asp Ala Phe Leu Gly Thr Trp Lys Leu Val Asp Ser Lys Asn
1               5                   10                  15

Phe Asp Asp Tyr Met Lys Ser Leu Gly Val Gly Phe Ala Thr Arg Gln
            20                  25                  30

Val Ala Ser Met Thr Lys Pro Thr Thr Ile Ile Glu Lys Asn Gly Asp
        35                  40                  45

Ile Leu Thr Leu Lys Thr His Ser Thr Phe Lys Asn Thr Glu Ile Ser
    50                  55                  60

Phe Lys Leu Gly Val Glu Phe Asp Glu Thr Thr Ala Asp Asp Arg Lys
65                  70                  75                  80

Val Lys Ser Ile Val Thr Leu Asp Gly Gly Lys Leu Val His Leu Gln
                85                  90                  95

Lys Trp Asp Gly Gln Glu Thr Thr Leu Val Arg Glu Leu Ile Asp Gly
            100                 105                 110

Lys Leu Ile Leu Thr Leu Thr His Gly Thr Ala Val Cys Thr Arg Thr
        115                 120                 125

Tyr Glu Lys Glu Ala
    130

<210> SEQ ID NO 3
<211> LENGTH: 728
<212> TYPE: PRT
<213> ORGANISM: Homo sapiens

<400> SEQUENCE: 3

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
```

```
            35                  40                  45
Thr Leu Ile Lys Ile Asp Pro Ala Leu Lys Ile Lys Thr Lys Val
 50                  55                  60

Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
                100                 105                 110

Gly His Glu Phe Asp Leu Tyr Glu Asn Lys Asp Tyr Ile Arg Asn Cys
             115                 120                 125

Ile Ile Gly Lys Gly Arg Ser Tyr Lys Gly Thr Val Ser Ile Thr Lys
130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
                180                 185                 190

Asn Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
                260                 265                 270

Thr Leu Asp Pro His Thr Arg Trp Glu Tyr Cys Ala Ile Lys Thr Cys
            275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
                340                 345                 350

Tyr Cys Arg Asn Pro Asp Gly Ser Glu Ser Pro Trp Cys Phe Thr Thr
            355                 360                 365

Asp Pro Asn Ile Arg Val Gly Tyr Cys Ser Gln Ile Pro Asn Cys Asp
370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
                420                 425                 430

Ser Lys Leu Asn Glu Asn Tyr Cys Arg Asn Pro Asp Asp Asp Ala His
            435                 440                 445

Gly Pro Trp Cys Tyr Thr Gly Asn Pro Leu Ile Pro Trp Asp Tyr Cys
450                 455                 460
```

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
            485                 490                 495

Asn Gly Ile Pro Thr Arg Thr Asn Ile Gly Trp Met Val Ser Leu Arg
        500                 505                 510

Tyr Arg Asn Lys His Ile Cys Gly Gly Ser Leu Ile Lys Glu Ser Trp
    515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 4
<211> LENGTH: 166
<212> TYPE: PRT
<213> ORGANISM: Homo sapiens

<400> SEQUENCE: 4

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg

```
            100                 105                 110
Asp Asp Phe Glu Lys Leu Thr Asn Tyr Ser Val Thr Asp Leu Asn Val
            115                 120                 125

Gln Arg Lys Ala Ile His Glu Leu Ile Gln Val Met Ala Glu Leu Ser
            130                 135             140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 5
<211> LENGTH: 328
<212> TYPE: PRT
<213> ORGANISM: Homo sapiens

<400> SEQUENCE: 5

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
        50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
                100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
        130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300
```

```
Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 6
<211> LENGTH: 631
<212> TYPE: PRT
<213> ORGANISM: Homo sapiens

<400> SEQUENCE: 6

Met Asp Tyr Ser Phe Asp Thr Thr Ala Glu Asp Pro Trp Val Arg Ile
1               5                   10                  15

Ser Asp Cys Ile Lys Asn Leu Phe Ser Pro Ile Met Ser Glu Asn His
                20                  25                  30

Gly His Met Pro Leu Gln Pro Asn Ala Ser Leu Asn Glu Glu Glu Gly
            35                  40                  45

Thr Gln Gly His Pro Asp Gly Thr Pro Pro Lys Leu Asp Thr Ala Asn
    50                  55                  60

Gly Thr Pro Lys Val Tyr Lys Ser Ala Asp Ser Ser Thr Val Lys Lys
65                  70                  75                  80

Gly Pro Pro Val Ala Pro Lys Pro Ala Trp Phe Arg Gln Ser Leu Lys
                85                  90                  95

Gly Leu Arg Asn Arg Ala Ser Asp Pro Arg Gly Leu Pro Asp Pro Ala
            100                 105                 110

Leu Ser Thr Gln Pro Ala Pro Ala Ser Arg Glu His Leu Gly Ser His
        115                 120                 125

Ile Arg Ala Ser Ser Ser Ser Ser Ile Arg Gln Arg Ile Ser Ser
130                 135                 140

Phe Glu Thr Phe Gly Ser Ser Gln Leu Pro Asp Lys Gly Ala Gln Arg
145                 150                 155                 160

Leu Ser Leu Gln Pro Ser Ser Gly Glu Ala Lys Pro Leu Gly Lys
                165                 170                 175

His Glu Glu Gly Arg Phe Ser Gly Leu Leu Gly Arg Gly Ala Ala Pro
            180                 185                 190

Thr Leu Val Pro Gln Gln Pro Glu Gln Val Leu Ser Ser Gly Ser Pro
        195                 200                 205

Ala Ala Ser Glu Ala Arg Asp Pro Gly Val Ser Glu Ser Pro Pro Pro
210                 215                 220

Gly Arg Gln Pro Asn Gln Lys Thr Leu Pro Pro Gly Pro Asp Pro Leu
225                 230                 235                 240

Leu Arg Leu Leu Ser Thr Gln Ala Glu Glu Ser Gln Gly Pro Val Leu
                245                 250                 255

Lys Met Pro Ser Gln Arg Ala Arg Ser Phe Pro Leu Thr Arg Ser Gln
            260                 265                 270

Ser Cys Glu Thr Lys Leu Leu Asp Glu Lys Thr Ser Lys Leu Tyr Ser
        275                 280                 285

Ile Ser Ser Gln Val Ser Ser Ala Val Met Lys Ser Leu Leu Cys Leu
290                 295                 300

Pro Ser Ser Ile Ser Cys Ala Gln Thr Pro Cys Ile Pro Lys Glu Gly
305                 310                 315                 320

Ala Ser Pro Thr Ser Ser Ser Asn Glu Asp Ser Ala Ala Asn Gly Ser
                325                 330                 335

Ala Glu Thr Ser Ala Leu Asp Thr Gly Phe Ser Leu Asn Leu Ser Glu
            340                 345                 350
```

```
Leu Arg Glu Tyr Thr Glu Gly Leu Thr Glu Ala Lys Glu Asp Asp
            355                 360                 365

Gly Asp His Ser Ser Leu Gln Ser Gly Gln Ser Val Ile Ser Leu Leu
    370                 375                 380

Ser Ser Glu Glu Leu Lys Lys Leu Ile Glu Glu Val Lys Val Leu Asp
385                 390                 395                 400

Glu Ala Thr Leu Lys Gln Leu Asp Gly Ile His Val Thr Ile Leu His
                405                 410                 415

Lys Glu Glu Gly Ala Gly Leu Gly Phe Ser Leu Ala Gly Gly Ala Asp
                420                 425                 430

Leu Glu Asn Lys Val Ile Thr Val His Arg Val Phe Pro Asn Gly Leu
            435                 440                 445

Ala Ser Gln Glu Gly Thr Ile Gln Lys Gly Asn Glu Val Leu Ser Ile
        450                 455                 460

Asn Gly Lys Ser Leu Lys Gly Thr Thr His His Asp Ala Leu Ala Ile
465                 470                 475                 480

Leu Arg Gln Ala Arg Glu Pro Arg Gln Ala Val Ile Val Thr Arg Lys
                485                 490                 495

Leu Thr Pro Glu Ala Met Pro Asp Leu Asn Ser Ser Thr Asp Ser Ala
            500                 505                 510

Ala Ser Ala Ser Ala Ala Ser Asp Val Ser Val Glu Ser Thr Ala Glu
        515                 520                 525

Ala Thr Val Cys Thr Val Thr Leu Glu Lys Met Ser Ala Gly Leu Gly
    530                 535                 540

Phe Ser Leu Glu Gly Gly Lys Gly Ser Leu His Gly Asp Lys Pro Leu
545                 550                 555                 560

Thr Ile Asn Arg Ile Phe Lys Gly Ala Ala Ser Glu Gln Ser Glu Thr
                565                 570                 575

Val Gln Pro Gly Asp Glu Ile Leu Gln Leu Gly Gly Thr Ala Met Gln
            580                 585                 590

Gly Leu Thr Arg Phe Glu Ala Trp Asn Ile Ile Lys Ala Leu Pro Asp
        595                 600                 605

Gly Pro Val Thr Ile Val Ile Arg Arg Lys Ser Leu Gln Ser Lys Glu
    610                 615                 620

Thr Thr Ala Ala Gly Asp Ser
625                 630

<210> SEQ ID NO 7
<211> LENGTH: 153
<212> TYPE: PRT
<213> ORGANISM: Homo sapiens

<400> SEQUENCE: 7

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
```

```
            85                  90                  95
Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
            130                 135                 140

Cys Gln Ser Ile Ile Ser Thr Leu Thr
145                 150
```

<210> SEQ ID NO 8
<211> LENGTH: 660
<212> TYPE: PRT
<213> ORGANISM: Homo sapiens

<400> SEQUENCE: 8

```
Met Glu Ala Leu Met Ala Arg Gly Ala Leu Thr Gly Pro Leu Arg Ala
1               5                   10                  15

Leu Cys Leu Leu Gly Cys Leu Leu Ser His Ala Ala Ala Ala Pro Ser
            20                  25                  30

Pro Ile Ile Lys Phe Pro Gly Asp Val Ala Pro Lys Thr Asp Lys Glu
        35                  40                  45

Leu Ala Val Gln Tyr Leu Asn Thr Phe Tyr Gly Cys Pro Lys Glu Ser
    50                  55                  60

Cys Asn Leu Phe Val Leu Lys Asp Thr Leu Lys Lys Met Gln Lys Phe
65                  70                  75                  80

Phe Gly Leu Pro Gln Thr Gly Asp Leu Asp Gln Asn Thr Ile Glu Thr
            85                  90                  95

Met Arg Lys Pro Arg Cys Gly Asn Pro Asp Val Ala Asn Tyr Asn Phe
            100                 105                 110

Phe Pro Arg Lys Pro Lys Trp Asp Lys Asn Gln Ile Thr Tyr Arg Ile
            115                 120                 125

Ile Gly Tyr Thr Pro Asp Leu Asp Pro Glu Thr Val Asp Asp Ala Phe
            130                 135                 140

Ala Arg Ala Phe Gln Val Trp Ser Asp Val Thr Pro Leu Arg Phe Ser
145                 150                 155                 160

Arg Ile His Asp Gly Glu Ala Asp Ile Met Ile Asn Phe Gly Arg Trp
            165                 170                 175

Glu His Gly Asp Gly Tyr Pro Phe Asp Gly Lys Asp Gly Leu Leu Ala
            180                 185                 190

His Ala Phe Ala Pro Gly Thr Gly Val Gly Gly Asp Ser His Phe Asp
            195                 200                 205

Asp Asp Glu Leu Trp Thr Leu Gly Glu Gly Gln Val Val Arg Val Lys
            210                 215                 220

Tyr Gly Asn Ala Asp Gly Glu Tyr Cys Lys Phe Pro Phe Leu Phe Asn
225                 230                 235                 240

Gly Lys Glu Tyr Asn Ser Cys Thr Asp Thr Gly Arg Ser Asp Gly Phe
            245                 250                 255

Leu Trp Cys Ser Thr Thr Tyr Asn Phe Glu Lys Asp Gly Lys Tyr Gly
            260                 265                 270

Phe Cys Pro His Glu Ala Leu Phe Thr Met Gly Gly Asn Ala Glu Gly
            275                 280                 285

Gln Pro Cys Lys Phe Pro Phe Arg Phe Gln Gly Thr Ser Tyr Asp Ser
            290                 295                 300
```

-continued

```
Cys Thr Thr Glu Gly Arg Thr Asp Gly Tyr Arg Trp Cys Gly Thr Thr
305                 310                 315                 320

Glu Asp Tyr Asp Arg Asp Lys Lys Tyr Gly Phe Cys Pro Glu Thr Ala
            325                 330                 335

Met Ser Thr Val Gly Asn Ser Glu Gly Ala Pro Cys Val Phe Pro
            340                 345                 350

Phe Thr Phe Leu Gly Asn Lys Tyr Glu Ser Cys Thr Ser Ala Gly Arg
            355                 360                 365

Ser Asp Gly Lys Met Trp Cys Ala Thr Thr Ala Asn Tyr Asp Asp Asp
370                 375                 380

Arg Lys Trp Gly Phe Cys Pro Asp Gln Gly Tyr Ser Leu Phe Leu Val
385                 390                 395                 400

Ala Ala His Glu Phe Gly His Ala Met Gly Leu Glu His Ser Gln Asp
                405                 410                 415

Pro Gly Ala Leu Met Ala Pro Ile Tyr Thr Tyr Lys Asn Phe Arg
            420                 425                 430

Leu Ser Gln Asp Asp Ile Lys Gly Ile Gln Glu Leu Tyr Gly Ala Ser
                435                 440                 445

Pro Asp Ile Asp Leu Gly Thr Gly Pro Thr Pro Thr Leu Gly Pro Val
450                 455                 460

Thr Pro Glu Ile Cys Lys Gln Asp Ile Val Phe Asp Gly Ile Ala Gln
465                 470                 475                 480

Ile Arg Gly Glu Ile Phe Phe Phe Lys Asp Arg Phe Ile Trp Arg Thr
                485                 490                 495

Val Thr Pro Arg Asp Lys Pro Met Gly Pro Leu Leu Val Ala Thr Phe
            500                 505                 510

Trp Pro Glu Leu Pro Glu Lys Ile Asp Ala Val Tyr Glu Ala Pro Gln
            515                 520                 525

Glu Glu Lys Ala Val Phe Phe Ala Gly Asn Glu Tyr Trp Ile Tyr Ser
530                 535                 540

Ala Ser Thr Leu Glu Arg Gly Tyr Pro Lys Pro Leu Thr Ser Leu Gly
545                 550                 555                 560

Leu Pro Pro Asp Val Gln Arg Val Asp Ala Ala Phe Asn Trp Ser Lys
            565                 570                 575

Asn Lys Lys Thr Tyr Ile Phe Ala Gly Asp Lys Phe Trp Arg Tyr Asn
            580                 585                 590

Glu Val Lys Lys Lys Met Asp Pro Gly Phe Pro Lys Leu Ile Ala Asp
            595                 600                 605

Ala Trp Asn Ala Ile Pro Asp Asn Leu Asp Ala Val Val Asp Leu Gln
610                 615                 620

Gly Gly Gly His Ser Tyr Phe Phe Lys Gly Ala Tyr Tyr Leu Lys Leu
625                 630                 635                 640

Glu Asn Gln Ser Leu Lys Ser Val Lys Phe Gly Ser Ile Lys Ser Asp
                645                 650                 655

Trp Leu Gly Cys
            660

<210> SEQ ID NO 9
<211> LENGTH: 707
<212> TYPE: PRT
<213> ORGANISM: Homo sapiens

<400> SEQUENCE: 9

Met Ser Leu Trp Gln Pro Leu Val Leu Val Leu Leu Val Leu Gly Cys
1               5                   10                  15
```

-continued

```
Cys Phe Ala Ala Pro Arg Gln Arg Gln Ser Thr Leu Val Leu Phe Pro
             20                  25                  30

Gly Asp Leu Arg Thr Asn Leu Thr Asp Arg Gln Leu Ala Glu Glu Tyr
         35                  40                  45

Leu Tyr Arg Tyr Gly Tyr Thr Arg Val Ala Glu Met Arg Gly Glu Ser
 50                  55                  60

Lys Ser Leu Gly Pro Ala Leu Leu Leu Gln Lys Gln Leu Ser Leu
 65                  70                  75                  80

Pro Glu Thr Gly Glu Leu Asp Ser Ala Thr Leu Lys Ala Met Arg Thr
                 85                  90                  95

Pro Arg Cys Gly Val Pro Asp Leu Gly Arg Phe Gln Thr Phe Glu Gly
            100                 105                 110

Asp Leu Lys Trp His His His Asn Ile Thr Tyr Trp Ile Gln Asn Tyr
        115                 120                 125

Ser Glu Asp Leu Pro Arg Ala Val Ile Asp Asp Ala Phe Ala Arg Ala
130                 135                 140

Phe Ala Leu Trp Ser Ala Val Thr Pro Leu Thr Phe Thr Arg Val Tyr
145                 150                 155                 160

Ser Arg Asp Ala Asp Ile Val Ile Gln Phe Gly Val Ala Glu His Gly
                165                 170                 175

Asp Gly Tyr Pro Phe Asp Gly Lys Asp Gly Leu Leu Ala His Ala Phe
            180                 185                 190

Pro Pro Gly Pro Gly Ile Gln Gly Asp Ala His Phe Asp Asp Asp Glu
        195                 200                 205

Leu Trp Ser Leu Gly Lys Gly Val Val Val Pro Thr Arg Phe Gly Asn
    210                 215                 220

Ala Asp Gly Ala Ala Cys His Phe Pro Phe Ile Phe Glu Gly Arg Ser
225                 230                 235                 240

Tyr Ser Ala Cys Thr Thr Asp Gly Arg Ser Asp Gly Leu Pro Trp Cys
                245                 250                 255

Ser Thr Thr Ala Asn Tyr Asp Thr Asp Asp Arg Phe Gly Phe Cys Pro
            260                 265                 270

Ser Glu Arg Leu Tyr Thr Gln Asp Gly Asn Ala Asp Gly Lys Pro Cys
        275                 280                 285

Gln Phe Pro Phe Ile Phe Gln Gly Gln Ser Tyr Ser Ala Cys Thr Thr
    290                 295                 300

Asp Gly Arg Ser Asp Gly Tyr Arg Trp Cys Ala Thr Thr Ala Asn Tyr
305                 310                 315                 320

Asp Arg Asp Lys Leu Phe Gly Phe Cys Pro Thr Arg Ala Asp Ser Thr
                325                 330                 335

Val Met Gly Gly Asn Ser Ala Gly Glu Leu Cys Val Phe Pro Phe Thr
            340                 345                 350

Phe Leu Gly Lys Glu Tyr Ser Thr Cys Thr Ser Glu Gly Arg Gly Asp
        355                 360                 365

Gly Arg Leu Trp Cys Ala Thr Thr Ser Asn Phe Asp Ser Asp Lys Lys
    370                 375                 380

Trp Gly Phe Cys Pro Asp Gln Gly Tyr Ser Leu Phe Leu Val Ala Ala
385                 390                 395                 400

His Glu Phe Gly His Ala Leu Gly Leu Asp His Ser Ser Val Pro Glu
                405                 410                 415

Ala Leu Met Tyr Pro Met Tyr Arg Phe Thr Glu Gly Pro Pro Leu His
            420                 425                 430
```

-continued

```
Lys Asp Asp Val Asn Gly Ile Arg His Leu Tyr Gly Pro Arg Pro Glu
            435                 440                 445

Pro Glu Pro Arg Pro Pro Thr Thr Thr Pro Gln Pro Thr Ala Pro
        450                 455                 460

Pro Thr Val Cys Pro Thr Gly Pro Pro Thr Val His Pro Ser Glu Arg
465                 470                 475                 480

Pro Thr Ala Gly Pro Thr Gly Pro Pro Ser Ala Gly Pro Thr Gly Pro
                485                 490                 495

Pro Thr Ala Gly Pro Ser Thr Ala Thr Val Pro Leu Ser Pro Val
                500                 505                 510

Asp Asp Ala Cys Asn Val Asn Ile Phe Asp Ala Ile Ala Glu Ile Gly
            515                 520                 525

Asn Gln Leu Tyr Leu Phe Lys Asp Gly Lys Tyr Trp Arg Phe Ser Glu
        530                 535                 540

Gly Arg Gly Ser Arg Pro Gln Gly Pro Phe Leu Ile Ala Asp Lys Trp
545                 550                 555                 560

Pro Ala Leu Pro Arg Lys Leu Asp Ser Val Phe Glu Glu Pro Leu Ser
                565                 570                 575

Lys Lys Leu Phe Phe Phe Ser Gly Arg Gln Val Trp Val Tyr Thr Gly
                580                 585                 590

Ala Ser Val Leu Gly Pro Arg Arg Leu Asp Lys Leu Gly Leu Gly Ala
            595                 600                 605

Asp Val Ala Gln Val Thr Gly Ala Leu Arg Ser Gly Arg Gly Lys Met
        610                 615                 620

Leu Leu Phe Ser Gly Arg Arg Leu Trp Arg Phe Asp Val Lys Ala Gln
625                 630                 635                 640

Met Val Asp Pro Arg Ser Ala Ser Glu Val Asp Arg Met Phe Pro Gly
                645                 650                 655

Val Pro Leu Asp Thr His Asp Val Phe Gln Tyr Arg Glu Lys Ala Tyr
                660                 665                 670

Phe Cys Gln Asp Arg Phe Tyr Trp Arg Val Ser Ser Arg Ser Glu Leu
            675                 680                 685

Asn Gln Val Asp Gln Val Gly Tyr Val Thr Tyr Asp Ile Leu Gln Cys
        690                 695                 700

Pro Glu Asp
705

<210> SEQ ID NO 10
<211> LENGTH: 143
<212> TYPE: PRT
<213> ORGANISM: Homo sapiens

<400> SEQUENCE: 10

Met Gln His Arg Gly Phe Leu Leu Leu Thr Leu Leu Ala Leu Leu Ala
1               5                   10                  15

Leu Thr Ser Ala Val Ala Lys Lys Lys Asp Lys Val Lys Lys Gly Gly
            20                  25                  30

Pro Gly Ser Glu Cys Ala Glu Trp Ala Trp Gly Pro Cys Thr Pro Ser
        35                  40                  45

Ser Lys Asp Cys Gly Val Gly Phe Arg Glu Gly Thr Cys Gly Ala Gln
    50                  55                  60

Thr Gln Arg Ile Arg Cys Arg Val Pro Cys Asn Trp Lys Lys Glu Phe
65                  70                  75                  80

Gly Ala Asp Cys Lys Tyr Lys Phe Glu Asn Trp Gly Ala Cys Asp Gly
                85                  90                  95
```

-continued

```
Gly Thr Gly Thr Lys Val Arg Gln Gly Thr Leu Lys Lys Ala Arg Tyr
            100                 105                 110

Asn Ala Gln Cys Gln Glu Thr Ile Arg Val Thr Lys Pro Cys Thr Pro
            115                 120                 125

Lys Thr Lys Ala Lys Ala Lys Ala Lys Lys Gly Lys Gly Lys Asp
        130                 135                 140

<210> SEQ ID NO 11
<211> LENGTH: 223
<212> TYPE: PRT
<213> ORGANISM: Homo sapiens

<400> SEQUENCE: 11

Met Asn Lys Pro Leu Leu Trp Ile Ser Val Leu Thr Ser Leu Leu Glu
1               5                   10                  15

Ala Phe Ala His Thr Asp Leu Ser Gly Lys Val Phe Val Phe Pro Arg
            20                  25                  30

Glu Ser Val Thr Asp His Val Asn Leu Ile Thr Pro Leu Glu Lys Pro
        35                  40                  45

Leu Gln Asn Phe Thr Leu Cys Phe Arg Ala Tyr Ser Asp Leu Ser Arg
    50                  55                  60

Ala Tyr Ser Leu Phe Ser Tyr Asn Thr Gln Gly Arg Asp Asn Glu Leu
65                  70                  75                  80

Leu Val Tyr Lys Glu Arg Val Gly Glu Tyr Ser Leu Tyr Ile Gly Arg
                85                  90                  95

His Lys Val Thr Ser Lys Val Ile Glu Lys Phe Pro Ala Pro Val His
            100                 105                 110

Ile Cys Val Ser Trp Glu Ser Ser Ser Gly Ile Ala Glu Phe Trp Ile
        115                 120                 125

Asn Gly Thr Pro Leu Val Lys Lys Gly Leu Arg Gln Gly Tyr Phe Val
    130                 135                 140

Glu Ala Gln Pro Lys Ile Val Leu Gly Gln Glu Gln Asp Ser Tyr Gly
145                 150                 155                 160

Gly Lys Phe Asp Arg Ser Gln Ser Phe Val Gly Glu Ile Gly Asp Leu
                165                 170                 175

Tyr Met Trp Asp Ser Val Leu Pro Pro Glu Asn Ile Leu Ser Ala Tyr
            180                 185                 190

Gln Gly Thr Pro Leu Pro Ala Asn Ile Leu Asp Trp Gln Ala Leu Asn
        195                 200                 205

Tyr Glu Ile Arg Gly Tyr Val Ile Ile Lys Pro Leu Val Trp Val
    210                 215                 220
```

METHODS AND COMPOSITIONS FOR DIAGNOSIS AND PROGNOSIS OF RENAL INJURY AND RENAL FAILURE

This application is filed under 35 U.S.C. §371 as the U.S. national phase of International Application No. PCT/US2009/063906, filed Nov. 10, 2009, which designated the U.S. and claims the benefit of priority to U.S. Provisional Patent Application 61/117,168 filed Nov. 22, 2008; U.S. Provisional Patent Application 61/115,049 filed Nov. 15, 2008; U.S. Provisional Patent Application 61/113,074 filed Nov. 10, 2008; U.S. Provisional Patent Application 61/117,160 filed Nov. 22, 2008; U.S. Provisional Patent Application 61/117,158 filed Nov. 22, 2008; U.S. Provisional Patent Application 61/117,162 filed Nov. 22, 2008; U.S. Provisional Patent Application 61/117,163 filed Nov. 22, 2008; U.S. Provisional Patent Application 61/117,180 filed Nov. 22, 2008; U.S. Provisional Patent Application 61/117,178 filed Nov. 22, 2008; U.S. Provisional Patent Application 61/117,151 filed Nov. 22, 2008; and U.S. Provisional Patent Application 61/117,161 filed Nov. 22, 2008, each of which is hereby incorporated in its entirety including all tables, figures, and claims.

BACKGROUND OF THE INVENTION

The following discussion of the background of the invention is merely provided to aid the reader in understanding the invention and is not admitted to describe or constitute prior art to the present invention.

The kidney is responsible for water and solute excretion from the body. Its functions include maintenance of acid-base balance, regulation of electrolyte concentrations, control of blood volume, and regulation of blood pressure. As such, loss of kidney function through injury and/or disease results in substantial morbidity and mortality. A detailed discussion of renal injuries is provided in Harrison's Principles of Internal Medicine, 17th Ed., McGraw Hill, N.Y., pages 1741-1830, which are hereby incorporated by reference in their entirety. Renal disease and/or injury may be acute or chronic. Acute and chronic kidney disease are described as follows (from Current Medical Diagnosis & Treatment 2008, 47th Ed, McGraw Hill, N.Y., pages 785-815, which are hereby incorporated by reference in their entirety): "Acute renal failure is worsening of renal function over hours to days, resulting in the retention of nitrogenous wastes (such as urea nitrogen) and creatinine in the blood. Retention of these substances is called azotemia. Chronic renal failure (chronic kidney disease) results from an abnormal loss of renal function over months to years".

Acute renal failure (ARF, also known as acute kidney injury, or AKI) is an abrupt (typically detected within about 48 hours to 1 week) reduction in glomerular filtration. This loss of filtration capacity results in retention of nitrogenous (urea and creatinine) and non-nitrogenous waste products that are normally excreted by the kidney, a reduction in urine output, or both. It is reported that ARF complicates about 5% of hospital admissions, 4-15% of cardiopulmonary bypass surgeries, and up to 30% of intensive care admissions. ARF may be categorized as prerenal, intrinsic renal, or postrenal in causation. Intrinsic renal disease can be further divided into glomerular, tubular, interstitial, and vascular abnormalities. Major causes of ARF are described in the following table, which is adapted from the Merck Manual, 17th ed., Chapter 222, and which is hereby incorporated by reference in their entirety:

| Type | Risk Factors |
| --- | --- |
| Prerenal | |
| ECF volume depletion | Excessive diuresis, hemorrhage, GI losses, loss of intravascular fluid into the extravascular space (due to ascites, peritonitis, pancreatitis, or burns), loss of skin and mucus membranes, renal salt- and water-wasting states |
| Low cardiac output | Cardiomyopathy, MI, cardiac tamponade, pulmonary embolism, pulmonary hypertension, positive-pressure mechanical ventilation |
| Low systemic vascular resistance | Septic shock, liver failure, antihypertensive drugs |
| Increased renal vascular resistance | NSAIDs, cyclosporines, tacrolimus, hypercalcemia, anaphylaxis, anesthetics, renal artery obstruction, renal vein thrombosis, sepsis, hepatorenal syndrome |
| Decreased efferent arteriolar tone (leading to decreased GFR from reduced glomerular transcapillary pressure, especially in patients with bilateral renal artery stenosis) | ACE inhibitors or angiotensin II receptor blockers |
| Intrinsic Renal | |
| Acute tubular injury | Ischemia (prolonged or severe prerenal state): surgery, hemorrhage, arterial or venous obstruction; Toxins: NSAIDs, cyclosporines, tacrolimus, aminoglycosides, foscarnet, ethylene glycol, hemoglobin, myoglobin, ifosfamide, heavy metals, methotrexate, radiopaque contrast agents, streptozotocin |
| Acute glomerulonephritis | ANCA-associated: Crescentic glomerulonephritis, polyarteritis nodosa, Wegener's granulomatosis; Anti-GBM glomerulonephritis: Goodpasture's syndrome; Immune-complex: Lupus glomerulonephritis, postinfectious glomerulonephritis, cryoglobulinemic glomerulonephritis |
| Acute tubulointerstitial nephritis | Drug reaction (eg, β-lactams, NSAIDs, sulfonamides, ciprofloxacin, thiazide diuretics, furosemide, phenytoin, allopurinol, pyelonephritis, papillary necrosis |
| Acute vascular nephropathy | Vasculitis, malignant hypertension, thrombotic microangiopathies, scleroderma, atheroembolism |
| Infiltrative diseases | Lymphoma, sarcoidosis, leukemia |
| Postrenal | |
| Tubular precipitation | Uric acid (tumor lysis), sulfonamides, triamterene, acyclovir, indinavir, methotrexate, ethylene glycol ingestion, myeloma protein, myoglobin |
| Ureteral obstruction | Intrinsic: Calculi, clots, sloughed renal tissue, fungus ball, edema, malignancy, congenital defects; Extrinsic: Malignancy, retroperitoneal fibrosis, ureteral trauma during surgery or high impact injury |
| Bladder obstruction | Mechanical: Benign prostatic hyperplasia, prostate cancer, bladder cancer, urethral strictures, phimosis, paraphimosis, urethral valves, obstructed indwelling urinary catheter; Neurogenic: Anticholinergic drugs, upper or lower motor neuron lesion |

In the case of ischemic ARF, the course of the disease may be divided into four phases. During an initiation phase, which lasts hours to days, reduced perfusion of the kidney is evolving into injury. Glomerular ultrafiltration reduces, the flow of filtrate is reduced due to debris within the tubules, and back leakage of filtrate through injured epithelium occurs. Renal injury can be mediated during this phase by reperfusion of the kidney. Initiation is followed by an extension phase which is characterized by continued ischemic injury and inflammation and may involve endothelial damage and vascular congestion. During the maintenance phase, lasting from 1 to 2 weeks, renal cell injury occurs, and glomerular filtration and urine output reaches a minimum. A recovery phase can follow in which the renal epithelium is repaired and GFR gradually recovers. Despite this, the survival rate of subjects with ARF may be as low as about 60%.

Acute kidney injury caused by radiocontrast agents (also called contrast media) and other nephrotoxins such as cyclosporine, antibiotics including aminoglycosides and anticancer drugs such as cisplatin manifests over a period of days to about a week. Contrast induced nephropathy (CIN, which is AKI caused by radiocontrast agents) is thought to be caused by intrarenal vasoconstriction (leading to ischemic injury) and from the generation of reactive oxygen species that are directly toxic to renal tubular epithelial cells. CIN classically presents as an acute (onset within 24-48 h) but reversible (peak 3-5 days, resolution within 1 week) rise in blood urea nitrogen and serum creatinine.

A commonly reported criteria for defining and detecting AKI is an abrupt (typically within about 2-7 days or within a period of hospitalization) elevation of serum creatinine. Although the use of serum creatinine elevation to define and detect AKI is well established, the magnitude of the serum creatinine elevation and the time over which it is measured to define AKI varies considerably among publications. Traditionally, relatively large increases in serum creatinine such as 100%, 200%, an increase of at least 100% to a value over 2 mg/dL and other definitions were used to define AKI. However, the recent trend has been towards using smaller serum creatinine rises to define AKI. The relationship between serum creatinine rise, AKI and the associated health risks are reviewed in Praught and Shlipak, *Curr Opin Nephrol Hypertens* 14:265-270, 2005 and Chertow et al, *J Am Soc Nephrol* 16: 3365-3370, 2005, which, with the references listed therein, are hereby incorporated by reference in their entirety. As described in these publications, acute worsening renal function (AKI) and increased risk of death and other detrimental outcomes are now known to be associated with very small increases in serum creatinine. These increases may be determined as a relative (percent) value or a nominal value. Relative increases in serum creatinine as small as 20% from the pre-injury value have been reported to indicate acutely worsening renal function (AKI) and increased health risk, but the more commonly reported value to define AKI and increased health risk is a relative increase of at least 25%. Nominal increases as small as 0.3 mg/dL, 0.2 mg/dL or even 0.1 mg/dL have been reported to indicate worsening renal function and increased risk of death. Various time periods for the serum creatinine to rise to these threshold values have been used to define AKI, for example, ranging from 2 days, 3 days, 7 days, or a variable period defined as the time the patient is in the hospital or intensive care unit. These studies indicate there is not a particular threshold serum creatinine rise (or time period for the rise) for worsening renal function or AKI, but rather a continuous increase in risk with increasing magnitude of serum creatinine rise.

One study (Lassnigg et all, J Am Soc Nephrol 15:1597-1605, 2004, hereby incorporated by reference in its entirety) investigated both increases and decreases in serum creatinine. Patients with a mild fall in serum creatinine of −0.1 to −0.3 mg/dL following heart surgery had the lowest mortality rate. Patients with a larger fall in serum creatinine (more than or equal to −0.4 mg/dL) or any increase in serum creatinine had a larger mortality rate. These findings caused the authors to conclude that even very subtle changes in renal function (as detected by small creatinine changes within 48 hours of surgery) seriously effect patient's outcomes. In an effort to reach consensus on a unified classification system for using serum creatinine to define AKI in clinical trials and in clinical practice, Bellomo et al., *Crit. Care.* 8(4):R204-12, 2004, which is hereby incorporated by reference in its entirety, proposes the following classifications for stratifying AKI patients:

"Risk": serum creatinine increased 1.5 fold from baseline OR urine production of <0.5 ml/kg body weight/hr for 6 hours;

"Injury": serum creatinine increased 2.0 fold from baseline OR urine production <0.5 ml/kg/hr for 12 h;

"Failure": serum creatinine increased 3.0 fold from baseline OR creatinine >355 μmol/l (with a rise of >44) or urine output below 0.3 ml/kg/hr for 24 h or anuria for at least 12 hours;

And included two clinical outcomes:

"Loss": persistent need for renal replacement therapy for more than four weeks.

"ESRD": end stage renal disease—the need for dialysis for more than 3 months.

These criteria are called the RIFLE criteria, which provide a useful clinical tool to classify renal status. As discussed in Kellum, *Crit. Care Med.* 36: S141-45, 2008 and Ricci et al., *Kidney Int.* 73, 538-546, 2008, each hereby incorporated by reference in its entirety, the RIFLE criteria provide a uniform definition of AKI which has been validated in numerous studies.

More recently, Mehta et al., *Crit. Care* 11:R31 (doi: 10.1186.cc5713), 2007, hereby incorporated by reference in its entirety, proposes the following similar classifications for stratifying AKI patients, which have been modified from RIFLE:

"Stage I": increase in serum creatinine of more than or equal to 0.3 mg/dL (≥26.4 μmol/L) or increase to more than or equal to 150% (1.5-fold) from baseline OR urine output less than 0.5 mL/kg per hour for more than 6 hours;

"Stage II": increase in serum creatinine to more than 200% (>2-fold) from baseline OR urine output less than 0.5 mL/kg per hour for more than 12 hours;

"Stage III": increase in serum creatinine to more than 300% (>3-fold) from baseline OR serum creatinine ≥354 μmol/L accompanied by an acute increase of at least 44 μmol/L OR urine output less than 0.3 mL/kg per hour for 24 hours or anuria for 12 hours.

The CIN Consensus Working Panel (McCollough et al, Rev Cardiovasc Med. 2006; 7(4):177-197, hereby incorporated by reference in its entirety) uses a serum creatinine rise of 25% to define Contrast induced nephropathy (which is a type of AKI). Although various groups propose slightly different criteria for using serum creatinine to detect AKI, the consensus is that small changes in serum creatinine, such as 0.3 mg/dL or 25%, are sufficient to detect AKI (worsening renal function) and that the magnitude of the serum creatinine change is an indicator of the severity of the AKI and mortality risk.

Although serial measurement of serum creatinine over a period of days is an accepted method of detecting and diagnosing AKI and is considered one of the most important tools to evaluate AKI patients, serum creatinine is generally regarded to have several limitations in the diagnosis, assessment and monitoring of AKI patients. The time period for serum creatinine to rise to values (e.g., a 0.3 mg/dL or 25% rise) considered diagnostic for AKI can be 48 hours or longer depending on the definition used. Since cellular injury in AKI can occur over a period of hours, serum creatinine elevations detected at 48 hours or longer can be a late indicator of injury, and relying on serum creatinine can thus delay diagnosis of AKI. Furthermore, serum creatinine is not a good indicator of the exact kidney status and treatment needs during the most acute phases of AKI when kidney function is changing rapidly. Some patients with AKI will recover fully, some will need dialysis (either short term or long term) and some will have other detrimental outcomes including death, major adverse cardiac events and chronic kidney disease. Because serum creatinine is a marker of filtration rate, it does not differentiate between the causes of AKI (pre-renal, intrinsic renal, post-renal obstruction, atheroembolic, etc) or the category or location of injury in intrinsic renal disease (for example, tubular, glomerular or interstitial in origin). Urine output is similarly limited, Knowing these things can be of vital importance in managing and treating patients with AKI.

These limitations underscore the need for better methods to detect and assess AKI, particularly in the early and subclinical stages, but also in later stages when recovery and repair of the kidney can occur. Furthermore, there is a need to better identify patients who are at risk of having an AKI.

BRIEF SUMMARY OF THE INVENTION

It is an object of the invention to provide methods and compositions for evaluating renal function in a subject. As described herein, measurement of one or more markers selected from the group consisting of Clusterin, Heart-type fatty acid binding protein, Hepatocyte growth factor, Interferon gamma, Interleukin-12 subunit beta, Interleukin-16, Interleukin-2, 72 kDa type IV collagenase, Matrix metalloproteinase-9, Midkine, and Serum amyloid P-component (collectively referred to herein as "kidney injury markers, and individually as a "kidney injury marker") can be used for diagnosis, prognosis, risk stratification, staging, monitoring, categorizing and determination of further diagnosis and treatment regimens in subjects suffering or at risk of suffering from an injury to renal function, reduced renal function, and/or acute renal failure (also called acute kidney injury).

These kidney injury markers may be used, individually or in panels comprising a plurality of kidney injury markers, for risk stratification (that is, to identify subjects at risk for a future injury to renal function, for future progression to reduced renal function, for future progression to ARF, for future improvement in renal function, etc.); for diagnosis of existing disease (that is, to identify subjects who have suffered an injury to renal function, who have progressed to reduced renal function, who have progressed to ARF, etc.); for monitoring for deterioration or improvement of renal function; and for predicting a future medical outcome, such as improved or worsening renal function, a decreased or increased mortality risk, a decreased or increased risk that a subject will require renal replacement therapy (i.e., hemodialysis, peritoneal dialysis, hemofiltration, and/or renal transplantation, a decreased or increased risk that a subject will recover from an injury to renal function, a decreased or increased risk that a subject will recover from ARF, a decreased or increased risk that a subject will progress to end stage renal disease, a decreased or increased risk that a subject will progress to chronic renal failure, a decreased or increased risk that a subject will suffer rejection of a transplanted kidney, etc.

In a first aspect, the present invention relates to methods for evaluating renal status in a subject. These methods comprise performing an assay method that is configured to detect one or more kidney injury markers of the present invention in a body fluid sample obtained from the subject. The assay result(s), for example a measured concentration of one or more markers selected from the group consisting of Clusterin, Heart-type fatty acid binding protein, Hepatocyte growth factor, Interferon gamma, Interleukin-12 subunit beta, Interleukin-16, Interleukin-2, 72 kDa type IV collagenase, Matrix metalloproteinase-9, Midkine, and Serum amyloid P-component is/are then correlated to the renal status of the subject. This correlation to renal status may include correlating the assay result(s) to one or more of risk stratification, diagnosis, prognosis, staging, classifying and monitoring of the subject as described herein. Thus, the present invention utilizes one or more kidney injury markers of the present invention for the evaluation of renal injury.

In certain embodiments, the methods for evaluating renal status described herein are methods for risk stratification of the subject; that is, assigning a likelihood of one or more future changes in renal status to the subject. In these embodiments, the assay result(s) is/are correlated to one or more such future changes. The following are preferred risk stratification embodiments.

In preferred risk stratification embodiments, these methods comprise determining a subject's risk for a future injury to renal function, and the assay result(s) is/are correlated to a likelihood of such a future injury to renal function. For example, the measured concentration(s) may each be compared to a threshold value. For a "positive going" kidney injury marker, an increased likelihood of suffering a future injury to renal function is assigned to the subject when the measured concentration is above the threshold, relative to a likelihood assigned when the measured concentration is below the threshold. For a "negative going" kidney injury marker, an increased likelihood of suffering a future injury to renal function is assigned to the subject when the measured concentration is below the threshold, relative to a likelihood assigned when the measured concentration is above the threshold.

In other preferred risk stratification embodiments, these methods comprise determining a subject's risk for future reduced renal function, and the assay result(s) is/are correlated to a likelihood of such reduced renal function. For example, the measured concentrations may each be compared to a threshold value. For a "positive going" kidney injury marker, an increased likelihood of suffering a future reduced renal function is assigned to the subject when the measured concentration is above the threshold, relative to a likelihood assigned when the measured concentration is below the threshold. For a "negative going" kidney injury marker, an increased likelihood of future reduced renal function is assigned to the subject when the measured concentration is below the threshold, relative to a likelihood assigned when the measured concentration is above the threshold.

In still other preferred risk stratification embodiments, these methods comprise determining a subject's likelihood for a future improvement in renal function, and the assay result(s) is/are correlated to a likelihood of such a future improvement in renal function. For example, the measured concentration(s) may each be compared to a threshold value. For a "positive going" kidney injury marker, an increased likelihood of a future improvement in renal function is assigned to the subject when the measured concentration is below the threshold, relative to a likelihood assigned when the measured concentration is above the threshold. For a "negative going" kidney injury marker, an increased likelihood of a future improvement in renal function is assigned to the subject when the measured concentration is above the threshold, relative to a likelihood assigned when the measured concentration is below the threshold.

In yet other preferred risk stratification embodiments, these methods comprise determining a subject's risk for progression to ARF, and the result(s) is/are correlated to a likelihood of such progression to ARF. For example, the measured concentration(s) may each be compared to a threshold value. For a "positive going" kidney injury marker, an increased likelihood of progression to ARF is assigned to the subject when the measured concentration is above the threshold, relative to a likelihood assigned when the measured concentration is below the threshold. For a "negative going" kidney injury marker, an increased likelihood of progression to ARF is assigned to the subject when the measured concentration is below the threshold, relative to a likelihood assigned when the measured concentration is above the threshold.

And in other preferred risk stratification embodiments, these methods comprise determining a subject's outcome risk, and the assay result(s) is/are correlated to a likelihood of the occurrence of a clinical outcome related to a renal injury suffered by the subject. For example, the measured concentration(s) may each be compared to a threshold value. For a "positive going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is above the threshold, relative to a likelihood assigned when the measured concentration is below the threshold. For a "negative going" kidney injury marker, an increased likelihood of one or more of: acute kidney injury, progression to a worsening stage of AKI, mortality, a requirement for renal replacement therapy, a requirement for withdrawal of renal toxins, end stage renal disease, heart failure, stroke, myocardial infarction, progression to chronic kidney disease, etc., is assigned to the subject when the measured concentration is below the threshold, relative to a likelihood assigned when the measured concentration is above the threshold.

In such risk stratification embodiments, preferably the likelihood or risk assigned is that an event of interest is more or less likely to occur within 180 days of the time at which the body fluid sample is obtained from the subject. In particularly preferred embodiments, the likelihood or risk assigned relates to an event of interest occurring within a shorter time period such as 18 months, 120 days, 90 days, 60 days, 45 days, 30 days, 21 days, 14 days, 7 days, 5 days, 96 hours, 72 hours, 48 hours, 36 hours, 24 hours, 12 hours, or less. A risk at 0 hours of the time at which the body fluid sample is obtained from the subject is equivalent to diagnosis of a current condition.

In preferred risk stratification embodiments, the subject is selected for risk stratification based on the pre-existence in the subject of one or more known risk factors for prerenal, intrinsic renal, or postrenal ARF. For example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin are all preferred subjects for monitoring risks according to the methods described herein. This list is not meant to be limiting. By "pre-existence" in this context is meant that the risk factor exists at the time the body fluid sample is obtained from the subject. In particularly preferred embodiments, a subject is chosen for risk stratification based on an existing diagnosis of injury to renal function, reduced renal function, or ARF.

In other embodiments, the methods for evaluating renal status described herein are methods for diagnosing a renal injury in the subject; that is, assessing whether or not a subject has suffered from an injury to renal function, reduced renal function, or ARF. In these embodiments, the assay result(s), for example a measured concentration of one or more markers selected from the group consisting of Clusterin, Heart-type fatty acid binding protein, Hepatocyte growth factor, Interferon gamma, Interleukin-12 subunit beta, Interleukin-16, Interleukin-2, 72 kDa type IV collagenase, Matrix metalloproteinase-9, Midkine, and Serum amyloid P-component is/are correlated to the occurrence or nonoccurrence of a change in renal status. The following are preferred diagnostic embodiments.

In preferred diagnostic embodiments, these methods comprise diagnosing the occurrence or nonoccurrence of an injury to renal function, and the assay result(s) is/are correlated to the occurrence or nonoccurrence of such an injury. For example, each of the measured concentration(s) may be compared to a threshold value. For a positive going marker, an increased likelihood of the occurrence of an injury to renal function is assigned to the subject when the measured concentration is above the threshold (relative to the likelihood assigned when the measured concentration is below the threshold); alternatively, when the measured concentration is below the threshold, an increased likelihood of the nonoccurrence of an injury to renal function may be assigned to the subject (relative to the likelihood assigned when the measured concentration is above the threshold). For a negative going marker, an increased likelihood of the occurrence of an injury to renal function is assigned to the subject when the measured concentration is below the threshold (relative to the likelihood assigned when the measured concentration is above the threshold); alternatively, when the measured concentration is above the threshold, an increased likelihood of the nonoccurrence of an injury to renal function may be assigned to the subject (relative to the likelihood assigned when the measured concentration is below the threshold).

In other preferred diagnostic embodiments, these methods comprise diagnosing the occurrence or nonoccurrence of reduced renal function, and the assay result(s) is/are correlated to the occurrence or nonoccurrence of an injury causing reduced renal function. For example, each of the measured concentration(s) may be compared to a threshold value. For a positive going marker, an increased likelihood of the occurrence of an injury causing reduced renal function is assigned to the subject when the measured concentration is above the threshold (relative to the likelihood assigned when the measured concentration is below the threshold); alternatively, when the measured concentration is below the threshold, an increased likelihood of the nonoccurrence of an injury causing reduced renal function may be assigned to the subject (relative to the likelihood assigned when the measured concentration is above the threshold). For a negative going marker, an increased likelihood of the occurrence of an injury causing reduced renal function is assigned to the subject when the measured concentration is below the threshold (relative to the likelihood assigned when the measured concentration is above the threshold); alternatively, when the measured concentration is above the threshold, an increased likelihood of the nonoccurrence of an injury causing reduced renal function may be assigned to the subject (relative to the likelihood assigned when the measured concentration is below the threshold).

In yet other preferred diagnostic embodiments, these methods comprise diagnosing the occurrence or nonoccurrence of ARF, and the assay result(s) is/are correlated to the occurrence or nonoccurrence of an injury causing ARF. For example, each of the measured concentration(s) may be compared to a threshold value. For a positive going marker, an increased likelihood of the occurrence of ARF is assigned to the subject when the measured concentration is above the threshold (relative to the likelihood assigned when the measured concentration is below the threshold); alternatively, when the measured concentration is below the threshold, an increased likelihood of the nonoccurrence of ARF may be assigned to the subject (relative to the likelihood assigned when the measured concentration is above the threshold). For a negative going marker, an increased likelihood of the occurrence of ARF is assigned to the subject when the measured concentration is below the threshold (relative to the likelihood assigned when the measured concentration is above the threshold); alternatively, when the measured concentration is above the threshold, an increased likelihood of the nonoccurrence of ARF may be assigned to the subject (relative to the likelihood assigned when the measured concentration is below the threshold).

In still other preferred diagnostic embodiments, these methods comprise diagnosing a subject as being in need of renal replacement therapy, and the assay result(s) is/are correlated to a need for renal replacement therapy. For example, each of the measured concentration(s) may be compared to a threshold value. For a positive going marker, an increased likelihood of the occurrence of an injury creating a need for renal replacement therapy is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal replacement therapy may be assigned to the subject (relative to the likelihood assigned when the measured concentration is above the threshold). For a negative going marker, an increased likelihood of the occurrence of an injury creating a need for renal replacement therapy is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal replacement therapy may be assigned to the subject (relative to the likelihood assigned when the measured concentration is below the threshold).

In still other preferred diagnostic embodiments, these methods comprise diagnosing a subject as being in need of renal transplantation, and the assay result(s) is/are correlated to a need for renal transplantation. For example, each of the measured concentration(s) may be compared to a threshold value. For a positive going marker, an increased likelihood of the occurrence of an injury creating a need for renal transplantation is assigned to the subject when the measured concentration is above the threshold (relative to the likelihood assigned when the measured concentration is below the threshold); alternatively, when the measured concentration is below the threshold, an increased likelihood of the nonoccurrence of an injury creating a need for renal transplantation may be assigned to the subject (relative to the likelihood assigned when the measured concentration is above the threshold). For a negative going marker, an increased likelihood of the occurrence of an injury creating a need for renal transplantation is assigned to the subject when the measured concentration is below the threshold (relative to the likelihood assigned when the measured concentration is above the threshold); alternatively, when the measured concentration is above the threshold, an increased likelihood of the nonoccurrence of an injury creating a need for renal transplantation may be assigned to the subject (relative to the likelihood assigned when the measured concentration is below the threshold).

In still other embodiments, the methods for evaluating renal status described herein are methods for monitoring a renal injury in the subject; that is, assessing whether or not renal function is improving or worsening in a subject who has suffered from an injury to renal function, reduced renal function, or ARF. In these embodiments, the assay result(s), for example a measured concentration of one or more markers selected from the group consisting of Clusterin, Heart-type fatty acid binding protein, Hepatocyte growth factor, Interferon gamma, Interleukin-12 subunit beta, Interleukin-16, Interleukin-2, 72 kDa type IV collagenase, Matrix metalloproteinase-9, Midkine, and Serum amyloid P-component is/are correlated to the occurrence or nonoccurrence of a change in renal status. The following are preferred monitoring embodiments.

In preferred monitoring embodiments, these methods comprise monitoring renal status in a subject suffering from an injury to renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other preferred monitoring embodiments, these methods comprise monitoring renal status in a subject suffering from reduced renal function, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In yet other preferred monitoring embodiments, these methods comprise monitoring renal status in a subject suffering from acute renal failure, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In other additional preferred monitoring embodiments, these methods comprise monitoring renal status in a subject at risk of an injury to renal function due to the pre-existence of one or more known risk factors for prerenal, intrinsic renal, or postrenal ARF, and the assay result(s) is/are correlated to the occurrence or nonoccurrence of a change in renal status in the subject. For example, the measured concentration(s) may be compared to a threshold value. For a positive going marker, when the measured concentration is above the threshold, a worsening of renal function may be assigned to the subject; alternatively, when the measured concentration is below the threshold, an improvement of renal function may be assigned to the subject. For a negative going marker, when the measured concentration is below the threshold, a worsening of renal function may be assigned to the subject; alternatively, when the measured concentration is above the threshold, an improvement of renal function may be assigned to the subject.

In still other embodiments, the methods for evaluating renal status described herein are methods for classifying a renal injury in the subject; that is, determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage. In these embodiments, the assay result(s), for example a measured concentration of one or more markers selected from the group consisting of Clusterin, Heart-type fatty acid binding protein, Hepatocyte growth factor, Interferon gamma, Interleukin-12 subunit beta, Interleukin-16, Interleukin-2, 72 kDa type IV collagenase, Matrix metalloproteinase-9, Midkine, and Serum amyloid P-component is/are correlated to a particular class and/or subclass. The following are preferred classification embodiments.

In preferred classification embodiments, these methods comprise determining whether a renal injury in a subject is prerenal, intrinsic renal, or postrenal; and/or further subdividing these classes into subclasses such as acute tubular injury, acute glomerulonephritis acute tubulointerstitial nephritis, acute vascular nephropathy, or infiltrative disease; and/or assigning a likelihood that a subject will progress to a particular RIFLE stage, and the assay result(s) is/are correlated to the injury classification for the subject. For example, the measured concentration may be compared to a threshold value, and when the measured concentration is above the threshold, a particular classification is assigned; alternatively, when the measured concentration is below the threshold, a different classification may be assigned to the subject.

A variety of methods may be used by the skilled artisan to arrive at a desired threshold value for use in these methods. For example, the threshold value may be determined from a population of normal subjects by selecting a concentration representing the $75^{th}$, $85^{th}$, $90^{th}$, $95^{th}$, or $99^{th}$ percentile of a kidney injury marker measured in such normal subjects. Alternatively, the threshold value may be determined from a "diseased" population of subjects, e.g., those suffering from an injury or having a predisposition for an injury (e.g., progression to ARF or some other clinical outcome such as death, dialysis, renal transplantation, etc.), by selecting a concentration representing the $75^{th}$, $85^{th}$, $90^{th}$, $95^{th}$, or $99^{th}$ percentile of a kidney injury marker measured in such subjects. In another alternative, the threshold value may be determined from a prior measurement of a kidney injury marker in the same subject; that is, a temporal change in the level of a kidney injury marker in the subject may be used to assign risk to the subject.

The foregoing discussion is not meant to imply, however, that the kidney injury markers of the present invention must be compared to corresponding individual thresholds. Methods for combining assay results can comprise the use of multivariate logistical regression, loglinear modeling, neural network analysis, n-of-m analysis, decision tree analysis, calculating ratios of markers, etc. This list is not meant to be limiting. In these methods, a composite result which is determined by combining individual markers may be treated as if it is itself a marker; that is, a threshold may be determined for the composite result as described herein for individual markers, and the composite result for an individual patient compared to this threshold.

The ability of a particular test to distinguish two populations can be established using ROC analysis. For example, ROC curves established from a "first" subpopulation which is predisposed to one or more future changes in renal status, and a "second" subpopulation which is not so predisposed can be used to calculate a ROC curve, and the area under the curve provides a measure of the quality of the test. Preferably, the tests described herein provide a ROC curve area greater than 0.5, preferably at least 0.6, more preferably 0.7, still more preferably at least 0.8, even more preferably at least 0.9, and most preferably at least 0.95.

In certain aspects, the measured concentration of one or more kidney injury markers, or a composite of such markers, may be treated as continuous variables. For example, any particular concentration can be converted into a corresponding probability of a future reduction in renal function for the subject, the occurrence of an injury, a classification, etc. In yet another alternative, a threshold that can provide an acceptable level of specificity and sensitivity in separating a population of subjects into "bins" such as a "first" subpopulation (e.g., which is predisposed to one or more future changes in renal status, the occurrence of an injury, a classification, etc.) and a "second" subpopulation which is not so predisposed. A threshold value is selected to separate this first and second population by one or more of the following measures of test accuracy:

an odds ratio greater than 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less;

a specificity of greater than 0.5, preferably at least about 0.6, more preferably at least about 0.7, still more preferably at least about 0.8, even more preferably at least about 0.9 and most preferably at least about 0.95, with a corresponding sensitivity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

a sensitivity of greater than 0.5, preferably at least about 0.6, more preferably at least about 0.7, still more preferably at least about 0.8, even more preferably at least about 0.9 and most preferably at least about 0.95, with a corresponding specificity greater than 0.2, preferably greater than about 0.3, more preferably greater than about 0.4, still more preferably at least about 0.5, even more preferably about 0.6, yet more preferably greater than about 0.7, still more preferably greater than about 0.8, more preferably greater than about 0.9, and most preferably greater than about 0.95;

at least about 75% sensitivity, combined with at least about 75% specificity;

a positive likelihood ratio (calculated as sensitivity/(1-specificity)) of greater than 1, at least about 2, more preferably at least about 3, still more preferably at least about 5, and most preferably at least about 10; or a negative likelihood ratio (calculated as (1-sensitivity)/specificity) of less than 1, less than or equal to about 0.5, more preferably less than or equal to about 0.3, and most preferably less than or equal to about 0.1.

The term "about" in the context of any of the above measurements refers to +/−5% of a given measurement.

Multiple thresholds may also be used to assess renal status in a subject. For example, a "first" subpopulation which is predisposed to one or more future changes in renal status, the occurrence of an injury, a classification, etc., and a "second" subpopulation which is not so predisposed can be combined into a single group. This group is then subdivided into three or more equal parts (known as tertiles, quartiles, quintiles, etc., depending on the number of subdivisions). An odds ratio is assigned to subjects based on which subdivision they fall into. If one considers a tertile, the lowest or highest tertile can be used as a reference for comparison of the other subdivisions. This reference subdivision is assigned an odds ratio of 1. The second tertile is assigned an odds ratio that is relative to that first tertile. That is, someone in the second tertile might be 3 times more likely to suffer one or more future changes in renal status in comparison to someone in the first tertile. The third tertile is also assigned an odds ratio that is relative to that first tertile.

In certain embodiments, the assay method is an immunoassay. Antibodies for use in such assays will specifically bind a full length kidney injury marker of interest, and may also bind one or more polypeptides that are "related" thereto, as that term is defined hereinafter. Numerous immunoassay formats are known to those of skill in the art. Preferred body fluid samples are selected from the group consisting of urine, blood, serum, saliva, tears, and plasma.

The foregoing method steps should not be interpreted to mean that the kidney injury marker assay result(s) is/are used in isolation in the methods described herein. Rather, additional variables or other clinical indicia may be included in the methods described herein. For example, a risk stratification, diagnostic, classification, monitoring, etc. method may combine the assay result(s) with one or more variables measured for the subject selected from the group consisting of demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a glomerular filtration rate, an estimated glomerular filtration rate, a urine production rate, a serum or plasma creatinine concentration, a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, a renal failure index calculated as urine sodium/(urine creatinine/plasma creatinine), a serum or plasma neutrophil gelatinase (NGAL) concentration, a urine NGAL concentration, a serum or plasma cystatin C concentration, a serum or plasma cardiac troponin concentration, a serum or plasma BNP concentration, a serum or plasma NTproBNP concentration, and a serum or plasma proBNP concentration. Other measures of renal function which may be combined with one or more kidney injury marker assay result(s) are described hereinafter and in Harrison's Principles of Internal Medicine, 17$^{th}$ Ed., McGraw Hill, N.Y., pages 1741-1830, and Current Medical Diagnosis & Treatment 2008, 47$^{th}$ Ed, McGraw Hill, N.Y., pages 785-815, each of which are hereby incorporated by reference in their entirety.

When more than one marker is measured, the individual markers may be measured in samples obtained at the same time, or may be determined from samples obtained at different (e.g., an earlier or later) times. The individual markers may also be measured on the same or different body fluid samples. For example, one kidney injury marker may be measured in a serum or plasma sample and another kidney injury marker may be measured in a urine sample. In addition, assignment of a likelihood may combine an individual kidney injury marker assay result with temporal changes in one or more additional variables.

In various related aspects, the present invention also relates to devices and kits for performing the methods described herein. Suitable kits comprise reagents sufficient for performing an assay for at least one of the described kidney injury markers, together with instructions for performing the described threshold comparisons.

In certain embodiments, reagents for performing such assays are provided in an assay device, and such assay devices may be included in such a kit. Preferred reagents can comprise one or more solid phase antibodies, the solid phase antibody comprising antibody that detects the intended biomarker target(s) bound to a solid support. In the case of sandwich immunoassays, such reagents can also include one or more detectably labeled antibodies, the detectably labeled antibody comprising antibody that detects the intended biomarker target(s) bound to a detectable label. Additional optional elements that may be provided as part of an assay device are described hereinafter.

Detectable labels may include molecules that are themselves detectable (e.g., fluorescent moieties, electrochemical labels, ecl (electrochemical luminescence) labels, metal chelates, colloidal metal particles, etc.) as well as molecules that may be indirectly detected by production of a detectable reaction product (e.g., enzymes such as horseradish peroxidase, alkaline phosphatase, etc.) or through the use of a specific binding molecule which itself may be detectable (e.g., a labeled antibody that binds to the second antibody, biotin, digoxigenin, maltose, oligohistidine, 2,4-dintrobenzene, phenylarsenate, ssDNA, dsDNA, etc.).

Generation of a signal from the signal development element can be performed using various optical, acoustical, and electrochemical methods well known in the art. Examples of detection modes include fluorescence, radiochemical detection, reflectance, absorbance, amperometry, conductance, impedance, interferometry, ellipsometry, etc. In certain of these methods, the solid phase antibody is coupled to a transducer (e.g., a diffraction grating, electrochemical sensor, etc) for generation of a signal, while in others, a signal is generated by a transducer that is spatially separate from the solid phase antibody (e.g., a fluorometer that employs an excitation light source and an optical detector). This list is not meant to be limiting. Antibody-based biosensors may also be employed to determine the presence or amount of analytes that optionally eliminate the need for a labeled molecule.

BRIEF DESCRIPTION OF THE FIGURES

FIG. 1 provides data tables determined in accordance with Example 6 for the comparison of marker levels in urine samples collected for Cohort 1 (patients that did not progress beyond RIFLE stage 0) and in urine samples collected from subjects at 0, 24 hours, and 48 hours prior to reaching stage R, I or F in Cohort 2. Tables provide descriptive statistics, AUC analysis, and sensitivity, specificity and odds ratio calculations at various threshold (cutoff) levels for the various markers.

FIG. 2 provides data tables determined in accordance with Example 7 for the comparison of marker levels in urine samples collected for Cohort 1 (patients that did not progress beyond RIFLE stage 0 or R) and in urine samples collected from subjects at 0, 24 hours, and 48 hours prior to reaching stage I or F in Cohort 2. Tables provide descriptive statistics, AUC analysis, and sensitivity, specificity and odds ratio calculations at various threshold (cutoff) levels for the various markers.

FIG. 3 provides data tables determined in accordance with Example 8 for the comparison of marker levels in urine samples collected for Cohort 1 (patients that reached, but did not progress beyond, RIFLE stage R) and in urine samples collected from subjects at 0, 24 hours, and 48 hours prior to reaching stage I or F in Cohort 2. Tables provide descriptive statistics, AUC analysis, and sensitivity, specificity and odds ratio calculations at various threshold (cutoff) levels for the various markers.

FIG. 4 provides data tables determined in accordance with Example 9 for the comparison of marker levels in urine samples collected for Cohort 1 (patients that did not progress beyond RIFLE stage 0) and in urine samples collected from subjects at 0, 24 hours, and 48 hours prior to reaching stage F in Cohort 2. Tables provide descriptive statistics, AUC analysis, and sensitivity, specificity and odds ratio calculations at various threshold (cutoff) levels for the various markers.

FIG. 5 provides data tables determined in accordance with Example 6 for the comparison of marker levels in plasma samples collected for Cohort 1 (patients that did not progress beyond RIFLE stage 0) and in plasma samples collected from subjects at 0, 24 hours, and 48 hours prior to reaching stage R, I or F in Cohort 2. Tables provide descriptive statistics, AUC analysis, and sensitivity, specificity and odds ratio calculations at various threshold (cutoff) levels for the various markers.

FIG. 6 provides data tables determined in accordance with Example 7 for the comparison of marker levels in plasma samples collected for Cohort 1 (patients that did not progress beyond RIFLE stage 0 or R) and in plasma samples collected from subjects at 0, 24 hours, and 48 hours prior to reaching stage I or F in Cohort 2. Tables provide descriptive statistics, AUC analysis, and sensitivity, specificity and odds ratio calculations at various threshold (cutoff) levels for the various markers.

FIG. 7 provides data tables determined in accordance with Example 8 for the comparison of marker levels in plasma samples collected for Cohort 1 (patients that reached, but did not progress beyond, RIFLE stage R) and in plasma samples collected from subjects at 0, 24 hours, and 48 hours prior to reaching stage I or F in Cohort 2. Tables provide descriptive statistics, AUC analysis, and sensitivity, specificity and odds ratio calculations at various threshold (cutoff) levels for the various markers.

FIG. 8 provides data tables determined in accordance with Example 9 for the comparison of marker levels in plasma samples collected for Cohort 1 (patients that did not progress beyond RIFLE stage 0) and in plasma samples collected from subjects at 0, 24 hours, and 48 hours prior to reaching stage F in Cohort 2. Tables provide descriptive statistics, AUC analysis, and sensitivity, specificity and odds ratio calculations at various threshold (cutoff) levels for the various markers.

DETAILED DESCRIPTION OF THE INVENTION

The present invention relates to methods and compositions for diagnosis, differential diagnosis, risk stratification, monitoring, classifying and determination of treatment regimens in subjects suffering or at risk of suffering from injury to renal function, reduced renal function and/or acute renal failure through measurement of one or more kidney injury markers. In various embodiments, a measured concentration of one or more markers selected from the group consisting of Clusterin, Heart-type fatty acid binding protein, Hepatocyte growth factor, Interferon gamma, Interleukin-12 subunit beta, Interleukin-16, Interleukin-2, 72 kDa type IV collagenase, Matrix metalloproteinase-9, Midkine, and Serum amyloid P-component, or one or more markers related thereto, are correlated to the renal status of the subject.

For purposes of this document, the following definitions apply:

As used herein, an "injury to renal function" is an abrupt (within 14 days, preferably within 7 days, more preferably within 72 hours, and still more preferably within 48 hours) measurable reduction in a measure of renal function. Such an injury may be identified, for example, by a decrease in glomerular filtration rate or estimated GFR, a reduction in urine output, an increase in serum creatinine, an increase in serum cystatin C, a requirement for renal replacement therapy, etc. "Improvement in Renal Function" is an abrupt (within 14 days, preferably within 7 days, more preferably within 72 hours, and still more preferably within 48 hours) measurable increase in a measure of renal function. Preferred methods for measuring and/or estimating GFR are described hereinafter. As used herein, "reduced renal function" is an abrupt (within 14 days, preferably within 7 days, more preferably within 72 hours, and still more preferably within 48 hours) reduction in kidney function identified by an absolute increase in serum creatinine of greater than or equal to 0.1 mg/dL ($\geq 8.8$ µmol/L), a percentage increase in serum creatinine of greater than or equal to 20% (1.2-fold from baseline), or a reduction in urine output (documented oliguria of less than 0.5 ml/kg per hour).

As used herein, "acute renal failure" or "ARF" is an abrupt (within 14 days, preferably within 7 days, more preferably within 72 hours, and still more preferably within 48 hours) reduction in kidney function identified by an absolute increase in serum creatinine of greater than or equal to 0.3 mg/dl ($\geq 26.4$ µmol/l), a percentage increase in serum creatinine of greater than or equal to 50% (1.5-fold from baseline), or a reduction in urine output (documented oliguria of less than 0.5 ml/kg per hour for at least 6 hours). This term is synonymous with "acute kidney injury" or "AKI."

In this regard, the skilled artisan will understand that the signals obtained from an immunoassay are a direct result of complexes formed between one or more antibodies and the target biomolecule (i.e., the analyte) and polypeptides containing the necessary epitope(s) to which the antibodies bind. While such assays may detect the full length biomarker and the assay result be expressed as a concentration of a biomarker of interest, the signal from the assay is actually a result of all such "immunoreactive" polypeptides present in the sample. Expression of biomarkers may also be determined by means other than immunoassays, including protein measurements (such as dot blots, western blots, chromatographic methods, mass spectrometry, etc.) and nucleic acid measurements (mRNA quatitation). This list is not meant to be limiting.

As used herein, the term "Clusterin" refers to one or more polypeptides present in a biological sample that are derived from the Clusterin precursor (Swiss-Prot P10909 (SEQ ID NO: 1)).

```
        10         20         30         40         50         60
MMKTLLLFVG LLLTWESGQV LGDQTVSDNE LQEMSNQGSK YVNKEIQNAV NGVKQIKTLI 70         80         90        100        110        120
EKTNEERKTL LSNLEEAKKK KEDALNETRE SETKLKELPG VCNETMMALW EECKPCLKQT 130        140        150        160        170        180
CMKFYARVCR SGSGLVGRQL EEFLNQSSPF YFWMNGDRID SLLENDRQQT HMLDVMQDHF 190        200        210        220        230        240
SRASSIIDEL FQDRFFTREP QDTYHYLPFS LPHRRPHFFF PKSRIVRSLM PFSPYEPLNF 250        260        270        280        290        300
HAMFQPFLEM IHEAQQAMDI HFHSPAFQHP PTEFIREGDD DRTVCREIRH NSTGCLRMKD 310        320        330        340        350        360
QCDKCREILS VDCSTNNPSQ AKLRRELDES LQVAERLTRK YNELLKSYQW KMLNTSSLLE 370        380        390        400        410        420
QLNEQFNWVS RLANLTQGED QYYLRVTTVA SHTSDSDVPS GVTEVVVKLF DSDPITVTVP 430        440
VEVSRKNPKF METVAEKALQ EYRKKHREE
```

The following domains have been identified in Clusterin:

| Residues | Length | Domain ID |
|---|---|---|
| 1-22 | 22 | Signal peptide |
| 23-449 | 427 | Clusterin |
| 23-227 | 205 | Clusterin beta chain |
| 228-449 | 222 | Clusterin alpha chain |

As used herein, the term "Heart-type fatty acid-binding protein" refers to one or more polypeptides present in a biological sample that are derived from the Heart-type fatty acid-binding protein precursor (Swiss-Prot P05413 (SEQ ID NO: 2)).

```
        10         20         30         40         50         60
MVDAFLGTWK LVDSKNFDDY MKSLGVGFAT RQVASMTKPT TIIEKNGDIL TLKTHSTFKN 70         80         90        100        110        120
TEISFKLGVE FDETTADDRK VKSIVTLDGG KLVHLQKWDG QETTLVRELI DGKLILTLTH

130
GTAVCTRTYE KEA
```

The following domains have been identified in Heart-type fatty acid-binding protein:

| Residues | Length | Domain ID |
|---|---|---|
| 1 | 1 | Initiator methionine |
| 2-133 | 132 | Heart-type fatty acid-binding protein |

As used herein, the term "Hepatocyte growth factor" refers to one or more polypeptides present in a biological sample that are derived from the Hepatocyte growth factor precursor (Swiss-Prot P14210 (SEQ ID NO: 3)).

```
          10         20         30         40         50         60
MWVTKLLPAL LLQHVLLHLL LLPIAIPYAE GQRKRRNTIH EFKKSAKTTL IKIDPALKIK 70         80         90        100        110        120
TKKVNTADQC ANRCTRNKGL PFTCKAFVFD KARKQCLWFP FNSMSSGVKK EFGHEFDLYE 130        140        150        160        170        180
NKDYIRNCII GKGRSYKGTV SITKSGIKCQ PWSSMIPHEH SFLPSSYRGK DLQENYCRNP 190        200        210        220        230        240
RGEEGGPWCF TSNPEVRYEV CDIPQCSEVE CMTCNGESYR GLMDHTESGK ICQRWDHQTP 250        260        270        280        290        300
HRHKFLPERY PDKGFDDNYC RNPDGQPRPW CYTLDPHTRW EYCAIKTCAD NTMNDTDVPL 310        320        330        340        350        360
ETTECIQGQG EGYRGTVNTI WNGIPCQRWD SQYPHEHDMT PENFKCKDLR ENYCRNPDGS 370        380        390        400        410        420
ESPWCFTTDP NIRVGYCSQI PNCDMSHGQD CYRGNGKNYM GNLSQTRSGL TCSMWDKNME 430        440        450        460        470        480
DLHRHIFWEP DASKLNENYC RNPDDDAHGP WCYTGNPLIP WDYCPISRCE GDTTPTIVNL 490        500        510        520        530        540
DHPVISCAKT KQLRVVNGIP TRTNIGWMVS LRYRNKHICG GSLIKESWVL TARQCFPSRD 550        560        570        580        590        600
LKDYEAWLGI HDVHGRGDEK CKQVLNVSQL VYGPEGSDLV LMKLARPAVL DDFVSTIDLP 610        620        630        640        650        660
NYGCTIPEKT SCSVYGWGYT GLINYDGLLR VAHLYIMGNE KCSQHHRGKV TLNESEICAG 670        680        690        700        710        720
AEKIGSGPCE GDYGGPLVCE QHKMRMVLGV IVPGRGCAIP NRPGIFVRVA YYAKWIHKII

LTYKVPQS
```

The following domains have been identified in Hepatocyte growth factor:

| Residues | Length | Domain ID |
|---|---|---|
| 1-31 | 31 | signal sequence |
| 32-494 | 463 | Hepatocyte growth factor alpha chain |
| 495-728 | 234 | Hepatocyte growth factor beta chain |

As used herein, the term "Interferon gamma" refers to one or more polypeptides present in a biological sample that are derived from the Interferon gamma precursor (Swiss-Prot P01579 (SEQ ID NO: 4)).

```
          10         20         30         40         50         60
MKYTSYILAF QLCIVLGSLG CYCQDPYVKE AENLKKYFNA GHSDVADNGT LFLGILKNWK 70         80         90        100        110        120
EESDRKIMQS QIVSFYFKLF KNFKDDQSIQ KSVETIKEDM NVKFFNSNKK KRDDFEKLTN 130        140        150        160
YSVTDLNVQR KAIHELIQVM AELSPAAKTG KRKRSQMLFR GRRASQ
```

The following domains have been identified in Interferon gamma:

| Residues | Length | Domain ID |
|---|---|---|
| 1-23 | 23 | Signal peptide |
| 24-161 | 138 | Interferon gamma |
| 162-166 | 5 | Propeptide |

As used herein, the term "Interleukin-12 subunit beta" (also known as "Interleukin-12 p40") refers to one or more polypeptides present in a biological sample that are derived from the Interleukin-12 subunit beta precursor (Swiss-Prot P29460 (SEQ ID NO: 5)).

```
                              10         20         30         40         50         60
                    MCHQQLVISW FSLVFLASPL VAIWELKKDV YVVELDWYPD APGEMVVLTC DTPEEDGITW 70         80         90        100        110        120
                    TLDQSSEVLG SGKTLTIQVK EFGDAGQYTC HKGGEVLSHS LLLLHKKEDG IWSTDILKDQ
```

```
           130        140        150        160        170        180
KEPKNKTFLR CEAKNYSGRF TCWWLTTIST DLTFSVKSSR GSSDPQGVTC GAATLSAERV 190        200        210        220        230        240
RGDNKEYEYS VECQEDSACP AAEESLPIEV MVDAVHKLKY ENYTSSFFIR DIIKPDPPKN 250        260        270        280        290        300
LQLKPLKNSR QVEVSWEYPD TWSTPHSYFS LTFCVQVQGK SKREKKDRVF TDKTSATVIC 310        320
RKNASISVRA QDRYYSSSWS EWASVPCS
```

The following domains have been identified in Interleukin-12 subunit beta:

| Residues | Length | Domain ID |
|---|---|---|
| 1-22 | 22 | Signal peptide |
| 23-328 | 306 | Interleukin-12 subunit beta |

As used herein, the term "Interleukin-16" refers to one or more polypeptides present in a biological sample that are derived from the Interleukin-16 precursor (Swiss-Prot Q14005 (SEQ ID NO: 6)).

```
           10         20         30         40         50         60
MDYSFDTTAE DPWVRISDCI KNLFSPIMSE NHGHMPLQPN ASLNEEEGTQ GHPDGTPPKL 70         80         90         100        110        120
DTANGTPKVY KSADSSTVKK GPPVAPKPAW FRQSLKGLRN RASDPRGLPD PALSTQPAPA 130        140        150        160        170        180
SREHLGSHIR ASSSSSSIRQ RISSFETFGS SQLPDKGAQR LSLQPSSGEA AKPLGKHEEG 190        200        210        220        230        240
RFSGLLGRGA APTLVPQQPE QVLSSGSPAA SEARDPGVSE SPPPGRQPNQ KTLPPGPDPL 250        260        270        280        290        300
LRLLSTQAEE SQGPVLKMPS QRARSFPLTR SQSCETKLLD EKTSKLYSIS SQVSSAVMKS 310        320        330        340        350        360
LLCLPSSISC AQTPCIPKEG ASPTSSSNED SAANGSAETS ALDTGFSLNL SELREYTEGL 370        380        390        400        410        420
TEAKEDDDGD HSSLQSGQSV ISLLSSEELK KLIEEVKVLD EATLKQLDGI HVTILHKEEG 430        440        450        460        470        480
AGLGFSLAGG ADLENKVITV HRVFPNGLAS QEGTIQKGNE VLSINGKSLK GTTHHDALAI 490        500        510        520        530        540
LRQAREPRQA VIVTRKLTPE AMPDLNSSTD SAASASAASD VSVESTAEAT VCTVTLEKMS 550        560        570        580        590        600
AGLGFSLEGG KGSLHGDKPL TINRIFKGAA SEQSETVQPG DEILQLGGTA MQGLTRFEAW 610        620        630
NIIKALPDGP VTIVIRRKSL QSKETTAAGD S
```

| | | |
|---|---|---|
| 1-1332 | 1332 | Pro-interleukin-16 |
| 1212-1332 | 121 | Interleukin-16 |

As used herein, the term "Interleukin-2" refers to one or more polypeptides present in a biological sample that are derived from the Interleukin-2 precursor (Swiss-Prot P60568 (SEQ ID NO: 7)).

```
           10         20         30         40         50         60
MYRMQLLSCI ALSLALVTNS APTSSSTKKT QLQLEHLLLD LQMILNGINN YKNPKLTRML 70         80         90         100        110        120
TFKFYMPKKA TELKHLQCLE EELKPLEEVL NLAQSKNFHL RPRDLISNIN VIVLELKGSE 130        140        150
TTFMCEYADE TATIVEFLNR WITFCQSIIS TLT
```

The following domains have been identified in Interleukin-2:

| Residues | Length | Domain ID |
| --- | --- | --- |
| 1-20 | 20 | Signal peptide |
| 21-153 | 133 | Interleukin-2 |

As used herein, the term "72 kDa type IV collagenase" (also known as "Matrix metalloproteinase-2") refers to one or more polypeptides present in a biological sample that are derived from the 72 kDa type IV collagenase precursor (Swiss-Prot P08253 (SEQ ID NO: 8)).

```
         10         20         30         40         50         60
MEALMARGAL TGPLRALCLL GCLLSHAAAA PSPIIKFPGD VAPKTDKELA VQYLNTFYGC 70         80         90        100        110        120
PKESCNLFVL KDTLKKMQKF FGLPQTGDLD QNTIETMRKP RCGNPDVANY NFFPRKPKWD 130        140        150        160        170        180
KNQITYRIIG YTPDLDPETV DDAFARAFQV WSDVTPLRFS RIHDGEADIM INFGRWEHGD 190        200        210        220        230        240
GYPFDGKDGL LAHAFAPGTG VGGDSHFDDD ELWTLGEGQV VRVKYGNADG EYCKFPFLFN 250        260        270        280        290        300
GKEYNSCTDT GRSDGFLWCS TTYNFEKDGK YGFCPHEALF TMGGNAEGQP CKFPFRFQGT 310        320        330        340        350        360
SYDSCTTEGR TDGYRWCGTT EDYDRDKKYG FCPETAMSTV GGNSEGAPCV FPFTFLGNKY 370        380        390        400        410        420
ESCTSAGRSD GKMWCATTAN YDDDRKWGFC PDQGYSLFLV AAHEFGHAMG LEHSQDPGAL 430        440        450        460        470        480
MAPIYTYTKN FRLSQDDIKG IQELYGASPD IDLGTGPTPT LGPVTPEICK QDIVFDGIAQ 490        500        510        520        530        540
IRGEIFFFKD RFIWRTVTPR DKPMGPLLVA TFWPELPEKI DAVYEAPQEE KAVFFAGNEY 550        560        570        580        590        600
WIYSASTLER GYPKPLTSLG LPPDVQRVDA AFNWSKNKKT YIFAGDKFWR YNEVKKKMDP 610        620        630        640        650        660
GFPKLIADAW NAIPDNLDAV VDLQGGGHSY FFKGAYYLKL ENQSLKSVKF GSIKSDWLGC
```

The following domains have been identified in 72 kDa type IV collagenase:

| Residues | Length | Domain ID |
| --- | --- | --- |
| 1-29 | 29 | Signal peptide |
| 30-109 | 90 | Activation peptide |
| 110-660 | 551 | 72 kDa type IV collagenase |

As used herein, the term "Matrix metalloproteinase-9" refers to one or more polypeptides present in a biological sample that are derived from the Matrix metalloproteinase-9 precursor (Swiss-Prot P14780 (SEQ ID NO: 9)).

```
                   10         20         30         40         50         60
          MSLWQPLVLV LLVLGCCFAA PRQRQSTLVL FPGDLRTNLT DRQLAEEYLY RYGYTRVAEM 70         80         90        100        110        120
          RGESKSLGPA LLLLQKQLSL PETGELDSAT LKAMRTPRCG VPDLGRFQTF EGDLKWHHHN 130        140        150        160        170        180
          ITYWIQNYSE DLPRAVIDDA FARAFALWSA VTPLTFTRVY SRDADIVIQF GVAEHGDGYP 190        200        210        220        230        240
          FDGKDGLLAH AFPPGPGIQG DAHFDDDELW SLGKGVVVPT RFGNADGAAC HFPFIFEGRS 250        260        270        280        290        300
          YSACTTDGRS DGLPWCSTTA NYDTDDRFGF CPSERLYTQD GNADGKPCQF PFIFQGQSYS 310        320        330        340        350        360
          ACTTDGRSDG YRWCATTANY DRDKLFGFCP TRADSTVMGG NSAGELCVFP FTFLGKEYST 370        380        390        400        410        420
          CTSEGRGDGR LWCATTSNFD SDKKWGFCPD QGYSLFLVAA HEFGHALGLD HSSVPEALMY 430        440        450        460        470        480
          PMYRFTEGPP LHKDDVNGIR HLYGPRPEPE PRPPTTTTPQ PTAPPTVCPT GPPTVHPSER
```

```
         490        500        510        520        530        540
  PTAGPTGPPS AGPTGPPTAG PSTATTVPLS PVDDACNVNI FDAIAEIGNQ LYLFKDGKYW 550        560        570        580        590        600
  RFSEGRGSRP QGPFLIADKW PALPRKLDSV FEEPLSKKLF FFSGRQVWVY TGASVLGPRR 610        620        630        640        650        660
  LDKLGLGADV AQVTGALRSG RGKMLLFSGR RLWRFDVKAQ MVDPRSASEV DRMFPGVPLD 670        680        690        700
  THDVFQYREK AYFCQDRFYW RVSSRSELNQ VDQVGYVTYD ILQCPED
```

The following domains have been identified in Matrix metalloproteinase-9:

| Residues | Length | Domain ID |
|---|---|---|
| 1-19 | 19 | Signal peptide |
| 20-93 | 74 | Activation peptide |
| 107-707 | 601 | Matrix metalloproteinase-9 82 kDa form |

In addition, a 67 kDa form of Matrix metalloproteinase-9 has been identified.

As used herein, the term "Midkine" refers to one or more polypeptides present in a biological sample that are derived from the Midkine precursor (Swiss-Prot P21741 (SEQ ID NO: 10)).

```
          10         20         30         40         50         60
  MQHRGFLLLT LLALLALTSA VAKKKDKVKK GGPGSECAEW AWGPCTPSSK DCGVGFREGT 70         80         90        100        110        120
  CGAQTQRIRC RVPCNWKKEF GADCKYKFEN WGACDGGTGT KVRQGTLKKA RYNAQCQETI 130        140
  RVTKPCTPKT KAKAKAKKGK GKD
```

The following domains have been identified in Midkine:

| Residues | Length | Domain ID |
|---|---|---|
| 1-20 | 20 | Signal peptide |
| 21-143 | 123 | Midkine |

As used herein, the term "Serum amyloid P-component" refers to one or more polypeptides present in a biological sample that are derived from the Serum amyloid P-component precursor (Swiss-Prot P02743 (SEQ ID NO: 11)).

```
          10         20         30         40         50         60
  MNKPLLWISV LTSLLEAFAH TDLSGKVFVF PRESVTDHVN LITPLEKPLQ NFTLCFRAYS 70         80         90        100        110        120
  DLSRAYSLFS YNTQGRDNEL LVYKERVGEY SLYIGRHKVT SKVIEKFPAP VHICVSWESS 130        140        150        160        170        180
  SGIAEFWING TPLVKKGLRQ GYFVEAQPKI VLGQEQDSYG GKFDRSQSFV GEIGDLYMWD 190        200        210        220
  SVLPPENILS AYQGTPLPAN ILDWQALNYE IRGYVIIKPL VWV
```

The following domains have been identified in Serum amyloid P-component:

| Residues | Length | Domain ID |
|---|---|---|
| 1-19 | 19 | Signal peptide |
| 20-223 | 204 | Serum amyloid P-component |
| 20-222 | 203 | Serum amyloid P-component (1-203) |

As used herein, the term "relating a signal to the presence or amount" of an analyte reflects this understanding. Assay signals are typically related to the presence or amount of an analyte through the use of a standard curve calculated using known concentrations of the analyte of interest. As the term is used herein, an assay is "configured to detect" an analyte if an assay can generate a detectable signal indicative of the presence or amount of a physiologically relevant concentration of the analyte. Because an antibody epitope is on the order of 8 amino acids, an immunoassay configured to detect a marker of interest will also detect polypeptides related to the marker sequence, so long as those polypeptides contain the epitope(s) necessary to bind to the antibody or antibodies used in the assay. The term "related marker" as used herein with regard to a biomarker such as one of the kidney injury markers described herein refers to one or more fragments, variants, etc., of a particular marker or its biosynthetic parent that may be detected as a surrogate for the marker itself or as independent biomarkers. The term also refers to one or more polypeptides present in a biological sample that are derived from the biomarker precursor complexed to additional species, such as binding proteins, receptors, heparin, lipids, sugars, etc.

The term "positive going" marker as that term is used herein refer to a marker that is determined to be elevated in subjects suffering from a disease or condition, relative to subjects not suffering from that disease or condition. The term "negative going" marker as that term is used herein refer to a marker that is determined to be reduced in subjects suffering from a disease or condition, relative to subjects not suffering from that disease or condition.

The term "subject" as used herein refers to a human or non-human organism. Thus, the methods and compositions described herein are applicable to both human and veterinary disease. Further, while a subject is preferably a living organism, the invention described herein may be used in postmortem analysis as well. Preferred subjects are humans, and most preferably "patients," which as used herein refers to living humans that are receiving medical care for a disease or condition. This includes persons with no defined illness who are being investigated for signs of pathology.

Preferably, an analyte is measured in a sample. Such a sample may be obtained from a subject, or may be obtained from biological materials intended to be provided to the subject. For example, a sample may be obtained from a kidney being evaluated for possible transplantation into a subject, and an analyte measurement used to evaluate the kidney for preexisting damage. Preferred samples are body fluid samples.

The term "body fluid sample" as used herein refers to a sample of bodily fluid obtained for the purpose of diagnosis, prognosis, classification or evaluation of a subject of interest, such as a patient or transplant donor. In certain embodiments, such a sample may be obtained for the purpose of determining the outcome of an ongoing condition or the effect of a treatment regimen on a condition. Preferred body fluid samples include blood, serum, plasma, cerebrospinal fluid, urine, saliva, sputum, and pleural effusions. In addition, one of skill in the art would realize that certain body fluid samples would be more readily analyzed following a fractionation or purification procedure, for example, separation of whole blood into serum or plasma components.

The term "diagnosis" as used herein refers to methods by which the skilled artisan can estimate and/or determine the probability ("a likelihood") of whether or not a patient is suffering from a given disease or condition. In the case of the present invention, "diagnosis" includes using the results of an assay, most preferably an immunoassay, for a kidney injury marker of the present invention, optionally together with other clinical characteristics, to arrive at a diagnosis (that is, the occurrence or nonoccurrence) of an acute renal injury or ARF for the subject from which a sample was obtained and assayed. That such a diagnosis is "determined" is not meant to imply that the diagnosis is 100% accurate. Many biomarkers are indicative of multiple conditions. The skilled clinician does not use biomarker results in an informational vacuum, but rather test results are used together with other clinical indicia to arrive at a diagnosis. Thus, a measured biomarker level on one side of a predetermined diagnostic threshold indicates a greater likelihood of the occurrence of disease in the subject relative to a measured level on the other side of the predetermined diagnostic threshold.

Similarly, a prognostic risk signals a probability ("a likelihood") that a given course or outcome will occur. A level or a change in level of a prognostic indicator, which in turn is associated with an increased probability of morbidity (e.g., worsening renal function, future ARF, or death) is referred to as being "indicative of an increased likelihood" of an adverse outcome in a patient.

Marker Assays

In general, immunoassays involve contacting a sample containing or suspected of containing a biomarker of interest with at least one antibody that specifically binds to the biomarker. A signal is then generated indicative of the presence or amount of complexes formed by the binding of polypeptides in the sample to the antibody. The signal is then related to the presence or amount of the biomarker in the sample. Numerous methods and devices are well known to the skilled artisan for the detection and analysis of biomarkers. See, e.g., U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, and *The Immunoassay Handbook*, David Wild, ed. Stockton Press, New York, 1994, each of which is hereby incorporated by reference in its entirety, including all tables, figures and claims.

The assay devices and methods known in the art can utilize labeled molecules in various sandwich, competitive, or non-competitive assay formats, to generate a signal that is related to the presence or amount of the biomarker of interest. Suitable assay formats also include chromatographic, mass spectrographic, and protein "blotting" methods. Additionally, certain methods and devices, such as biosensors and optical immunoassays, may be employed to determine the presence or amount of analytes without the need for a labeled molecule. See, e.g., U.S. Pat. Nos. 5,631,171; and 5,955,377, each of which is hereby incorporated by reference in its entirety, including all tables, figures and claims. One skilled in the art also recognizes that robotic instrumentation including but not limited to Beckman ACCESS®, Abbott AXSYM®, Roche ELECSYS®, Dade Behring STRATUS® systems are among the immunoassay analyzers that are capable of performing immunoassays. But any suitable immunoassay may be utilized, for example, enzyme-linked immunoassays (ELISA), radioimmunoassays (RIAs), competitive binding assays, and the like.

Antibodies or other polypeptides may be immobilized onto a variety of solid supports for use in assays. Solid phases that may be used to immobilize specific binding members include include those developed and/or used as solid phases in solid phase binding assays. Examples of suitable solid phases include membrane filters, cellulose-based papers, beads (including polymeric, latex and paramagnetic particles), glass, silicon wafers, microparticles, nanoparticles, TentaGel™ resins (Rapp Polymere GmbH), AgroGel™ resins (I.L.S.A. Industria Lavorazione Sottoprodotti Animali S.P.A.), polyethylene glycol and acrylamide (PEGA) gels, SPOCC gels, and multiple-well plates. An assay strip could be prepared by coating the antibody or a plurality of antibodies in an array on solid support. This strip could then be dipped into the test sample and then processed quickly through washes and detection steps to generate a measurable signal, such as a colored spot. Antibodies or other polypeptides may be bound to specific zones of assay devices either by conjugating directly to an assay device surface, or by indirect binding. In an example of the later case, antibodies or other polypeptides may be immobilized on particles or other solid supports, and that solid support immobilized to the device surface.

Biological assays require methods for detection, and one of the most common methods for quantitation of results is to conjugate a detectable label to a protein or nucleic acid that has affinity for one of the components in the biological system being studied. Detectable labels may include molecules that are themselves detectable (e.g., fluorescent moieties, electrochemical labels, metal chelates, etc.) as well as molecules that may be indirectly detected by production of a detectable reaction product (e.g., enzymes such as horseradish peroxidase, alkaline phosphatase, etc.) or by a specific binding molecule which itself may be detectable (e.g., biotin, digoxigenin, maltose, oligohistidine, 2,4-dintrobenzene, phenylarsenate, ssDNA, dsDNA, etc.).

Preparation of Solid Phases and Detectable Label Conjugates Often Comprise the use of chemical cross-linkers. Cross-linking reagents contain at least two reactive groups, and are divided generally into homofunctional cross-linkers (containing identical reactive groups) and heterofunctional cross-linkers (containing non-identical reactive groups). Homobifunctional cross-linkers that couple through amines, sulfhydryls or react non-specifically are available from many commercial sources. Maleimides, alkyl and aryl halides, alpha-haloacyls and pyridyl disulfides are thiol reactive groups. Maleimides, alkyl and aryl halides, and alpha-haloacyls react with sulfhydryls to form thiol ether bonds, while pyridyl disulfides react with sulfhydryls to produce mixed disulfides. The pyridyl disulfide product is cleavable. Imidoesters are also very useful for protein-protein cross-links. A variety of heterobifunctional cross-linkers, each combining different attributes for successful conjugation, are commercially available.

In certain aspects, the present invention provides kits for the analysis of the described kidney injury markers. The kit comprises reagents for the analysis of at least one test sample which comprise at least one antibody that a kidney injury marker. The kit can also include devices and instructions for performing one or more of the diagnostic and/or prognostic correlations described herein. Preferred kits will comprise an antibody pair for performing a sandwich assay, or a labeled species for performing a competitive assay, for the analyte. Preferably, an antibody pair comprises a first antibody conjugated to a solid phase and a second antibody conjugated to a detectable label, wherein each of the first and second antibodies that bind a kidney injury marker. Most preferably each of the antibodies are monoclonal antibodies. The instructions for use of the kit and performing the correlations can be in the form of labeling, which refers to any written or recorded material that is attached to, or otherwise accompanies a kit at any time during its manufacture, transport, sale or use. For example, the term labeling encompasses advertising leaflets and brochures, packaging materials, instructions, audio or video cassettes, computer discs, as well as writing imprinted directly on kits.

Antibodies

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Antibodies used in the immunoassays described herein preferably specifically bind to a kidney injury marker of the present invention. The term "specifically binds" is not intended to indicate that an antibody binds exclusively to its intended target since, as noted above, an antibody binds to any polypeptide displaying the epitope(s) to which the antibody binds. Rather, an antibody "specifically binds" if its affinity for its intended target is about 5-fold greater when compared to its affinity for a non-target molecule which does not display the appropriate epitope(s). Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In preferred embodiments, Preferred antibodies bind with affinities of at least about $10^7 M^{-1}$, and preferably between about $10^8 M^{-1}$ to about $10^9 M^{-1}$, about $10^9 M^{-1}$ to about $10^{10} M^{-1}$, or about $10^{10} M^{-1}$ to about $10^{12} M^{-1}$.

Affinity is calculated as $K_d = k_{off}/k_{on}$ ($k_{off}$ is the dissociation rate constant, $K_{on}$ is the association rate constant and $K_d$ is the equilibrium constant). Affinity can be determined at equilibrium by measuring the fraction bound (r) of labeled ligand at various concentrations (c). The data are graphed using the Scatchard equation: $r/c=K(n-r)$: where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Antibody affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988.

The term "epitope" refers to an antigenic determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents.

Numerous publications discuss the use of phage display technology to produce and screen libraries of polypeptides for binding to a selected analyte. See, e.g, Cwirla et al., *Proc. Natl. Acad. Sci. USA* 87, 6378-82, 1990; Devlin et al., *Science* 249, 404-6, 1990, Scott and Smith, *Science* 249, 386-88, 1990; and Ladner et al., U.S. Pat. No. 5,571,698. A basic concept of phage display methods is the establishment of a physical association between DNA encoding a polypeptide to be screened and the polypeptide. This physical association is provided by the phage particle, which displays a polypeptide as part of a capsid enclosing the phage genome which encodes the polypeptide. The establishment of a physical association between polypeptides and their genetic material allows simultaneous mass screening of very large numbers of phage bearing different polypeptides. Phage displaying a polypeptide with affinity to a target bind to the target and these phage are enriched by affinity screening to the target. The identity of polypeptides displayed from these phage can be determined from their respective genomes. Using these methods a polypeptide identified as having a binding affinity for a desired target can then be synthesized in bulk by conventional means. See, e.g., U.S. Pat. No. 6,057,098, which is hereby incorporated in its entirety, including all tables, figures, and claims.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labeled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) are present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g., in sandwich assays) may interfere with one another sterically, etc., assay performance of an antibody may be a more important measure than absolute affinity and specificity of an antibody.

Assay Correlations

The term "correlating" as used herein in reference to the use of biomarkers refers to comparing the presence or amount of the biomarker(s) in a patient to its presence or amount in persons known to suffer from, or known to be at risk of, a given condition; or in persons known to be free of a given condition. Often, this takes the form of comparing an assay result in the form of a biomarker concentration to a predetermined threshold selected to be indicative of the occurrence or nonoccurrence of a disease or the likelihood of some future outcome.

Selecting a diagnostic threshold involves, among other things, consideration of the probability of disease, distribution of true and false diagnoses at different test thresholds, and estimates of the consequences of treatment (or a failure to treat) based on the diagnosis. For example, when considering administering a specific therapy which is highly efficacious and has a low level of risk, few tests are needed because clinicians can accept substantial diagnostic uncertainty. On the other hand, in situations where treatment options are less effective and more risky, clinicians often need a higher degree of diagnostic certainty. Thus, cost/benefit analysis is involved in selecting a diagnostic threshold.

Suitable thresholds may be determined in a variety of ways. For example, one recommended diagnostic threshold for the diagnosis of acute myocardial infarction using cardiac troponin is the $97.5^{th}$ percentile of the concentration seen in a normal population. Another method may be to look at serial samples from the same patient, where a prior "baseline" result is used to monitor for temporal changes in a biomarker level.

Population studies may also be used to select a decision threshold. Receiver Operating Characteristic ("ROC") arose from the field of signal detection theory developed during World War II for the analysis of radar images, and ROC analysis is often used to select a threshold able to best distinguish a "diseased" subpopulation from a "nondiseased" subpopulation. A false positive in this case occurs when the person tests positive, but actually does not have the disease. A false negative, on the other hand, occurs when the person tests negative, suggesting they are healthy, when they actually do have the disease. To draw a ROC curve, the true positive rate (TPR) and false positive rate (FPR) are determined as the decision threshold is varied continuously. Since TPR is equivalent with sensitivity and FPR is equal to 1-specificity, the ROC graph is sometimes called the sensitivity vs (1-specificity) plot. A perfect test will have an area under the ROC curve of 1.0; a random test will have an area of 0.5. A threshold is selected to provide an acceptable level of specificity and sensitivity.

In this context, "diseased" is meant to refer to a population having one characteristic (the presence of a disease or condition or the occurrence of some outcome) and "nondiseased" is meant to refer to a population lacking the characteristic. While a single decision threshold is the simplest application of such a method, multiple decision thresholds may be used. For example, below a first threshold, the absence of disease may be assigned with relatively high confidence, and above a second threshold the presence of disease may also be assigned with relatively high confidence. Between the two thresholds may be considered indeterminate. This is meant to be exemplary in nature only.

In addition to threshold comparisons, other methods for correlating assay results to a patient classification (occurrence or nonoccurrence of disease, likelihood of an outcome, etc.) include decision trees, rule sets, Bayesian methods, and neural network methods. These methods can produce probability values representing the degree to which a subject belongs to one classification out of a plurality of classifications.

Measures of test accuracy may be obtained as described in Fischer et al., *Intensive Care Med.* 29: 1043-51, 2003, and used to determine the effectiveness of a given biomarker. These measures include sensitivity and specificity, predictive values, likelihood ratios, diagnostic odds ratios, and ROC curve areas. The area under the curve ("AUC") of a ROC plot is equal to the probability that a classifier will rank a randomly chosen positive instance higher than a randomly chosen negative one. The area under the ROC curve may be thought of as equivalent to the Mann-Whitney U test, which tests for the median difference between scores obtained in the two groups considered if the groups are of continuous data, or to the Wilcoxon test of ranks.

As discussed above, suitable tests may exhibit one or more of the following results on these various measures: a specificity of greater than 0.5, preferably at least 0.6, more preferably at least 0.7, still more preferably at least 0.8, even more preferably at least 0.9 and most preferably at least 0.95, with a corresponding sensitivity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; a sensitivity of greater than 0.5, preferably at least 0.6, more preferably at least 0.7, still more preferably at least 0.8, even more preferably at least 0.9 and most preferably at least 0.95, with a corresponding specificity greater than 0.2, preferably greater than 0.3, more preferably greater than 0.4, still more preferably at least 0.5, even more preferably 0.6, yet more preferably greater than 0.7, still more preferably greater than 0.8, more preferably greater than 0.9, and most preferably greater than 0.95; at least 75% sensitivity, combined with at least 75% specificity; a ROC curve area of greater than 0.5, preferably at least 0.6, more preferably 0.7, still more preferably at least 0.8, even more preferably at least 0.9, and most preferably at least 0.95; an odds ratio different from 1, preferably at least about 2 or more or about 0.5 or less, more preferably at least about 3 or more or about 0.33 or less, still more preferably at least about 4 or more or about 0.25 or less, even more preferably at least about 5 or more or about 0.2 or less, and most preferably at least about 10 or more or about 0.1 or less; a positive likelihood ratio (calculated as sensitivity/(1−specificity)) of greater than 1, at least 2, more preferably at least 3, still more preferably at least 5, and most preferably at least 10; and or a negative likelihood ratio (calculated as (1−sensitivity)/specificity) of less than 1, less than or equal to 0.5, more preferably less than or equal to 0.3, and most preferably less than or equal to 0.1

Additional clinical indicia may be combined with the kidney injury marker assay result(s) of the present invention. These include other biomarkers related to renal status. Examples include the following, which recite the common biomarker name, followed by the Swiss-Prot entry number for that biomarker or its parent: Actin (P68133); Adenosine deaminase binding protein (DPP4, P27487); Alpha-1-acid glycoprotein 1 (P02763); Alpha-1-microglobulin (P02760); Albumin (P02768); Angiotensinogenase (Renin, P00797); Annexin A2 (P07355); Beta-glucuronidase (P08236); B-2-microglobulin (P61679); Beta-galactosidase (P16278); BMP-7 (P18075); Brain natriuretic peptide (proBNP, BNP-32, NTproBNP; P16860); Calcium-binding protein Beta (S100-beta, P04271); Carbonic anhydrase (Q16790); Casein Kinase 2 (P68400); Cathepsin B (P07858); Ceruloplasmin (P00450); Clusterin (P10909); Complement C3 (P01024); Cysteine-rich protein (CYR61, O00622); Cytochrome C (P99999); Epidermal growth factor (EGF, P01133); Endothelin-1 (P05305); Exosomal Fetuin-A (P02765); Fatty acid-binding protein, heart (FABP3, P05413); Fatty acid-binding protein, liver (P07148); Ferritin (light chain, P02793; heavy chain P02794); Fructose-1,6-biphosphatase (P09467); GRO-alpha (CXCL1, (P09341); Growth Hormone (P01241); Hepatocyte growth factor (P14210); Insulin-like growth factor I (P01343); Immunoglobulin G; Immunoglobulin Light Chains (Kappa and Lambda); Interferon gamma (P01308); Lysozyme (P61626); Interleukin-1alpha (P01583); Interleukin-2 (P60568); Interleukin-4 (P60568); Interleukin-9 (P15248); Interleukin-12p40 (P29460); Interleukin-13 (P35225); Interleukin-16 (Q14005); L1 cell adhesion molecule (P32004); Lactate dehydrogenase (P00338); Leucine Aminopeptidase (P28838); Meprin A-alpha subunit (Q16819); Meprin A-beta subunit (Q16820); Midkine (P21741); MIP2-alpha (CXCL2, P19875); MMP-2 (P08253); MMP-9 (P14780); Netrin-1 (O95631); Neutral endopeptidase (P08473); Osteopontin (P10451); Renal papillary antigen 1 (RPA1); Renal papillary antigen 2 (RPA2); Retinol binding protein (P09455); Ribonuclease; S100 calcium-binding protein A6 (P06703); Serum Amyloid P Component (P02743); Sodium/Hydrogen exchanger isoform (NHE3, P48764); Spermidine/spermine N1-acetyltransferase (P21673); TGF-Beta1 (P01137); Transferrin (P02787); Trefoil factor 3 (TFF3, Q07654); Toll-Like protein 4 (O00206); Total protein; Tubulointerstitial nephritis antigen (Q9UJW2); Uromodulin (Tamm-Horsfall protein, P07911).

For purposes of risk stratification, Adiponectin (Q15848); Alkaline phosphatase (P05186); Aminopeptidase N (P15144); CalbindinD28k (P05937); Cystatin C (P01034); 8 subunit of F1FO ATPase (P03928); Gamma-glutamyltransferase (P19440); GSTa (alpha-glutathione-S-transferase, P08263); GSTpi (Glutathione-S-transferase P; GST class-pi; P09211); IGFBP-1 (P08833); IGFBP-2 (P18065); IGFBP-6 (P24592); Integral membrane protein 1 (Itm1, P46977); Interleukin-6 (P05231); Interleukin-8 (P10145); Interleukin-18 (Q14116); IP-10 (10 kDa interferon-gamma-induced protein, P02778); IRPR (IFRD1, O00458); Isovaleryl-CoA dehydrogenase (IVD, P26440); I-TAC/CXCL11 (O14625); Keratin 19 (P08727); Kim-1 (Hepatitis A virus cellular receptor 1, O43656); L-arginine:glycine amidinotransferase (P50440); Leptin (P41159); Lipocalin2 (NGAL, P80188); MCP-1 (P13500); MIG (Gamma-interferon-induced monokine Q07325); MIP-1a (P10147); MIP-3a (P78556); MIP-1beta (P13236); MIP-1d (Q16663); NAG (N-acetyl-beta-D-glucosaminidase, P54802); Organic ion transporter (OCT2, O15244); Osteoprotegerin (O14788); P8 protein (O60356); Plasminogen activator inhibitor 1 (PAI-1, P05121); ProANP (1-98) (P01160); Protein phosphatase 1-beta (PPI-beta, P62140); Rab GDI-beta (P50395); Renal kallikrein (Q86U61); RT1.B-1 (alpha) chain of the integral membrane protein (Q5Y7A8); Soluble tumor necrosis factor receptor superfamily member 1A (sTNFR-I, P19438); Soluble tumor necrosis factor receptor superfamily member 1B (sTNFR-II, P20333); Tissue inhibitor of metalloproteinases 3 (TIMP-3, P35625); uPAR (Q03405) may be combined with the kidney injury marker assay result(s) of the present invention.

Other clinical indicia which may be combined with the kidney injury marker assay result(s) of the present invention includes demographic information (e.g., weight, sex, age, race), medical history (e.g., family history, type of surgery, pre-existing disease such as aneurism, congestive heart failure, preeclampsia, eclampsia, diabetes mellitus, hypertension, coronary artery disease, proteinuria, renal insufficiency, or sepsis, type of toxin exposure such as NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin), clinical variables (e.g., blood pressure, temperature, respiration rate), risk scores (APACHE score, PREDICT score, TIMI Risk Score for UA/NSTEMI, Framingham Risk Score), a urine total protein measurement, a glomerular filtration rate, an estimated glomerular filtration rate, a urine production rate, a serum or plasma creatinine concentration, a renal papillary antigen 1 (RPA1) measurement; a renal papillary antigen 2 (RPA2) measurement; a urine creatinine concentration, a fractional excretion of sodium, a urine sodium concentration, a urine creatinine to serum or plasma creatinine ratio, a urine specific gravity, a urine osmolality, a urine urea nitrogen to plasma urea nitrogen ratio, a plasma BUN to creatnine ratio, and/or a renal failure index calculated as urine sodium/(urine creatinine/plasma creatinine). Other measures of renal function which may be combined with the kidney injury marker assay result(s) are described hereinafter and in Harrison's Principles of Internal Medicine, 17$^{th}$ Ed., McGraw Hill, N.Y., pages 1741-1830, and Current Medical Diagnosis & Treatment 2008, 47$^{th}$ Ed, McGraw Hill, N.Y., pages 785-815, each of which are hereby incorporated by reference in their entirety.

Combining assay results/clinical indicia in this manner can comprise the use of multivariate logistical regression, loglinear modeling, neural network analysis, n-of-m analysis, decision tree analysis, etc. This list is not meant to be limiting.

Diagnosis of Acute Renal Failure

As noted above, the terms "acute renal (or kidney) injury" and "acute renal (or kidney) failure" as used herein are defined in part in terms of changes in serum creatinine from a baseline value. Most definitions of ARF have common elements, including the use of serum creatinine and, often, urine output. Patients may present with renal dysfunction without an available baseline measure of renal function for use in this comparison. In such an event, one may estimate a baseline serum creatinine value by assuming the patient initially had a normal GFR. Glomerular filtration rate (GFR) is the volume of fluid filtered from the renal (kidney) glomerular capillaries into the Bowman's capsule per unit time. Glomerular filtration rate (GFR) can be calculated by measuring any chemical that has a steady level in the blood, and is freely filtered but neither reabsorbed nor secreted by the kidneys. GFR is typically expressed in units of ml/min:

$$GFR = \frac{\text{Urine Concentration} \times \text{Urine Flow}}{\text{Plasma Concentration}}$$

By normalizing the GFR to the body surface area, a GFR of approximately 75-100 ml/min per 1.73 m² can be assumed. The rate therefore measured is the quantity of the substance in the urine that originated from a calculable volume of blood.

There are several different techniques used to calculate or estimate the glomerular filtration rate (GFR or eGFR). In clinical practice, however, creatinine clearance is used to measure GFR. Creatinine is produced naturally by the body (creatinine is a metabolite of creatine, which is found in muscle). It is freely filtered by the glomerulus, but also actively secreted by the renal tubules in very small amounts such that creatinine clearance overestimates actual GFR by 10-20%. This margin of error is acceptable considering the ease with which creatinine clearance is measured.

Creatinine clearance (CCr) can be calculated if values for creatinine's urine concentration ($U_{Cr}$), urine flow rate (V), and creatinine's plasma concentration ($P_{Cr}$) are known. Since the product of urine concentration and urine flow rate yields creatinine's excretion rate, creatinine clearance is also said to be its excretion rate ($U_{Cr} \times V$) divided by its plasma concentration. This is commonly represented mathematically as:

$$C_{Cr} = \frac{U_{Cr} \times V}{P_{Cr}}$$

Commonly a 24 hour urine collection is undertaken, from empty-bladder one morning to the contents of the bladder the following morning, with a comparative blood test then taken:

$$C_{Cr} = \frac{U_{Cr} \times 24\text{-hour volume}}{P_{Cr} \times 24 \times 60 \text{ mins}}$$

To allow comparison of results between people of different sizes, the CCr is often corrected for the body surface area (BSA) and expressed compared to the average sized man as ml/min/1.73 m2. While most adults have a BSA that approaches 1.7 (1.6-1.9), extremely obese or slim patients should have their CCr corrected for their actual BSA:

$$C_{Cr-corrected} = \frac{C_{Cr} \times 1.73}{BSA}$$

The accuracy of a creatinine clearance measurement (even when collection is complete) is limited because as glomerular filtration rate (GFR) falls creatinine secretion is increased, and thus the rise in serum creatinine is less. Thus, creatinine excretion is much greater than the filtered load, resulting in a potentially large overestimation of the GFR (as much as a twofold difference). However, for clinical purposes it is important to determine whether renal function is stable or getting worse or better. This is often determined by monitoring serum creatinine alone. Like creatinine clearance, the serum creatinine will not be an accurate reflection of GFR in the non-steady-state condition of ARF. Nonetheless, the degree to which serum creatinine changes from baseline will reflect the change in GFR. Serum creatinine is readily and easily measured and it is specific for renal function.

For purposes of determining urine output on a Urine output on a mL/kg/hr basis, hourly urine collection and measurement is adequate. In the case where, for example, only a cumulative 24-h output was available and no patient weights are provided, minor modifications of the RIFLE urine output criteria have been described. For example, Bagshaw et al., Nephrol. Dial. Transplant. 23: 1203-1210, 2008, assumes an average patient weight of 70 kg, and patients are assigned a RIFLE classification based on the following: <35 mL/h (Risk), <21 mL/h (Injury) or <4 mL/h (Failure).

Selecting a Treatment Regimen

Once a diagnosis is obtained, the clinician can readily select a treatment regimen that is compatible with the diagnosis, such as initiating renal replacement therapy, withdrawing delivery of compounds that are known to be damaging to the kidney, kidney transplantation, delaying or avoiding procedures that are known to be damaging to the kidney, modifying diuretic administration, initiating goal directed therapy, etc. The skilled artisan is aware of appropriate treatments for numerous diseases discussed in relation to the methods of diagnosis described herein. See, e.g., Merck Manual of Diagnosis and Therapy, 17th Ed. Merck Research Laboratories, Whitehouse Station, N.J., 1999. In addition, since the methods and compositions described herein provide prognostic information, the markers of the present invention may be used to monitor a course of treatment. For example, improved or worsened prognostic state may indicate that a particular treatment is or is not efficacious.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

Example 1

Contrast-Induced Nephropathy Sample Collection

The objective of this sample collection study is to collect samples of plasma and urine and clinical data from patients before and after receiving intravascular contrast media. Approximately 250 adults undergoing radiographic/angiographic procedures involving intravascular administration of iodinated contrast media are enrolled. To be enrolled in the study, each patient must meet all of the following inclusion criteria and none of the following exclusion criteria:

Inclusion Criteria males and females 18 years of age or older;
undergoing a radiographic/angiographic procedure (such as a CT scan or coronary intervention) involving the intravascular administration of contrast media;
expected to be hospitalized for at least 48 hours after contrast administration.
able and willing to provide written informed consent for study participation and to comply with all study procedures.

Exclusion Criteria
renal transplant recipients;
acutely worsening renal function prior to the contrast procedure;
already receiving dialysis (either acute or chronic) or in imminent need of dialysis at enrollment;
expected to undergo a major surgical procedure (such as involving cardiopulmonary bypass) or an additional imaging procedure with contrast media with significant risk for further renal insult within the 48 hrs following contrast administration;
participation in an interventional clinical study with an experimental therapy within the previous 30 days;
known infection with human immunodeficiency virus (HIV) or a hepatitis virus.

Immediately prior to the first contrast administration (and after any pre-procedure hydration), an EDTA anti-coagulated blood sample (10 mL) and a urine sample (10 mL) are collected from each patient. Blood and urine samples are then collected at 4 (±0.5), 8 (±1), 24 (±2) 48 (±2), and 72 (±2) hrs following the last administration of contrast media during the index contrast procedure. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Serum creatinine is assessed at the site immediately prior to the first contrast administration (after any pre-procedure hydration) and at 4 (±0.5), 8 (±1), 24 (±2) and 48 (±2)), and 72 (±2) hours following the last administration of contrast (ideally at the same time as the study samples are obtained). In addition, each patient's status is evaluated through day 30 with regard to additional serum and urine creatinine measurements, a need for dialysis, hospitalization status, and adverse clinical outcomes (including mortality).

Prior to contrast administration, each patient is assigned a risk based on the following assessment: systolic blood pressure <80 mm Hg=5 points; intra-arterial balloon pump=5 points; congestive heart failure (Class III-IV or history of pulmonary edema)=5 points; age >75 yrs=4 points; hematocrit level <39% for men, <35% for women=3 points; diabetes=3 points; contrast media volume=1 point for each 100 mL; serum creatinine level >1.5 g/dL=4 points OR estimated GFR 40-60 mL/min/1.73 m$^2$=2 points, 20-40 mL/min/1.73 m$^2$=4 points, <20 mL/min/1.73 m$^2$=6 points. The risks assigned are as follows: risk for CIN and dialysis: 5 or less total points=risk of CIN−7.5%, risk of dialysis−0.04%; 6-10 total points=risk of CIN−14%, risk of dialysis−0.12%; 11-16 total points=risk of CIN−26.1%, risk of dialysis−1.09%; >16 total points=risk of CIN−57.3%, risk of dialysis−12.8%.

Example 2

Cardiac Surgery Sample Collection

The objective of this sample collection study is to collect samples of plasma and urine and clinical data from patients before and after undergoing cardiovascular surgery, a procedure known to be potentially damaging to kidney function. Approximately 900 adults undergoing such surgery are enrolled. To be enrolled in the study, each patient must meet all of the following inclusion criteria and none of the following exclusion criteria:
Inclusion Criteria
males and females 18 years of age or older;
undergoing cardiovascular surgery;
Toronto/Ottawa Predictive Risk Index for Renal Replacement risk score of at least 2 (Wijeysundera et al., *JAMA* 297: 1801-9, 2007); and
able and willing to provide written informed consent for study participation and to comply with all study procedures.
Exclusion Criteria
known pregnancy;
previous renal transplantation;
acutely worsening renal function prior to enrollment (e.g., any category of RIFLE criteria);
already receiving dialysis (either acute or chronic) or in imminent need of dialysis at enrollment;
currently enrolled in another clinical study or expected to be enrolled in another clinical study within 7 days of cardiac surgery that involves drug infusion or a therapeutic intervention for AKI;
known infection with human immunodeficiency virus (HIV) or a hepatitis virus.

Within 3 hours prior to the first incision (and after any pre-procedure hydration), an EDTA anti-coagulated blood sample (10 mL), whole blood (3 mL), and a urine sample (35 mL) are collected from each patient. Blood and urine samples are then collected at 3 (±0.5), 6 (±0.5), 12 (±1), 24 (±2) and 48 (±2) hrs following the procedure and then daily on days 3 through 7 if the subject remains in the hospital. Blood is collected via direct venipuncture or via other available venous access, such as an existing femoral sheath, central venous line, peripheral intravenous line or hep-lock. These study blood samples are frozen and shipped to Astute Medical, Inc., San Diego, Calif. The study urine samples are frozen and shipped to Astute Medical, Inc.

Example 3

Acutely Ill Subject Sample Collection

The objective of this study is to collect samples from acutely ill patients. Approximately 900 adults expected to be in the ICU for at least 48 hours will be enrolled. To be enrolled in the study, each patient must meet all of the following inclusion criteria and none of the following exclusion criteria:
Inclusion Criteria
males and females 18 years of age or older;
Study population 1: approximately 300 patients that have at least one of:
shock (SBP<90 mmHg and/or need for vasopressor support to maintain MAP>60 mmHg and/or documented drop in SBP of at least 40 mmHg); and sepsis;
Study population 2: approximately 300 patients that have at least one of:
IV antibiotics ordered in computerized physician order entry (CPOE) within 24 hours of enrollment;
contrast media exposure within 24 hours of enrollment;
increased Intra-Abdominal Pressure with acute decompensated heart failure; and
severe trauma as the primary reason for ICU admission and likely to be hospitalized in the ICU for 48 hours after enrollment;
Study population 3: approximately 300 patients
expected to be hospitalized through acute care setting (ICU or ED) with a known risk factor for acute renal injury (e.g. sepsis, hypotension/shock (Shock=systolic BP<90 mmHg and/or the need for vasopressor support to maintain a MAP>60 mmHg and/or a documented drop in SBP>40 mmHg), major trauma, hemorrhage, or major surgery); and/or expected to be hospitalized to the ICU for at least 24 hours after enrollment.

Exclusion Criteria known pregnancy;
institutionalized individuals;
previous renal transplantation;
known acutely worsening renal function prior to enrollment (e.g., any category of RIFLE criteria);
received dialysis (either acute or chronic) within 5 days prior to enrollment or in imminent need of dialysis at the time of enrollment;
known infection with human immunodeficiency virus (HIV) or a hepatitis virus;
meets only the SBP<90 mmHg inclusion criterion set forth above, and does not have shock in the attending physician's or principal investigator's opinion.

After providing informed consent, an EDTA anti-coagulated blood sample (10 mL) and a urine sample (25-30 mL) are collected from each patient. Blood and urine samples are then collected at 4 (±0.5) and 8 (±1) hours after contrast administration (if applicable); at 12 (±1), 24 (±2), and 48 (±2) hours after enrollment, and thereafter daily up to day 7 to day 14 while the subject is hospitalized. Blood is collected via direct venipuncture or via other available venous access, such as an existing femoral sheath, central venous line, peripheral intravenous line or hep-lock. These study blood samples are processed to plasma at the clinical site, frozen and shipped to Astute Medical, Inc., San Diego, Calif. The study urine samples are frozen and shipped to Astute Medical, Inc.

Example 4

Immunoassay Format

Analytes are is measured using standard sandwich enzyme immunoassay techniques. A first antibody which binds the analyte is immobilized in wells of a 96 well polystyrene microplate. Analyte standards and test samples are pipetted into the appropriate wells and any analyte present is bound by the immobilized antibody. After washing away any unbound substances, a horseradish peroxidase-conjugated second antibody which binds the analyte is added to the wells, thereby forming sandwich complexes with the analyte (if present) and the first antibody. Following a wash to remove any unbound antibody-enzyme reagent, a substrate solution comprising tetramethylbenzidine and hydrogen peroxide is added to the wells. Color develops in proportion to the amount of analyte present in the sample. The color development is stopped and the intensity of the color is measured at 540 nm or 570 nm. An analyte concentration is assigned to the test sample by comparison to a standard curve determined from the analyte standards.

Concentrations are expressed in the following examples as follows: Clusterin ng/mL, Heart-type fatty acid binding protein ng/mL, Hepatocyte growth factor pg/mL, Interferon gamma pg/mL, Interleukin-12 subunit beta pg/mL, Interleukin-16 pg/mL, Interleukin-2 pg/mL, 72 kDa type IV collagenase ng/mL, Matrix metalloproteinase-9 pg/mL (urine) and ng/mL (plasma), Midkine ng/mL, and Serum amyloid P-component ng/mL.

Example 5

Apparently Healthy Donor and Chronic Disease Patient Samples

Human urine samples from donors with no known chronic or acute disease ("Apparently Healthy Donors") were purchased from two vendors (Golden West Biologicals, Inc., 27625 Commerce Center Dr., Temecula, Calif. 92590 and Virginia Medical Research, Inc., 915 First Colonial Rd., Virginia Beach, Va. 23454). The urine samples were shipped and stored frozen at less than −20° C. The vendors supplied demographic information for the individual donors including gender, race (Black/White), smoking status and age.

Human urine samples from donors with various chronic diseases ("Chronic Disease Patients") including congestive heart failure, coronary artery disease, chronic kidney disease, chronic obstructive pulmonary disease, diabetes mellitus and hypertension were purchased from Virginia Medical Research, Inc., 915 First Colonial Rd., Virginia Beach, Va. 23454. The urine samples were shipped and stored frozen at less than −20 degrees centigrade. The vendor provided a case report form for each individual donor with age, gender, race (Black/White), smoking status and alcohol use, height, weight, chronic disease(s) diagnosis, current medications and previous surgeries.

Example 6

Kidney Injury Markers for Evaluating Renal Status in Patients at RIFLE Stage 0

Patients from the intensive care unit (ICU) were classified by kidney status as non-injury (0), risk of injury (R), injury (I), and failure (F) according to the maximum stage reached within 7 days of enrollment as determined by the RIFLE criteria.

Two cohorts were defined as (Cohort 1) patients that did not progress beyond stage 0, and (Cohort 2) patients that reached stage R, I, or F within 10 days. To address normal marker fluctuations that occur within patients at the ICU and thereby assess utility for monitoring AKI status, marker levels were measured in urine samples collected for Cohort 1. Marker concentrations were measured in urine samples collected from a subject at 0, 24 hours, and 48 hours prior to reaching stage R, I or F in Cohort 2. In the following tables, the time "prior max stage" represents the time at which a sample is collected, relative to the time a particular patient reaches the lowest disease stage as defined for that cohort, binned into three groups which are +/−12 hours. For example, 24 hr prior for this example (0 vs R, I, F) would mean 24 hr (+/−12 hours) prior to reaching stage R (or I if no sample at R, or F if no sample at R or I).

Each marker was measured by standard immunoassay methods using commercially available assay reagents. A receiver operating characteristic (ROC) curve was generated for each marker and the area under each ROC curve (AUC) was determined. Patients in Cohort 2 were also separated according to the reason for adjudication to stage R, I, or F as being based on serum creatinine measurements (sCr), being based on urine output (UO), or being based on either serum creatinine measurements or urine output. That is, for those patients adjudicated to stage R, I, or F on the basis of serum creatinine measurements alone, the stage 0 cohort may have included patients adjudicated to stage R, I, or F on the basis of urine output; for those patients adjudicated to stage R, I, or F on the basis of urine output alone, the stage 0 cohort may have included patients adjudicated to stage R, I, or F on the basis of serum creatinine measurements; and for those patients adjudicated to stage R, I, or F on the basis of serum creatinine measurements or urine output, the stage 0 cohort contains only patients in stage 0 for both serum creatinine measurements and urine output. Also, for those patients adjudicated to stage R, I, or F on the basis of serum creatinine measurements or urine output, the adjudication method which yielded the most severe RIFLE stage was used.

The ability to distinguish cohort 1 (subjects remaining in RIFLE 0) from Cohort 2 (subjects progressing to RIFLE R, I or F) was determined using ROC analysis. SE is the standard error of the AUC, n is the number of sample or individual patients ("pts," as indicated). Standard errors were calculated as described in Hanley, J. A., and McNeil, B. J., The meaning and use of the area under a receiver operating characteristic (ROC) curve. Radiology (1982) 143: 29-36; p values were calculated with a two-tailed Z-test. An AUC<0.5 is indicative of a negative going marker for the comparison, and an AUC>0.5 is indicative of a positive going marker for the comparison.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 1.

Example 7

Kidney Injury Markers for Evaluating Renal Status in Patients at RIFLE Stages 0 and R Patients were classified and analyzed as described in Example 6. However, patients that reached stage R but did not progress to stage I or F were grouped with patients from non-injury stage 0 in Cohort 1. Cohort 2 in this example included only patients that progressed to stage I or F. Marker concentrations in urine samples were included for Cohort 1. Marker concentrations in urine samples collected within 0, 24, and 48 hours of reaching stage I or F were included for Cohort 2.

The ability to distinguish cohort 1 (subjects remaining in RIFLE 0 or R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 2.

Example 8

Kidney Injury Markers for Evaluating Renal Status in Patients Progressing from Stage R to Stages I and F Patients were classified and analyzed as described in Example 6, but only those patients that reached Stage R were included in this example. Cohort 1 contained patients that reached stage R but did not progress to stage I or F within 10 days, and Cohort 2 included only patients that progressed to stage I or F. Marker concentrations in urine samples collected within 12 hours of reaching stage R were included in the analysis for both Cohort 1 and 2.

The ability to distinguish cohort 1 (subjects remaining in RIFLE R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 3.

Example 9

Kidney Injury Markers for Evaluating Renal Status in Patients at RIFLE Stage 0

Patients were classified and analyzed as described in Example 6. However, patients that reached stage R or I but did not progress to stage F were eliminated from the analysis. Patients from non-injury stage 0 are included in Cohort 1. Cohort 2 in this example included only patients that progressed to stage F. The maximum marker concentrations in urine samples were included for each patient in Cohort 1. The maximum marker concentrations in urine samples collected within 0, 24, and 48 hours of reaching stage F were included for each patient in Cohort 2.

The ability to distinguish cohort 1 (subjects remaining in RIFLE 0 or R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 4.

Example 10

Kidney Injury Markers for Evaluating Renal Status in Patients at RIFLE Stage 0

Patients from the intensive care unit (ICU) were classified by kidney status as non-injury (0), risk of injury (R), injury (I), and failure (F) according to the maximum stage reached within 7 days of enrollment as determined by the RIFLE criteria.

Two cohorts were defined as (Cohort 1) patients that did not progress beyond stage 0, and (Cohort 2) patients that reached stage R, I, or F within 10 days. To address normal marker fluctuations that occur within patients at the ICU and thereby assess utility for monitoring AKI status, marker levels were measured in the plasma component of blood samples collected for Cohort 1. Marker concentrations were measured in the plasma component of blood samples collected from a subject at 0, 24 hours, and 48 hours prior to reaching stage R, I or F in Cohort 2. In the following tables, the time "prior max stage" represents the time at which a sample is collected, relative to the time a particular patient reaches the lowest disease stage as defined for that cohort, binned into three groups which are +/−12 hours. For example, 24 hr prior for this example (0 vs R, I, F) would mean 24 hr (+/−12 hours) prior to reaching stage R (or I if no sample at R, or F if no sample at R or I).

Each marker was measured by standard immunoassay methods using commercially available assay reagents. A receiver operating characteristic (ROC) curve was generated for each marker and the area under each ROC curve (AUC) was determined. Patients in Cohort 2 were also separated according to the reason for adjudication to stage R, I, or F as being based on serum creatinine measurements (sCr), being based on urine output (UO), or being based on either serum creatinine measurements or urine output. That is, for those patients adjudicated to stage R, I, or F on the basis of serum creatinine measurements alone, the stage 0 cohort may have included patients adjudicated to stage R, I, or F on the basis of urine output; for those patients adjudicated to stage R, I, or F on the basis of urine output alone, the stage 0 cohort may have included patients adjudicated to stage R, I, or F on the basis of serum creatinine measurements; and for those patients adjudicated to stage R, I, or F on the basis of serum creatinine measurements or urine output, the stage 0 cohort contains only patients in stage 0 for both serum creatinine measurements and urine output. Also, for those patients adjudicated to stage R, I, or F on the basis of serum creatinine measurements or urine output, the adjudication method which yielded the most severe RIFLE stage was used.

The ability to distinguish cohort 1 (subjects remaining in RIFLE 0) from Cohort 2 (subjects progressing to RIFLE R, I or F) was determined using ROC analysis. SE is the standard error of the AUC, n is the number of sample or individual patients ("pts," as indicated). Standard errors were calculated as described in Hanley, J. A., and McNeil, B. J., The meaning and use of the area under a receiver operating characteristic (ROC) curve. Radiology (1982) 143: 29-36; p values were calculated with a two-tailed Z-test. An AUC<0.5 is indicative of a negative going marker for the comparison, and an AUC>0.5 is indicative of a positive going marker for the comparison.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 5.

Example 11

Kidney Injury Markers for Evaluating Renal Status in Patients at RIFLE Stages 0 and R Patients were classified and analyzed as described in Example 10. However, patients that reached stage R but did not progress to stage I or F were grouped with patients from non-injury stage 0 in Cohort 1. Cohort 2 in this example included only patients that progressed to stage I or F. Marker concentrations in the plasma component of blood samples were included for Cohort 1. Marker concentrations in the plasma component of blood samples collected within 0, 24, and 48 hours of reaching stage I or F were included for Cohort 2.

The ability to distinguish cohort 1 (subjects remaining in RIFLE 0 or R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 6.

Example 12

Kidney Injury Markers for Evaluating Renal Status in Patients Progressing from Stage R to Stages I and F Patients were classified and analyzed as described in Example 10, but only those patients that reached Stage R were included in this example. Cohort 1 contained patients that reached stage R but did not progress to stage I or F within 10 days, and Cohort 2 included only patients that progressed to stage I or F. Marker concentrations in the plasma component of blood samples collected within 12 hours of reaching stage R were included in the analysis for both Cohort 1 and 2.

The ability to distinguish cohort 1 (subjects remaining in RIFLE R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 7.

Example 13

Kidney Injury Markers for Evaluating Renal Status in Patients at RIFLE Stage 0

Patients were classified and analyzed as described in Example 10. However, patients that reached stage R or I but did not progress to stage F were eliminated from the analysis. Patients from non-injury stage 0 are included in Cohort 1. Cohort 2 in this example included only patients that progressed to stage F. The maximum marker concentrations in the plasma component of blood samples were included from each patient in Cohort 1. The maximum marker concentrations in the plasma component of blood samples collected within 0, 24, and 48 hours of reaching stage F were included from each patient in Cohort 2.

The ability to distinguish cohort 1 (subjects remaining in RIFLE 0 or R) from Cohort 2 (subjects progressing to RIFLE I or F) was determined using ROC analysis.

Various threshold (or "cutoff") concentrations were selected, and the associated sensitivity and specificity for distinguishing cohort 1 from cohort 2 were determined. OR is the odds ratio calculated for the particular cutoff concentration, and 95% CI is the confidence interval for the odds ratio.

The results of these three analyses for various markers of the present invention are presented in FIG. 8.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method for evaluating renal status in a subject, comprising:
    obtaining a urine sample from a subject selected for evaluation based on a determination that the subject is at risk of a future acute renal injury;
    performing one or more assays configured to detect a kidney injury marker selected from the group consisting of Clusterin, Heart-type fatty acid binding protein, Hepatocyte growth factor, Interferon gamma, Interleukin-12 subunit beta, Interleukin-16, Interleukin-2, 72 kDa type IV collagenase, Matrix metalloproteinase-9, Midkine, and Serum amyloid P-component by introducing the urine sample obtained from the subject into an assay instrument which (i) contacts the urine sample with one or more antibodies which specifically bind for detection the biomarker(s) which are assayed, and (ii) generates one or more assay results indicative of binding of each biomarker which is assayed to a respective antibody to provide one or more assay results; and
    correlating the assay result(s) generated by the assay instrument to the renal status of the subject, wherein said correlation step comprises correlating the assay result(s) to one or more of risk stratification, staging, prognosis, classifying and monitoring of the renal status of the subject, wherein said correlating step comprises assigning a likelihood of one or more future changes in renal status to the subject based on the assay result(s).

2. A method according to claim 1, wherein said one or more future changes in renal status comprise one or more of a future injury to renal function, future reduced renal function, future improvement in renal function, and future acute renal failure (ARF).

3. A method according to claim 2, wherein said assay result(s) comprise one or more of:
  (i) a measured concentration of Clusterin,
  (ii) a measured concentration of Heart-type fatty acid binding protein,
  (iii) a measured concentration of Hepatocyte growth factor,
  (iv) a measured concentration of Interferon gamma,
  (v) a measured concentration of Interleukin-12 subunit beta,
  (vi) a measured concentration of Interleukin-16,
  (vii) a measured concentration of Interleukin-2,
  (viii) a measured concentration of 72 kDa type IV collagenase,
  (ix) a measured concentration of Matrix metalloproteinase-9,
  (x) a measured concentration of Midkine, or
  (xi) a measured concentration of Serum amyloid P-component,
  and said correlation step comprises, for each assay result, comparing said measure concentration to a threshold concentration, and
  for a positive going marker, assigning an increased likelihood of suffering a future injury to renal function, future reduced renal function, future ARF, or a future improvement in renal function to the subject when the measured concentration is above the threshold, relative to a likelihood assigned when the measured concentration is below the threshold or assigning a decreased likelihood of suffering a future injury to renal function, future reduced renal function, future ARF, or a future improvement in renal function to the subject when the measured concentration is below the threshold, relative to a likelihood assigned when the measured concentration is above the threshold, or
  for a negative going marker, assigning an increased likelihood of suffering a future injury to renal function, future reduced renal function, future ARF, or a future improvement in renal function to the subject when the measured concentration is below the threshold, relative to a likelihood assigned when the measured concentration is above the threshold or assigning a decreased likelihood of suffering a future injury to renal function, future reduced renal function, future ARF, or a future improvement in renal function to the subject when the measured concentration is above the threshold, relative to a likelihood assigned when the measured concentration is below the threshold.

4. A method according to claim 1, wherein said one or more future changes in renal status comprise a clinical outcome related to a renal injury suffered by the subject.

5. A method according to claim 1, wherein said assay result(s) comprise one or more of:
  (i) a measured concentration of Clusterin,
  (ii) a measured concentration of Heart-type fatty acid binding protein,
  (iii) a measured concentration of Hepatocyte growth factor,
  (iv) a measured concentration of Interferon gamma,
  (v) a measured concentration of Interleukin-12 subunit beta,
  (vi) a measured concentration of Interleukin-16,
  (vii) a measured concentration of Interleukin-2,
  (viii) a measured concentration of 72 kDa type IV collagenase,
  (ix) a measured concentration of Matrix metalloproteinase-9,
  (x) a measured concentration of Midkine, or
  (xi) a measured concentration of Serum amyloid P-component,
  and said correlation step comprises, for each assay result, comparing said measure concentration to a threshold concentration, and
  for a positive going marker, assigning an increased likelihood of subsequent acute kidney injury, worsening stage of AKI, mortality, need for renal replacement therapy, need for withdrawal of renal toxins, end stage renal disease, heart failure, stroke, myocardial infarction, or chronic kidney disease to the subject when the measured concentration is above the threshold, relative to a likelihood assigned when the measured concentration is below the threshold, or assigning a decreased likelihood of subsequent acute kidney injury, worsening stage of AKI, mortality, need for renal replacement therapy, need for withdrawal of renal toxins, end stage renal disease, heart failure, stroke, myocardial infarction, or chronic kidney disease to the subject when the measured concentration is below the threshold, relative to a likelihood assigned when the measured concentration is above the threshold, or
  for a negative going marker, assigning an increased likelihood of subsequent acute kidney injury, worsening stage of AKI, mortality, need for renal replacement therapy, need for withdrawal of renal toxins, end stage renal disease, heart failure, stroke, myocardial infarction, or chronic kidney disease to the subject when the measured concentration is below the threshold, relative to a likelihood assigned when the measured concentration is above the threshold, or assigning a decreased likelihood of subsequent acute kidney injury, worsening stage of AKI, mortality, need for renal replacement therapy, need for withdrawal of renal toxins, end stage renal disease, heart failure, stroke, myocardial infarction, or chronic kidney disease to the subject when the measured concentration is above the threshold, relative to a likelihood assigned when the measured concentration is below the threshold.

6. A method according to claim 1, wherein the likelihood of one or more future changes in renal status is that an event of interest is more or less likely to occur within 30 days of the time at which the urine sample is obtained from the subject.

7. A method according to claim 6, wherein the likelihood of one or more future changes in renal status is that an event of interest is more or less likely to occur within a period selected from the group consisting of 21 days, 14 days, 7 days, 5 days, 96 hours, 72 hours, 48 hours, 36 hours, 24 hours, and 12 hours.

8. A method according to claim 1, wherein the subject is selected for evaluation of renal status based on the pre-existence in the subject of one or more known risk factors for prerenal, intrinsic renal, or postrenal ARF.

9. A method according to claim 1, wherein the subject is selected for evaluation of renal status based on an existing diagnosis of one or more of congestive heart failure, preeclampsia, eclampsia, diabetes mellitus, hypertension, coronary artery disease, proteinuria, renal insufficiency, glomerular filtration below the normal range, cirrhosis, serum creatinine above the normal range, sepsis, injury to renal function, reduced renal function, or ARF, or based on undergoing or having undergone major vascular surgery, coronary artery bypass, or other cardiac surgery, or based on exposure to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin.

10. A method according to claim 1, wherein said correlating step comprises assigning a diagnosis of the occurrence or nonoccurrence of one or more of an injury to renal function, reduced renal function, or ARF to the subject based on the assay result(s).

11. A method according to claim 1, wherein said correlating step comprises assessing whether or not renal function is improving or worsening in a subject who has suffered from an injury to renal function, reduced renal function, or ARF based on the assay result(s).

12. A method according to claim 11, wherein said assay result(s) comprise one or more of:
(i) a measured concentration of Clusterin,
(ii) a measured concentration of Heart-type fatty acid binding protein,
(iii) a measured concentration of Hepatocyte growth factor,
(iv) a measured concentration of Interferon gamma,
(v) a measured concentration of Interleukin-12 subunit beta,
(vi) a measured concentration of Interleukin-16,
(vii) a measured concentration of Interleukin-2,
(viii) a measured concentration of 72 kDa type IV collagenase,
(ix) a measured concentration of Matrix metalloproteinase-9,
(x) a measured concentration of Midkine, or
(xi) a measured concentration of Serum amyloid P-component,
and said correlation step comprises, for each assay result, comparing said measure concentration to a threshold concentration, and
for a positive going marker, assigning a worsening of renal function to the subject when the measured concentration is above the threshold, or assigning an improvement of renal function when the measured concentration is below the threshold, or
for a negative going marker, assigning a worsening of renal function to the subject when the measured concentration is below the threshold, or assigning an improvement of renal function when the measured concentration is above the threshold.

13. A method according to claim 1, wherein said method is a method of assigning a risk of the future occurrence or nonoccurrence of an injury to renal function in said subject.

14. A method according to claim 1, wherein said method is a method of assigning a risk of the future occurrence or nonoccurrence of reduced renal function in said subject.

15. A method according to claim 1, wherein said method is a method of assigning a risk of the future occurrence or nonoccurrence of acute renal failure in said subject.

16. A method according to claim 1, wherein said method is a method of assigning a risk of the future occurrence or nonoccurrence of a need for renal replacement therapy in said subject.

17. A method according to claim 1, wherein said method is a method of assigning a risk of the future occurrence or nonoccurrence of a need for renal transplantation in said subject.

18. A method according to claim 3, wherein said one or more future changes in renal status comprise one or more of a future injury to renal function, future reduced renal function, future improvement in renal function, and future acute renal failure (ARF) within 72 hours of the time at which the urine sample is obtained.

19. A method according to claim 3, wherein said one or more future changes in renal status comprise one or more of a future injury to renal function, future reduced renal function, future improvement in renal function, and future acute renal failure (ARF) within 48 hours of the time at which the urine sample is obtained.

20. A method according to claim 3, wherein said one or more future changes in renal status comprise one or more of a future injury to renal function, future reduced renal function, future improvement in renal function, and future acute renal failure (ARF) within 72 hours of the time at which the urine sample is obtained.

21. A method according to claim 3, wherein said one or more future changes in renal status comprise one or more of a future injury to renal function, future reduced renal function, future improvement in renal function, and future acute renal failure (ARF) within 48 hours of the time at which the urine sample is obtained.

22. A method according to claim 3, wherein said one or more future changes in renal status comprise one or more of a future injury to renal function, future reduced renal function, future improvement in renal function, and future acute renal failure (ARF) within 24 hours of the time at which the urine sample is obtained.

23. A method according to claim 5, wherein the increased or decreased likelihood of subsequent acute kidney injury, worsening stage of AKI, mortality, need for renal replacement therapy, need for withdrawal of renal toxins, end stage renal disease, heart failure, stroke, myocardial infarction, or chronic kidney disease assigned to the subject is a likelihood that an event of interest is more or less likely to occur within 30 days of the time at which the urine sample is obtained from the subject.

24. A method according to claim 5, wherein the increased or decreased likelihood of subsequent acute kidney injury, worsening stage of AKI, mortality, need for renal replacement therapy, need for withdrawal of renal toxins, end stage renal disease, heart failure, stroke, myocardial infarction, or chronic kidney disease assigned to the subject is a likelihood that an event of interest is more or less likely to occur within 72 hours of the time at which the urine sample is obtained from the subject.

25. A method according to claim 5, wherein the increased or decreased likelihood of subsequent acute kidney injury, worsening stage of AKI, mortality, need for renal replacement therapy, need for withdrawal of renal toxins, end stage renal disease, heart failure, stroke, myocardial infarction, or chronic kidney disease assigned to the subject is a likelihood that an event of interest is more or less likely to occur within 24 hours of the time at which the urine sample is obtained from the subject.

* * * * *